(12) United States Patent
Lennox et al.

(10) Patent No.: US 9,271,960 B2
(45) Date of Patent: Mar. 1, 2016

(54) TETRAHYDROCARBAZOLES AS ACTIVE AGENTS FOR INHIBITING VEGF PRODUCTION BY TRANSLATIONAL CONTROL

(71) Applicant: PTC Therapeutics, Inc., South Plainfield, NJ (US)

(72) Inventors: William Lennox, South Plainfield, NJ (US); Hongyan Qi, Plainsboro, NJ (US); Duck-Hyung Lee, Seoul (KR); Soongyu Choi, Skillman, NJ (US); Young-Choon Moon, Belle Mead, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 14/605,721

(22) Filed: Jan. 26, 2015

(65) Prior Publication Data
US 2015/0141418 A1    May 21, 2015

Related U.S. Application Data

(63) Continuation of application No. 11/720,055, filed as application No. PCT/US2005/042483 on Nov. 23, 2005, now Pat. No. 8,946,444.

(60) Provisional application No. 60/639,283, filed on Dec. 27, 2004, provisional application No. 60/633,738, filed on Dec. 6, 2004, provisional application No. 60/629,889, filed on Nov. 23, 2004.

(51) Int. Cl.
| | |
|---|---|
| *A61K 31/403* | (2006.01) |
| *C07D 209/90* | (2006.01) |
| *C07D 209/08* | (2006.01) |
| *C07D 471/04* | (2006.01) |
| *A61K 31/343* | (2006.01) |
| *A61K 31/4035* | (2006.01) |
| *A61K 31/407* | (2006.01) |
| *A61K 31/4162* | (2006.01) |
| *A61K 31/4184* | (2006.01) |
| *A61K 31/4188* | (2006.01) |
| *A61K 31/424* | (2006.01) |
| *A61K 31/4245* | (2006.01) |
| *A61K 31/506* | (2006.01) |
| *A61K 31/5377* | (2006.01) |

(52) U.S. Cl.
CPC ............. *A61K 31/403* (2013.01); *A61K 31/343* (2013.01); *A61K 31/407* (2013.01); *A61K 31/4035* (2013.01); *A61K 31/4162* (2013.01); *A61K 31/4184* (2013.01); *A61K 31/4188* (2013.01); *A61K 31/424* (2013.01); *A61K 31/4245* (2013.01); *A61K 31/506* (2013.01); *A61K 31/5377* (2013.01); *C07D 209/08* (2013.01); *C07D 209/90* (2013.01); *C07D 471/04* (2013.01)

(58) Field of Classification Search
CPC ..................................................... A61K 31/403
See application file for complete search history.

(56) References Cited

U.S. PATENT DOCUMENTS 5,451,600 A * 9/1995 Banner et al. ................. 514/414

FOREIGN PATENT DOCUMENTS

WO      WO2004110999      * 12/2004      ........... C07D 209/82

OTHER PUBLICATIONS

Perspicace et al. (European Journal of Medicinal Chemistry, 63 (2013), p. 765-781).*
Kubinyi (3D QSAR in Drug Design: Ligand-Protein Interactions and Molecular Similarity, vol. 2-3, Springer, 1998, 800 pages). p. 243 provided.*
Wermuth, The Practice of Medicinal Chemsitry, 2d ed. (2003), 768 pages. Chs. 9-10 provided.*
Park et al. (Toxicology Lett., 120 (2001), 281-91).*

* cited by examiner

*Primary Examiner* — Robert Havlin
(74) *Attorney, Agent, or Firm* — Hoffmann & Baron, LLP

(57) ABSTRACT

The present invention relates to methods, compounds, and compositions for inhibiting angiogenesis. More particularly, the present invention relates to methods, compounds, and compositions for inhibiting VEGF production.

4 Claims, 1 Drawing Sheet

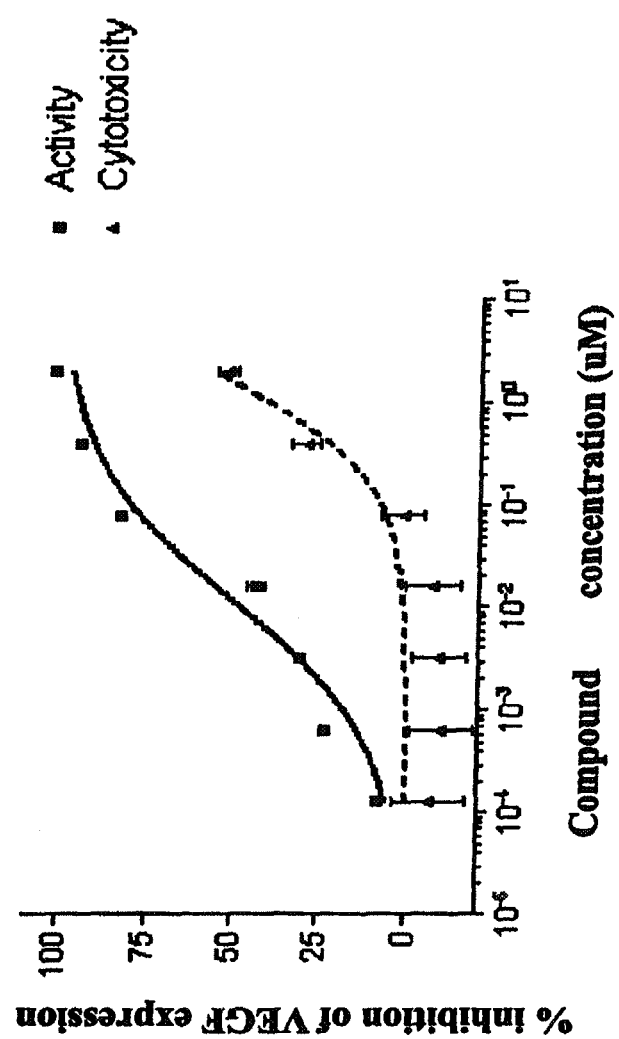

TETRAHYDROCARBAZOLES AS ACTIVE AGENTS FOR INHIBITING VEGF PRODUCTION BY TRANSLATIONAL CONTROL

CROSS-REFERENCE TO RELATED APPLICATIONS

The present application is a continuation of U.S. application Ser. No. 11/720,055, filed May 23, 2007, and afforded a 371(c) date of Apr. 28, 2008, now U.S. Pat. No. 8,946,444, which U.S. application Ser. No. 11/720,055 is a national phase application under 35 U.S.C. §371 of International Application No. PCT/US2005/042483, filed Nov. 23, 2005, which claims priority to and the benefit under 35 U.S.C. §119 of U.S. Provisional Application No. 60/633,738, filed Dec. 6, 2004, U.S. Provisional Application No. 60/629,889, filed Nov. 23, 2004, and U.S. Provisional Application No. 60/639,283, filed Dec. 27, 2004, the entire contents of all of which applications are incorporated herein by reference.

FIELD OF THE INVENTION

The present invention relates to methods, compounds, and compositions for inhibiting angiogenesis. More particularly, the present invention relates to methods, compounds, and compositions for inhibiting VEGF production.

BACKGROUND OF THE INVENTION

Aberrant angiogenesis plays a critical role in the pathogenesis of numerous diseases, including malignant, ischemic, inflammatory and immune disorders (1, 2). The best-known of these disorders are cancer, exudative macular degeneration and diabetic retinopathy (DR), the last two of which are leading cause of blindness in the United States (3, 4). During the last decade our understanding of the molecular basis of angiogenesis has grown considerably. Numerous cytokines and growth factors that stimulate angiogenesis, such as VEGF, FGF-2, PDGF, IGF-1, TGF, TNFα, G-CSF have been identified (5-7). Among these growth factors, Vascular Endothelial Growth Factor (VEGF) plays a central role in angiogenesis (2).

VEGF, also known as VEGF-A, was initially identified for its ability to induce vascular permeability and to promote vascular endothelial cell proliferation (8-10). VEGF is encoded by a single gene that gives rise to four isoforms by alternative splicing (11). All four isoforms share the same unusually long and GC rich 5'-UTR, as well as a 3'-UTR that includes multiple RNA stability determinants. The receptors VEGFR-2 (also known as KDR or Flk-1) and VEGFR-1 (previously known as Flt1) recognize the dimeric form of VEGF (12, 13). The highly specific VEGFR-2 receptor is expressed on endothelial cells. VEGF binding to the VEGFR-2 receptor activates the receptor's tyrosine kinase activity, leading to endothelial cell proliferation, differentiation and primitive vessel formation (14). VEGFR-1 inhibits growth either by acting as a decoy or by suppressing signaling pathways through VEGFR-2 (15).

Over 30 years ago, it was proposed that inhibition of tumor angiogenesis could be an effective approach for the treatment of cancer (16). Subsequent studies have demonstrated that angiogenesis regulators, including VEGF, the FGFs, PDGF, TGF, EGF, IL-8, IL-6, and the angiopoietins, etc, are involved in tumor growth and metastasis (17, 18). VEGF and its receptor have been demonstrated to have a central role in tumor angiogenesis, especially in the early stages of tumor growth (19). Indeed, increased levels of VEGF expression have been correlated with microvessel density in primary tumor tissues (20). Moreover, increased levels of the VEGF transcript are found in virtually all of the common solid tumors (21). In general, tumor-bearing patients have higher levels of VEGF compared to those in tumor-free individuals, and high VEGF levels in serum/plasma are associated with poor prognosis (22). Consistent with the role of VEGF in tumor angiogenesis, VEGF null embryonic stem cells showed a dramatically reduced ability to form tumors in nude mice (23). Direct evidence for the involvement of VEGF in tumorigenesis was demonstrated by using specific antibodies against VEGF in human xenografts implanted in nude mice (24, 25). In these studies, the inhibition of tumor growth correlated positively with decreased vessel formation in the antibody-treated tumors. Subsequent experiments using the soluble receptors substantiated the importance of VEGF activity in tumor growth (26), and demonstrated that inactivation of VEGF by specific antibody treatment directly resulted in a nearly complete suppression of tumor-associated neovascularization (27, 28).

In exudative macular degeneration and diabetic retinopathy, pre-clinical experiments and clinical trials have demonstrated that over production of VEGF is critical for aberrant retinal or choroidal neovascularization (reviewed in 3). Evidence has been obtained that intra-ocular VEGF levels are strongly correlated with active retinal/choroidal neovascularization (CNV) in patients with diseases such as diabetic retinopathy and wet form macular degeneration (29, 30). In addition, studies using transgenic mice demonstrated that overexpression of VEGF in retinal pigment epithelial cells or photoreceptor cells results in choroidal or retinal neovascularization (31, 32). In recent studies neutralizing antibodies, soluble receptor, receptor antagonists, or siRNA have proven efficacious in reducing VEGF-mediated blood vessel formation in animal models and in the clinic (33, 34-37).

VEGF expression is regulated by a number of factors and agents including cytokines, growth factors, steroid hormones and chemicals, and mutations that modulate the activity of oncogenes such as ras or the tumor suppressor gene VHL (38, 39). Nevertheless, hypoxia is the most significant physiologic signal for regulating VEGF expression. Hypoxia results in enhanced VEGF expression by increasing both the transcription rate and stability of the VEGF transcript (40-42). Hypoxia-inducible factor 1α (HIF-1α) is a transcription factor that increases VEGF gene expression in cells undergoing hypoxia by binding to the hypoxia response element (HRE) located in the VEGF promoter (43, 44). The stability of VEGF mRNA is also greatly enhanced as a consequence of the binding of factors to elements in the 3'-UTR (45). In addition, the translation initiation of the VEGF transcript is uniquely regulated. Under hypoxic conditions, translation of most cellular transcripts mediated by cap-dependent translation initiation process is greatly impaired (46). Initiation of translation of the VEGF mRNA, however, is unique under hypoxic conditions in that it is mediated via an internal ribosome entry site (IRES) within the VEGF 5'UTR (41, 42, 47, 48).

There is a large body of experimental evidence indicating that tumor growth can be inhibited by the prevention of neovascularization (26, 49). Tumor vessels are generally immature and constantly undergo remodeling (1, 50). Active and aberrant angiogenesis is the result of a disruption in the normal balance of proangiogenic and anti-angiogenic factors, including various cytokines, growth factors and steroid hormones. Despite the complexity of the regulation of tumor angiogenesis, accumulated evidence indicates that targeting a single proangiogenic factor might be sufficient to inhibit tumor angiogenesis and suppress tumor growth (24, 51, 52). Among many angiogenesis targets, VEGF and its receptor are most attractive (1, 12). As noted above, treatment with a monoclonal antibody specifically targeting VEGF inhibited the growth of tumors in human xenografts implanted in nude mice. Subsequently, various approaches designed to inactivate VEGF have been tested in tumor models and have proven to be highly effective in a broad range of tumor cell lines including carcinomas, sarcomas and gliomas (21, 24, 51-53). In addition, inhibition of VEGF by anti-VEGF antibody did not result in significant side effects in fully developed rodents or primates (54, 55). Taken together, these results indicate that VEGF is a valid target for the development of tumor therapy. Indeed, a number of clinical trials are underway using VEGF inhibitors (17, 25).

Although several pro-angiogenic factors are implicated in the pathology of exudative age-related macular degeneration, VEGF appears to be the most critical in the pathogenesis and development of this disease (3, 56). Data from preclinical experiments and clinical trials have demonstrated that blockade of VEGF alone is sufficient to alleviate or stabilize disease progression (33, 34-37). For example, inhibition of VEGFR signaling by a specific tyrosine kinase inhibitor is sufficient to completely prevent retinal neovascularization in a murine retinopathy of prematurity model (57). Furthermore, it has recently been demonstrated that small interfering RNAs (siRNA) directed against murine VEGF significantly inhibited ocular neovascularization after laser photocoagulation in a mouse model (58). These results indicate that selective inhibition of VEGF expression is achievable and offers validation of this approach for the treatment of ocular neovascular diseases such as exudative macular degeneration and diabetic retinopathy.

Three approaches have been used to inhibit VEGF activity, including (1) neutralization of VEGF activity by using a specific antibody, soluble VEGF receptor or aptamer oligos against the VEGF/VEGFR interaction (24, 26, 27, 49, 51, 59, 60); (2) inhibition of VEGFR mediated signal transduction by specific small molecule tyrosine kinase inhibitors (52, 61, 62); and (3) inhibition of VEGF/VEGFR expression by using antisense, siRNA or ribozyme (58, 63-65). Although all of these approaches show significant inhibition of angiogenesis in vivo, they all possess significant limitations. For example, therapeutic proteins (antibody and soluble receptors) or oligos (antisense, siRNA and ribozyme) are large molecules with poor permeability that usually require parenteral administration and are costly to produce. For treatment of chronic ocular neovascularization, multiple injections may be impractical due to potential complications such as retinal detachment and procedure related infection. Moreover, tyrosine kinase inhibitors have the potential for limited specificity. VEGF is constitutively expressed at a low level in normal eyes and other tissues and thus it may be harmful to completely suppress VEGF function by administration of antibody or tyrosine kinase inhibitors systemically, especially for patients with AMD and RD many of whom are also hypertensive (66-69).

Thus, there remains a need to develop characterize and optimize lead molecules for the development of novel anti-angiogenesis drugs. Accordingly, it is an object of the present invention to provide such compounds.

SUMMARY OF THE INVENTION

In accordance with the present invention, compounds that inhibit the expression of VEGF post-transcriptionally have been identified, and methods for their use provided.

In one aspect of the invention, compounds of Formulas (I) to (VIII) are provided which are useful in the inhibition of VEGF production and/or in the inhibition of angiogenesis, and/or in the treatment of cancer, diabetic retinopathy, rheumatoid arthritis, psoriasis, atherosclerosis, obesity, chronic inflammation or exudative macular degeneration.

In another aspect of the invention, methods are provided for the inhibition of VEGF production and/or the inhibition of angiogenesis, and/or the treatment of cancer, diabetic retinopathy, rheumatoid arthritis, psoriasis, atherosclerosis, obesity, chronic inflammation or exudative macular degeneration using the compounds described herein.

In one embodiment, the invention is directed to methods for inhibiting VEGF production comprising administering a VEGF-inhibiting amount of at least one compound of the invention to a subject in need thereof.

In another embodiment, methods for inhibiting angiogenesis are provided comprising administering an anti-angiogenic amount of at least one compound of the invention to a subject in need thereof.

In yet another embodiment, methods for treating cancer, diabetic retinopathy, rheumatoid arthritis, psoriasis, atherosclerosis, obesity, chronic inflammation or exudative macular degeneration are provided comprising administering a therapeutically effective amount of at least one compound of the invention to a subject in need thereof.

These and other aspects of the invention will be more clearly understood with reference to the following preferred embodiments and detailed description.

Certain Embodiments

Embodiment 1. A method for inhibiting VEGF production in a subject, comprising administering a VEGF-inhibiting amount of a compound selected from the group consisting of the compounds of Formula (I) to Formula (VIII), or an enantiomer, a diastereomer, a pharmaceutically acceptable salt, a prodrug, a solvate or a mixture thereof to a subject in need thereof.

Embodiment 2. A method for inhibiting angiogenesis in a subject, comprising administering an anti-angiogenic amount of a compound selected from the group consisting of the compounds of Formula (I) to Formula (VIII), or an enantiomer, a diastereomer, a pharmaceutically acceptable salt, a prodrug, a solvate or a mixture thereof to a subject in need thereof.

Embodiment 3. A method for treating cancer in a subject, comprising administering a therapeutically effective amount of a compound selected from the group consisting of the compounds of Formula (I) to Formula (VIII), or an enantiomer, a diastereomer, a pharmaceutically acceptable salt, a prodrug, a solvate or a mixture thereof to a subject in need thereof.

Embodiment 4. A method for treating diabetic retinopathy in a subject, comprising administering a therapeutically effective amount of a compound selected from the group consisting of the compounds of Formula (I) to Formula (VIII), or an enantiomer, a diastereomer, a pharmaceutically acceptable salt, a prodrug, a solvate or a mixture thereof to a subject in need thereof.

Embodiment 5. A method for treating exudative macular degeneration in a subject, comprising administering a therapeutically effective amount of a compound selected from the group consisting of the compounds of Formula (I) to Formula (VIII), or an enantiomer, a diastereomer, a pharmaceutically acceptable salt, a prodrug, a solvate or a mixture thereof to a subject in need thereof.

Embodiment 6. A method for treating rheumatoid arthritis in a subject, comprising administering a therapeutically effective amount of a compound selected from the group consisting of the compounds of Formula (I) to Formula (VIII), or an enantiomer, a diastereomer, a pharmaceutically acceptable salt, a prodrug, a solvate or a mixture thereof to a subject in need thereof.

Embodiment 7. A method for treating psoriasis in a subject, comprising administering a therapeutically effective amount of a compound selected from the group consisting of the compounds of Formula (I) to Formula (VIII), or an enantiomer, a diastereomer, a pharmaceutically acceptable salt, a prodrug, a solvate or a mixture thereof to a subject in need thereof.

Embodiment 8. A method for atherosclerosis in a subject, comprising administering a therapeutically effective amount of a compound selected from the group consisting of the compounds of Formula (I) to Formula (VIII), or an enantiomer, a diastereomer, a pharmaceutically acceptable salt, a prodrug, a solvate or a mixture thereof to a subject in need thereof.

Embodiment 9. A method for treating obesity in a subject, comprising administering a therapeutically effective amount of a compound selected from the group consisting of the compounds of Formula (I) to Formula (VIII), or an enantiomer, a diastereomer, a pharmaceutically acceptable salt, a prodrug, a solvate or a mixture thereof to a subject in need thereof.

Embodiment 10. A method for treating chronic inflammation in a subject, comprising administering a therapeutically effective amount of a compound selected from the group consisting of the compounds of Formula (I) to Formula (VIII), or an enantiomer, a diastereomer, a pharmaceutically acceptable salt, a prodrug, a solvate or a mixture thereof to a subject in need thereof.

Embodiment 11. A method of selectively inhibiting VEGF in cells comprising exposing the cells to an effective amount of at least one compound of Formula (I) to Formula (VIII), or an enantiomer, a diastereomer, a pharmaceutically acceptable salt, a prodrug, a solvate or a mixture thereof, under conditions and for a time sufficient to selectively inhibit VEGF therein.

Embodiment 12. A method of selectively inhibiting VEGF in cells which comprises exposing the cells to an effective amount of a composition including a pharmaceutically acceptable excipient and at least one compound of Formula (I) to Formula (VIII), or an enantiomer, a diastereomer, a pharmaceutically acceptable salt, a prodrug, a solvate or a mixture thereof, under conditions and for a time sufficient to selectively inhibit VEGF therein.

Embodiment 13. A method for treating or preventing a disease whose onset or progress is aided by aberrant VEGF production, which comprises administering to a subject in need thereof a therapeutically effective amount of at least one compound of Formula (I) to Formula (VIII), or an enantiomer, a diastereomer, a pharmaceutically acceptable salt, a prodrug, a solvate or a mixture thereof, under conditions and for a time sufficient to selectively inhibit VEGF therein.

Embodiment 14. A method for inhibiting aberrant angiogenesis, which comprises administering to a subject in need thereof a therapeutically effective amount of at least one compound of Formula (I) to Formula (VIII), or an enantiomer, a diastereomer, a pharmaceutically acceptable salt, a prodrug, a solvate or a mixture thereof, under conditions and for a time sufficient to selectively inhibit VEGF therein.

Embodiment 15. A pharmaceutical composition comprising a compound selected from the group consisting of the compounds of Formula (I) to Formula (VIII), or enantiomer, a diastereomer, a pharmaceutically acceptable salt, a prodrug, a solvate or a mixture thereof and a pharmaceutically acceptable excipient.

Embodiment 16. A VEGF-inhibiting composition, comprising at least one compound of Formula (I) to Formula (VIII), or an enantiomer, a diastereomer, a pharmaceutically acceptable salt, a prodrug, a solvate or a mixture thereof. The VEGF-inhibiting composition can include a pharmaceutically acceptable excipient.

Embodiment 17. The use of a compound of Formula (I) through Formula (VIII) for the preparation of a pharmaceutical composition.

Embodiment 18. The use of a compound selected from Compounds 191 through 239.

In accordance with the present invention, compounds that inhibit the expression of VEGF post-transcriptionally have been identified, and methods for their use provided. Compounds of the present invention may be useful in the inhibition of VEGF production and/or in the inhibition of angiogenesis and/or in the treatment or prevention of diseases whose onset or progress is aided by aberrant VEGF production or abberant angiogenesis.

As recognized by one of skill in the art, certain compounds of the invention may be include a chiral center, and as such may exist as racemic mixtures or as enantiomerically pure compositions. For example, the compounds may exist as R or S isomers in enantiomerically pure compositions.

BRIEF DESCRIPTION OF THE DRAWINGS

FIG. 1 is a graph showing a dose-response ELISA assay and, in parallel, a dose-response cytotoxicity assay for a typical compound of the present invention. Dose-response curves were plotted using percentage inhibition of VEGF post-transcriptional expression versus concentration of a compound of the present invention.

DETAILED DESCRIPTION OF THE INVENTION

Up-regulation of Vascular Endothelial Growth Factor (VEGF), a key factor for angiogenesis, is an important contributor to the pathogenesis of cancers, diabetic retinopathy and exudative macular degeneration. In accordance with the present invention, compounds that inhibit the expression of VEGF post-transcriptionally have been identified and methods for their use provided. The compounds of the invention have low nonomolar activity for the inhibition of VEGF expression.

Compounds of the Invention

In one embodiment of the invention, compounds are provided which are useful in the inhibition of VEGF production and/or in the inhibition of angiogenesis, and/or in the treatment of cancer, diabetic retinopathy, rheumatoid arthritis, psoriasis, atherosclerosis, obesity, chronic inflammation or exudative macular degeneration. In certain embodiments, the compounds of the invention specifically inhibit VEGF production. In other embodiments, the compounds of the invention inhibit VEGF production as well as that of other angiogenesis factors such as FGF-2. In this regard, pan-angiogenic inhibitors may be preferred for the treatment of ocular neovascular disorders.

As recognized by one of skill in the art, certain compounds of the invention may be include a chiral center, and as such may exist as racemice mixtures or as enantiomerically pur compositions. For example, the compounds may exist as R or S isomers in enantiomerically pure compositions.

As used herein, "enantiomerically pure" refers to compositions consisting substantially of a single isomer, preferably consisting of 75%, 80%, 85%, 90%, 92%, 95%, 98%, 99%, or 100% of a single isomer.

Preferred compounds of the present invention include those of Formula (I) as shown below:

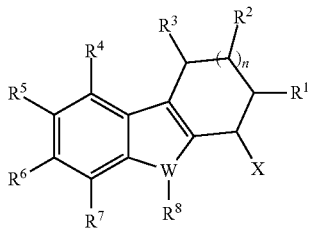

Formula (I)

an enantiomer, a diastereomer, a pharmaceutically acceptable salt, a prodrug, a solvate or a mixture thereof, wherein:

(a) X is —NR$^9$R$^{10}$, —N(alkyl)-C(O)-aryl, —N(alkyl)-C(O)-halogen substituted aryl, oxo, OR$^9$, H, substituted or unsubstituted phenylaminocarbonyl, substituted or unsubstituted phenyl, oxime, substituted or unsubstituted alkoxycarbonyl, hydroxycarbonyl (i.e., —COOH), or a substituted or unsubstituted heterocyclic ring; where R$^9$ and R$^{10}$ are each independently H, substituted or unsubstituted C$_{1-6}$ alkyl, substituted or unsubstituted C$_1$-C$_6$ alcohol, substituted or unsubstituted carbonyl (i.e., —C(O)H), substituted or unsubstituted mono- or bi-cyclic cycloalkyl, substituted or unsubstituted mono- or bi-cyclic heterocyclic ring, substituted or unsubstituted aryl, substituted or unsubstituted alkenyl, substituted or unsubstituted sulfonyl, substituted or unsubstituted arylalkyl, substituted or unsubstituted heterocycloalkyl, substituted or unsubstituted aminothiocarbonyl wherein at least one of R$^9$ and R$^{10}$ is H, or R$^9$ and R$^{10}$ together with the atom to which they are attached form a mono- or bi-cyclic heterocyclic ring, wherein at least one ring contains one or two heteroatoms;

(b) R$^1$, R$^2$ and R$^3$ are each independently —H, —OH, or alkyl, wherein R$^1$ may optionally form a substituted or unsubstituted 5-11 membered mono- or bi-heterocyclic ring with X;

(c) n is 0, 1 or 2, wherein when n is 0 then R$^2$ is absent;

(d) R$^4$, R$^5$, R$^6$ and R$^7$ are each independently —H, —OH, substituted or unsubstituted C$_{1-6}$ alkyl, substituted or unsubstituted carbonyl (i.e., —C(O)H), substituted or unsubstituted alkoxy, halo, haloalkyl, haloalkoxy, nitro, cyano, substituted or unsubstituted heterocyclic ring, substituted or unsubstituted amino, substituted or unsubstituted phenyl, substituted or unsubstituted phenoxy, substituted or unsubstituted cycloalkyl, substituted or unsubstituted alkenyl, substituted or unsubstituted alkynyl, or substituted or unsubstituted alkoxycarbonyl, or hydroxycarbonyl;

(e) W is N, O, or S;

(f) R$^8$ is H, C$_{1-3}$ alkyl, substituted or unsubstituted cycloalkyl, substituted or unsubstituted carbonyl (i.e. —C(O)H), or together with X forms a substituted or unsubstituted 5-11 membered mono- or bi-cyclic heterocyclic ring, with the proviso that when W is O or S, R$^8$ is absent; and (g) with the proviso that a compound of Formula I is not a compound selected from compounds 156-188.

As used herein, the term "alkyl" denotes an optionally substituted, branched or straight-chained saturated hydrocarbon radical. For example, without limitation, embodiments of alkyl include a C$_1$ to C$_4$ alkyl, a C$_1$ to C$_8$ alkyl, or C$_1$ to C$_{12}$ alkyl.

As used herein, the term "alkenyl" denotes an optionally substituted, branched or straight-chained unsaturated hydrocarbon radical having at least one carbon-carbon double bond.

As used herein, the term "alkynyl" denotes an optionally substituted, branched or straight-chained aliphatic hydrocarbon radical having at least one carbon-carbon triple bond.

As used herein, the term "aromatic ring" denotes an optionally substituted, monocyclic aromatic hydrocarbon ring. The aromatic ring may be a part of an aromatic bicyclic ring system, such as napthyl. Alternatively, the ring to which the aromatic ring is attached in the bicyclic ring system may be an aliphatic ring.

As used herein, the term "aryl" denotes an optionally substituted, stable 5 to 7 membered monocyclic hydrocarbon radical or a stable 8 to 11 membered bicyclic aromatic hydrocarbon radical.

As used herein, the term "cycloalkyl" denotes the radical of an optionally substituted, aliphatic hydrocarbon ring having three to ten carbon atoms.

As used herein, the term "cycloalkylalkyl" denotes an optionally substituted alkyl radical having a cycloalkyl substituent.

As used herein, the term "heteroatom" denotes an atom that is any element other than carbon or hydrogen.

As used herein, the terms "heterocycle" and "heterocyclic ring" denote an optionally substituted stable 5 to 7 membered monocyclic hydrocarbon ring or an optionally substituted stable 8 to 11 membered bicyclic hydrocarbon ring, in which one to four carbon atoms have been replaced with a heteroatom selected from the group consisting of N, O, and S. In the case of bicyclic heterocycles, substitution may take place on either ring. Furthermore, the heterocycle may be saturated or unsaturated, and aliphatic or aromatic.

As used herein, the term "oxime" denotes the radical of the oxime group =NOR$^{26}$ wherein R$^{26}$ is H or C$_1$-C$_6$ alkyl, in which the oxime radical is connected to the specified atom through a double bond to the oxime nitrogen. In a preferred embodiment, R$^{26}$ is H.

As used herein, the phrase "pharmaceutically acceptable salts" refers to those salts derived from organic and inorganic acids such as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly acceptable acids.

As used herein, the term "aminothiocarbonyl" denotes a radical in which an amino group is bonded to the carbon of a thiocarbonyl group. A thiocarbonyl group is one in which a carbon atom is connected to a sulfur atom through a double bond. The point of attachment of the aminothiocarbonyl radical to the indicated atom is the carbon atom of the thiocarbonyl moiety.

As used herein, the term "substituted" denotes that a moiety has one or more of its hydrogen atoms replaced by one or more substituents. Examples of suitable substituents include, but are not limited to:

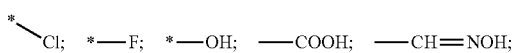

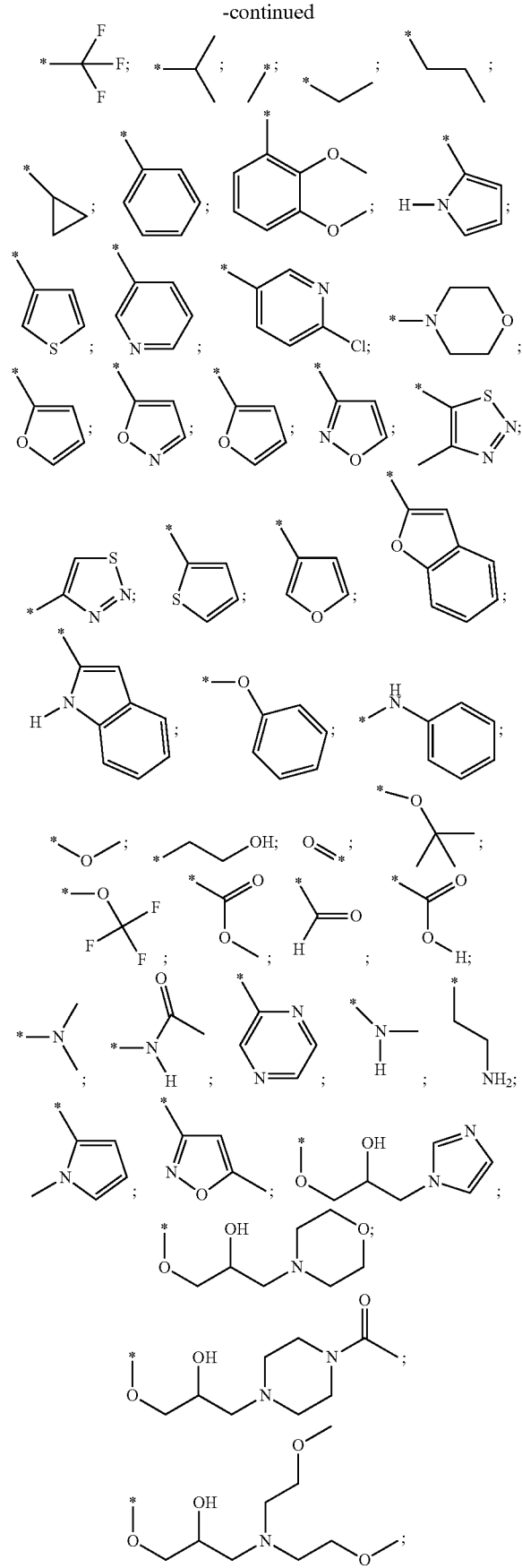
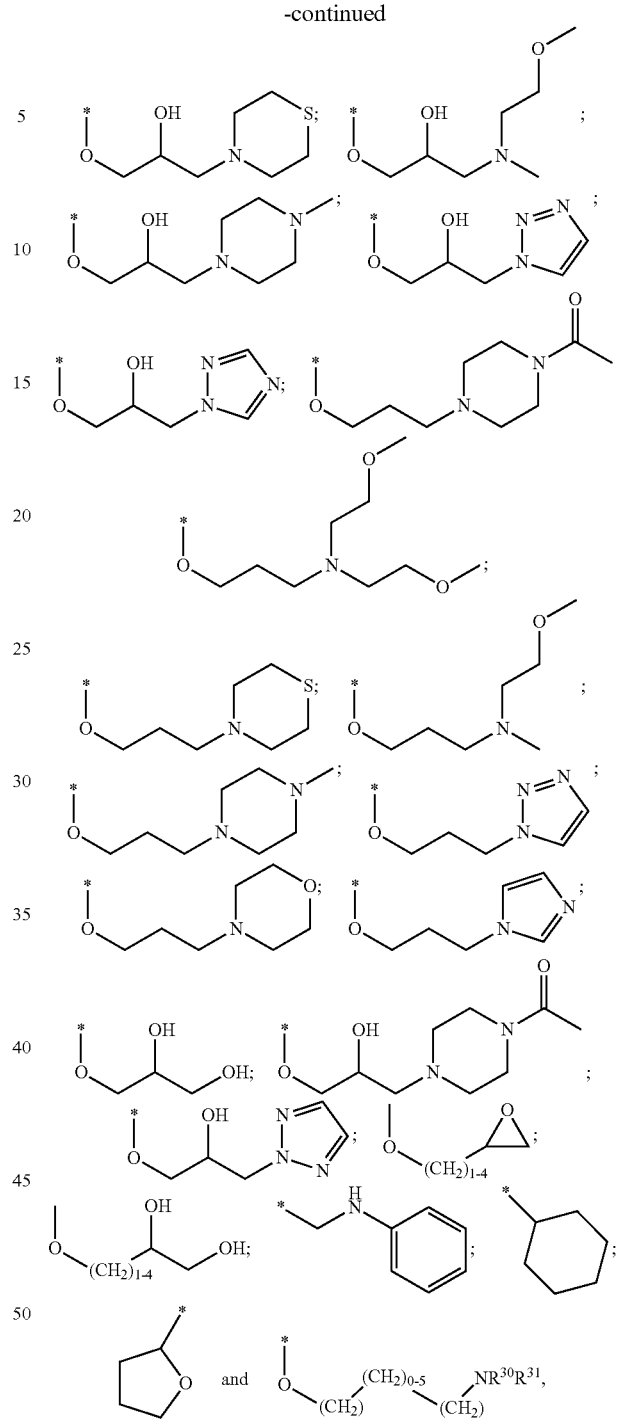

wherein

R[30] and R[31] are each independently H or alkyl; or

R[30] and R[31] together with the nitrogen to which they are bound may form a 5-7 membered nitrogen containing heterocyclic ring.

In an embodiment of Formula (I), X is phenyl. In another embodiment of Formula (I), X is substituted phenyl. In a preferred embodiment of compounds of Formula (I), where X is substituted phenyl, the substituted phenyl may also bear one or more $R_a$ groups alone or in combination with those moieties recited for the term "substituted" above.

$R_a$ is independently selected from halogen; —$OR_d$ group; a 5 to 6 membered heterocycle; a 5 to 6 membered heteroaryl; or a $C_1$ to $C_6$ alkyl group, wherein the alkyl group is optionally substituted with one or more independently selected halogen groups;

$R_b$ is hydroxyl; an amino; an alkylamino, wherein the alkylamino is optionally substituted with a hydroxyl, an amino, an alkylamino, a $C_1$ to $C_4$ alkoxy, a 3 to 12 membered heterocycle optionally substituted with at least one independently selected $C_1$ to $C_6$ alkyl, oxo, —C(O)O—$R_{cc}$, or a 5 to 12 membered heteroaryl optionally substituted with a $C_1$ to $C_4$ alkyl; a $C_1$ to $C_4$ alkoxy; a $C_2$ to $C_8$ alkenyl; a $C_2$ to $C_8$ alkynyl; a $C_6$ to $C_{10}$ aryl, wherein the aryl is optionally substituted with at least one independently selected halogen or $C_1$ to $C_4$ alkoxy; a 5 to 12 membered heteroaryl; 3 to 12 membered heterocycle group, wherein the heterocycle is optionally substituted with at least one independently selected acetamide, —C(O)—$R_{cc}$, 5 to 6 membered heterocycle, or $C_1$ to $C_6$ alkyl optionally substituted with a hydroxyl, $C_1$ to $C_4$ alkoxy, amino group, or alkylamino group; or a $C_1$ to $C_8$ alkyl, wherein the alkyl is optionally substituted with at least one independently selected $C_1$ to $C_4$ alkoxy, $C_6$ to $C_{10}$ aryl, amino, or 3 to 12 membered heterocycle group, wherein the amino and heterocycle groups are optionally substituted with at least one independently selected $C_1$ to $C_6$ alkyl, oxo, or —C(O)O—$R_{cc}$ group;

$R_{bb}$ is hydrogen, alkylamino, wherein the alkylamino is optionally substituted with a hydroxyl, an amino, an alkylamino, a $C_1$ to $C_4$ alkoxy, a 3 to 12 membered heterocycle optionally substituted with at least one independently selected $C_1$ to $C_6$ alkyl, oxo, or a 5 to 12 membered heteroaryl optionally substituted with a $C_1$ to $C_4$ alkyl; a $C_2$ to $C_8$ alkenyl; a $C_2$ to $C_8$ alkynyl; a $C_6$ to $C_{10}$ aryl, wherein the aryl is optionally substituted with at least one independently selected halogen or $C_1$ to $C_4$ alkoxy; a 5 to 12 membered heteroaryl; 3 to 12 membered heterocycle group, wherein the heterocycle is optionally substituted with at least one independently selected acetamide, —C(O)O—Rdcc, 5 to 6 membered heterocycle, or $C_1$ to $C_6$ alkyl optionally substituted with a hydroxyl, $C_1$ to $C_4$ alkoxy, amino group, or alkylamino group; or a $C_1$ to $C_8$ alkyl, wherein the alkyl is optionally substituted with at least one independently selected $C_1$ to $C_4$ alkoxy, $C_6$ to $C_{10}$ aryl, amino, or 3 to 12 membered heterocycle group, wherein the amino and heterocycle groups are optionally substituted with at least one independently selected $C_1$ to $C_6$ alkyl, oxo, or —C(O)O—$R_{cc}$, group;

$R_c$ is a hydroxyl, $C_1$ to $C_4$ alkoxy, amino, or $C_1$ to $C_6$ alkyl;

$R_{cc}$ is hydrogen, or $C_1$ to $C_6$ alkyl; and $R_d$ is hydrogen; $C_2$ to $C_8$ alkylene; $C_2$ to $C_8$ alkynyl; —C(O)O—$R_{bb}$; —C(O)—NH—$R_{bb}$; a five to six membered heterocycle; a five to six membered heteroaryl; a $C_1$ to $C_8$ alkyl group, wherein the alkyl group is optionally substituted with at least one independently selected hydroxyl, halogen, $C_1$ to $C_4$ alkoxy, amino, alkylamino, acetamide, —C(O)—$R_b$, —C(O)O—$R_{bb}$, $C_6$ to $C_{10}$ aryl, 3 to 12 membered heterocycle, or 5 to 12 heteroaryl group; further wherein the alkylamino is optionally substituted with a hydroxyl, a $C_1$ to $C_4$ alkoxy, or a 5 to 12 membered heteroaryl optionally substituted with a $C_1$ to $C_4$ alkyl; further wherein the acetamide is optionally substituted with a $C_1$ to $C_4$ alkoxy, sulfonyl, or alkylsulfonyl; and further wherein the heterocycle group is optionally substituted with a $C_1$ to $C_4$ alkyl optionally substituted with a hydroxyl group, —C(O)—$R_c$, —C(O)O—$R_{cc}$, or an oxo group.

In another preferred embodiment, the present invention provides compounds, including a preferred class of compounds within Formula (I), including those compounds of Formula (Ia) shown below:

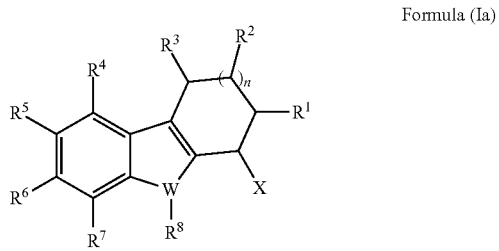

Formula (Ia)

an enantiomer, a diastereomer, a pharmaceutically acceptable salt, a prodrug, a solvate or a mixture thereof, wherein:

(a) X is $NR^9R^{10}$, —N(alkyl)-C(O)-aryl, —N(alkyl)-C(O)-halogen substituted aryl, oxo, $OR^9$, H, substituted or unsubstituted phenylaminocarbonyl, substituted or unsubstituted phenyl, oxime, substituted or unsubstituted alkoxycarbonyl, hydroxycarbonyl or a substituted or unsubstituted heterocyclic ring;

$R^9$ and $R^{10}$ are each independently H, substituted or unsubstituted $C_{1-6}$ alkyl, substituted or unsubstituted carbonyl (i.e., —C(O)H), substituted or unsubstituted mono- or bi-cyclic cycloalkyl, substituted or unsubstituted mono- or bi-cyclic heterocyclic ring, substituted or unsubstituted aryl, substituted or unsubstituted sulfonyl, substituted or unsubstituted arylalkyl, substituted or unsubstituted heterocycloalkyl, wherein at least one of $R^9$ and $R^{10}$ is H, or $R^9$ and $R^{10}$ together with the atom to which they are attached form a mono- or bi-cyclic heterocyclic ring, wherein at least one ring contains one or two heteroatoms;

(b) $R^1$, $R^2$ and $R^3$ are each independently H or alkyl, wherein $R^1$ may optionally form a substituted or unsubstituted 5-11 membered mono- or bi-heterocyclic ring with X;

(c) n is 0, 1 or 2, wherein when n is 0 then $R^2$ is absent;

(d) $R^4$, $R^6$ and $R^7$ are each independently H, OH, $C_{1-6}$ alkyl, substituted or unsubstituted carbonyl (i.e. —C(O)H), halo, haloalkyl, haloalkoxy, cyano, substituted or unsubstituted mono-cyclic heterocyclic ring, substituted or unsubstituted amino, substituted or unsubstituted phenyl, substituted or unsubstituted phenoxy, substituted or unsubstituted alkenyl, or substituted or unsubstituted alkynyl;

(e) $R^5$ are each independently H, OH, substituted or unsubstituted $C_{2-6}$ alkyl, substituted or unsubstituted alkoxy, substituted or unsubstituted carbonyl (i.e. —C(O)H), halo, haloalkyl, haloalkoxy, cyano, substituted or unsubstituted heterocyclic ring, substituted or unsubstituted amino, substituted or unsubstituted phenyl, substituted or unsubstituted phenoxy, substituted or unsubstituted cycloalkyl, substituted or unsubstituted alkenyl, substituted or unsubstituted alkynyl, or substituted or unsubstituted alkoxycarbonyl, or hydroxycarbonyl;

(f) $R^8$ is H, $C_{1-3}$ alkyl, substituted or unsubstituted cycloalkyl, substituted or unsubstituted carbonyl (i.e. —C(O)H), or $R^8$ together with X forms a substituted or unsubstituted 5-11 membered mono- or bi-cyclic heterocyclic ring, with the proviso that when X, $R^9$ and $R^{10}$ form an unsubstituted pyrrole, then $R_5$ is not bromine when $R^8$ is H, and $R^8$ may together with X form a substituted or unsubstituted heterocyclic ring; and (g) W is N, O, or S, with the proviso that when W is O or S, $R^8$ is absent.

In yet another embodiment, the present invention provides VEGF-inhibiting compounds, including a compound of Formula (Ib):

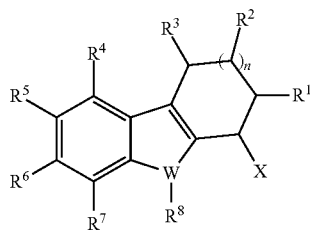

Formula (Ib)

an enantiomer, a diastereomer, a pharmaceutically acceptable salt, a prodrug, a solvate or a mixture thereof, wherein:

(a) X is $NR^9R^{10}$, —N(alkyl)-C(O)-aryl, —N(alkyl)-C(O)-halogen substituted aryl, oxo, $OR^9$, H, substituted or unsubstituted phenylaminocarbonyl, substituted or unsubstituted phenyl, oxime, substituted or unsubstituted alkoxycarbonyl, hydroxycarbonyl, or a substituted or unsubstituted heterocyclic ring;

$R^9$ and $R^{10}$ are each independently H, substituted or unsubstituted $C_{1-6}$ alkyl, substituted or unsubstituted carbonyl (i.e., —C(O)H), substituted or unsubstituted mono- or bi-cyclic cycloalkyl, substituted or unsubstituted mono- or bi-cyclic heterocyclic ring, substituted or unsubstituted aryl, substituted or unsubstituted arylalkyl, substituted or unsubstituted heterocycloalkyl, substituted or unsubstituted aminothiocarbonyl, wherein at least one of $R^9$ and $R^{10}$ is H, or $R^9$ and $R^{10}$ together with the atom to which they are attached form a mono- or bi-cyclic heterocyclic ring, wherein at least one ring contains one or two heteroatoms;

(b) $R^1$, $R^2$ and $R^3$ are each independently H or alkyl, wherein $R^1$ may optionally form a substituted or unsubstituted 5-11 membered mono- or bi-heterocyclic ring with X;

(c) n is 0, 1 or 2, wherein when n is 0 then $R^2$ is absent;

(d) $R^4$, $R^5$, $R^6$ and $R^7$ are each independently H, OH, substituted or unsubstituted $C_{1-6}$ alkyl, substituted or unsubstituted carbonyl (i.e., —C(O)H), substituted or unsubstituted alkoxy, halo, haloalkyl, haloalkoxy, nitro, cyano, substituted or unsubstituted mono-cyclic heterocyclic ring, substituted or unsubstituted amino, substituted or unsubstituted phenyl, substituted or unsubstituted phenoxy, substituted or unsubstituted cycloalkyl, substituted or unsubstituted alkenyl, or substituted or unsubstituted alkynyl;

(e) $R^8$ is H, $C_{1-3}$ alkyl, substituted or unsubstituted cycloalkyl, substituted or unsubstituted carbonyl (i.e., —C(O)H), with the proviso that when X, $R^9$ and $R^{10}$ form an unsubstituted pyrrole, then $R^5$ is not bromine when $R^8$ is H;

(f) W is N, O or S, with the proviso that when W is O or S, $R^8$ is absent.

In a preferred embodiment, X is selected from the following:

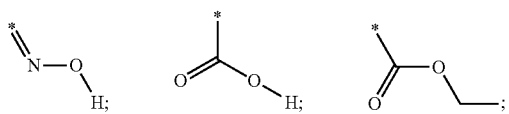

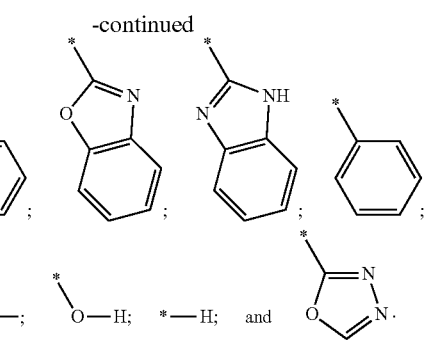

In another preferred embodiment, X is $NR^9R^{10}$. Preferable substituents for $NR^9R^{10}$ include the following:

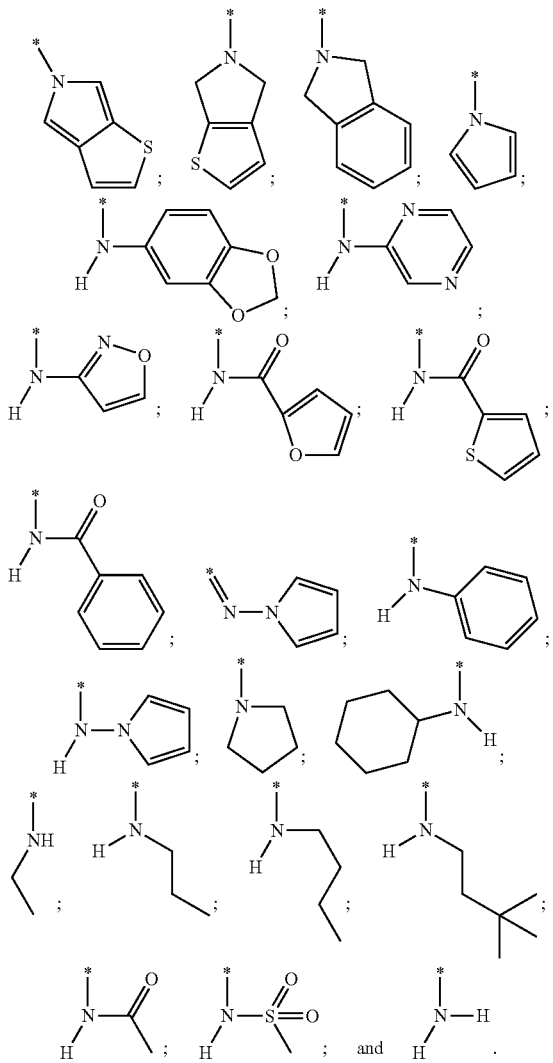

In another preferred embodiment, X is —$OR^9$, wherein $R^9$ is phenol.

It will be apparent to those skilled in the art that certain of the above-indicated preferred embodiments of X, including those preferred embodiments where X is —$NR^9R^{10}$, and —$OR^9$, are themselves capable of being substituted with substituents including for example:

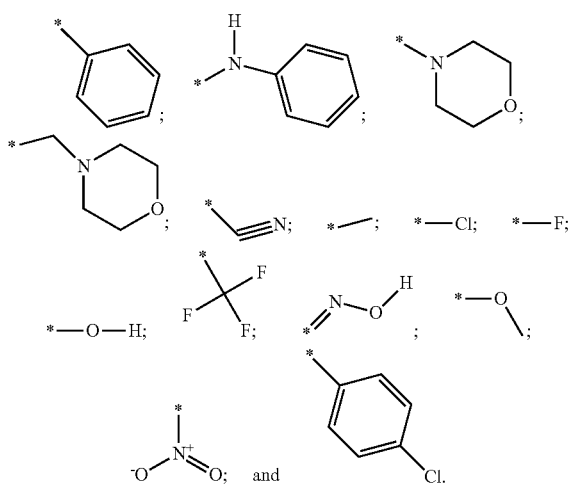

In another embodiment of Formula (I), $R^9$ and $R^{10}$, except when hydrogen, may be substituted with one or more of the same or different: halogen, $C_{1-6}$ alkyl, $C_{1-6}$ alcohol, hydroxyl, cyano, oxo, alkoxy, carbonyl (i.e., —C(O)H), substituted or unsubstituted alkoxycarbonyl, haloalkyl, haloalkoxy, substituted or unsubstituted heterocyclic ring, substituted or unsubstituted cycloalkyl, substituted or unsubstituted amino, or substituted or unsubstituted phenyl.

In still another embodiment Formula (I), $R^9$ and $R^{10}$, except when hydrogen, may be substituted with one or more of the same or different halogen, methyl, isopropyl, ethyl, —$(CH_2)_3CH_3$ or —$C(CH_3)_3$, —$OCH_3$, —$COCH_3$, —$COOCH_3$, trifluoromethyl (—$CF_3$), trifluoromethoxy (—$OCF_3$), —$NHCOCH_3$ or —$N(CH_3)_2$, —$(CH_2)_2OH$.

In a preferred embodiment Formula (I), $R^1$ is H or methyl.

In a preferred embodiment Formula (I), $R^2$ and $R^3$ are H.

In a preferred embodiment Formula (I), $R^4$ is H, Br, or Cl.

In a preferred embodiment Formula (I), $R^3$ is Br, Cl, methyl, trifluoromethyl, trifluoromethoxy, methoxy, methoxycarbonyl, hydroxycarbonyl, morpholino, pyrrolidino, or —C(O)$NH_2$.

In a preferred embodiment Formula (I), $R^6$ is H or Br.

In a preferred embodiment Formula (I), $R^7$ is H or Br.

In a preferred embodiment Formula (I), $R^8$ is H, methyl, acyl, or t-butoxycarbonyl.

In a preferred embodiment of Formula (I), $R^5$ is halogen, and $R^1$, $R^2$, and $R^3$ are H or —OH. In a more preferred embodiment, $R^5$ is Br, $R^1$ is H or —OH, and $R^2$, $R^3$, $R^4$, $R^6$, $R^7$ and $R^8$ are H.

In a preferred embodiment of compounds of Formula (I), $R^5$ is halogen, n is 1 or 2, and $R^1$, $R^2$, and $R^3$ are H or —OH.

In another preferred embodiment of compounds of Formula (I), $R^5$ is —$CF_3$, Br or Cl, $R^1$ is H or —OH, n is 1 or 2, and $R^2$, $R^3$, $R^4$, $R^6$, $R^7$ and $R^8$ are H.

In a more preferred embodiment of compounds of Formula (I), X is phenyl substituted with a substituent selected from the group consisting of:

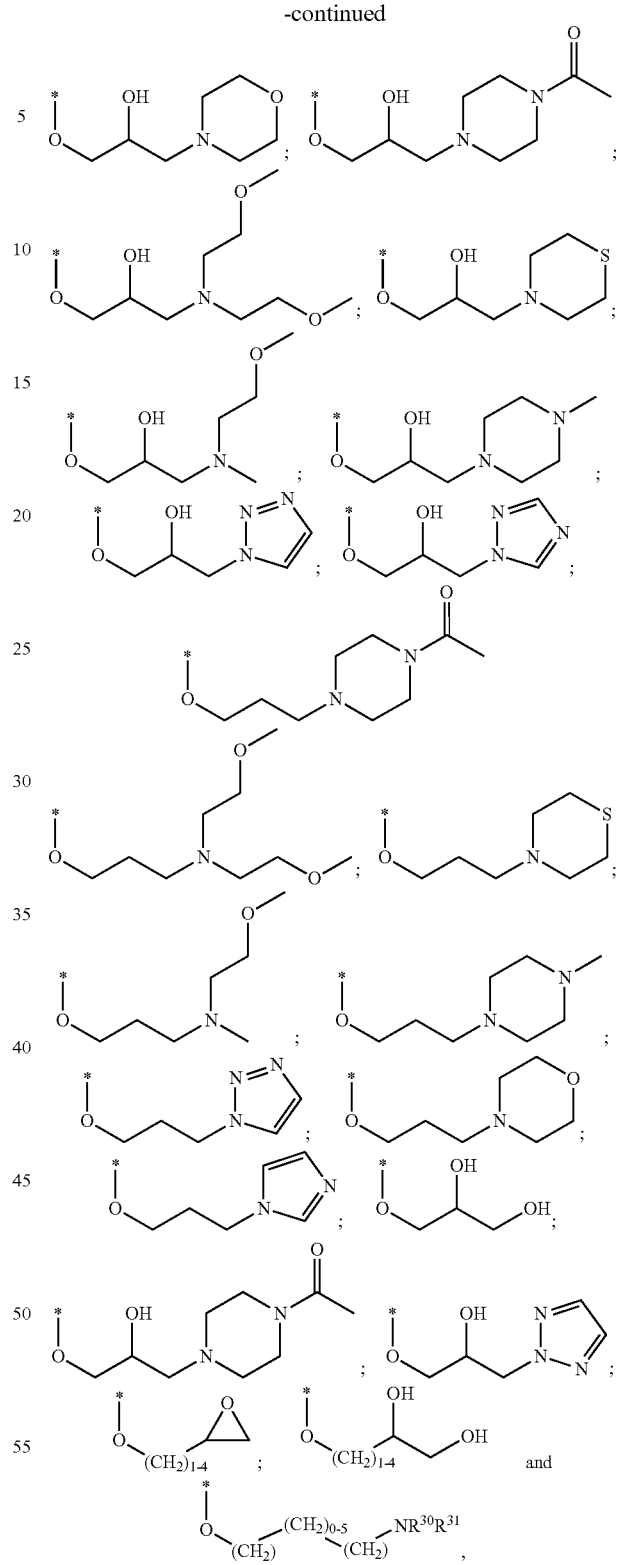

In another preferred embodiment of compounds of Formula (I), X is —$NR^9R^{10}$; wherein $R^9$ and $R^{10}$ are each independently H, substituted carbonyl, substituted or unsubstituted mono- or bi-cyclic cycloalkyl, substituted or unsubstituted mono- or bi-cyclic heterocyclic ring, substituted or unsubstituted aryl, substituted or unsubstituted arylalkyl, substituted or unsubstituted heterocycloalkyl, wherein at least one of $R^9$ and $R^{10}$ is H, or $R^9$ and $R^{10}$ together with the atom to which they are attached form a mono- or bi-cyclic heterocyclic ring, wherein at least one ring contains one or two heteroatoms.

In another more preferred embodiment of compounds of Formula (I) where X is —$NR^9R^{10}$, $R^9$ is H, and $R^{10}$ is a substituted carbonyl.

In another more preferred embodiment of compounds of Formula (I) where X is —$NR^9R^{10}$, $R^9$ is H, and $R^{10}$ is a substituted or unsubstituted aryl.

In another more preferred embodiment of compounds of Formula (I) where X is —$NR^9R^{10}$, $R^9$ is H, and $R^{10}$ is a substituted or unsubstituted mono- or bi-cyclic heterocyclic ring.

In another more preferred embodiment of compounds of Formula (I) where X is —$NR^9R^{10}$, $R^9$ is H, and $R^{10}$ is a substituted or unsubstituted mono-cyclic heterocyclic ring.

In another more preferred embodiment of compounds of Formula (I) where X is —$NR^9R^{10}$, $R^9$ is H, and $R^{10}$ is a substituted or unsubstituted bi-cyclic heterocyclic ring.

In another more preferred embodiment of compounds of Formula (I) where X is —$NR^9R^{10}$, $R^9$ is H, and $R^{10}$ is a substituted or unsubstituted arylalkyl.

The present invention also provides for other preferred compounds of Formula (I) where X is oxo. The present invention also provides for further preferred compounds of Formula (I) where X is —$OR^9$. In other embodiments of compounds of Formula (I), X is substituted or unsubstituted phenylaminocarbonyl or oxime.

In an embodiment of the present invention, compounds of Formulas (I), (Ia), and (Ib) are provided, wherein X is —N(alkyl)-C(O)-aryl or —N(alkyl)-C(O)-halogen substituted aryl. In another embodiment, —N(alkyl)-C(O)-aryl is —N($C_1$ to $C_6$ alkyl)-C(O)—($C_6$ to $C_8$ aryl). In another embodiment, —N(alkyl)-C(O)— halogen substituted aryl is —N($C_1$ to $C_6$ alkyl)-C(O)—($C_6$ to $C_8$ halogen substituted aryl).

In a further preferred embodiment of the present invention, compounds of Formulas (I), (Ia), and (Ib) are provided, wherein X is not —N(alkyl)-C(O)-aryl.

In another preferred embodiment of Formulas (I), (Ia) and (Ib), compounds are provided wherein X is not —N(alkyl)-C(O)-halogen substituted aryl.

A more preferred embodiment of the invention provides for compounds of Formula (I) where X is substituted or unsubstituted phenyl.

In another preferred embodiment of compounds of Formula (I), X is substituted or unsubstituted alkoxycarbonyl, or a hydroxycarbonyl.

In still other preferred embodiments of compounds of Formula (I), X is a substituted or unsubstituted heterocyclic ring.

Other preferred embodiments of compounds of Formula (I) include compounds of Formula (Ia) and compounds of Formula (Ib).

In other preferred embodiments of Formula (I), Formula (Ia) or Formula (Ib), $R^5$ is Br or Cl.

Another preferred class of compounds include those compounds of Formula (II) as shown below:

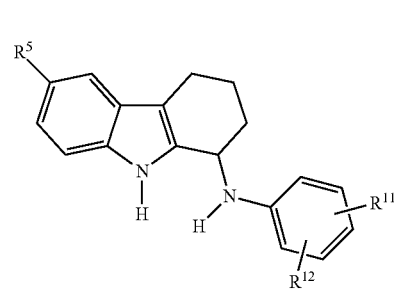

Formula (II)

wherein
(a) $R^5$ is halo, $C_1$-$C_3$ haloalkyl, or substituted or unsubstituted $C_1$-$C_6$ alkyl;
(b) $R^{11}$ and $R^{12}$ are each, independently, H, halo, substituted or unsubstituted $C_1$-$C_6$ alkyl, substituted or unsubstituted $C_1$-$C_6$ alkoxy, phenoxy, and substituted or unsubstituted phenyl; or
$R^{11}$ and $R^{12}$ taken together with the atom or atoms to which they are attached, may optionally form a five or six membered carbocyclic or heterocyclic ring, containing, including the atoms to which $R^{11}$ and $R^{12}$ are attached, one to three heteroatoms selected from the group consisting of N, O, and S.

Another preferred class of compounds includes those of Formula (III):

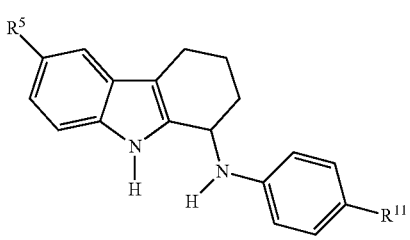

Formula (III)

wherein
(a) $R^5$ is halo and substituted or unsubstituted $C_1$-$C_6$ alkyl; and
(b) $R^{11}$ is H, halo, substituted or unsubstituted $C_1$-$C_6$ alkyl, substituted or unsubstituted phenoxy, substituted or unsubstituted $C_1$-$C_6$ alkoxy, and substituted or unsubstituted phenyl.

In yet another preferred class of compounds, compounds of Formula (IV) are provided:

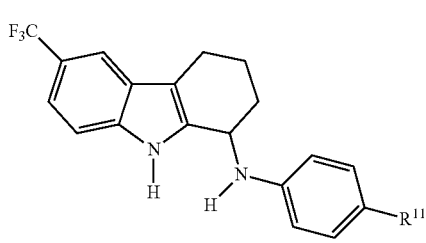

Formula (IV)

wherein
(a) $R^{11}$ is H, halo, substituted or unsubstituted $C_1$-$C_6$ alkoxy, or substituted or unsubstituted $C_1$-$C_6$ alkyl.

In yet another embodiment, preferred compounds include those compounds of Formula (V):

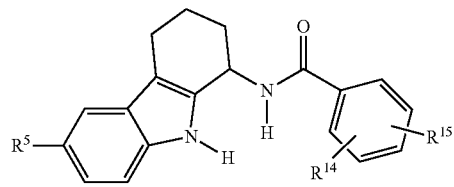

Formula (V)

wherein
(a) $R^5$ is halo or substituted or unsubstituted $C_1$-$C_6$ alkyl;
(b) $R^{14}$ and $R^{15}$ are each, independently, H, halo, substituted or unsubstituted phenoxy, cyano, substituted or unsubstituted $C_1$-$C_6$ alkyl; or
$R^{14}$ and $R^{15}$ taken together with the atom or atoms to which they are attached, may optionally form a five or six membered heterocyclic ring, containing, including the atoms to which $R^{14}$ and $R^{15}$ are attached, one to three heteroatoms selected from the group consisting of N, O, and S.

In another embodiment, preferred compounds include those of Formula (VI):

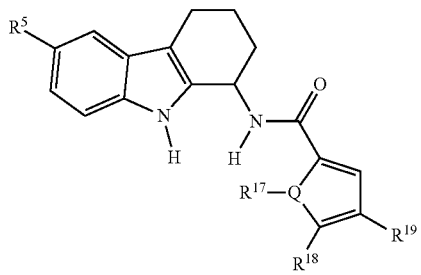

Formula (VI)

wherein
(a) $R^5$ is halo or substituted or unsubstituted $C_1$-$C_6$ alkyl;
(b) Q is N, O, or S,
with the proviso that when Q is O or S, $R^{17}$ is absent;
(c) $R^{17}$ is H or alkyl;
(d) $R^{18}$ and $R^{19}$ are each, independently, selected from the group consisting of H, halo, substituted or unsubstituted $C_1$-$C_6$ alkyl, substituted or unsubstituted phenyl, and nitro; or
$R^{18}$ and $R^{19}$ taken together with the atoms to which they are attached, may optionally form a carbocyclic aromatic ring.

Still other preferred compounds include those of Formula (VII):

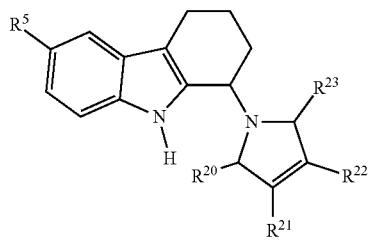

Formula (VII)

wherein
(a) $R^5$ is halo or $C_1$-$C_6$ alkyl;
(b) $R^{20}$ is H or oxo;
(c) $R^{21}$ and $R^{22}$ are H; or
$R^{21}$ and $R^{22}$, taken together with the atoms to which they are attached, may optionally form a carbocyclic aromatic ring, or a five or six membered heterocyclic ring, the heterocyclic ring containing, including the atoms to which $R^{21}$ and $R^{22}$ are attached, one to three heteroatoms selected from the group consisting of N, O, and S; and
(d) $R^{23}$ is H or oxo.

In another preferred embodiment, compounds of the present invention include those of Formula (VIII):

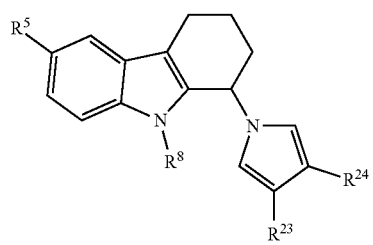

Formula (VIII)

wherein
(a) $R^5$ is halo or $C_1$-$C_6$ alkyl;
(b) $R^{23}$ and $R^{24}$ are selected from the group consisting of H, substituted of unsubstituted alkoxycarbonyl, substituted or unsubstituted alkylcarbonyl, formyl, cyano, and substituted or unsubstituted phenylaminoalkyl; or
$R^{23}$ and $R^{24}$, taken together with the atoms to which they are attached, may optionally form a carbocyclic aromatic ring, or a five or six membered heterocyclic ring, the heterocyclic ring containing, including the atoms to which $R^{23}$ and $R^{24}$ are attached, one to three heteroatoms selected from the group consisting of N, O, and S; and
(c) $R^8$ is substituted or unsubstituted carbonyl.

In an embodiment of the present invention, compounds of Formula (II) through Formula (VIII) are provided with the proviso that the compounds are not any of Compounds 156 through 188.

In a more preferred embodiment of the present invention, a compound is selected from Compounds 191 through 239, or an enantiomer, a diastereomer, a pharmaceutically acceptable salt, a prodrug, a solvate or a mixture thereof.

Methods of the Invention

In another aspect of the invention, methods are provided for the inhibition of VEGF production and/or the inhibition of angiogenesis, and/or the treatment of cancer, diabetic retinopathy, rheumatoid arthritis, psoriasis, atherosclerosis, obesity, chronic inflammation or exudative macular degeneration using one or more compounds of the present invention.

In another embodiment, the present invention relates to a method for treating aberrant angiogenesis, including administering to a mammal in need thereof a compound of the invention.

In still another embodiment, the present invention relates to a method for treating overexpression of vascular endothelial growth factor, including administering to a mammal in need thereof a compound of the invention.

In yet another embodiment, the present invention relates to a method for treating cancer, including administering to a mammal suffering from such a condition a compound of the invention.

In a further embodiment, the present invention relates to a method for treating ocular neovascular disorders, including administering to a mammal suffering from such a condition a compound of the invention.

In one embodiment, the invention is directed to methods for inhibiting VEGF in cells, which methods include exposing the cells to an effective amount of at least one compound of the invention. A compound of the present invention may be administered to a subject in need of inhibition of VEGF production. Compounds of the present invention can be administered neat or can be formulated with a pharmaceutically acceptable excipient.

By the terms "inhibiting VEGF", "inhibition of VEGF", and the like, it is meant that the post-transcriptional expression or production of VEGF in cells treated with a compound of the present invention for a sufficient period of time is lower in relation to untreated cells. As such, VEGF activity (e.g., its pro-angiogenic activity) would also be reduced. Desirably, compounds of the present invention inhibit VEGF expression in cells during culture by an amount at least 10% relative to untreated cells. In one embodiment, compounds of the present invention inhibit VEGF expression in cells by an amount at least about 25% relative to untreated cells. In another embodiment, the compounds inhibit VEGF expression in cells by an amount at least about 50% relative to untreated cells. In a further embodiment, the compounds inhibit VEGF expression in cells by an amount of at least about 75% relative to untreated cells.

In another embodiment, methods for inhibiting aberrant angiogenesis are provided, which methods include administering to a subject in need thereof a therapeutically effective amount of at least one compound of the invention.

In yet another embodiment, methods for treating or preventing a disease whose onset or progress is aided by aberrant VEGF production are provided, which methods include administering to a subject in need thereof a therapeutically effective amount of at least one compound of the invention. In some embodiments, the disease is selected from cancer, diabetic retinopathy, rheumatoid arthritis, psoriasis, atherosclerosis, obesity, chronic inflammation and exudative macular degeneration. Without intending to be limited by theory, it is believed that the methods of the present invention act through a combination of mechanisms that modulate the activity of VEGF.

According to the methods of the invention, one or more compounds may be administered to the subject via any drug delivery route known in the art. Specific exemplary administration routes include oral, ocular, rectal, buccal, topical, nasal, opthamalic, subcutaneous, intramuscular, intravenous (bolus and infusion), intracerebral, transdermal and pulmonary.

The term "therapeutically effective amount", as used herein, refers to an amount of a pharmaceutical agent to treat, meliorate or prevent the identified disease or condition, or to exhibit a detectable therapeutic or inhibitory effect. The effect can be detected by, for example, assays disclosed in the following examples. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred. The data obtained from cell culture assays and animal studies may be used in formulating a range of dosage for human use. The dosage contained in such compositions is preferably within a range of circulating concentrations that include an $ED_{50}$ with little or no toxicity. The dosage may vary within this range depending upon the dosage form employed, sensitivity of the patient, and the route of administration.

More specifically, the concentration-biological effect relationships observed with regard to the compound(s) of the present invention indicate an initial target plasma concentration ranging from approximately 5 µg/mL to approximately 100 µg/mL, preferably from approximately 10 µg/mL to approximately 50 µg/mL, more preferably from approximately 10 µg/mL to approximately 25 µg/mL. To achieve such plasma concentrations, the compounds of the invention may be administered at doses that vary from 0.1 µg to 100,000 mg, depending upon the route of administration. Guidance as to particular dosages and methods of delivery is provided in the literature and is generally available to practitioners in the art. In general the dose will be in the range of about 1 mg/day to about 10 g/day, or about 0.1 g to about 3 g/day, or about 0.3 g to about 3 g/day, or about 0.5 g to about 2 g/day, in single, divided, or continuous doses for a patient weighing between about 40 to about 100 kg (which dose may be adjusted for patients above or below this weight range, particularly children below 40 kg).

The exact dosage will be determined by the practitioner, in light of factors related to the subject that requires treatment. Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

A method of inhibiting VEGF production comprising administering to a patient in need thereof a pharmaceutical composition comprising a compound selected from any of compounds 156 through 188, a compound of Formula I,

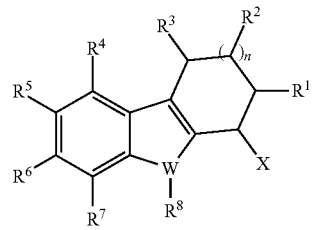

Formula (I)

an enantiomer, a diastereomer, a pharmaceutically acceptable salt, a prodrug, a solvate or a mixture thereof,
wherein
(a) X is —NR$^9$R$^{10}$, —N(alkyl)-C(O)-aryl, —N(alkyl)-C(O)-halogen substituted aryl, oxo, OR$^9$, H, substituted or unsubstituted phenylaminocarbonyl, substituted or unsubstituted phenyl, oxime, substituted or unsubstituted alkoxycarbonyl, hydroxycarbonyl (i.e., —COOH), or a substituted or unsubstituted heterocyclic ring; where $R^9$ and $R^{10}$ are each independently H, substituted or unsubstituted $C_{1-6}$ alkyl, substituted or unsubstituted $C_1$-$C_6$ alcohol, substituted or unsubstituted carbonyl (i.e., —C(O)H), substituted or unsubstituted mono- or bi-cyclic cycloalkyl, substituted or unsubstituted mono- or bi-cyclic heterocyclic ring, substituted or unsubstituted aryl, substituted or unsubstituted alkenyl, substituted or unsubstituted sulfonyl, substituted or unsubstituted arylalkyl, substituted or unsubstituted heterocycloalkyl, substituted or unsubstituted aminothiocarbonyl wherein at least one of $R^9$ and $R^{10}$ is H, or $R^9$ and $R^{10}$ together with the atom to which they are attached form a mono- or bi-cyclic heterocyclic ring, wherein at least one ring contains one or two heteroatoms;

(b) $R^1$, $R^2$ and $R^3$ are each independently —H, —OH, or alkyl, wherein $R^1$ may optionally form a substituted or unsubstituted 5-11 membered mono- or bi-heterocyclic ring with X;

(c) n is 0, 1 or 2, wherein when n is 0 then $R^2$ is absent;

(d) $R^4$, $R^5$, $R^6$ and $R^7$ are each independently —H, —OH, substituted or unsubstituted $C_{1-6}$ alkyl, substituted or unsubstituted carbonyl (i.e., —C(O)H), substituted or unsubstituted alkoxy, halo, haloalkyl, haloalkoxy, nitro, cyano, substituted or unsubstituted heterocyclic ring, substituted or unsubstituted amino, substituted or unsubstituted phenyl, substituted or unsubstituted phenoxy, substituted or unsubstituted cycloalkyl, substituted or unsubstituted alkenyl, substituted or unsubstituted alkynyl, or substituted or unsubstituted alkoxycarbonyl, or hydroxycarbonyl;

(e) W is N, O, or S; and (f) $R^8$ is H, $C_{1-3}$ alkyl, substituted or unsubstituted cycloalkyl, substituted or unsubstituted carbonyl (i.e., —C(O)H), or together with X forms a substituted or unsubstituted 5-11 membered mono- or bi-cyclic heterocyclic ring, with the proviso that when W is O or S, $R^8$ is absent.

In a preferred embodiment, the present invention provides a method of inhibiting VEGF production comprising administering to a patient in need thereof a pharmaceutical composition comprising a compound selected from any of compounds 156 through 188. A method of inhibiting VEGF production comprising administering to a patient in need thereof a pharmaceutical composition comprising a compound of Formula (I) with the proviso that the compound is not selected from any of compounds 156 through 188.

A method of inhibiting angiogenesis comprising administering to a patient in need thereof a pharmaceutical composition comprising a compound selected from any of compounds 156 through 188, a compound of Formula I,

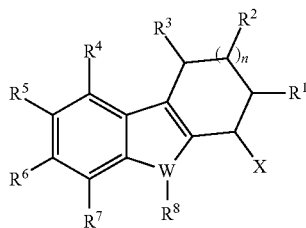

Formula (I)

an enantiomer, a diastereomer, a pharmaceutically acceptable salt, a prodrug, a solvate or a mixture thereof, wherein (a) X is —$NR^9R^{10}$, —N(alkyl)-C(O)-aryl, —N(alkyl)-C(O)-halogen substituted aryl, oxo, $OR^9$, H, substituted or unsubstituted phenylaminocarbonyl, substituted or unsubstituted phenyl, oxime, substituted or unsubstituted alkoxycarbonyl, hydroxycarbonyl (i.e., —COOH), or a substituted or unsubstituted heterocyclic ring; where $R^9$ and $R^{10}$ are each independently H, substituted or unsubstituted $C_{1-6}$ alkyl, substituted or unsubstituted $C_1$-$C_6$ alcohol, substituted or unsubstituted carbonyl (i.e., —C(O)H), substituted or unsubstituted mono- or bi-cyclic cycloalkyl, substituted or unsubstituted mono- or bi-cyclic heterocyclic ring, substituted or unsubstituted aryl, substituted or unsubstituted alkenyl, substituted or unsubstituted sulfonyl, substituted or unsubstituted arylalkyl, substituted or unsubstituted heterocycloalkyl, substituted or unsubstituted aminothiocarbonyl wherein at least one of $R^9$ and $R^{10}$ is H, or $R^9$ and $R^{10}$ together with the atom to which they are attached form a mono- or bi-cyclic heterocyclic ring, wherein at least one ring contains one or two heteroatoms;

(b) $R^1$, $R^2$ and $R^3$ are each independently —H, —OH, or alkyl, wherein $R^1$ may optionally form a substituted or unsubstituted 5-11 membered mono- or bi-heterocyclic ring with X;

(c) n is 0, 1 or 2, wherein when n is 0 then $R^2$ is absent;

(d) $R^4$, $R^5$, $R^6$ and $R^7$ are each independently —H, —OH, substituted or unsubstituted $C_{1-6}$ alkyl, substituted or unsubstituted carbonyl (i.e., —C(O)H), substituted or unsubstituted alkoxy, halo, haloalkyl, haloalkoxy, nitro, cyano, substituted or unsubstituted heterocyclic ring, substituted or unsubstituted amino, substituted or unsubstituted phenyl, substituted or unsubstituted phenoxy, substituted or unsubstituted cycloalkyl, substituted or unsubstituted alkenyl, substituted or unsubstituted alkynyl, or substituted or unsubstituted alkoxycarbonyl, or hydroxycarbonyl;

(e) W is N, O, or S; and (f) $R^8$ is H, $C_{1-3}$ alkyl, substituted or unsubstituted cycloalkyl, substituted or unsubstituted carbonyl (i.e., —C(O)H), or together with X forms a substituted or unsubstituted 5-11 membered mono- or bi-cyclic heterocyclic ring, with the proviso that when W is O or S, $R^8$ is absent.

In a preferred embodiment, the present invention provides a method of inhibiting angiogenesis comprising administering to a patient in need thereof a pharmaceutical composition comprising a compound selected from any of compounds 156 through 188. A method of inhibiting angiogenesis comprising administering to a patient in need thereof a pharmaceutical composition comprising a compound of Formula (I) with the proviso that the compound is not selected from any of compounds 156 through 188.

A method of treating cancer, diabetic retinopathy, rheumatoid arthritis, psoriasis, atherosclerosis, obesity, chronic inflammation or exudative macular degeneration comprising administering to a patient in need thereof a pharmaceutical composition comprising a compound selected from any of compounds 156 through 188, a compound of Formula I,

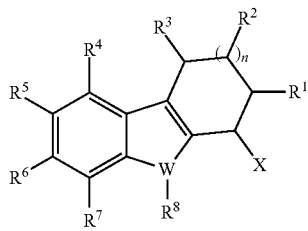

Formula (I)

an enantiomer, a diastereomer, a pharmaceutically acceptable salt, a prodrug, a solvate or a mixture thereof,
wherein
(a) X is —NR$^9$R$^{10}$, —N(alkyl)-C(O)-aryl, —N(alkyl)-C(O)-halogen substituted aryl, oxo, OR$^9$, H, substituted or unsubstituted phenylaminocarbonyl, substituted or unsubstituted phenyl, oxime, substituted or unsubstituted alkoxycarbonyl, hydroxycarbonyl (i.e., —COOH), or a substituted or unsubstituted heterocyclic ring; where
R$^9$ and R$^{10}$ are each independently H, substituted or unsubstituted C$_{1-6}$ alkyl, substituted or unsubstituted C$_1$-C$_6$ alcohol, substituted or unsubstituted carbonyl (i.e., —C(O)H), substituted or unsubstituted mono- or bi-cyclic cycloalkyl, substituted or unsubstituted mono- or bi-cyclic heterocyclic ring, substituted or unsubstituted aryl, substituted or unsubstituted alkenyl, substituted or unsubstituted sulfonyl, substituted or unsubstituted arylalkyl, substituted or unsubstituted heterocycloalkyl, substituted or unsubstituted aminothiocarbonyl wherein at least one of R$^9$ and R$^{16}$ is H,
or R$^9$ and R$^{10}$ together with the atom to which they are attached form a mono- or bi-cyclic heterocyclic ring, wherein at least one ring contains one or two heteroatoms;
(b) R$^1$, R$^2$ and R$^3$ are each independently —H, —OH, or alkyl, wherein R$^1$ may optionally form a substituted or unsubstituted 5-11 membered mono- or bi-heterocyclic ring with X;
(c) n is 0, 1 or 2, wherein when n is 0 then R$^2$ is absent;
(d) R$^4$, R$^5$, R$^6$ and R$^7$ are each independently —H, —OH, substituted or unsubstituted C$_{1-6}$ alkyl, substituted or unsubstituted carbonyl (i.e., —C(O)H), substituted or unsubstituted alkoxy, halo, haloalkyl, haloalkoxy, nitro, cyano, substituted or unsubstituted heterocyclic ring, substituted or unsubstituted amino, substituted or unsubstituted phenyl, substituted or unsubstituted phenoxy, substituted or unsubstituted cycloalkyl, substituted or unsubstituted alkenyl, substituted or unsubstituted alkynyl, or substituted or unsubstituted alkoxycarbonyl, or hydroxycarbonyl;
(e) W is N, O, or S; and
(f) R$^8$ is H, C$_{1-3}$ alkyl, substituted or unsubstituted cycloalkyl, substituted or unsubstituted carbonyl (i.e., —C(O)H), or together with X forms a substituted or unsubstituted 5-11 membered mono- or bi-cyclic heterocyclic ring, with the proviso that when W is O or S, R$^8$ is absent.

In a preferred embodiment, the present invention provides a method of treating cancer, diabetic retinopathy, rheumatoid arthritis, psoriasis, atherosclerosis, obesity, chronic inflammation or exudative macular degeneration comprising administering to a patient in need thereof a pharmaceutical composition comprising a compound selected from any of compounds 156 through 188. A method of treating cancer, diabetic retinopathy, rheumatoid arthritis, psoriasis, atherosclerosis, obesity, chronic inflammation or exudative macular degeneration comprising administering to a patient in need thereof a pharmaceutical composition comprising a compound of Formula (I) with the proviso that the compound is not selected from any of compounds 156 through 188.

A method of inhibiting VEGF production comprising administering to a patient in need thereof a pharmaceutical composition comprising a compound selected from any of compounds 156 through 188, a compound of Formula (II) through Formula (VIII).

A method of inhibiting VEGF production comprising administering to a patient in need thereof a pharmaceutical composition comprising a compound of Formula (II) through Formula (VIII) with the proviso that the compound is not selected from any of compounds 156 through 188.

A method of inhibiting angiogenesis comprising administering to a patient in need thereof a pharmaceutical composition comprising a compound selected from any of compounds 156 through 188, a compound of Formula (II) through Formula (VIII).

A method of inhibiting angiogenesis comprising administering to a patient in need thereof a pharmaceutical composition comprising a compound of Formula (II) through Formula (VIII) with the proviso that the compound is not selected from any of compounds 156 through 188.

A method of treating cancer, diabetic retinopathy, rheumatoid arthritis, psoriasis, atherosclerosis, obesity, chronic inflammation or exudative macular degeneration comprising administering to a patient in need thereof a pharmaceutical composition comprising a compound selected from any of compounds 156 through 188, a compound of Formula (II) through Formula (VIII).

A method of treating cancer, diabetic retinopathy, rheumatoid arthritis, psoriasis, atherosclerosis, obesity, chronic inflammation or exudative macular degeneration comprising administering to a patient in need thereof a pharmaceutical composition comprising a compound of Formula (II) through Formula (VIII) with the proviso that the compound is not selected from any of compounds 156 through 188.

In a further embodiment, the present invention provides a method for selectively inhibiting VEGF in cells, by exposing the cells to an effective amount of at least one compound selected from the following:
6-Bromo-1-thieno[2,3-c]pyrrol-5-yl-2,3,4,9-tetrahydro-1H-carbazole;
(6-Bromo-2,3,4,9-tetrahydro-1H-carbazol-1-yl)-phenyl-amine;
(6-Bromo-2,3,4,9-tetrahydro-1H-carbazol-1-yl)-(4-chlorophenyl)-amine;
(6-Bromo-2,3,4,9-tetrahydro-1H-carbazol-1-yl)-(4-methoxy-phenyl)-amine;
5-(6-Bromo-2,3,4,9-tetrahydro-1H-carbazol-1-yl)-4,5-dihydro-thieno[2,3-c]pyrrol-6-one;
(6-Bromo-2,3,4,9-tetrahydro-1H-carbazol-1-yl)-(4-trifluoromethyl-phenyl)-amine;
6-Bromo-1-(1,3-dihydro-isoindol-2-yl)-2,3,4,9-tetrahydro-1H-carbazole;
(6-Bromo-2,3,4,9-tetrahydro-1H-carbazol-1-yl)-(4-isopropyl-phenyl)-amine;
(6-Bromo-2,3,4,9-tetrahydro-1H-carbazol-1-yl)-(4-phenoxy-phenyl)-amine;
(6-Bromo-2,3,4,9-tetrahydro-1H-carbazol-1-yl)-(3-methoxy-phenyl)-amine;
(6-Methyl-2,3,4,9-tetrahydro-1H-carbazol-1-yl)-phenyl-amine;
(6-Bromo-2,3,4,9-tetrahydro-1H-carbazol-1-yl)-(3-fluoro-phenyl)-amine;
1-(6-Bromo-1-pyrrol-1-yl-1,2,3,4-tetrahydro-carbazol-9-yl)-ethanone;

Phenyl-(6-trifluoromethyl-2,3,4,9-tetrahydro-1H-carbazol-1-yl)-amine;
6-Bromo-1-phenyl-2,3,4,9-tetrahydro-1H-carbazole;
6-Bromo-1-(3-methoxy-phenyl)-2,3,4,9-tetrahydro-1H-carbazole;
(6-Bromo-2,3,4,9-tetrahydro-1H-carbazol-1-yl)-(2-fluoro-phenyl)-amine;
Benzo[1,3]dioxol-5-yl-(6-bromo-2,3,4,9-tetrahydro-1H-carbazol-1-yl)-amine;
(6-Bromo-2,3,4,9-tetrahydro-1H-carbazol-1-yl)-(4-trifluoromethoxy-phenyl)-amine;
(6-Bromo-2,3,4,9-tetrahydro-1H-carbazol-1-yl)-(3-chloro-phenyl)-amine;
N-(6-Bromo-2,3,4,9-tetrahydro-1H-carbazol-1-yl)-benzamide;
N-(6-Bromo-2,3,4,9-tetrahydro-1H-carbazol-1-yl)-3-chloro-benzamide;
(6-Bromo-2,3,4,9-tetrahydro-1H-carbazol-1-yl)-(3,5-dimethyl-phenyl)-amine;
(6-Bromo-2,3,4,9-tetrahydro-1H-carbazol-1-yl)-(4-fluoro-phenyl)-amine;
2-(6-Bromo-2,3,4,9-tetrahydro-1H-carbazol-1-yl)-2,3-dihydro-isoindol-1-one;
1-(6-Bromo-2,3,4,9-tetrahydro-1H-carbazol-1-yl)-1H-pyrrole-3-carboxylic acid methyl ester;
(6-Bromo-2,3,4,9-tetrahydro-1H-carbazol-1-yl)-(4-phenyl-cyclohexyl)-amine;
Biphenyl-4-yl-(6-bromo-2,3,4,9-tetrahydro-1H-carbazol-1-yl)-amine;
(6-Bromo-2,3,4,9-tetrahydro-1H-carbazol-1-yl)-(2-chloro-phenyl)-amine;
N-(6-Bromo-2,3,4,9-tetrahydro-1H-carbazol-1-yl)-3-phenoxy-benzamide;
(6-Bromo-2,3,4,9-tetrahydro-1H-carbazol-1-yl)-pyrazin-2-yl-amine;
(6-Bromo-2,3,4,9-tetrahydro-1H-carbazol-1-yl)-(2,3-difluoro-phenyl)-amine;
(2-Bromo-5,6,7,8,9,10-hexahydro-cyclohepta[b]indol-6-yl)-phenyl-amine;
Phenyl-(6-trifluoromethoxy-2,3,4,9-tetrahydro-1H-carbazol-1-yl)-amine;
Furan-2-carboxylic acid (6-bromo-2,3,4,9-tetrahydro-1H-carbazol-1-yl)-amide;
Thiophene-2-carboxylic acid (6-bromo-2,3,4,9-tetrahydro-1H-carbazol-1-yl)-amide;
1-Benzooxazol-2-yl-6-bromo-2,3,4,9-tetrahydro-1H-carbazole;
N-(6-Bromo-2,3,4,9-tetrahydro-1H-carbazol-1-yl)-4-methoxy-benzamide;
N-(6-Bromo-2,3,4,9-tetrahydro-1H-carbazol-1-yl)-4-trifluoromethyl-benzamide;
N-(6-Bromo-2,3,4,9-tetrahydro-1H-carbazol-1-yl)-4-cyano-benzamide;
N-(6-Bromo-2,3,4,9-tetrahydro-1H-carbazol-1-yl)-2,4-difluoro-benzamide;
N-(6-Bromo-2,3,4,9-tetrahydro-1H-carbazol-1-yl)-4-chloro-benzamide;
(4-Chloro-phenyl)-(6-chloro-2,3,4,9-tetrahydro-1H-carbazol-1-yl)-amine;
(6-Chloro-2,3,4,9-tetrahydro-1H-carbazol-1-yl)-(4-methoxy-phenyl)-amine;
(6-Chloro-2,3,4,9-tetrahydro-1H-carbazol-1-yl)-(4-trifluoromethyl-phenyl)-amine;
(4-Chloro-phenyl)-(6-trifluoromethyl-2,3,4,9-tetrahydro-1H-carbazol-1-yl)-amine;
(4-Methoxy-phenyl)-(6-trifluoromethyl-2,3,4,9-tetrahydro-1H-carbazol-1-yl)-amine;
(4-Trifluoromethyl-phenyl)-(6-trifluoromethyl-2,3,4,9-tetrahydro-1H-carbazol-1-yl)-amine;
(6-Bromo-2,3,4,9-tetrahydro-1H-carbazol-1-yl)-pyrimidin-2-yl-amine;
1-(1H-Benzoimidazol-2-yl)-6-bromo-2,3,4,9-tetrahydro-1H-carbazole;
N-(6-Chloro-2,3,4,9-tetrahydro-1H-carbazol-1-yl)-4-methoxy-benzamide;
5-(6-Chloro-2,3,4,9-tetrahydro-1H-carbazol-1-yl)-4,5-dihydro-thieno[2,3-c]pyrrol-6-one;
Isoxazole-5-carboxylic acid (6-bromo-2,3,4,9-tetrahydro-1H-carbazol-1-yl)-amide;
5-Methyl-isoxazole-3-carboxylic acid (6-bromo-2,3,4,9-tetrahydro-1H-carbazol-1-yl)-amide;
5-Chloro-thiophene-2-carboxylic acid (6-bromo-2,3,4,9-tetrahydro-1H-carbazol-1-yl)-amide; and
1-Methyl-1H-pyrrole-2-carboxylic acid (6-bromo-2,3,4,9-tetrahydro-1H-carbazol-1-yl)-amide.

In yet a further embodiment, the compound of Formula (I) is selected from the following:
6-Bromo-1-thieno[2,3-c]pyrrol-5-yl-2,3,4,9-tetrahydro-1H-carbazole;
(6-Bromo-2,3,4,9-tetrahydro-1H-carbazol-1-yl)-phenyl-amine;
(6-Bromo-2,3,4,9-tetrahydro-1H-carbazol-1-yl)-(4-chloro-phenyl)-amine;
(6-Bromo-2,3,4,9-tetrahydro-1H-carbazol-1-yl)-(4-methoxy-phenyl)-amine;
5-(6-Bromo-2,3,4,9-tetrahydro-1H-carbazol-1-yl)-4,5-dihydro-thieno[2,3-c]pyrrol-6-one;
(6-Bromo-2,3,4,9-tetrahydro-1H-carbazol-1-yl)-(4-trifluoromethyl-phenyl)-amine;
6-Bromo-1-(1,3-dihydro-isoindol-2-yl)-2,3,4,9-tetrahydro-1H-carbazole;
(6-Bromo-2,3,4,9-tetrahydro-1H-carbazol-1-yl)-(4-isopropyl-phenyl)-amine;
(6-Bromo-2,3,4,9-tetrahydro-1H-carbazol-1-yl)-(4-phenoxy-phenyl)-amine;
(6-Bromo-2,3,4,9-tetrahydro-1H-carbazol-1-yl)-(3-methoxy-phenyl)-amine;
(6-Methyl-2,3,4,9-tetrahydro-1H-carbazol-1-yl)-phenyl-amine;
(6-Bromo-2,3,4,9-tetrahydro-1H-carbazol-1-yl)-(3-fluoro-phenyl)-amine;
1-(6-Bromo-1-pyrrol-1-yl-1,2,3,4-tetrahydro-carbazol-9-yl)-ethanone;
Phenyl-(6-trifluoromethyl-2,3,4,9-tetrahydro-1H-carbazol-1-yl)-amine;
6-Bromo-1-phenyl-2,3,4,9-tetrahydro-1H-carbazole;
6-Bromo-1-(3-methoxy-phenyl)-2,3,4,9-tetrahydro-1H-carbazole;
(6-Bromo-2,3,4,9-tetrahydro-1H-carbazol-1-yl)-(2-fluoro-phenyl)-amine;
Benzo[1,3]dioxol-5-yl-(6-bromo-2,3,4,9-tetrahydro-1H-carbazol-1-yl)-amine;
(6-Bromo-2,3,4,9-tetrahydro-1H-carbazol-1-yl)-(4-trifluoromethoxy-phenyl)-amine;
(6-Bromo-2,3,4,9-tetrahydro-1H-carbazol-1-yl)-(3-chloro-phenyl)-amine;
N-(6-Bromo-2,3,4,9-tetrahydro-1H-carbazol-1-yl)-benzamide;
N-(6-Bromo-2,3,4,9-tetrahydro-1H-carbazol-1-yl)-3-chloro-benzamide;
(6-Bromo-2,3,4,9-tetrahydro-1H-carbazol-1-yl)-(3,5-dimethyl-phenyl)-amine;
(6-Bromo-2,3,4,9-tetrahydro-1H-carbazol-1-yl)-(4-fluoro-phenyl)-amine;

2-(6-Bromo-2,3,4,9-tetrahydro-1H-carbazol-1-yl)-2,3-dihydro-isoindol-1-one;
1-(6-Bromo-2,3,4,9-tetrahydro-1H-carbazol-1-yl)-1H-pyrrole-3-carboxylic acid methyl ester;
(6-Bromo-2,3,4,9-tetrahydro-1H-carbazol-1-yl)-(4-phenyl-cyclohexyl)-amine;
Biphenyl-4-yl-(6-bromo-2,3,4,9-tetrahydro-1H-carbazol-1-yl)-amine;
(6-Bromo-2,3,4,9-tetrahydro-1H-carbazol-1-yl)-(2-chloro-phenyl)-amine;
N-(6-Bromo-2,3,4,9-tetrahydro-1H-carbazol-1-yl)-3-phenoxy-benzamide;
(6-Bromo-2,3,4,9-tetrahydro-1H-carbazol-1-yl)-pyrazin-2-yl-amine;
(6-Bromo-2,3,4,9-tetrahydro-1H-carbazol-1-yl)-(2,3-difluoro-phenyl)-amine;
(2-Bromo-5,6,7,8,9,10-hexahydro-cyclohepta[b]indol-6-yl)-phenyl-amine;
Phenyl-(6-trifluoromethoxy-2,3,4,9-tetrahydro-1H-carbazol-1-yl)-amine;
Furan-2-carboxylic acid (6-bromo-2,3,4,9-tetrahydro-1H-carbazol-1-yl)-amide;
Thiophene-2-carboxylic acid (6-bromo-2,3,4,9-tetrahydro-1H-carbazol-1-yl)-amide;
1-Benzooxazol-2-yl-6-bromo-2,3,4,9-tetrahydro-1H-carbazole;
N-(6-Bromo-2,3,4,9-tetrahydro-1H-carbazol-1-yl)-4-methoxy-benzamide;
N-(6-Bromo-2,3,4,9-tetrahydro-1H-carbazol-1-yl)-4-trifluoromethyl-benzamide;
N-(6-Bromo-2,3,4,9-tetrahydro-1H-carbazol-1-yl)-4-cyano-benzamide;
N-(6-Bromo-2,3,4,9-tetrahydro-1H-carbazol-1-yl)-2,4-difluoro-benzamide;
N-(6-Bromo-2,3,4,9-tetrahydro-1H-carbazol-1-yl)-4-chloro-benzamide;
(4-Chloro-phenyl)-(6-chloro-2,3,4,9-tetrahydro-1H-carbazol-1-yl)-amine;
(6-Chloro-2,3,4,9-tetrahydro-1H-carbazol-1-yl)-(4-methoxy-phenyl)-amine;
(6-Chloro-2,3,4,9-tetrahydro-1H-carbazol-1-yl)-(4-trifluoromethyl-phenyl)-amine;
(4-Chloro-phenyl)-(6-trifluoromethyl-2,3,4,9-tetrahydro-1H-carbazol-1-yl)-amine;
(4-Methoxy-phenyl)-(6-trifluoromethyl-2,3,4,9-tetrahydro-1H-carbazol-1-yl)-amine;
(4-Trifluoromethyl-phenyl)-(6-trifluoromethyl-2,3,4,9-tetrahydro-1H-carbazol-1-yl)-amine;
(6-Bromo-2,3,4,9-tetrahydro-1H-carbazol-1-yl)-pyrimidin-2-yl-amine;
1-(1H-Benzoimidazol-2-yl)-6-bromo-2,3,4,9-tetrahydro-1H-carbazole;
N-(6-Chloro-2,3,4,9-tetrahydro-1H-carbazol-1-yl)-4-methoxy-benzamide;
5-(6-Chloro-2,3,4,9-tetrahydro-1H-carbazol-1-yl)-4,5-dihydro-thieno[2,3-c]pyrrol-6-one;
Isoxazole-5-carboxylic acid (6-bromo-2,3,4,9-tetrahydro-1H-carbazol-1-yl)-amide;
5-Methyl-isoxazole-3-carboxylic acid (6-bromo-2,3,4,9-tetrahydro-1H-carbazol-1-yl)-amide;
5-Chloro-thiophene-2-carboxylic acid (6-bromo-2,3,4,9-tetrahydro-1H-carbazol-1-yl)-amide; and
1-Methyl-1H-pyrrole-2-carboxylic acid (6-bromo-2,3,4,9-tetrahydro-1H-carbazol-1-yl)-amide.

Metabolites of the Compounds of the Invention

Also falling within the scope of the present invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammalian tissue or a mammal for a period of time sufficient to yield a metabolic product thereof. Such products typically are identified by preparing a radio-labeled (e.g. $C^{14}$ or $H^3$) compound of the invention, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of the invention even if they possess no biological activity of their own.

Pharmaceutical Compositions of the Invention

While it is possible for the compounds of the present invention to be administered neat, it may be preferable to formulate the compounds as pharmaceutical compositions. As such, in yet another aspect of the invention, pharmaceutical compositions useful in the methods of the invention are provided. The pharmaceutical compositions of the invention may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5 to about pH 8. In an embodiment, the pH is adjusted to a range from about pH 4 to about pH 7.

More particularly, the pharmaceutical compositions of the invention comprise a therapeutically or prophylactically effective amount of one or more, two or more, or three or more compounds of the present invention, together with one or more pharmaceutically acceptable excipients. For example, in an embodiment, pharmaceutical compositions of the invention may comprise one or more compounds of Formula (I) through Formula (VIII) and one or more pharmaceutically acceptable excipients. In an embodiment, pharmaceutical compositions of the invention may comprise one or more of Compounds 159 through 188 and one or more pharmaceutically acceptable excipients. In another embodiment, pharmaceutical compositions of the invention may comprise one or more compounds of Formula (I) through Formula (VIII) and one or more of Compounds 159 through 188 together with one or more pharmaceutically acceptable excipients. In an embodiment of the present invention, a pharmaceutical composition comprises one or more compounds of the invention and one ore more pharmaceutical excipients, with the proviso that the pharmaceutical composition does not comprise Compounds 159 through 188.

In a more preferred embodiment, a pharmaceutical composition is provided that comprises one or more, two or more, or three or more compounds selected from the group consisting of Compound No. 191 to 239, or a hydrate, enantiomer, a diastereomer, a pharmaceutically acceptable salt, prodrug, solvate or a mixture of said one or more, two or more, or three or more compounds, and one or more pharmaceutically acceptable excipients.

Optionally, the pharmaceutical compositions of the invention may comprise a combination of compounds of the present invention, or may include a second active ingredient useful in the treatment of cancer, diabetic retinopathy, rheumatoid arthritis, psoriasis, atherosclerosis, obesity, chronic inflammation, or exudative macular degeneration.

Formulations of the present invention, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition of the invention may also be formulated as a lyophilized solid that is reconstituted with a physiologically compatible solvent prior to administration. Alternative pharmaceutical compositions of the invention may be formulated as syrups, creams, ointments, tablets, and the like.

The term "pharmaceutically acceptable excipient" refers to an excipient for administration of a pharmaceutical agent, such as the compounds of the present invention. The term refers to any pharmaceutical excipient that may be administered without undue toxicity. Pharmaceutically acceptable excipients are determined in part by the particular composition being administered, as well as by the particular method used to administer the composition. Accordingly, there exists a wide variety of suitable formulations of pharmaceutical compositions of the present invention (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions of the invention may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as croscarmellose sodium, cross-linked povidone, *maize* starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions of the invention may be formulated as suspensions comprising a compound of the present invention in admixture with at least one pharmaceutically acceptable excipient suitable for the manufacture of a suspension. In yet another embodiment, pharmaceutical compositions of the invention may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum *acacia* and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions of the invention may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may likewise be used in the preparation of injectables.

Generally, the compounds of the present invention useful in the methods of the present invention are substantially insoluble in water and are sparingly soluble in most pharmaceutically acceptable protic solvents and in vegetable oils. However, the compounds are generally soluble in medium chain fatty acids (e.g., caprylic and capric acids) or triglycerides and have high solubility in propylene glycol esters of medium chain fatty acids. Also contemplated in the invention are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In a preferred embodiment, the compounds of the present invention may be formulated for oral administration in a lipid-based formulation suitable for low solubility compounds. Lipid-based formulations can generally enhance the oral bioavailability of such compounds. As such, a preferred pharmaceutical composition of the invention comprises a therapeutically or prophylactically effective amount of a compound of the present invention, together with at least one pharmaceutically acceptable excipient selected from the group consisting of: medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-β-cyclodextrin (HPBC), which may be added to any of the above-described compositions to further improve the aqueous solubility characteristics of the compounds of the present invention. In one embodiment, the composition comprises 0.1% to 20% hydroxypropyl-β-cyclodextrin, more preferably 1% to 15% hydroxypropyl-β-cyclodextrin, and even more preferably from 2.5% to 10% hydroxypropyl-3-cyclodextrin. The amount of solubility enhancer employed will depend on the amount of the compound of the present invention in the composition.

Combination Therapy

It is also possible to combine any compound of the present invention with one or more other active ingredients useful in the treatment of cancer, exudative macular degeneration, rheumatoid arthritis, psoriasis, atherosclerosis, obesity, chronic inflammation or diabetic retinopathy, including compounds, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of the present invention and one or more additional active ingredients by different routes.

The skilled artisan will recognize that a variety of active ingredients may be administered in combination with the compounds of the present invention that may act to augment or synergistically enhance the VEGF-inhibiting and/or anti-angiogenesis activity of the compounds of the invention.

According to the methods of the invention, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

EXAMPLES

The present invention is described in more detail with reference to the following non-limiting examples, which are offered to more fully illustrate the invention, but are not to be construed as limiting the scope thereof. The examples illustrate the preparation of certain compounds of the invention, and the testing of these compounds in vitro and/or in vivo. Those of skill in the art will understand that the techniques described in these examples represent techniques described by the inventors to function well in the practice of the invention, and as such constitute preferred modes for the practice thereof. However, it should be appreciated that those of skill in the art should in, in light of the present disclosure, appreciate that many changes can be made in the specific methods that are disclosed and still obtain a like or similar result without departing from the spirit and scope of the invention.

Example 1

Preparation of the Compounds of the Invention

Compounds of the invention may be produced in any manner known in the art. By way of example, compounds of the invention may be prepared according to the following general schemes. More specifically, Schemes A, C, D and E may be used to make compounds of Formula I or preferred classes thereof when X is $NR^9R^{10}$. Scheme B may be used to make compounds of Formula I when X is O, Scheme F depicts syntheses using starting compounds in which $R^5$ is Br.

General Synthetic Methods

The following Schemes are intended to present typical synthetic approaches to preparation of the compounds of the invention. In all cases, except where otherwise stated, substituents W, X, R, and $R^1$ to $R^{23}$ are as defined above. The substituent "L" denotes a leaving group. Y includes, but is not limited to, substituted or substituted $C_1$-$C_6$ alkyl, substituted or unsubstituted $C_2$-$C_6$ alkenyl, or substituted or unsubstituted aryl. Z includes, but is not limited to, substituted or unsubstituted carbonyl (i.e., unsubstituted carbonyl is —C(O)H), $C_1$-$C_6$ alkoxycarbonyl, substituted or unsubstituted aminocarbonyl, or sulfonyl.

Scheme A

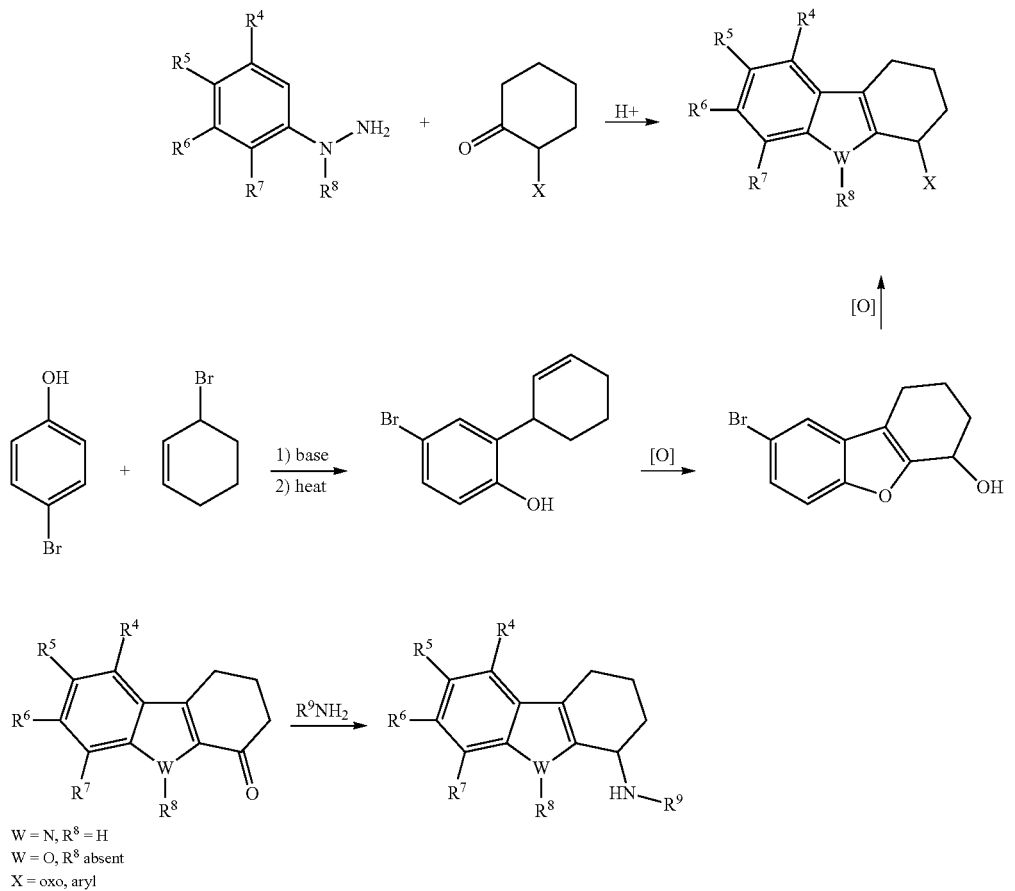

W = N, R⁸ = H
W = O, R⁸ absent
X = oxo, aryl

Scheme A depicts two pathways by which compounds encompassed by Formulas (I), (Ia), and I(b) are obtained. Also shown is a standard procedure for converting carbonyl compounds of the invention to amino compounds of the invention.

Scheme B

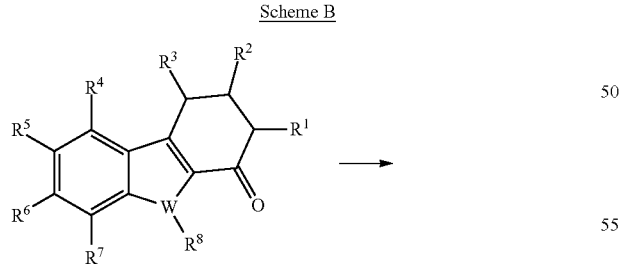

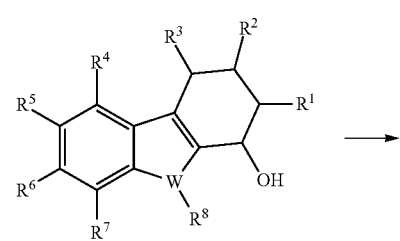

-continued

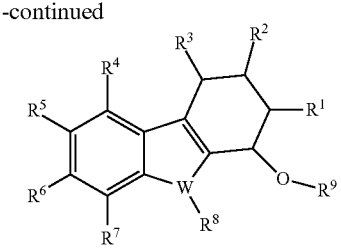

Scheme B depicts a carbonyl compound encompassed by formulas (I), I(a), and I(b), which, by means of a typical synthetic strategy, may be oxidized to an alcohol compound of the invention. Further compounds of the invention may then be obtained from the alcohol. For example, in Scheme B, the alcohol compound of the invention is converted to a variety of other compounds, including, among other compounds, ethers and esters.

Scheme C

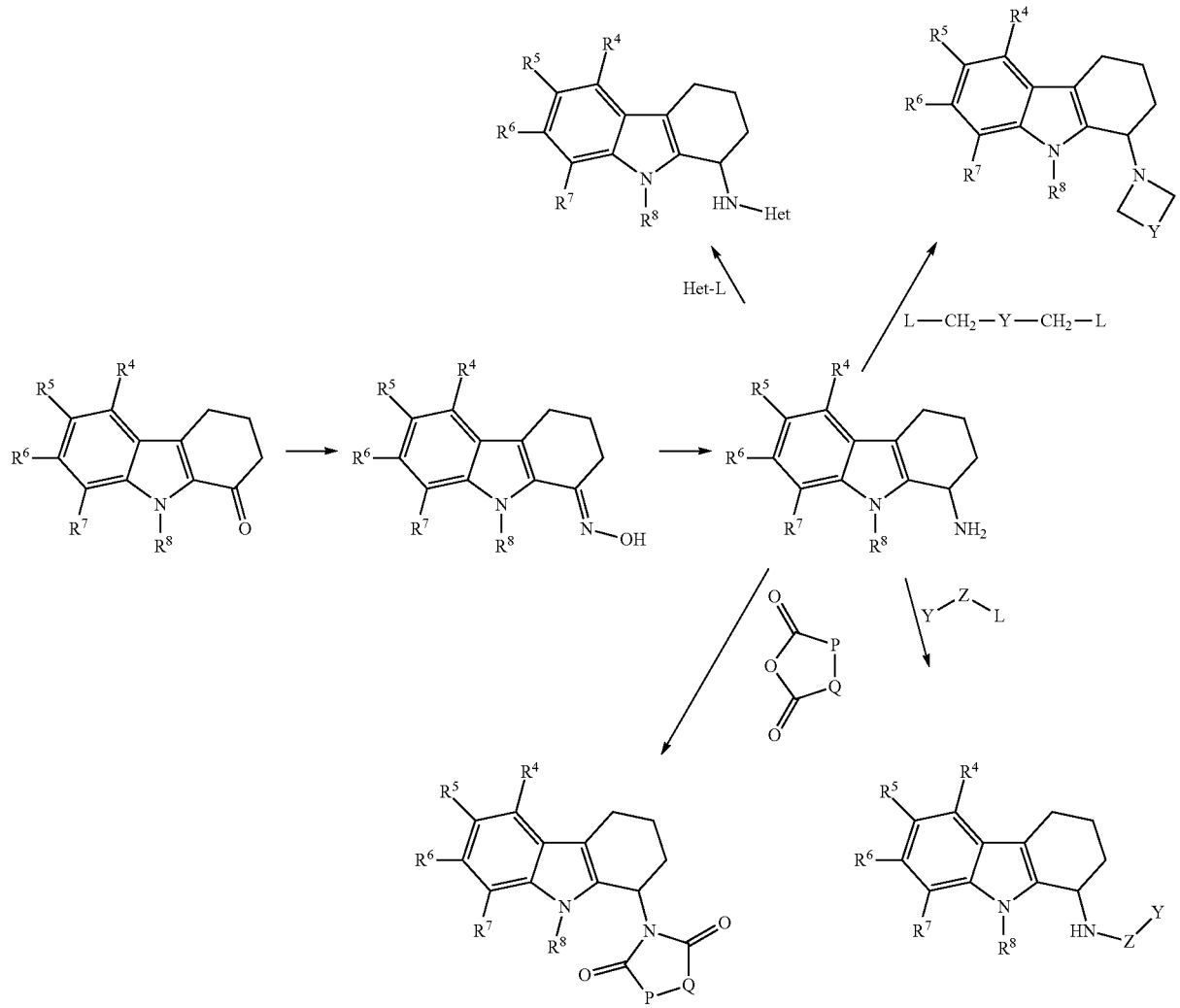

Scheme C depicts a typical synthetic sequence used in the preparation of an amino substituted compound of the invention. The amino substituted compound of the invention may itself serve as an intermediate for a large variety of compounds encompassed by Formulas (Ia), (Ib), and (Ic).

Scheme D

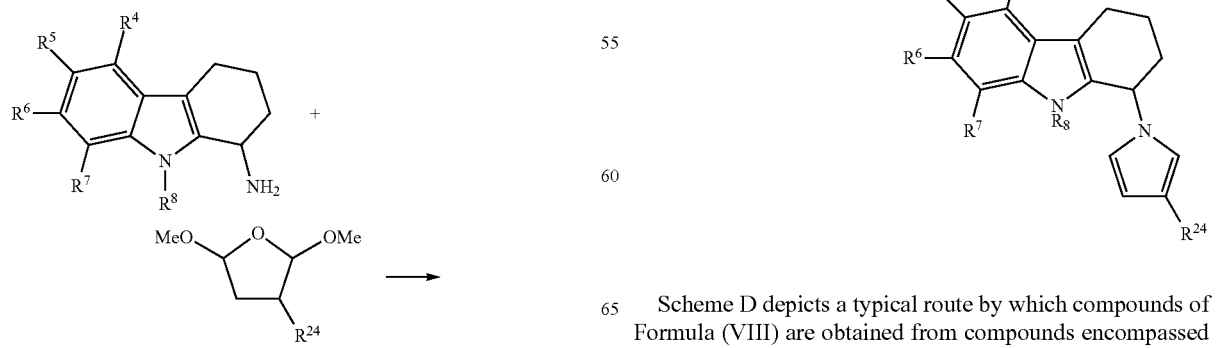

Scheme D depicts a typical route by which compounds of Formula (VIII) are obtained from compounds encompassed by Formulas (Ia), (Ib), and (Ic).

Scheme E

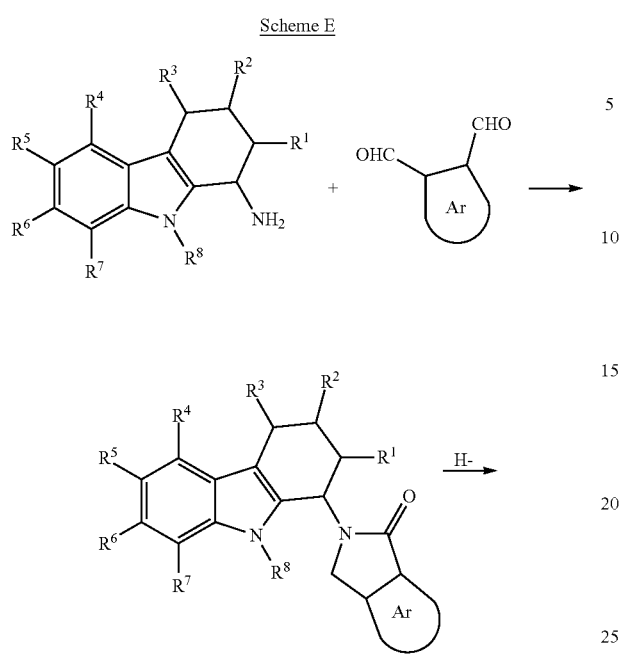

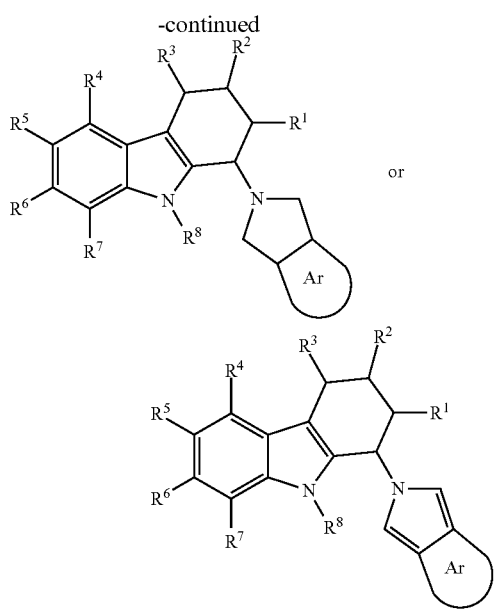

Scheme E depicts typical syntheses of compounds of the invention wherein the amino substituent is incorporated into various bicyclic ring systems.

Scheme F

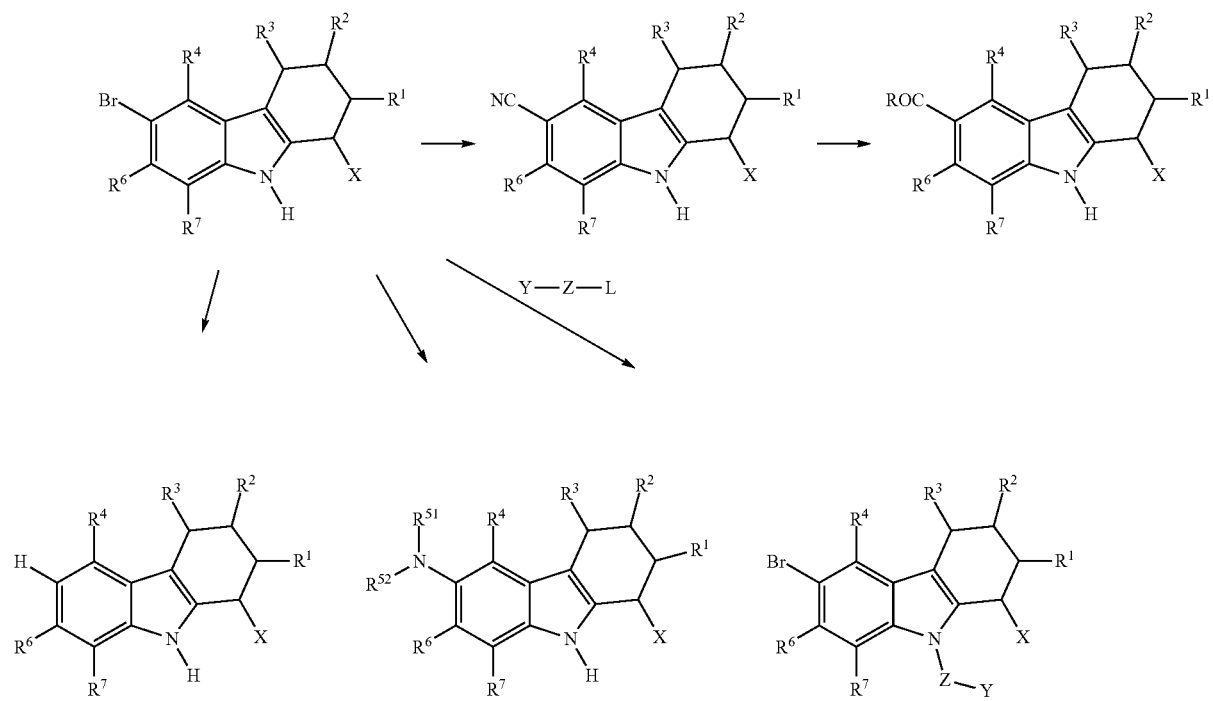

Scheme F depicts some of the various compounds of the invention which may be obtained from a starting compound of the invention wherein $R^5$=Br. The Br substituent may be replaced with a variety of substituents, including, for example, cyano, amino, and carbonyl. $R^{51}$ and $R^{52}$ are selected from the group consisting of H, substituted and unsubstituted $C_1$-$C_6$ alkyl, and substituted and unsubstituted $C_1$-$C_6$ alkylcarbonyl.

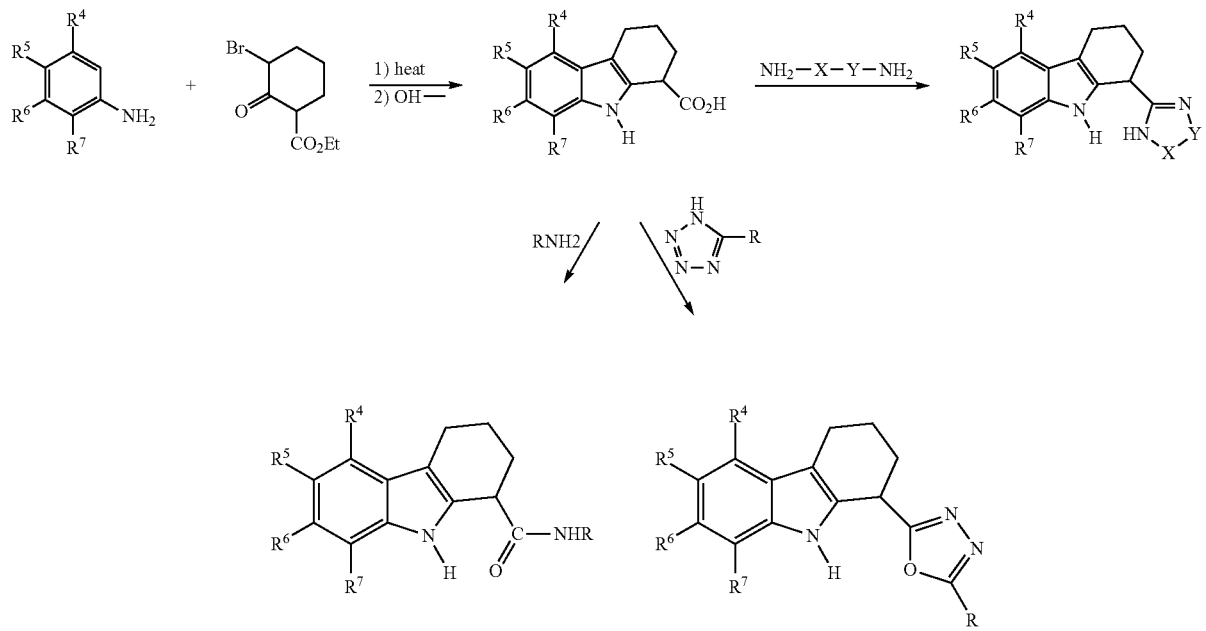

Scheme G depicts the synthesis of a typical intermediate, and compounds of the invention obtained from the intermediate. The intermediate is itself a compound of the invention.

Scheme H depicts a typical synthetic pathway in which the carbonyl moiety of the cyclohexenone ring portion of the starting compound provides a basis for the incorporation of a fourth ring into tricyclic ring system, providing a compound of the invention.

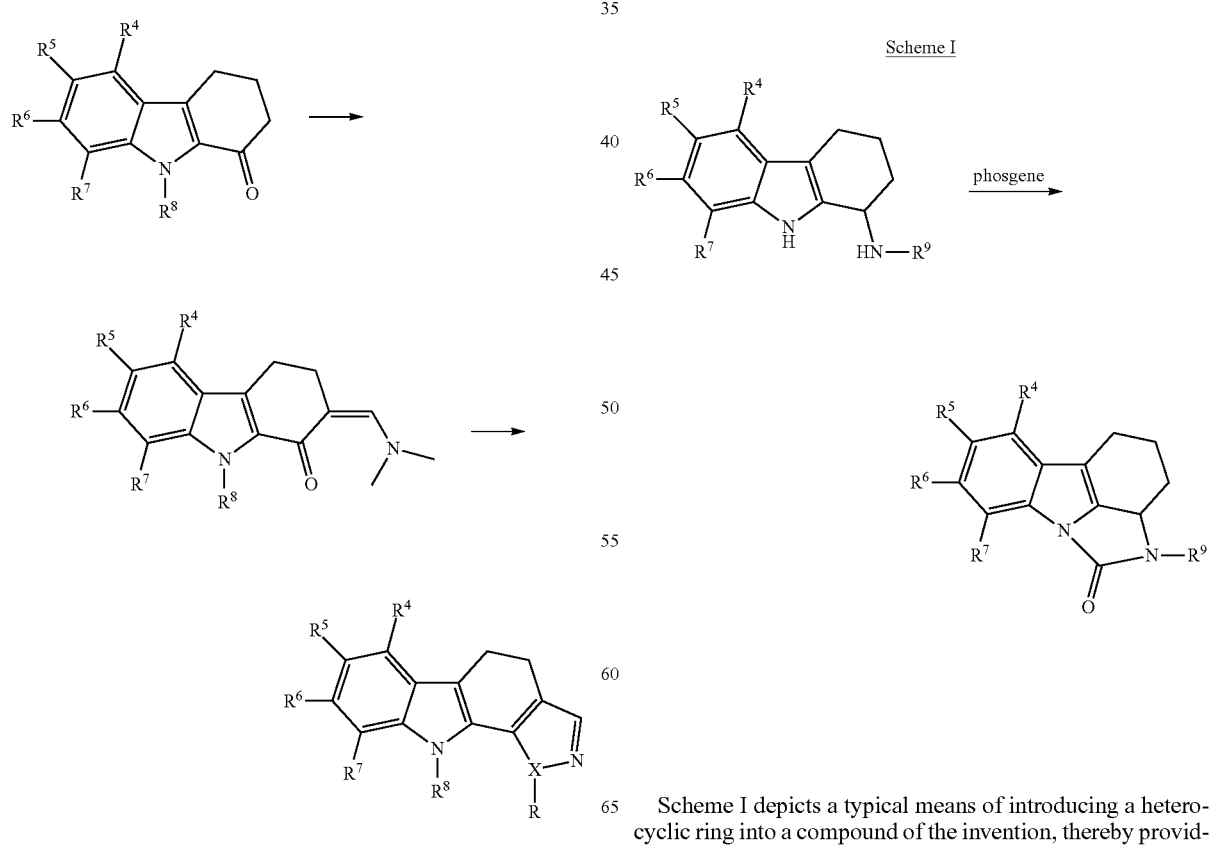

Scheme I depicts a typical means of introducing a heterocyclic ring into a compound of the invention, thereby providing a new compound of the invention.

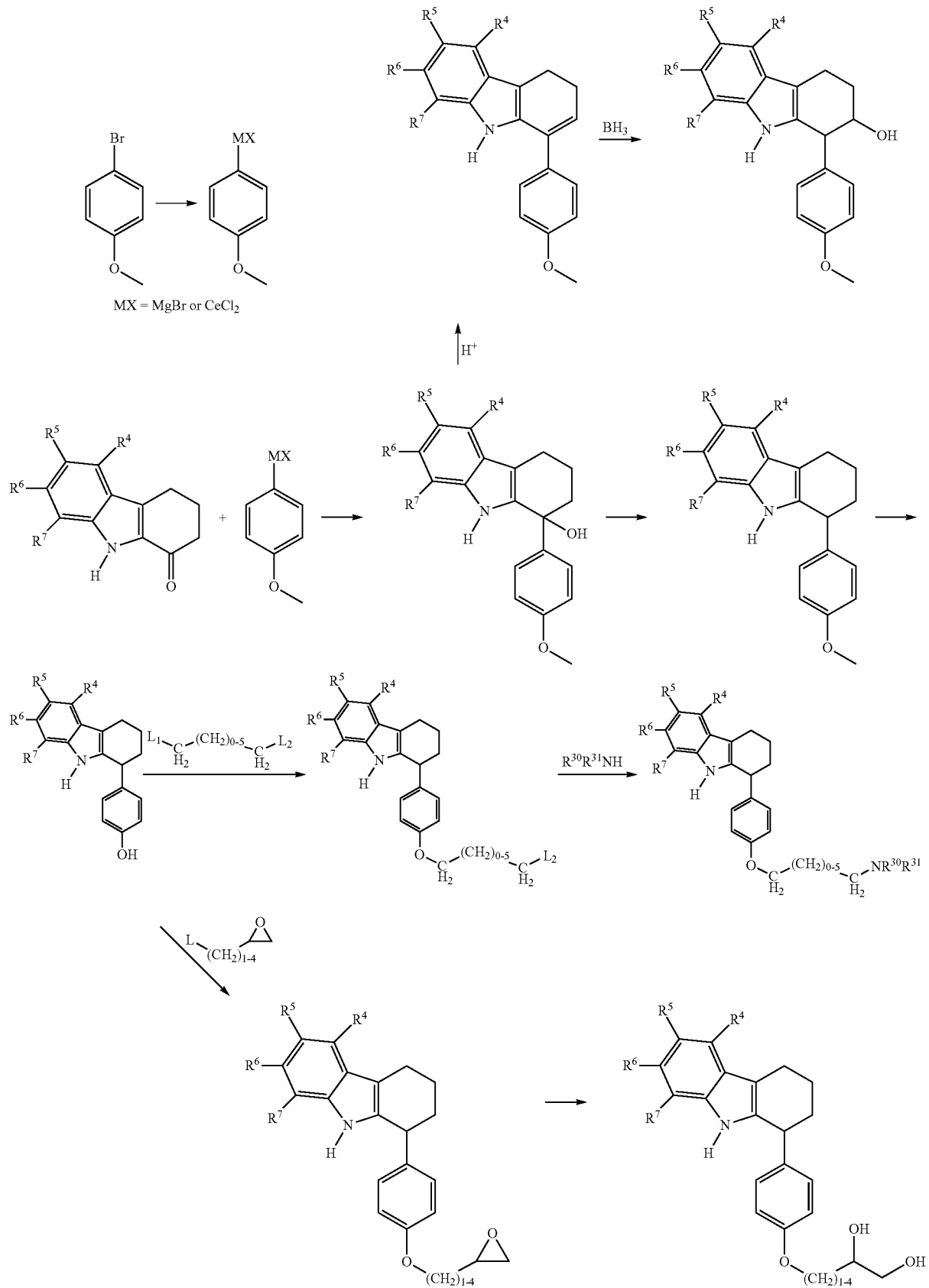

Scheme J depicts typical syntheses of compounds having a phenol or phenyl ether group.

These and other reaction methodologies may be useful in preparing the compounds of the invention, as recognized by one of skill in the art. Various modifications to the above schemes and procedures will be apparent to one of skill in the art, and the invention is not limited specifically by the method of preparing the compounds of the invention.

In general, the synthesis methods described herein may employ a variety of commercially available starting materials, starting materials known in the literature, and readily-prepared starting materials prepared by employing standard synthetic methods and procedures. Standard synthetic methods and procedures for the preparation of organic molecules and functional group transformations and manipulations can be obtained from the relevant scientific literature or from standard reference textbooks in the field. Although not limited to any one or several sources, recognized reference textbooks of organic synthesis include for example: Smith, M. B.; March, J. March's Advanced Organic Chemistry: Reactions, Mechanisms, and Structure, 5$^{th}$ ed.; John Wiley & Sons: New York, 2001; and Greene, T.W.; Wuts, P.G.M. Protective Groups in Organic Synthesis, 3$^{rd}$; John Wiley & Sons: New York, 1999. The foregoing descriptions of synthetic methods are designed to illustrate, but not limit, general procedures for the preparation of compounds of the invention.

Synthesis of Carbazole Compounds
Procedure I:

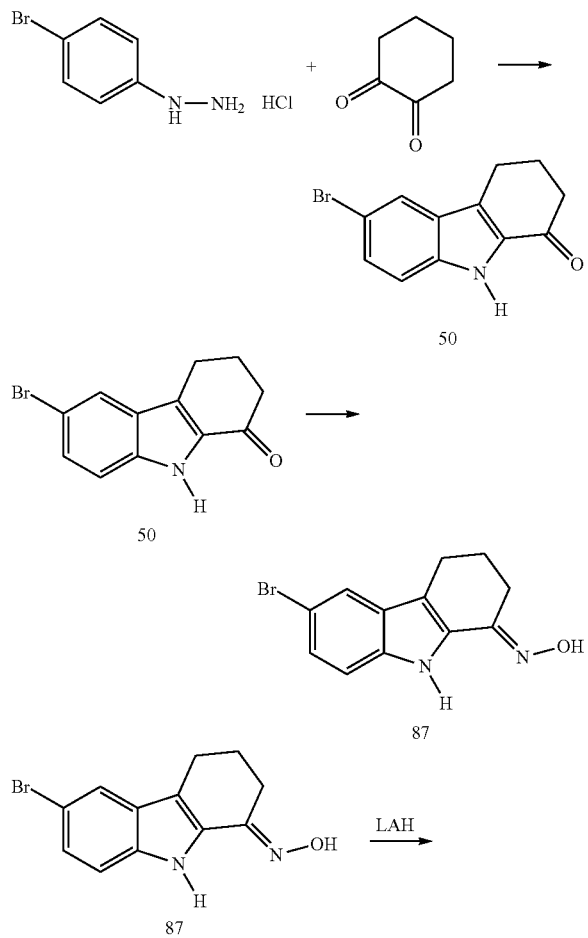

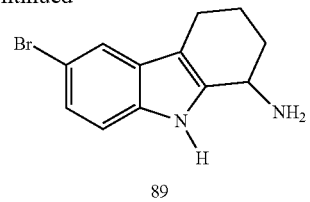

To a solution of 1,2-cyclohexanedione (10.0 g, 84 mmol) in acetic acid (220 mL) and concentrated HCl (80 mL) at 60° C. is added a solution of 4-bromophenylhydrazine HCl salt (9.5 g, 42.5 mmol) in methanol (200 mL) by addition funnel over 1.5 hours. After the addition, the resulting dark brown mixture is heated at 60° C. for an additional 1 hour. The reaction mixture is cooled to room temperature, then placed in a refrigerator to cool overnight. The brown precipitate which settles at the bottom of the flask is collected by filtration, washed with minimal MeOH (2×) to give a light brown powder, 5.25 g (LC-MS >95% pure). The dark brown filtrate is concentrated on rotavap to about half of its original volume, the brown precipitate is filtrated and washed with MeOH (4×) to give a brownish powder, 1.73 g (LC-MS, 95% pure). Total yield of 50: 62%.

Compounds 60, 71, 73, 76, 97 and 110 are prepared in the same manner.

To a mixture of the ketone 50 (5.25 g, 19.9 mmol) and hydroxylamine HCl salt (2.76 g, 39.8 mmol) in EtOH (100 mL) is added pyridine (5.64 mL, 39.8 mmol). The mixture is refluxed for 1 hour. The solids dissolve upon heating. The reaction mixture is concentrated under vacuum to dryness. The resulting sticky solid is treated and washed with hexanes (3×) to give a tan colored power of the oxime 87, 6.1 g, 100%.

Compounds 84, 92, 93 and 98 are prepared in the same manner.

To a suspension of LAH (3.02 g, 79.6 mmol) in ether (75 mL) at 0° C. is added a solution of oxime 87 (6.1 g, 19.9 mmol) in DCM (90 mL) and THF (12 mL). After the addition, the mixture is stirred at 0° C. for 30 min and then is heated at 50° C. for 10 hours. Cooled to 0° C., the mixture is quenched with water (3.2 mL), 20% NaOH (2.4 mL) and water (11.2 mL) sequentially. The white cloudy mixture is stirred at room temperature for 2 hours, and then filtered and washed thoroughly with THF until the filtrate shows no UV absorption. The combined filtrate is concentrated under vacuum to dryness and washed with ether (4×) to give 97% pure amine 89 by LC MS. Yield: 4.14 g, 90%. Compounds 94, 95, 96 and 99 are prepared in the same manner.

Procedure II:

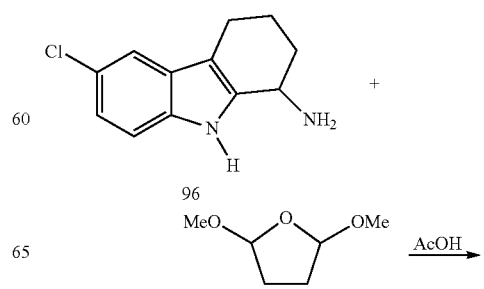

-continued

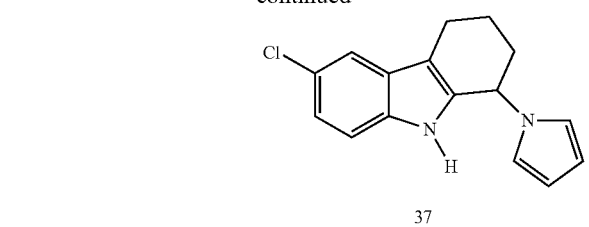
37

Procedure III:

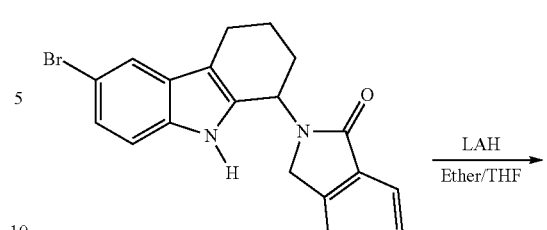
25

→ LAH / Ether/THF

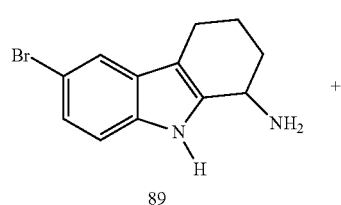
89
+

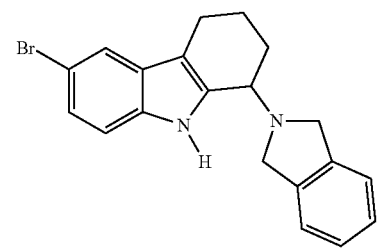
7

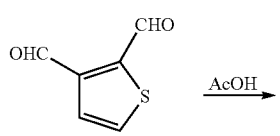

AcOH →

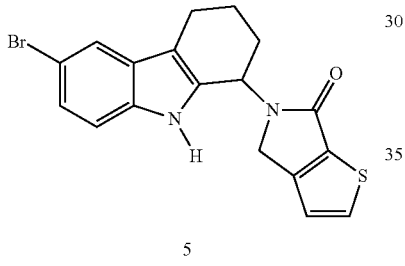
5

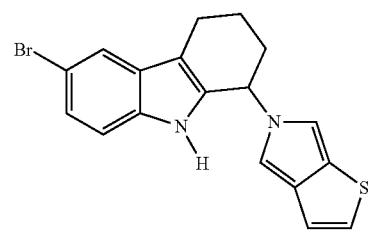 [SMILES: Brc1ccc2[nH]c3c(c2c1)CCCC3n1cc2ccsc2c1]
5

→ LAH / ether/THF

A solution of amine 96 (0.110 g, 0.5 mmol) and 2,5-dimethoxy-tetrahydro-furan (78 mL, 0.6 mmol) in AcOH (5 mL) is heated at 62° C. for 6 hours. The dark brown reaction mixture is concentrated under vacuum and chromatographed to give 37 as an off-white solid. Yield: 68.6 mg, 51%.

Compounds 5, 25, 38, 48, 56, 70, 118, 121 and 149 are made in the same manner.

Compound 5 structure assignment is based on the following references: JOC, 1997, 5392 and JCS, CC, 1985, 1183.

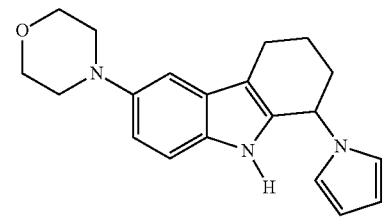
104

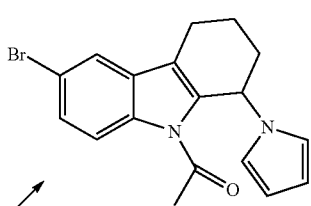
13

↑ Pd(OAc)₂

To a suspension of LAH (15.4 mg, 0.4 mmol) in ether (2 mL) at 0° C. is added a solution of lactam 25 (76 mg, 0.2 mmol) in THF (2 mL) The mixture is stirred at 50° C. overnight, cooled to 0° C. and quenched with saturated Na₂SO₄ (1 mL). The mixture is filtered. The filtrate is concentrated under vacuum and chromatographed (25% EtOAc in hexanes) to give compound 7. Yield: 51 mg, 70%.

Compound 1 is prepared by the same procedure.

Procedure IV:

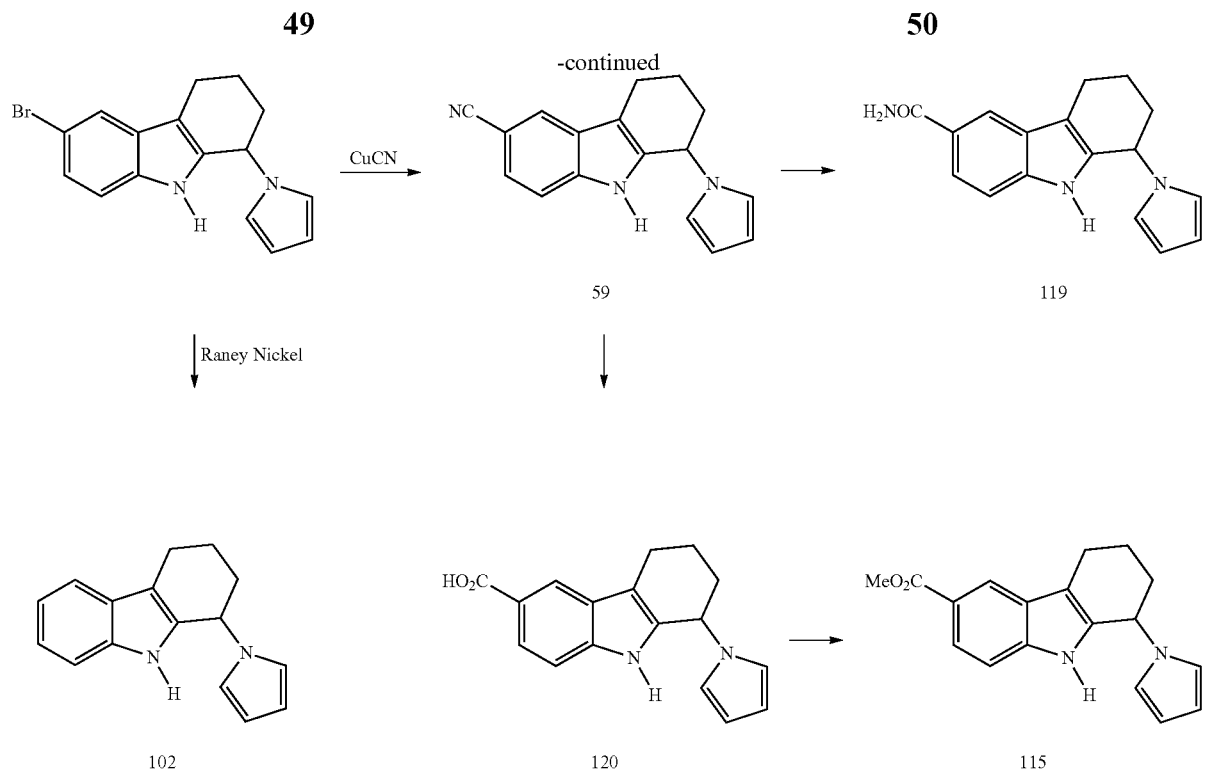

To a suspension of 1-pyrrolyl-6-bromo-1,2,3,4-tetrahydrocarbazole (1.226 g, 4.0 mmol) in NMP (7 mL) is added CuCN (2.86 g, 32 mmol) in a capped tube. The mixture is heated at 220° C. for 30 min. The solids dissolve upon heating, yielding a dark brown oil. The mixture is diluted with EtOAc (50 mL), filtered through celite, washed by water (4×) and brine. The organics are concentrated under vacuum to give nitrite 59 as an off-white solid. Yield: 0.961 g, 92%.

To a suspension of nitrile 59 (0.522 g, 2.0 mmol) in EtOH (8 mL) is added a solution of KOH (1.12 g, 20.0 mmol) in $H_2O$ (4 mL). After refluxing for 40 hours, the mixture is concentrated under vacuum to remove EtOH. The mixture is diluted in $H_2O$ (4 mL) and washed with EtOAc. The aqueous portion is acidified to pH 2-3 using 6N HCl. Compound 120 precipitates out as an off-white solid. The solid is filtered, washed with $H_2O$, and dried under vacuum. Yield: 0.58 g, 93.2%.

To a solution of the acid 120 in DMF is added MeI and $K_2CO_3$. After stirring at room temperature for 3 days, the mixture is diluted with EtOAc and washed with water (2×). The organics are concentrated under vacuum and chromatographed to give the ester 115 as a white powder. Yield: 48 mg, 82%.

To a solution of nitrile 59 (0.13 g, 0.5 mmol) in MeOH (0.5 mL) and THF (3 mL) at 0° C. is added hydrogen peroxide (1 mL). The mixture is stirred at 15° C. for 15 min and then cooled to 0° C. After the addition of 20% NaOH, the mixture is stirred at 15-20° C. for 3.5 hours, then at room temperature for 24 hours. The mixture is neutralized to pH 6-7, diluted with EtOAc and washed with brine. The organics are concentrated under vacuum and chromatographed (EtOAc: Hexanes=1:1) to give amide 119 as a white solid. Yield: 65 mg, 47%.

To a suspension of 1-pyrrolyl-6-bromo-1,2,3,4-tetrahydrocarbazole (157 mg, 0.5 mmol) in MeOH (10 mL) is added Raney Nickel (20 mg). The mixture is shaken on a Parr shaker at 40 psi for 30 min. The mixture is filtered. The filtrate is concentrated under vacuum and chromatographed (10% EtOAc in hexanes) to give 102 as an off-white solid. Yield: 25 mg, 21%.

To a solution of 1-pyrrolyl-6-bromo-1,2,3,4-tetrahydrocarbazole (157 mg, 0.5 mmol) and morpholine (0.1 mL, 1.0 mmol) in xylene (3.0 mL) under $N_2$ is added sodium t-butoxide (67 mg, 0.7 mmol), $Pd(OAc)_2$ (8.9 mg, 0.04 mmol) and $P(Ot-Bu)_3$ (0.53 mL, 0.16 mmol). After refluxing for 7 hours, the mixture is diluted with water and EtOAc. The organics are separated, concentrated under vacuum and chromatographed (20% EtOAc in hexanes) to give 104 as yellowish oil. Yield: 30 mg, 18.6%.

Compound 106 is prepared in the same manner.

To a solution of 1-pyrrolyl-6-bromo-1,2,3,4-tetrahydrocarbazole (94 mg, 0.3 mmol) and acetyl chloride (26 mL, 0.36 mmol) in THF (5 mL) are added DIEA (0.11 mL, 0.6 mmol) and DMAP (36.6 mg, 0.3 mmol) in a capped tube. The mixture is heated at 100° C. for 24 hours, concentrated under vacuum and chromatographed to give 13 as a white solid. Yield: 45.5 mg, 46%.

Procedure V:

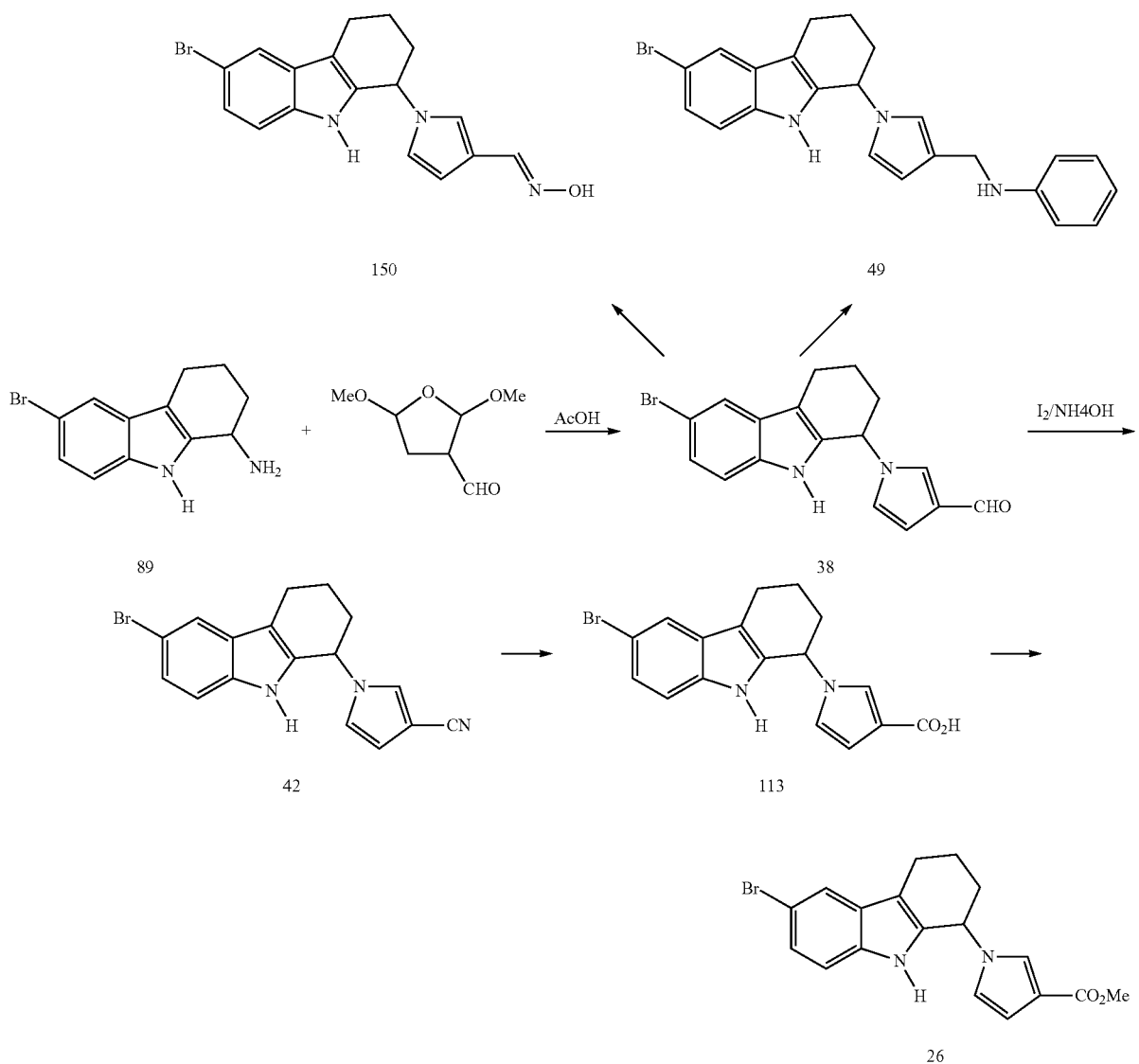

Compound 38 is prepared in the same manner as that of compound 37, Procedure II. Compound 49 is prepared in the same manner as that of compound 17, Procedure VI.

Compound 149 is prepared in the same manner as that of compound 87, Procedure I.

Compound 113 is prepared in the same manner as that of compound 120, Procedure IV.

Compound 26 is prepared in the same manner as that of compound 115, Procedure IV.

Compound 42: To a solution of the aldehyde 38 (102.6 g, 0.3 mmol) in THF (1.3 mL) is added saturated ammonium hydroxide (6 mL) and iodine (238 mg, 0.93 mmol). After stirring at room temperature for 24 hours, the mixture is treated with saturated $Na_2SO_3$ and extracted with EtOAc. The organics are concentrated under vacuum to give 42 as a grayish solid. Yield: 94 mg, 92%.

Procedure VIa:

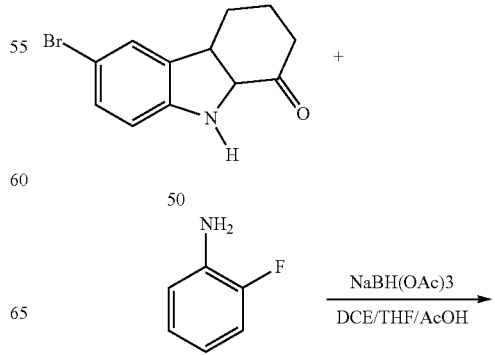

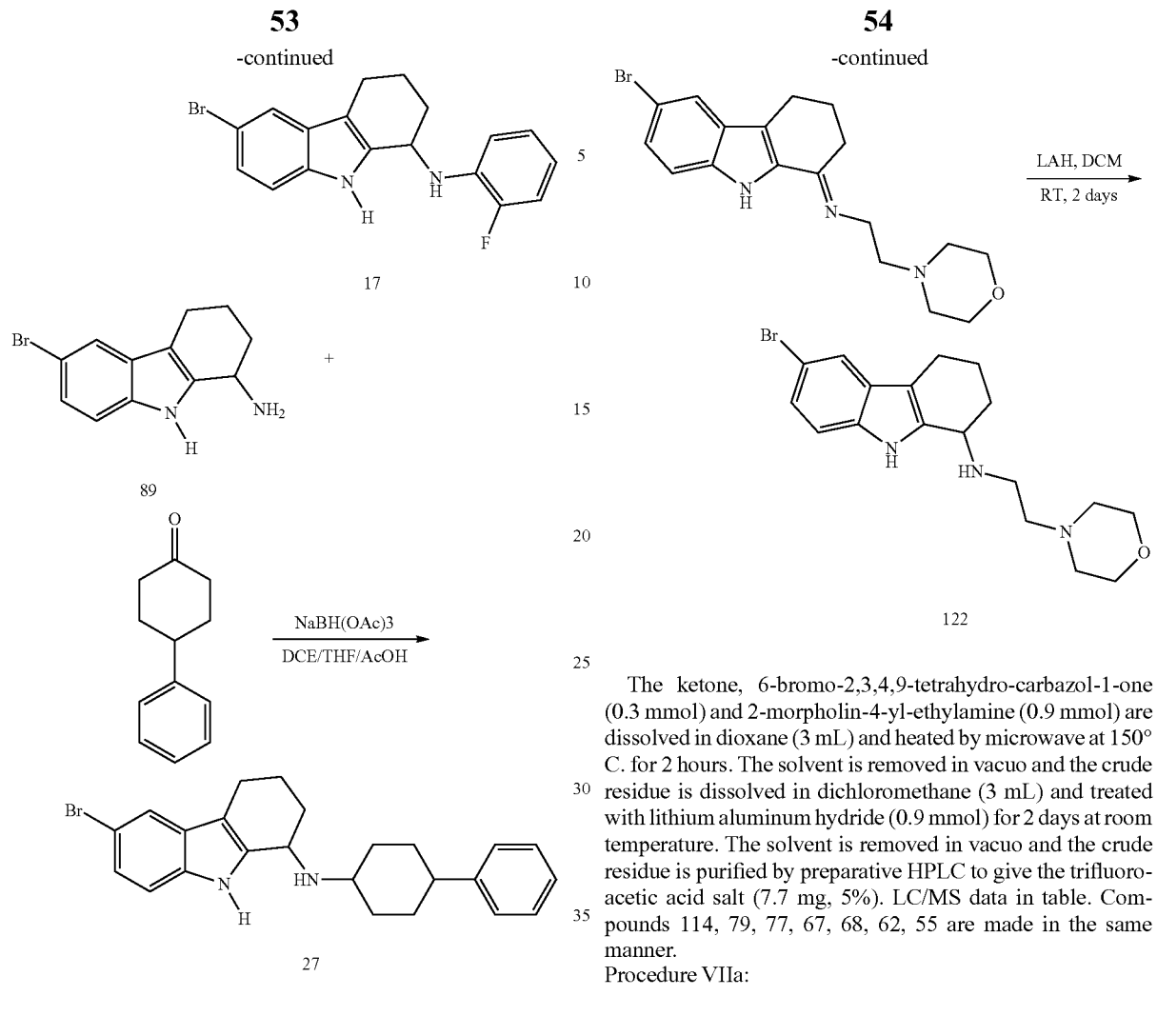

To a mixture of ketone 50 (105 mg, 0.4 mmol) and 2-fluoroaniline (43 ml, 0.44 mmol) in THF (0.8 mL) is added a solution of AcOH in 1,2-dichloroethane (1.6 mL, 0.5 M) and NaBH(OAc)₃ (169 mg, 0.8 mmol). After stirring at 28-30° C. for 6 days, the mixture is quenched with water (2 mL) and diluted with DCM (7 mL). The organics are separated and concentrated under vacuum. Chromatography (5% EA in hexanes) of the crude mixture gives the product 17 as off-white solid. Yield: 72 mg, 50%.

Compounds 2, 3, 4, 6, 8, 9, 10, 11, 12, 14, 18, 19, 20, 23, 24, 28, 29, 31, 32, 33, 34, 36, 40, 43, 44, 45, 47, 51, 57, 61, 63, 107 were made in the same manner.

Procedure VIb:

The ketone, 6-bromo-2,3,4,9-tetrahydro-carbazol-1-one (0.3 mmol) and 2-morpholin-4-yl-ethylamine (0.9 mmol) are dissolved in dioxane (3 mL) and heated by microwave at 150° C. for 2 hours. The solvent is removed in vacuo and the crude residue is dissolved in dichloromethane (3 mL) and treated with lithium aluminum hydride (0.9 mmol) for 2 days at room temperature. The solvent is removed in vacuo and the crude residue is purified by preparative HPLC to give the trifluoroacetic acid salt (7.7 mg, 5%). LC/MS data in table. Compounds 114, 79, 77, 67, 68, 62, 55 are made in the same manner.

Procedure VIIa:

To a mixture of amine 89 (52.8 mg, 0.2 mmol) and 3-phenoxy-benzoic acid (64 mg, 0.3 mmol) in DCM (4 mL) is added a solution of DMAP in DMF (1 mL, 0.1 M). The mixture is shaken at room temperature for 7 days, filtered, washed alternatively with DCM and MeOH (4×). The combined filtrate is concentrated on speed-vac and chromatographed to give 30 as a white powder. Yield: 91 mg, 99%.

Compounds 21, 22, 35, 39, 52, 58, 74, 91, 103, 123, 124, 125, 126, 127, 128, 129, 130, 131, 132, 133, 134, 141, 143, 144, 145, 146, 147, 150, 151, 152, 153, 154 and 155 were made in the same manner.

Procedure VIIb:

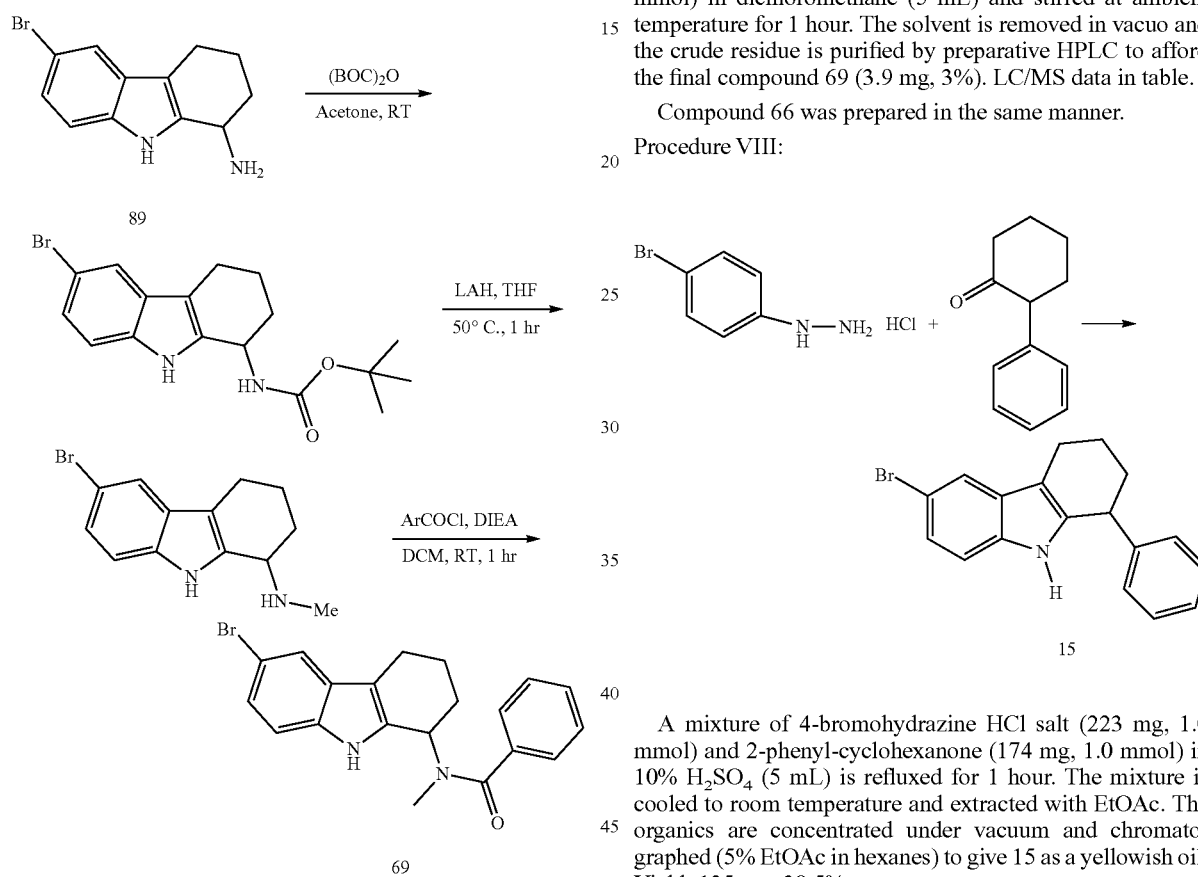

(6-Bromo-2,3,4,9-tetrahydro-1H-carbazol-1-yl)-carbamic acid tert-butyl ester

6-Bromo-2,3,4,9-tetrahydro-1H-carbazol-1-ylamine 89 (1.0 g, 3.77 mmol) and BOC anhydride (0.91 g, 4.15 mmol) are dissolved in 10 mL of acetone and stirred at ambient temperature for 3 hours under nitrogen. The solvent is removed in vacuo and the residue is purified on silica gel with 7.5% ethyl acetate in hexane as the mobile phase to afford the desired product (550 mg, 40%). LC/MS RT=4.20 min (M+Na$^+$: 387).

(6-Bromo-2,349-tetrahydro-1H-carbazol-1-yl)-methyl-amine

The BOC-protected compound (550 mg, 1.51 mmol) is dissolved in dry THF (5 mL) at ambient temperature under nitrogen. To the mixture is added a solution of lithium aluminum hydride (6 mL 1.0 M in diethyl ether, 6.02 mmol). The reaction is heated to 50° C. until all the starting material is consumed (1 hour). The reaction is quenched with saturated aqueous sodium sulfate (5 mL), filtered, and washed with THF (10 mL) to produce the crude final product (331 mg). LC/MS RT=2.23 min (M$^-$: 277/279).

N-(6-Bromo-2,3,4,9-tetrahydro-1H-carbazol-1-yl)-N-methyl-benzamide

The crude amine (0.35 mmol) is combined with diisopropylethylamine (1.05 mmol) and benzoyl chloride (0.70 mmol) in dichloromethane (5 mL) and stirred at ambient temperature for 1 hour. The solvent is removed in vacuo and the crude residue is purified by preparative HPLC to afford the final compound 69 (3.9 mg, 3%). LC/MS data in table.

Compound 66 was prepared in the same manner.

Procedure VIII:

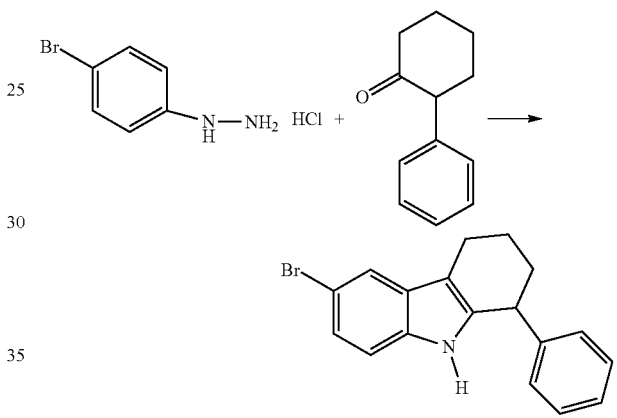

A mixture of 4-bromohydrazine HCl salt (223 mg, 1.0 mmol) and 2-phenyl-cyclohexanone (174 mg, 1.0 mmol) in 10% $H_2SO_4$ (5 mL) is refluxed for 1 hour. The mixture is cooled to room temperature and extracted with EtOAc. The organics are concentrated under vacuum and chromatographed (5% EtOAc in hexanes) to give 15 as a yellowish oil. Yield: 125 mg, 38.5%.

Compound 16 is made in the same manner.

Procedure IX:

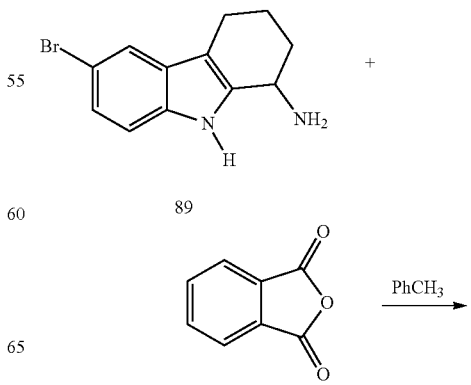

-continued

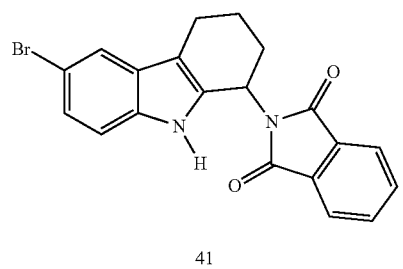

41

A mixture of amine 89 (98.4 mg, 0.6 mmol) and phthalic anhydride (110 mg, 0.74 mmol) in toluene (10 mL) is refluxed with a Dead-Stark trap. The solids dissolve upon heating. After 16 hours, the mixture is concentrated under vacuum and chromatographed (25% EtOAc in hexanes) to give 41 as a yellow powder. Yield: 95 mg, 40%.

Procedure X:

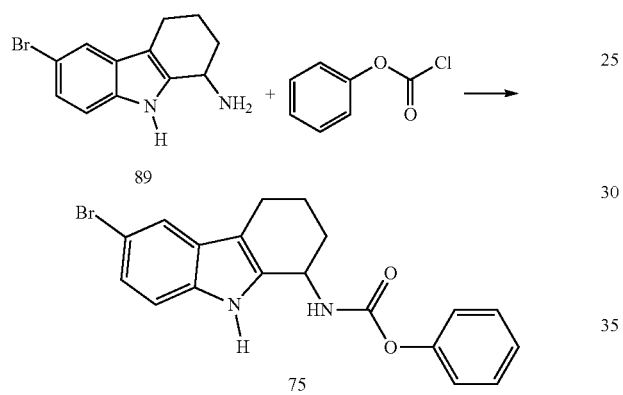

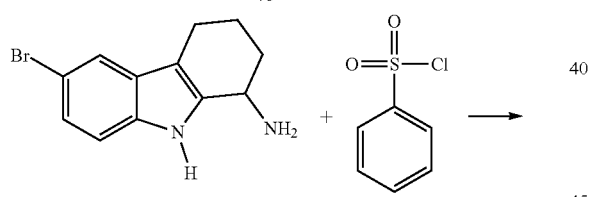

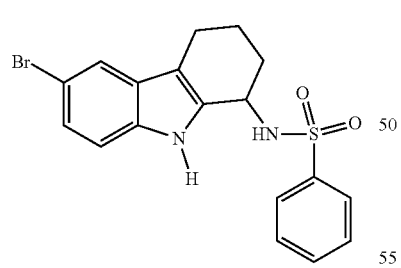

46

To a solution of amine 89 (53 mg, 0.2 mmol) and phenyl chloroformate (38 mL, 0.3 mmol) in DCM (2 mL) and THF (2 mL) at 0° C. is added DIEA (70 mL, 0.4 mmol). After stirring at room temperature for 2 hours, the mixture is diluted with DCM and water. The organics are separated, concentrated under vacuum and chromatographed to give 75 as a white solid. Yield: 68 mg, 89%.

Compound 46 is prepared in the same manner.

Procedure XI:

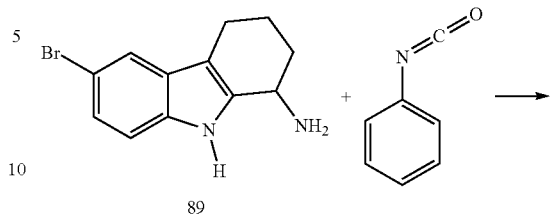

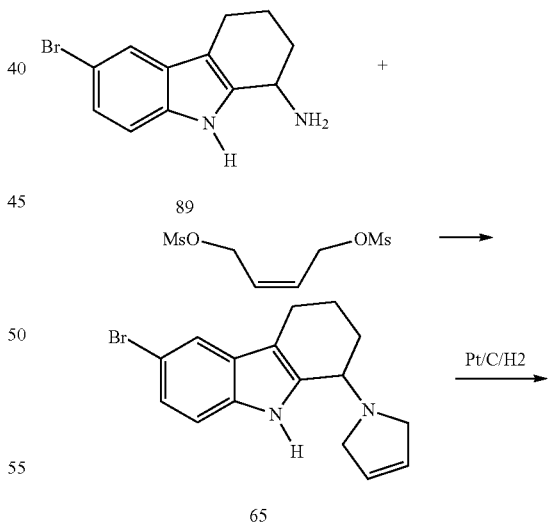

81

To a solution of amine 89 (53 mg, 0.2 mmol) and phenyl isocyanate (26 mL, 0.24 mmol) in THF (2 mL) is added DIEA (70 mL, 0.4 mmol). After refluxing overnight, the mixture is concentrated under vacuum. About 30 mg of the crude product is purified by preparative HPLC to give 11.5 mg of compound 81 as a white solid.

Procedure XII:

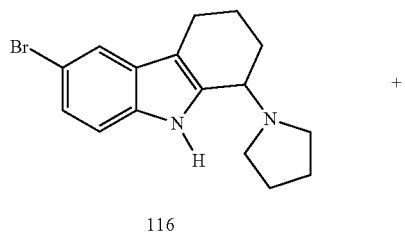

116

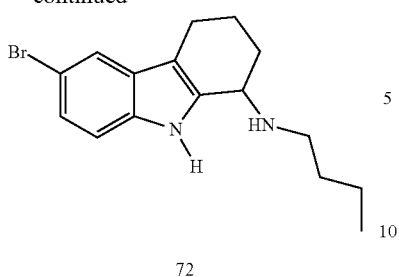

72

To a solution of amine 89 (0.133 g, 0.5 mmol) and the dimesylate (0.122 g, 0.5 mmol) in DCM (10 mL) is added DIEA (0.26 mL, 1.5 mmol). After stirring at room temperature overnight, the mixture is concentrated under vacuum and chromatographed (5% MeOH in DCM) to give 65 as yellowish oil. Yield: 88 mg, 56%.

To a solution of 65 (20 mg, 63%) in THF is added platinum on carbon (10 mg). The mixture is shaken on a Parr shaker under 40 psi H₂ for 3 hours. The mixture is filtered through celite, concentrated under vacuum and chromatographed to give 72 and 116, both as oil. Yield of 72: 9.2 mg, 46%. Yield of 116: 11.2 mg, 54%.

Procedure XIII:

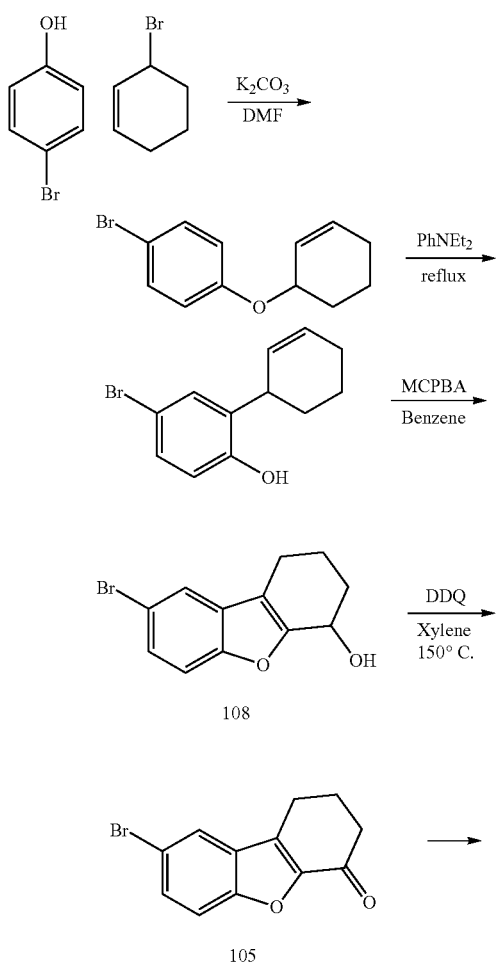

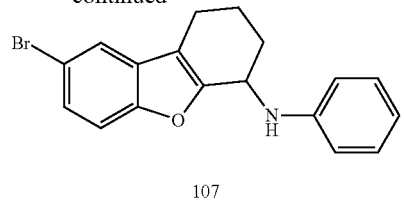

107

To a solution of 4-bromo-phenol (2.595 g, 15.0 mmol) and 3-bromo-cyclohexene (1.93 mL, 15.0 mmol) in DMF (50 mL) is added K₂CO₃ (4.15 g, 30 mmol). After overnight stirring at room temperature, the mixture is concentrated under vacuum, dissolved in EtOAc, and washed with water and brine. The organics are concentrated under vacuum to give the ether as brownish oil, 3.80 g, 100%.

A solution of the ether (1.8 g, 7.1 mmol) in N,N-diethyl-aniline (10 mL) is heated at 200° C. for 7 hours. The mixture is cooled to room temperature, poured into cold 6N HCl (50 mL) and extracted with ether (2×). The combined organics are washed with 1N HCl and brine, concentrated under vacuum and chromatographed (10% EtOAc in hexanes) to give 4-bromo-2-cyclohex-2-enyl-phenol as clear oil, 1.70 g, 94.4%.

A solution of the phenol and MCPBA in benzene is refluxed overnight. A solid is precipitated out and filtered. The filtrate is concentrated under vacuum and chromatographed (10% EtOAc in hexanes) to give 8-bromo-1,2,3,4-tetrahydro-dibenzofuran-4-ol 108 as clear oil, 0.66 g, 39%.

To a solution of the alcohol (70 mg, 0.26 mmol) in xylene (3.0 mL) is added DDQ (100 mg, 0.44 mmol). The solution turns dark red and is refluxed for 6 hours. The dark red color disappears and a light brown solid precipitates out. The mixture is filtered. The filtrate is concentrated under vacuum and chromatographed to give 105 as a white solid, 50 mg, 72%.

Compound 107 is prepared from 105 in the same manner of that of compound 17, procedure VIa.

Procedure XIV:

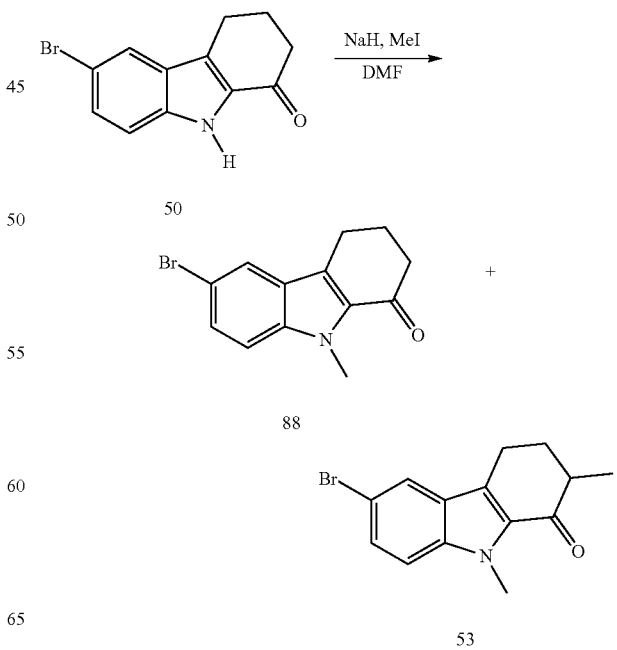

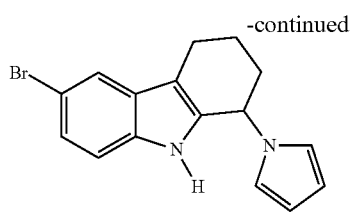

117

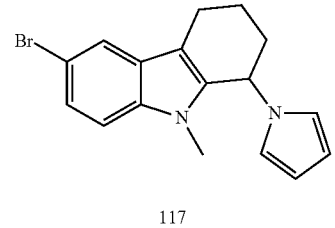

To a solution of 50 (0.795 g, 3.0 mmol) in DMF (20 mL) at 0° C. is added NaH (60% in mineral oil, 0.18 g, 4.5 mmol). After stirring at room temperature for 30 minutes and MeI (0.56 mL, 9.0 mmol) is added. The mixture is stirred at room temperature for 2 days, quenched with water, and concentrated under vacuum to remove most of the DMF. The residue is taken into EtOAc, washed with saturated NH$_4$Cl and brine. The organics are concentrated under vacuum and chromatographed (10% EtOAc in hexanes) to give compounds 53 and 88 as white solids. Yield of 53: 0.25 g, 32%. Yield of 88: 0.27 g, 34%.

Compound 117 is prepared in the same manner.
Procedure XV:

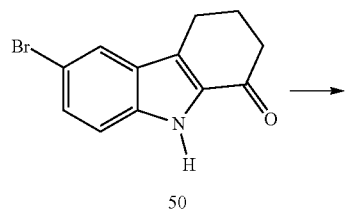

50

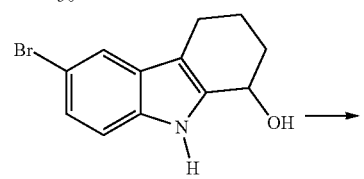

82

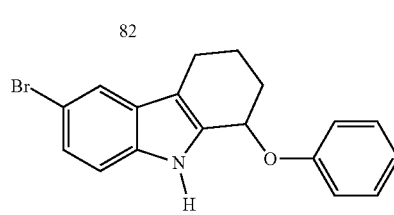

54

To a solution of ketone 50 (0.40 g, 1.5 mmol) in MeOH (20 mL) is added NaBH$_4$ (0.56 g, 15 mmol) at 0° C. in portions. After stirring at room temperature overnight, the mixture is quenched with water and concentrated under vacuum to remove MeOH. The aqueous layer is extracted with DCM (3×). The combined organics are concentrated under vacuum and chromatographed to give alcohol 82 as an off-white solid. Yield: 0.23 g, 57%.

To a solution of alcohol 82 (105 mg, 0.4 mmol) and 4-fluoro-phenol (54 mg, 0.48 mmol) in THF (5 mL) at 0° C. are added ADDP (303 mg, 1.2 mmol) and (n-Bu)$_3$P (0.30 mL, 1.2 mmol). The resulting yellow mixture is stirred overnight. The mixture is concentrated under vacuum and treated with EtOAc, producing a white solid. The white solid is removed by filtration. The filtrate is concentrated under vacuum and chromatographed to give ether 54 as a off-white solid. Yield: 12 mg, 8.3%.

Procedure XVI:

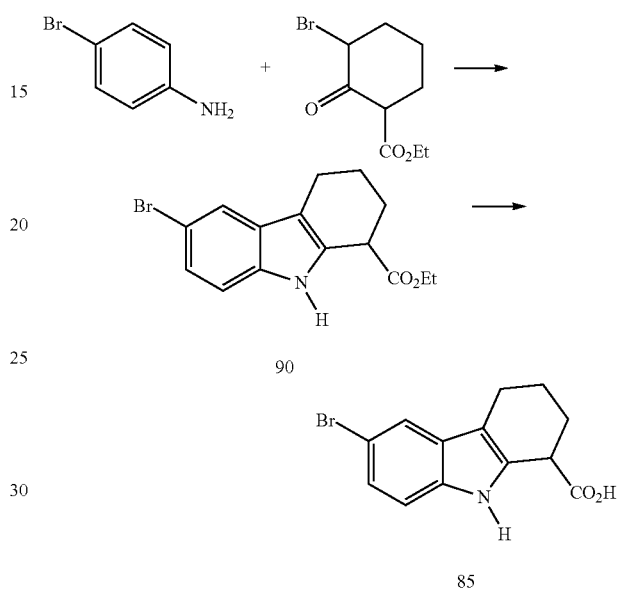

85

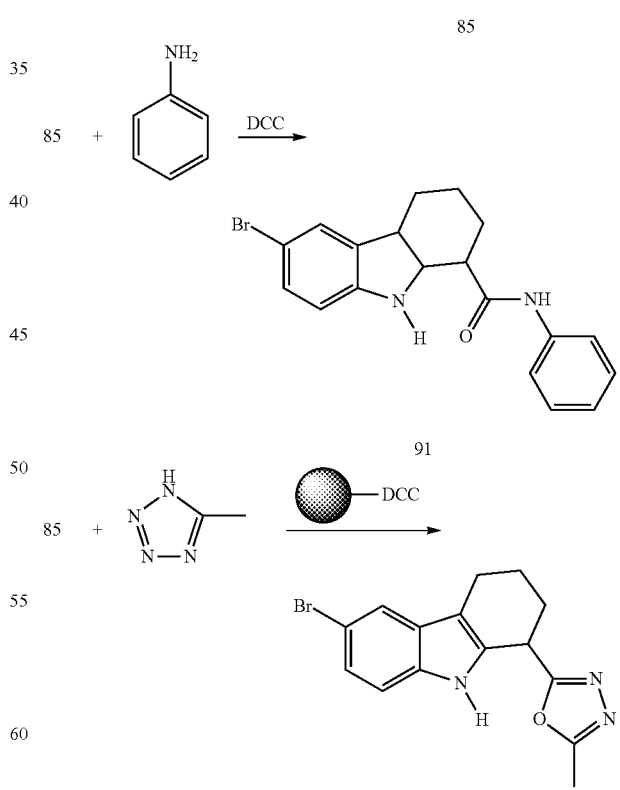

A mixture of the 4-bromo-aniline (solid) and 3-bromo-2-oxo-cyclohexanecarboxylic acid ethyl ester (oil) is heated at 150° C. under high vacuum. The solid is dissolved, whereupon the whole mass becomes solid. After about 1 hour, the solid melts into dark brown oil. Upon cooling to room temperature, the reaction mixture solidifies. The solids are treated with DCM and partially dissolved. The mixture is filtered and washed with DCM. The filtrate is concentrated under vacuum and chromatographed to give 90 as a yellow solid. Yield: 1.4 g, 36%.

To a solution of ester 90 (0.85 g, 2.64 mmol) in THF (10 mL) is added 5 N NaOH (2.6 mL, 13 mmol). After heating at 90° C. for 2 hours, the mixture is concentrated under vacuum to remove THF, diluted with water and washed with EtOAc. The aqueous layer is acidified to pH 3 with 6N HCl and extracted with DCM (3×). The combined organics are concentrated under vacuum to give 85 as a brownish solid. Yield: 0.71 g, 92%.

To a solution of acid 85 (88 mg, 0.3 mmol) and aniline (40 mL, 0.45 mmol) in DCM (4 mL) and THF (1 mL) are added HOBt (61 mg, 0.45 mmol) and DCC (93 mg, 0.45 mmol). After stirring at room temperature overnight, the mixture is concentrated under vacuum and then diluted with EtOAc, resulting in a white solid. The solid is filtered. The filtrate is concentrated under vacuum and chromatographed (25% EtOAc in hexanes) to give 91 as a brownish solid. Yield: 101 mg, 91%.

To a solution of acid 85 (88 mg, 0.3 mmol) and methyl tetrazole (37.8 mg, 0.45 mmol) in BCE (8 mL) is added poly-supported DCC (0.36 g, 0.45 mmol, 1.26 mmol/g). After heating at 80° C. overnight, the mixture is filtered. The resin is washed with DCM and MeOH alternatively. The filtrate is concentrated under vacuum and chromatographed (EtOAc: hex=1:1) to give 100 as an off-white solid. Yield: 33 mg, 33%.

Procedure XVII:

Br-[structure]-N(H)-C(=O) 50

(Boc)2O, DMAP, THF →

Br-[structure]-N(Boc)-C(=O) 80

To a solution of 50 (0.795 g, 3.0 mmol) and Boc anhydride (0.785 g, 3.6 mmol) in THF (30 mL) is added DMAP (0.55 g, 4.5 mmol). After stirring at room temperature for 2 days, the solution is concentrated under vacuum. The residue is taken into EtOAc, washed with saturated NH4Cl and brine. Evaporation of the solvents gives 80 as an oil, 1.148 g, 100%.

Procedure XVIII:

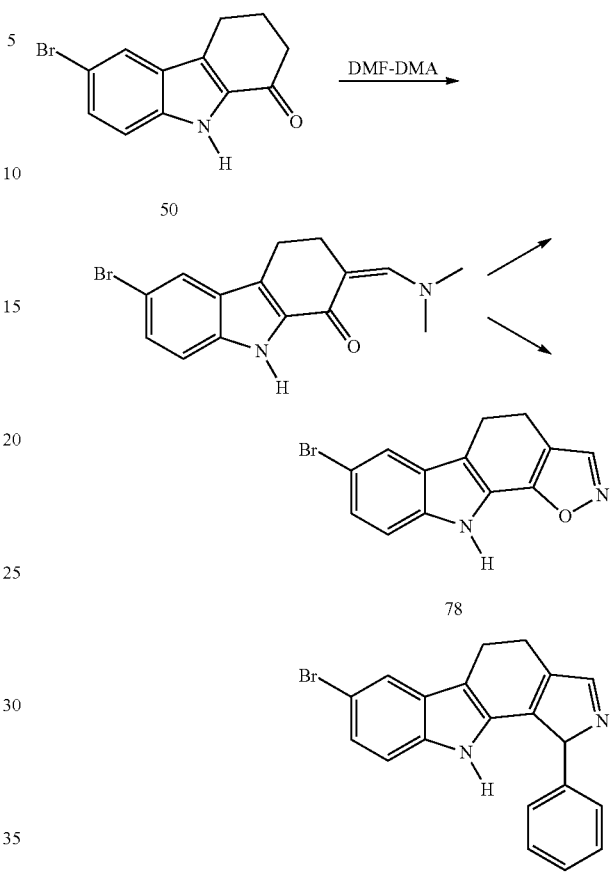

A solution of ketone 50 (264 mg, 1.0 mmol) in DMF-DMA (dimethyl formamide dimethyl acetal) (5.4 mL, 40 mmol) is refluxed for 7 hours. Upon cooling to room temperature, a yellow solid precipitates out. The solid is filtered and washed by EtOAc and dried in air at room temperature. Yield: 22 mg, 7%.

To a suspension of this solid in EtOH is added water and NH2OH HCl salt. The mixture is refluxed overnight. The mixture is cooled to room temperature and concentrated under vacuum. The residue is dissolved in DCM and washed with water. The organics are concentrated under vacuum and chromatographed to give 109 as a white solid. Yield: 26 mg, 100%.

Compound 78 is prepared in the same manner.

Procedure XIX:

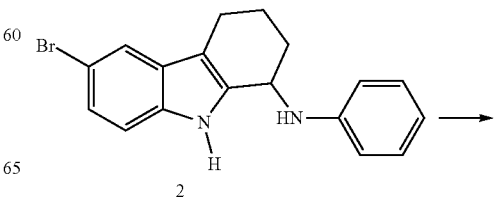

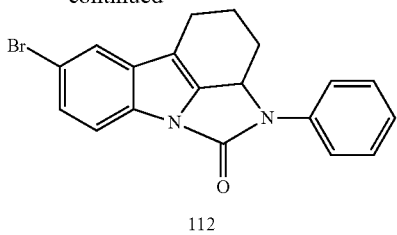

To a solution of compound 2 (34 mg, 0.1 mmol) in THF (2 mL) at 0° C. is added NaH (60% in mineral oil) (0.10 g, 0.4 mmol). After evolution of the bubbles ceases, CDI is added. After stirring at room temperature overnight, the mixture is quenched with water and extracted with DCM. The combined organics are concentrated under vacuum and chromatographed to give 112 as an off-white solid. Yield: 26 mg, 72%.
Procedure XX:

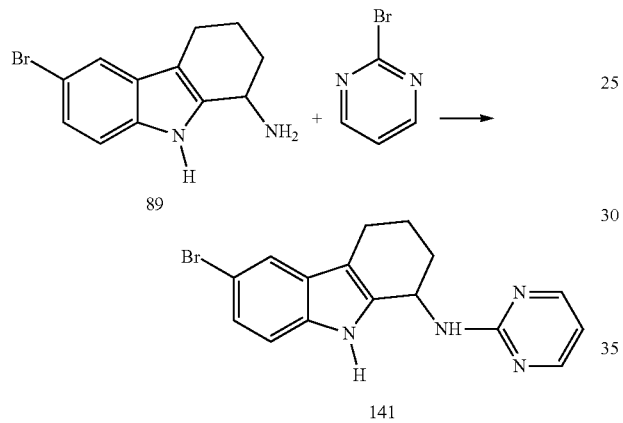

To a solution of amine 89 and 2-bromopyrimidine in DMF is added TEA. After heating at 100° C. overnight, the mixture is concentrated under vacuum and chromatographed (25% EtOAc in hexanes) to give 141 as an off-white solid. Yield: 61 mg, 60%.
Procedure XXI:

A mixture of acid 85 (20 mg, 0.07 mmol) and 1,2-diaminobenzene in (10 mg, 0.1 mmol) POCl$_3$ (1 mL) is heated at 100° C. for 4 hours. The mixture is cooled to room temperature and poured into ice-water. The pH is adjusted to about 11 by adding 20% NaOH, resulting in a brown solid. The solid is collected by filtration and purified by chromatography (10% EtOAc in hexanes) to give 142 as a brownish solid. Yield: 5 mg, 20%.
Procedure XXII:

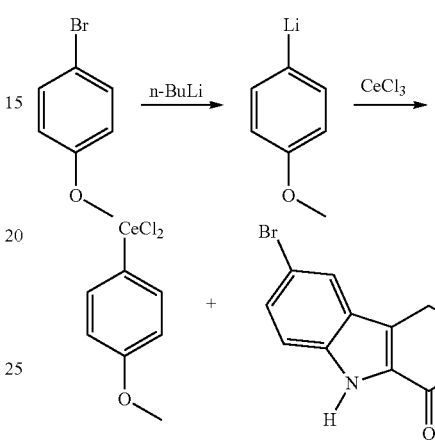

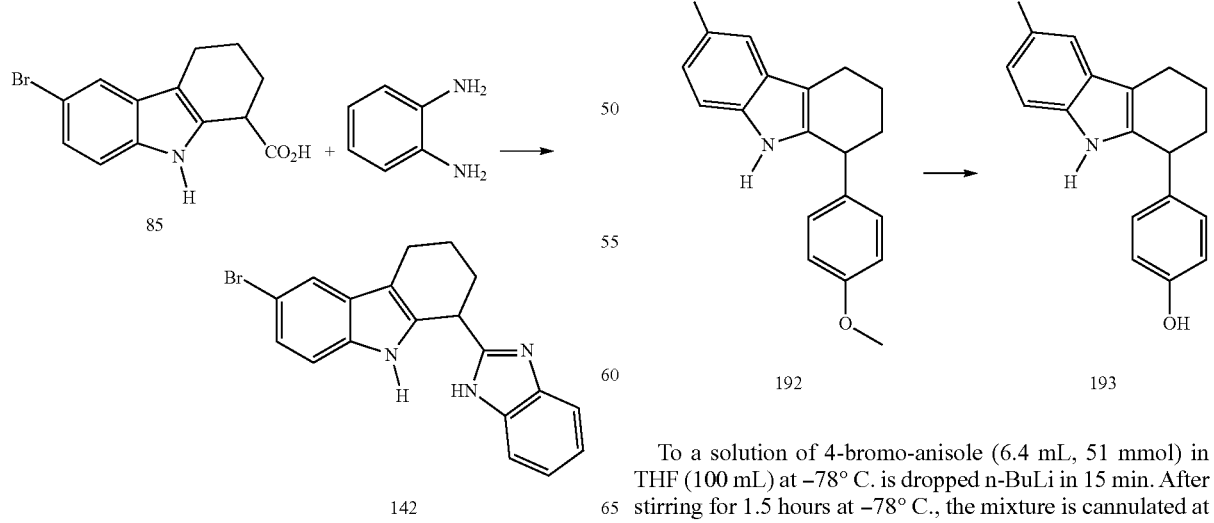

To a solution of 4-bromo-anisole (6.4 mL, 51 mmol) in THF (100 mL) at −78° C. is dropped n-BuLi in 15 min. After stirring for 1.5 hours at −78° C., the mixture is cannulated at −78° C. for 20 min to a mixture of anhydrous CeCl$_3$ (4.4 g, 99 mmol) in THF (50 mL), which had been vigorously stirred for 2 hours at room temperature. After stirring for 1.5 hours at −78° C., the ketone 50 (3.96 g, 15 mmol) in THF (60 mL) is dropped into this yellow suspension. The mixture is then stirred at room temperature overnight. The mixture is cooled to 0° C., quenched with saturated aqueous NH₄Cl, stirred at room temperature for 10 minutes and decanted. The remaining suspension is filtered through celite and washed with EtOAc. The combined organics are dried under Na₂SO₄ and concentrated under vacuum. The crude product XXII-1 is dissolved in a solution of Et₃SiH (7.20 mL, 45 mmol) and DCM (50 mL) at 0° C. TFA is dropped in, and the mixture is stirred at room temperature overnight. The mixture is quenched with saturated aqueous NaHCO₃ and extracted with EtOAc. The organic layer is washed with saturated aqueous NaHCO₃ and brine, dried over Na₂SO₄, and concentrated under vacuum. The residue is chromatographed with DCM in hexanes (30% to 50%) to give compound 192 as an off-white powder, 4.16 g, 82% yield. LC-MS: data in table.

To a solution of compound 192 (4.16 g, 11.7 mmol) in DCM at 0° C. is added BBr₃ in 15 minutes. The mixture is stirred at room temperature overnight. The dark purple mixture is concentrated, treated with saturated aqueous NaHCO₃. The organic layer is washed with brine, dried over Na₂SO₄, and concentrated under vacuum. The residue is chromatographed (10-25% EtOAc in hexanes) to give 193 as a purplish solid, 2.84 g, 71%.
Procedure XXIII:

To a solution of 193 (766 mg, 2.25 mmol) and 1-bromo-3-chloro-propane (2.24 mL, 22.5 mmol) in DMF (20 mL) is added K₂CO₃ (1.57 g, 11.35 mmol). The mixture is stirred at room temperature for 2 days and concentrated under vacuum. The residue is taken into EtOAc and washed with H₂O and brine. The organics are dried over Na₂SO₄ and concentrated under vacuum. The residue is chromatographed (10% EtOAc in hexanes) to give 5 as a white solid, 0.40 g, 42.6%.

To a solution of XXIII-1 (50 mg, 0.12 mmol) in methyl ethyl ketone (2 mL) is added N—Ac-piperazine (25.6 mg, 0.2 mmol), DIEA (70 ul, 0.4 mmol) and NaI (75 mg, 0.5 mmol). The mixture is stirred at 90° C. overnight and concentrated under vacuum. The residue is taken into EtOAc and washed with H₂O and brine. The organics are dried over Na₂SO₄ and concentrated under vacuum. The residue is chromatographed (10% MeOH in EtOAc) to give 204 as a yellowish solid, 40 mg, 54%.

Compound 194 is prepared in the same way as compound XXIII-1.

To a slightly cloudy mixture of 7 (40 mg, 0.1 mmol) in acetone (0.9 mL) and water (0.3 mL) is added ferric perchlorate. The rusty colored solution is stirred at room temperature overnight and then heated at 60° C. for 7 hours. The mixture is concentrated under vacuum. The residue is chromatographed (100% EtOAc) to give 212 as a white solid, 23.3 mg g, 56%.

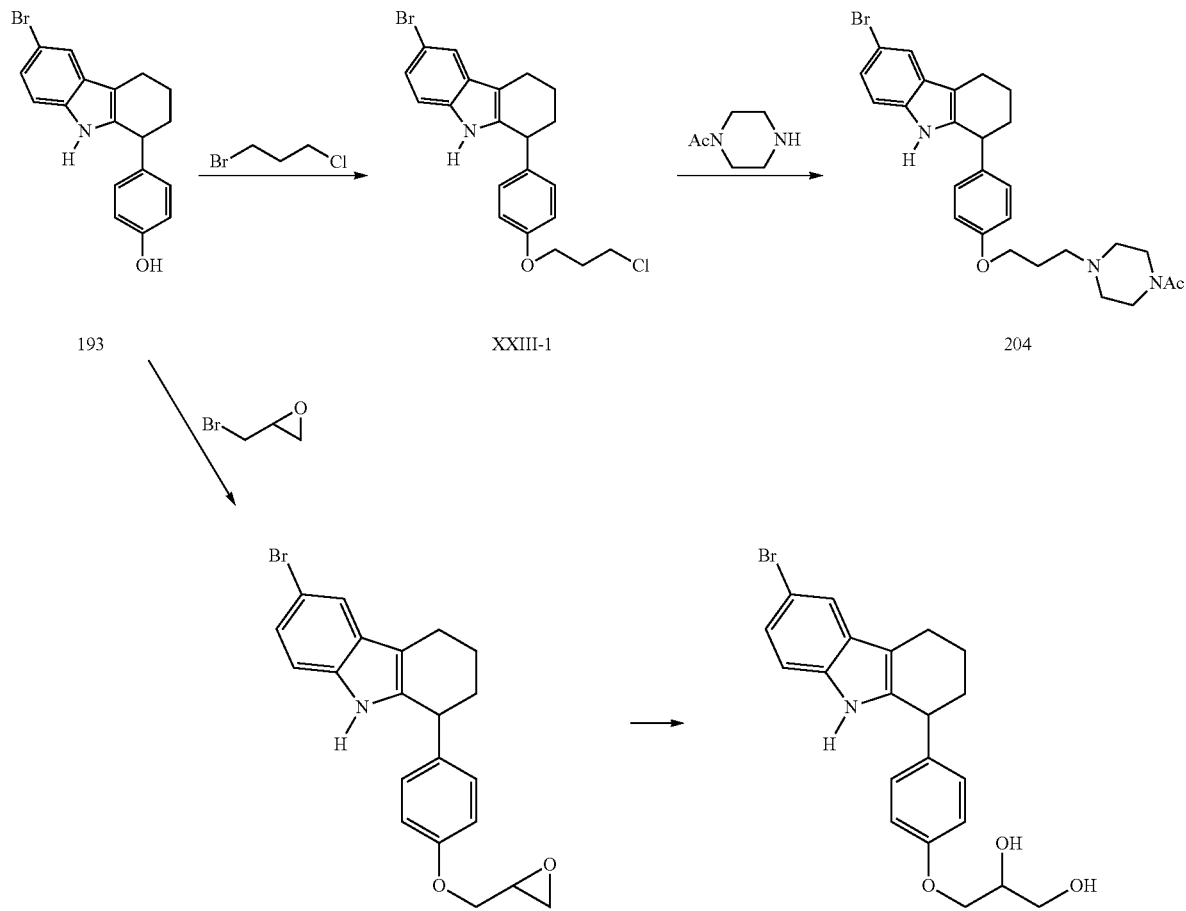

Example 2

Assay to Evaluate Effect on Hypoxia-Inducible Endogenous VEGF Expression

The ability of compounds of the invention to modulate hypoxia-inducible endogenous VEGF expression is analyzed as follows. VEGF protein levels are monitored by an ELISA assay (R&D Systems). Briefly, HeLa cells are cultured for 24-48 hours under hypoxic conditions (1% $O_2$, 5% $CO_2$, balanced with nitrogen) in the presence or absence of a compound of the invention. The conditioned media is then assayed by ELISA, and the concentration of VEGF is calculated from the standard ELISA curve of each assay.

A dose-response analysis is performed using the ELISA assay and conditions described above. A series of different concentrations (e.g., seven) are analyzed. In parallel, a dose-response cytotoxicity assay is performed using Cell Titer Glo (Promega) under the same conditions as the ELISA to ensure that the inhibition of VEGF expression is not due to cytotoxicity. Dose-response curves are plotted using percentage inhibition versus concentration of the compound, and $EC_{50}$ and $CC_{50}$ values are generated for each compound with the maximal inhibition set as 100% and the minimal inhibition as 0%.

FIG. 1 and Table 1 below show the ability of a typical compound of the invention to inhibit endogenous VEGF production in tumor cells under hypoxic conditions. In FIG. 1, the ELISA $EC_{50}$ is 0.0098 µm, while its $CC_{50}$ (50% cytotoxicity) is greater than 1.68 µm.

The $EC_{50}$ values for a series of compounds, which can be employed in the compositions and methods of the invention, are provided in Table 1 below. Compounds 156-188 in Table 1 are commercially available. In Table 1, each of the represented compounds is followed by one to five stars. The number of stars next to a particular compound indicates that compound's EC 50 (the effective concentration required to lower the amount of VEGF translation by 50%), according to the following scale:

>1 µM: *
0.2 µM to 1 µM: **
0.04 µM to 0.2 µM: ***
0.01 µM to 0.04 µM: ****
<0.01 µM: ***** (most preferred compounds of the invention)

TABLE 1

Representative Compounds and the Effective Concentration Required to Lower the Amount of VEGF Translation by 50%

| Compound | Compound Name | [M − H]⁻ | RT (min) | ELISA Activity |
|---|---|---|---|---|
| 1 | 6-Bromo-1-thieno[2,3-c]pyrrol-5-yl-2,3,4,9-tetrahydro-1H-carbazole | 371.02 | 4.49 | ***** |
| 2 | (6-Bromo-2,3,4,9-tetrahydro-1H-carbazol-1-yl)-phenyl-amine | 339.06 | 4.45 | ***** |
| 3 | (6-Bromo-2,3,4,9-tetrahydro-1H-carbazol-1-yl)-(4-chloro-phenyl)-amine | 373.02 | 4.68 | ***** |
| 4 | (6-Bromo-2,3,4,9-tetrahydro-1H-carbazol-1-yl)-(4-methoxy-phenyl)-amine | 369.06 | 3.93 | ***** |

TABLE 1-continued

| | | | | |
|---|---|---|---|---|
| 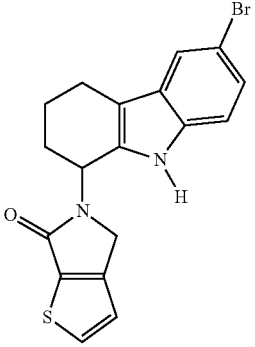 [SMILES: O=C1c2sccc2CN1C1CCCc2c1[nH]c1ccc(Br)cc21]<br>5 | 5-(6-Bromo-2,3,4,9-tetrahydro-1H-carbazol-1-yl)-4,5-dihydro-thieno[2,3-c]pyrrol-6-one | 385.02 | 3.92 | ***** |
| 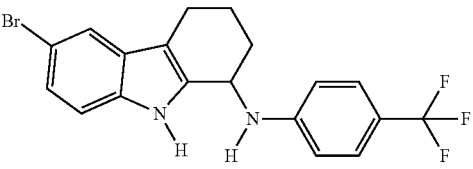 [SMILES: FC(F)(F)c1ccc(NC2CCCc3c2[nH]c2ccc(Br)cc32)cc1]<br>6 | (6-Bromo-2,3,4,9-tetrahydro-1H-carbazol-1-yl)-(4-trifluoromethyl-phenyl)-amine | 407.10 | 4.57 | ***** |
| 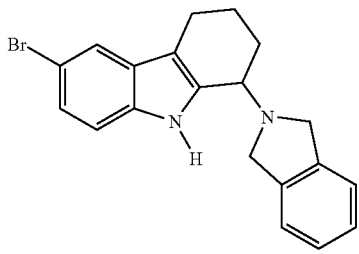 [SMILES: Brc1ccc2[nH]c3c(c2c1)CCCC3N1Cc2ccccc2C1]<br>7 | 6-Bromo-1-(1,3-dihydro-isoindol-2-yl)-2,3,4,9-tetrahydro-1H-carbazole | 365.21 | 2.49 | ***** |
| 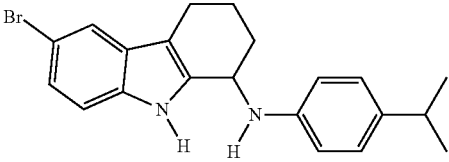 [SMILES: CC(C)c1ccc(NC2CCCc3c2[nH]c2ccc(Br)cc32)cc1]<br>8 | (6-Bromo-2,3,4,9-tetrahydro-1H-carbazol-1-yl)-(4-isopropyl-phenyl)-amine | 382.31 | 4.50 | ***** |
| 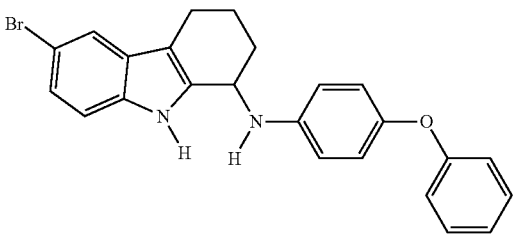 [SMILES: Brc1ccc2[nH]c3c(c2c1)CCCC3Nc1ccc(Oc2ccccc2)cc1]<br>9 | (6-Bromo-2,3,4,9-tetrahydro-1H-carbazol-1-yl)-(4-phenoxy-phenyl)-amine | | | ***** |
| 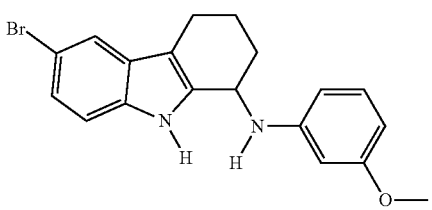 [SMILES: COc1cccc(NC2CCCc3c2[nH]c2ccc(Br)cc32)c1] | (6-Bromo-2,3,4,9-tetrahydro-1H-carbazol-1-yl)-(3-methoxy-phenyl)-amine | 369.25 | 3.94 | ***** |

TABLE 1-continued
| | | | | |
|---|---|---|---|---|
| 10 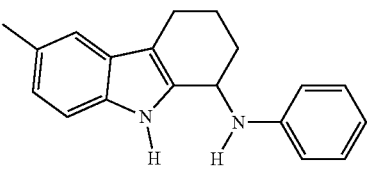 [SMILES: Cc1ccc2[nH]c3c(c2c1)CCCC3Nc1ccccc1] | (6-Methyl-2,3,4,9-tetrahydro-1H-carbazol-1-yl)-phenyl-amine | 375.03 | 4.47 | ***** |
| 11 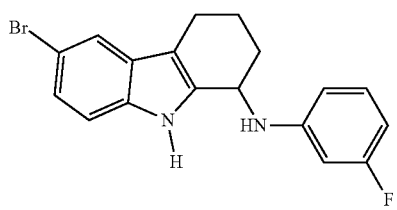 [SMILES: Fc1cccc(NC2CCCc3c2[nH]c2ccc(Br)cc32)c1] | (6-Bromo-2,3,4,9-tetrahydro-1H-carbazol-1-yl)-(3-fluoro-phenyl)-amine | 357.23 | 4.00 | ***** |
| 12 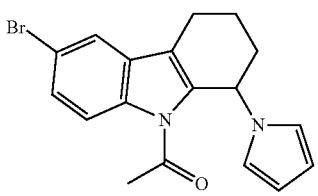 [SMILES: CC(=O)n1c2c(c3cc(Br)ccc31)CCCC2n1cccc1] | 1-(6-Bromo-1-pyrrol-1-yl-1,2,3,4-tetrahydro-carbazol-9-yl)ethanone | 313.07 | 4.36 | ***** |
| 13 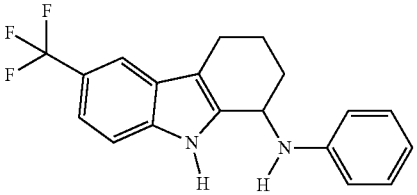 [SMILES: FC(F)(F)c1ccc2[nH]c3c(c2c1)CCCC3Nc1ccccc1] | Phenyl-(6-trifluoromethyl-2,3,4,9-tetrahydro-1H-carbazol-1-yl)-amine | 438.13 [M + H]+ | 4.41 | ***** |
| 14 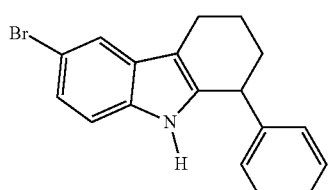 | 6-Bromo-1-phenyl-2,3,4,9-tetrahydro-1H-carbazole | 324.17 | 4.45 | ***** |
| 15 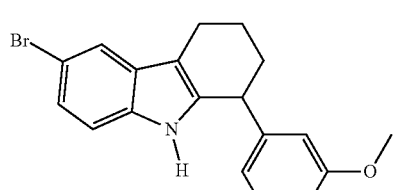 | 6-Bromo-1-(3-methoxy-phenyl)-2,3,4,9-tetrahydro-1H-carbazole | 354.12 | 4.51 | ***** |
| 16 | | | | |

TABLE 1-continued
| | | | | |
|---|---|---|---|---|
| 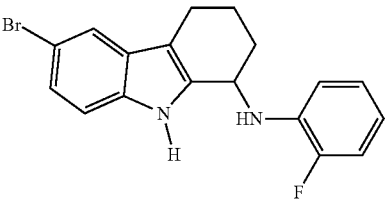 [SMILES: Fc1ccccc1NC1CCCc2c1[nH]c1ccc(Br)cc21] 17 | (6-Bromo-2,3,4,9-tetrahydro-1H-carbazol-1-yl)-(2-fluoro-phenyl)-amine | 257.21 | 4.10 | ***** |
| 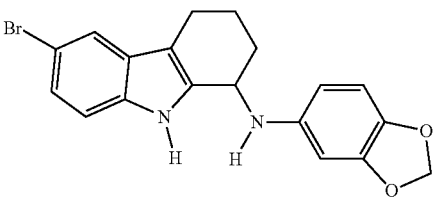 [SMILES: Brc1ccc2[nH]c3c(c2c1)CCCC3Nc1ccc2c(c1)OCO2] 18 | Benzo[1,3]dioxol-5-yl-(6-bromo-2,3,4,9-tetrahydro-1H-carbazol-1-yl)-amine | 383.11 | 4.12 | ***** |
| 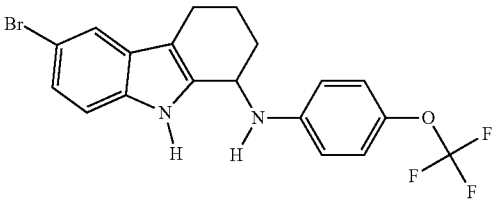 [SMILES: FC(F)(F)Oc1ccc(NC2CCCc3c2[nH]c2ccc(Br)cc32)cc1] 19 | (6-Bromo-2,3,4,9-tetrahydro-1H-carbazol-1-yl)-(4-trifluoromethoxy-phenyl)-amine | 423.08 | 4.67 | ***** |
| 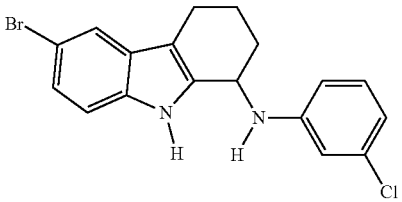 [SMILES: Clc1cccc(NC2CCCc3c2[nH]c2ccc(Br)cc32)c1] 20 | (6-Bromo-2,3,4,9-tetrahydro-1H-carbol-1-yl)-(3-chloro-phenyl)-amine | 373.22 | 4.19 | ***** |
| 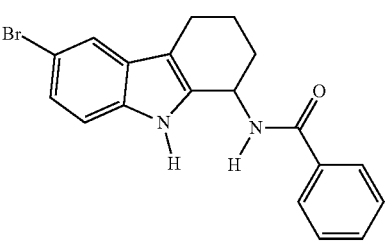 [SMILES: O=C(NC1CCCc2c1[nH]c1ccc(Br)cc21)c1ccccc1] 21 | N-(6-Bromo-2,3,4,9-tetrahydro-1H-carbazol-1-yl)-benzamide | 367.21 | 3.54 | ***** |
| 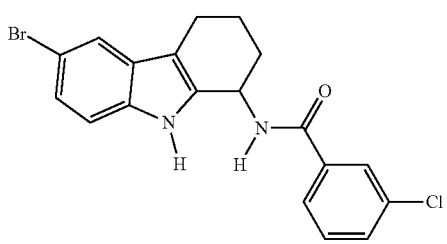 [SMILES: O=C(NC1CCCc2c1[nH]c1ccc(Br)cc21)c1cccc(Cl)c1] 22 | N-(6-Bromo-2,3,4,9-tetrahydro-1H-carbazol-1-yl)-3-chloro-benzamide | 401.10 | 4.16 | ***** |

TABLE 1-continued
| | | | | |
|---|---|---|---|---|
| 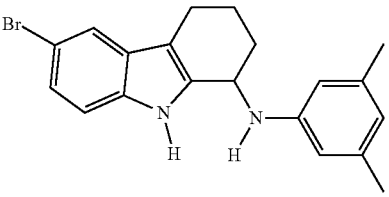 [SMILES: Cc1cc(C)cc(NC2CCCc3c2[nH]c2ccc(Br)cc32)c1] 23 | (6-Bromo-2,3,4,9-tetrahydro-1H-carbazol-1-yl)-(3,5-dimethyl-phenyl)-amine | 367.17 | 4.72 | **** |
| 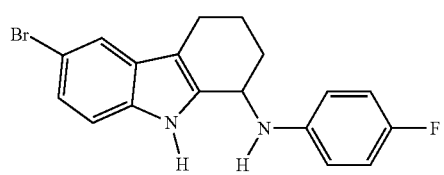 [SMILES: Fc1ccc(NC2CCCc3c2[nH]c2ccc(Br)cc32)cc1] 24 | (6-Bromo-2,3,4,9-tetrahydro-1H-carbazol-1-yl)-(4-fluoro-phenyl)-amine | 357.25 | 3.97 | **** |
| 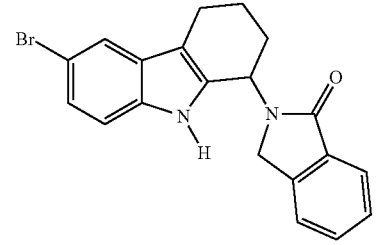 [SMILES: O=C1c2ccccc2CN1C1CCCc2c1[nH]c1ccc(Br)cc21] 25 | 2-(6-Bromo-2,3,4,9-tetrahydro-1H-carbazol-1-yl)-2,3-dihydro-isoindol-1-one | 379.18 | 3.84 | **** |
| 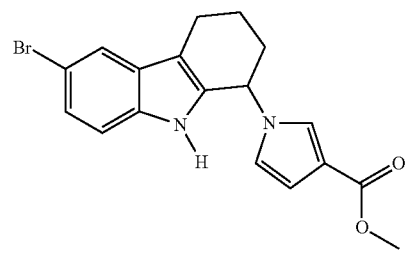 [SMILES: COC(=O)c1ccn(C2CCCc3c2[nH]c2ccc(Br)cc32)c1] 26 | 1-(6-Bromo-2,3,4,9-tetrahydro-1H-carbazol-1-yl)-1H-pyrrole-3-carboxylic acid methyl ester | 371.06 | 3.76 | **** |
| 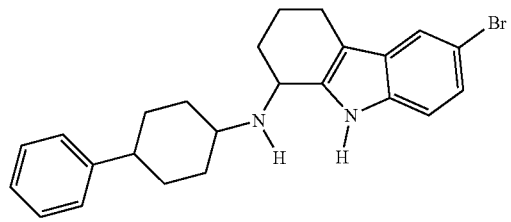 [SMILES: Brc1ccc2[nH]c3c(c2c1)CCCC3NC1CCC(c2ccccc2)CC1] 27 | (6-Bromo-2,3,4,9-tetrahydro-1H-carbazol-1-yl)-(4-phenyl-cyclohexyl)-amine | 421.12 | 2.83 | **** |
| 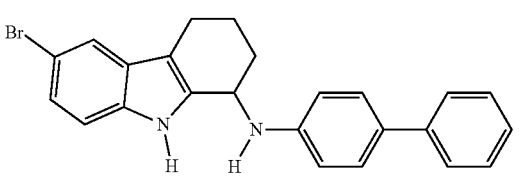 [SMILES: Brc1ccc2[nH]c3c(c2c1)CCCC3Nc1ccc(-c2ccccc2)cc1] 28 | Biphenyl-4-yl-(6-bromo-2,3,4,9-tetrahydro-1H-carbazol-1-yl)-amine | 415.17 | 4.94 | **** |

TABLE 1-continued
| | | | | |
|---|---|---|---|---|
| 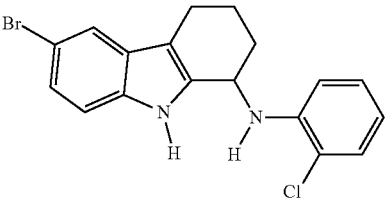 [SMILES: Clc1ccccc1NC1CCCc2c1[nH]c1ccc(Br)cc21] 29 | (6-Bromo-2,3,4,9-tetrahydro-1H-carbazol-1-yl)-(2-chloro-phenyl)-amine | 373.20 | 4.39 | **** |
| 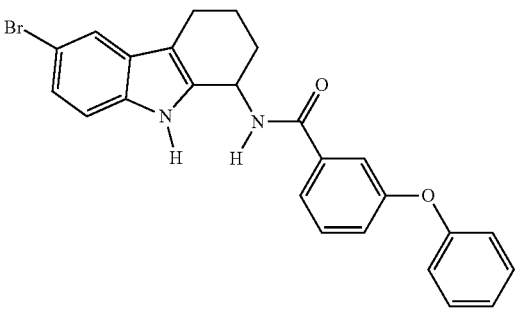 [SMILES: O=C(NC1CCCc2c1[nH]c1ccc(Br)cc21)c1cccc(Oc2ccccc2)c1] 30 | N-(6-Bromo-2,3,4,9-tetrahydro-1H-carbazol-1-yl)-3-phenoxy-benzamide | | | **** |
| 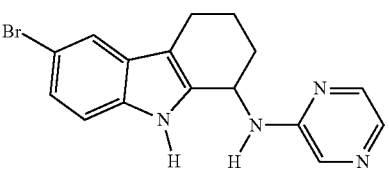 31 | (6-Bromo-2,3,4,9-tetrahydro-1H-carbazol-1-yl)-pyrazin-2-yl-amine | 343.16 | 3.77 | **** |
| 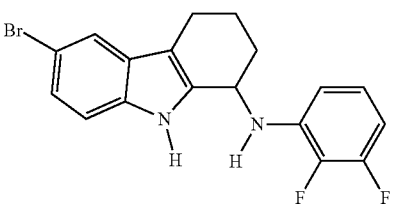 [SMILES: Fc1cccc(NC2CCCc3c2[nH]c2ccc(Br)cc32)c1F] 32 | (6-Bromo-2,3,4,9-tetrahydro-1H-carbazol-1-yl)-(2,3-difluoro-phenyl)-amine | | | **** |
| 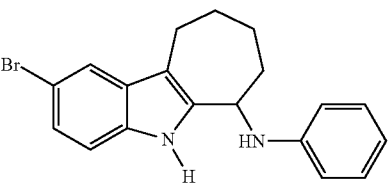 [SMILES: Brc1ccc2[nH]c3c(c2c1)CCCCC3Nc1ccccc1] 33 | (2-Bromo-5,6,7,8,9,10-hexahydro-cyclohepta[b]indol-6-yl)-phenyl-amine | 353.20 | 4.57 | **** |
| 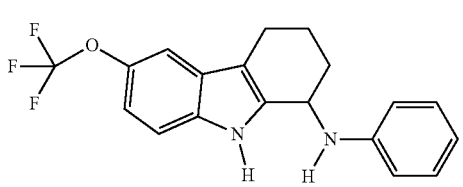 34 | Phenyl-(6-trifluoromethoxy-2,3,4,9-tetrahydro-1H-carbazol-1-yl)-amine | 345.14 | 4.36 | **** |

TABLE 1-continued
| | Compound Name | MS | RT | Activity |
|---|---|---|---|---|
| 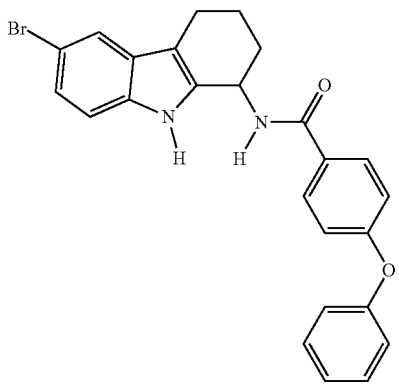 [SMILES: O=C(NC1CCCc2c1[nH]c1ccc(Br)cc21)c1ccc(Oc2ccccc2)cc1]<br>35 | N-(6-Bromo-2,3,4,9-tetrahydro-1H-carbazol-1-yl)-4-phenoxy-benzamide | 248.1<br>[M − C$_{13}$H$_9$NO$_2$]$^+$ | 4.35 | *** |
| 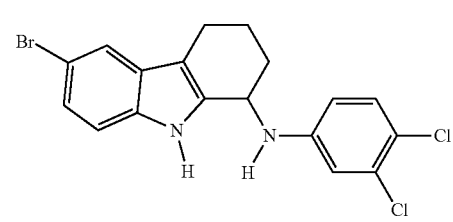 [SMILES: Clc1ccc(NC2CCCc3c2[nH]c2ccc(Br)cc32)cc1Cl]<br>36 | (6-Bromo-2,3,4,9-tetrahydro-1H-carbazol-1-yl)-(3,4-dichloro-phenyl)-amine | 409.07 | 4.80 | *** |
| 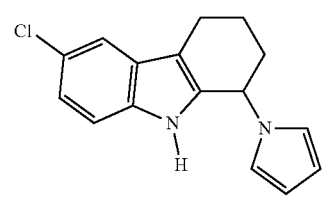 [SMILES: Clc1ccc2[nH]c3c(c2c1)CCCC3n1cccc1]<br>37 | 6-Chloro-1-pyrrol-1-yl-2,3,4,9-tetrahydro-1H-carbazole | 269.11 | 4.23 | *** |
| 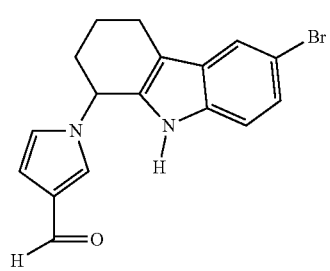 [SMILES: O=Cc1ccn(C2CCCc3c2[nH]c2ccc(Br)cc32)c1]<br>38 | 1-(6-Bromo-2,3,4,9-tetrahydro-1H-carbazol-1-yl)-1H-pyrrole-3-carbaldehyde | 341.06 | 3.85 | *** |
| 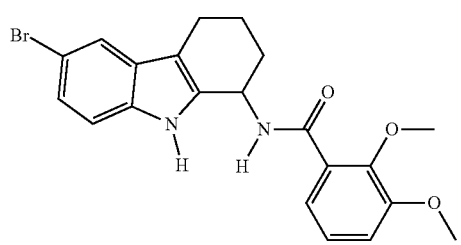 [SMILES: COc1cccc(C(=O)NC2CCCc3c2[nH]c2ccc(Br)cc32)c1OC]<br>39 | N-(6-Bromo-2,3,4,9-tetrahydro-1H-carbazol-1-yl)-2,3-dimethoxy-benzamide | 427.11 | 4.15 | *** |

TABLE 1-continued
| Structure | Name | MW | RT | Act |
|---|---|---|---|---|
| 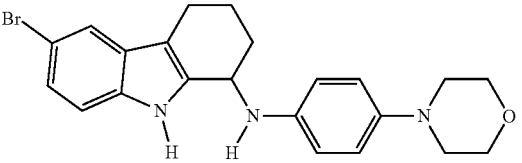 [SMILES: Brc1ccc2[nH]c3c(c2c1)CCCC3Nc1ccc(N2CCOCC2)cc1] 40 | (6-Bromo-2,3,4,9-tetrahydro-1H-carbazol-1-yl)-(4-morpholin-4-yl-phenyl)-amine | 424.26 | 3.01 | *** |
| 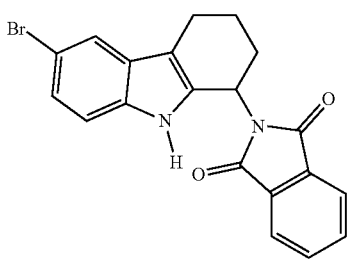 [SMILES: O=C1c2ccccc2C(=O)N1C1CCCc2c1[nH]c1ccc(Br)cc21] 41 | 2-(6-Bromo-2,3,4,9-tetrahydro-1H-carbazol-1-yl)-isoindole-1,3-dione | 393.12 | 4.01 | *** |
| 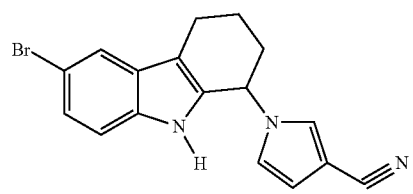 [SMILES: N#Cc1ccn(C2CCCc3c2[nH]c2ccc(Br)cc32)c1] 42 | 1-(6-Bromo-2,3,4,9-tetrahydro-1H-carbazol-1-yl)-1H-pyrrole-3-carbonitrile | 338.15 | 3.93 | *** |
| 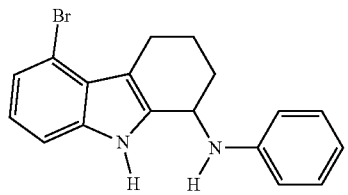 [SMILES: Brc1cccc2[nH]c3c(c12)CCCC3Nc1ccccc1] 43 | (5-Bromo-2,3,4,9-tetrahydro-1H-carbazol-1-yl)-phenyl-amine | 339.27 | 3.99 | *** |
| 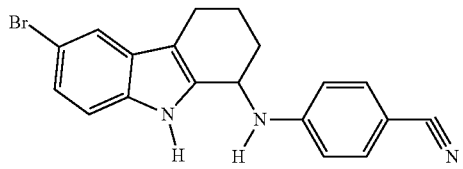 [SMILES: N#Cc1ccc(NC2CCCc3c2[nH]c2ccc(Br)cc32)cc1] 44 | 4-(6-Bromo-2,3,4,9-tetrahydro-1H-carbazol-1-ylamino)-benzonitrile | 364.19 | 4.09 | *** |
| 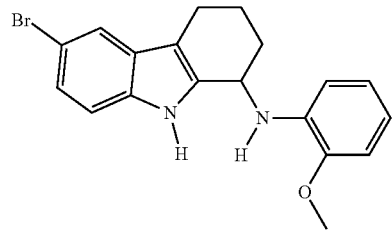 [SMILES: COc1ccccc1NC1CCCc2c1[nH]c1ccc(Br)cc21] 45 | (6-Bromo-2,3,4,9-tetrahydro-1H-carbazol-1-yl)-(2-methoxy-phenyl)-amine | 369.29 | 4.15 | *** |

TABLE 1-continued
| | | | | |
|---|---|---|---|---|
| 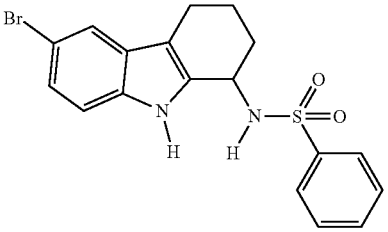 [SMILES: O=S(=O)(NC1CCCc2c1[nH]c1ccc(Br)cc21)c1ccccc1]<br>46 | N-(6-Bromo-2,3,4,9-tetrahydro-1H-carbazol-1-yl)-benzenesulfonamide | 403.19 | 3.64 | *** |
| 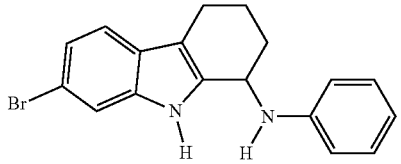<br>47 | (7-Bromo-2,3,4,9-tetrahydro-1H-carbazol-1-yl)-phenyl-amine | 339.27 | 3.95 | *** |
| 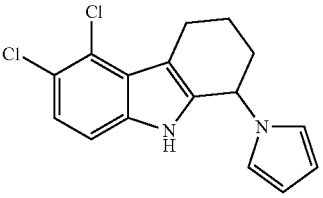 [SMILES: Clc1ccc2[nH]c3c(c2c1Cl)CCCC3n1cccc1]<br>48 | 5,6-Dichloro-1-pyrrol-1-yl-2,3,4,9-tetrahydro-1H-carbazole | 306.05 | 4.45 | *** |
| 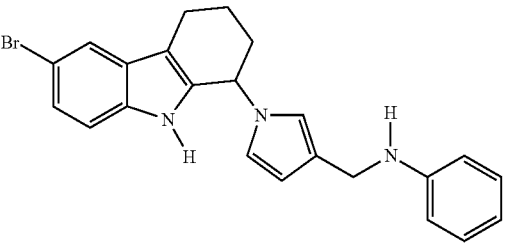 [SMILES: Brc1ccc2[nH]c3c(c2c1)CCCC3n1ccc(CNc2ccccc2)c1]<br>49 | [1-(6-Bromo-2,3,4,9-tetrahydro-1H-carbazol-1-yl)-1H-pyrrol-3-ylmethyl]-phenyl-amine | 418.24 | 3.47 | *** |
| 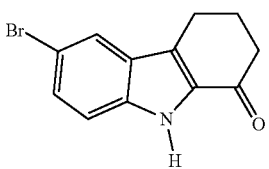 [SMILES: O=C1CCCc2c1[nH]c1ccc(Br)cc21]<br>50 | 6-Bromo-2,3,4,9-tetrahydro-carbazol-1-one | 264.15<br>[M + H]+ | 3.50 | *** |
| 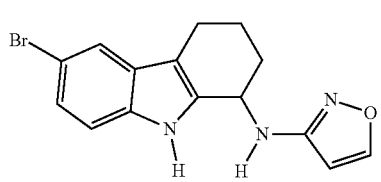 [SMILES: Brc1ccc2[nH]c3c(c2c1)CCCC3Nc1ccon1]<br>51 | (6-Bromo-2,3,4,9-tetrahydro-1H-carbazol-1-yl)-isoxazol-3-yl-amine | 248.08<br>$(M - C_3H_3N_2O)^+$ | 3.82 | *** |

TABLE 1-continued

| | | | | |
|---|---|---|---|---|
| 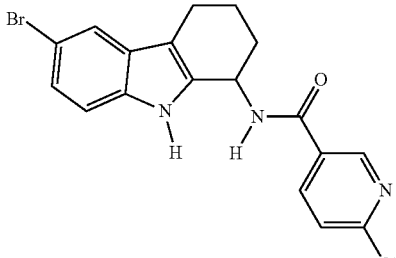<br>52 | N-(6-Bromo-2,3,4,9-tetrahydro-1H-carbazol-1-yl)-6-chloro-nicotinamide | 403.22 | 3.44 | *** |
| 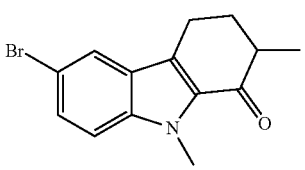 [SMILES: CC1CCc2c(n(C)c3ccc(Br)cc23)C1=O]<br>53 | 6-Bromo-2,9-dimethyl-2,3,4,9-tetrahydro-carbazol-1-one | 292.05<br>[M + H]+ | 4.32 | *** |
| 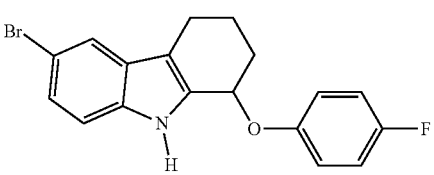 [SMILES: Fc1ccc(OC2CCCc3c2[nH]c2ccc(Br)cc32)cc1]<br>54 | 6-Bromo-1-(4-fluoro-phenoxy)-2,3,4,9-tetrahydro-1H-carbazole | 248.08<br>(M − C$_6$H$_4$FO) | 4.50 | *** |
| 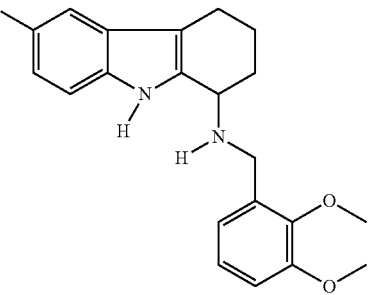<br>55 | (6-Bromo-2,3,4,9-tetrahydro-1H-carbazol-1-yl)-(2,3-dimethoxy-benzyl)-amine | 413/415<br>1:1 | 2.70 | *** |
| 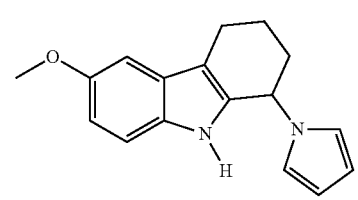 [SMILES: COc1ccc2[nH]c3c(c2c1)CCCC3n1cccc1]<br>56 | 6-Methoxy-1-pyrrol-1-yl-2,3,4,9-tetrahydro-1H-carbazole | 522.02 | 3.85 | *** |
| 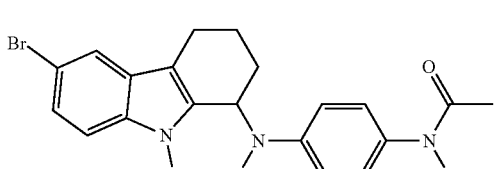<br>57 | N-[4-(6-Bromo-2,3,4,9-tetrahydro-1H-carbazol-1-ylamino)-phenyl]-acetamide | 396.19 | 3.51 | ** |

TABLE 1-continued
| | | | | |
|---|---|---|---|---|
| 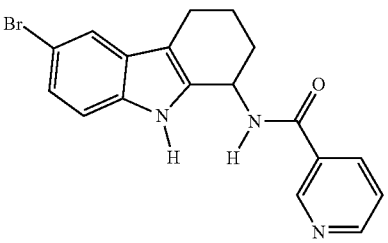 [SMILES: O=C(NC1CCCc2c1[nH]c1ccc(Br)cc21)c1cccnc1]<br>58 | N-(6-Bromo-2,3,4,9-tetrahydro-1H-carbazol-1-yl)-nicotinamide | 368.06 | 3.26 | *** |
| 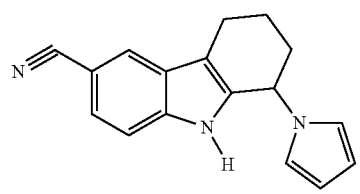 [SMILES: N#Cc1ccc2[nH]c3c(c2c1)CCCC3n1cccc1]<br>59 | 8-Pyrrol-1-yl-6,7,8,9-tetrahydro-5H-carbazole-3-carbonitrile | 260.29 | 3.34 | ** |
| 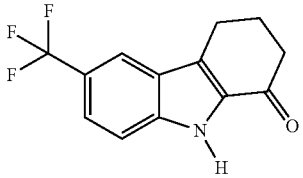 [SMILES: O=C1CCCc2c1[nH]c1ccc(C(F)(F)F)cc21]<br>60 | 6-Trifluoromethyl-2,3,4,9-tetrahydro-carbazol-1-one | 254.14 [M + H]+ | 3.58 | ** |
| 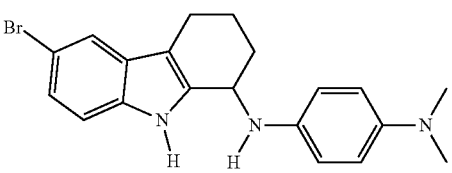<br>61 | N-(6-Bromo-2,3,4,9-tetrahydro-1H-carbazol-1-yl)-N',N'-dimethyl-benzene-1,4-diamine | 382.22 | 2.65 | ** |
| 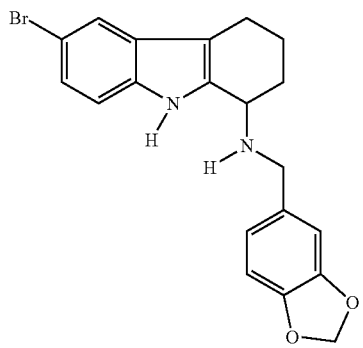 [SMILES: Brc1ccc2[nH]c3c(c2c1)CCCC3NCc1ccc2c(c1)OCO2]<br>62 | Benzo[1,3]dioxo-5-ylmethyl-(6-bromo-2,3,4,9-tetrahydro-1H-carbazol-1-yl)-amine | 397/399 1:1 | 2.63 | ** |
| 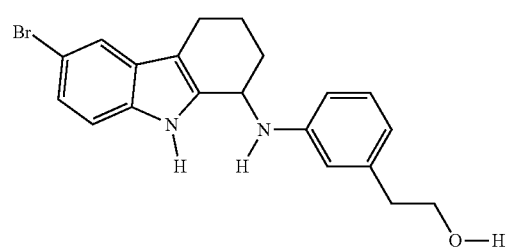 [SMILES: OCCc1cccc(NC2CCCc3c2[nH]c2ccc(Br)cc32)c1]<br>63 | 2-[3-(6-Bromo-2,3,4,9-tetrahydro-1H-carbazol-1-ylamino)-phenyl]-ethanol | 383.24 | 3.78 | ** |

TABLE 1-continued
| | | | | |
|---|---|---|---|---|
| 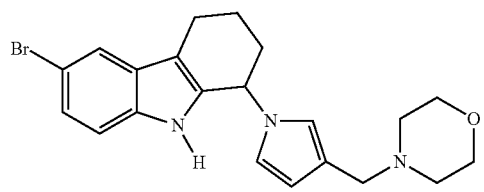 [SMILES: Brc1ccc2[nH]c3c(c2c1)CCCC3n1ccc(CN2CCOCC2)c1] 64 | 6-Bromo-1-(3-morpholin-4-ylmethyl-pyrrol-1-yl)-2,3,4,9-tetrahydro-1H-carbazole | 412.24 | 2.59 | ** |
| 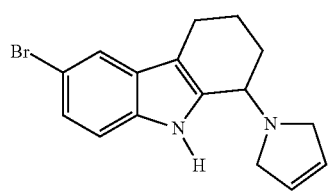 [SMILES: Brc1ccc2[nH]c3c(c2c1)CCCC3N1CC=CC1] 65 | 6-Bromo-1-(2,5-dihydro-pyrrol-1-yl)-2,3,4,9-tetrahydro-1H-carbazole | 315.07 | 2.45 | ** |
| 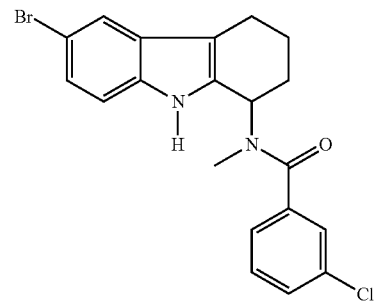 [SMILES: CN(C(=O)c1cccc(Cl)c1)C1CCCc2c1[nH]c1ccc(Br)cc21] 66 | N-(6-Bromo-2,3,4,9-tetrahydro-1H-carbazol-1-yl)-3-chloro-N-methyl-benzamide | 415/417 1:1 | 4.11 | ** |
| 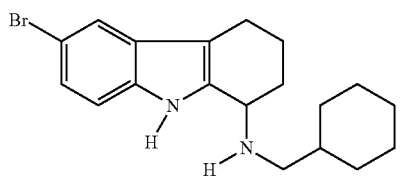 [SMILES: Brc1ccc2[nH]c3c(c2c1)CCCC3NCC1CCCCC1] 67 | (6-Bromo-2,3,4,9-tetrahydro-1H-carbazol-1-yl)-cyclohexylmethyl-amine | 359/361 1:1 | 2.73 | ** |
| 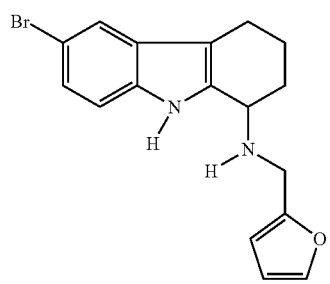 [SMILES: Brc1ccc2[nH]c3c(c2c1)CCCC3NCc1ccco1] 68 | (6-Bromo-2,3,4,9-tetrahydro-1H-carbazol-1-yl)-furan-2-ylmethyl-amine | 343/345 1:1 | 2.50 | ** |

| | | | | |
|---|---|---|---|---|
| 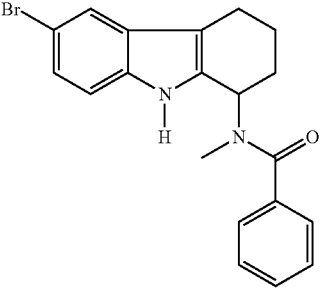 [SMILES: CN(C(=O)c1ccccc1)C1CCCc2c1[nH]c1ccc(Br)cc21] 69 | N-(6-Bromo-2,3,4,9-tetrahydro-1H-carbazol-1-yl)-N-methyl-benzamide | 381/383 1:1 | 3.46 | ** |
| 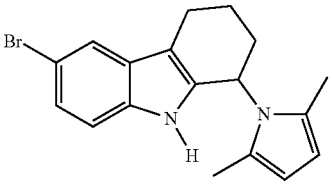 [SMILES: Cc1ccc(C)n1C1CCCc2c1[nH]c1ccc(Br)cc21] 70 | 6-Bromo-1-(2,5-dimethyl pyrrol-1-yl)-2,3,4,9-tetrahydro-1H-carbazole | 248.11 [M − C$_6$H$_5$]+ | 4.05 | ** |
| 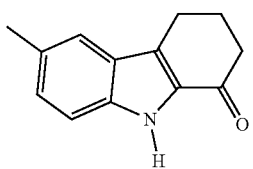 71 | 6-Methyl-2,3,4,9-tetrahydro-carbazol-1-one | 198.16 | 3.29 | ** |
| 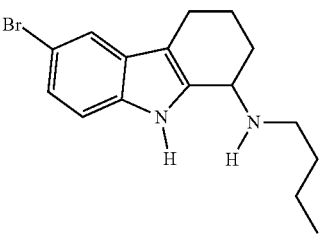 [SMILES: CCCCNC1CCCc2c1[nH]c1ccc(Br)cc21] 72 | (6-Bromo-2,3,4,9-tetrahydro-1H-carbazol-1-yl)-butyl-amine | 319.10 | 2.63 | ** |
| 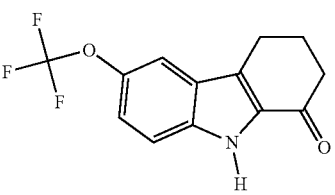 [SMILES: O=C1CCCc2c1[nH]c1ccc(OC(F)(F)F)cc21] 73 | 6-Trifluoromethoxy-2,3,4,9-tetrahydro-carbazol-1-one | 268.14 | 3.52 | ** |
| 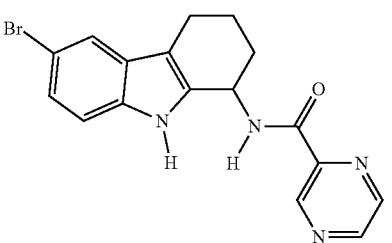 [SMILES: O=C(NC1CCCc2c1[nH]c1ccc(Br)cc21)c1cnccn1] 74 | Pyrazine-2-carboxylic acid (6-bromo-2,3,4,9-tetrahydro-1H-carbazol-1-yl)-amide | 369.12 | 3.60 | ***** |

TABLE 1-continued

| | | | | |
|---|---|---|---|---|
| 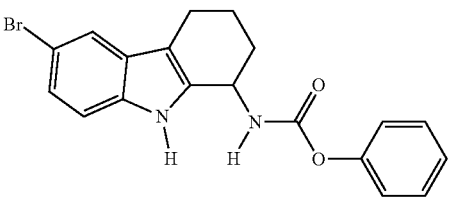 [SMILES: O=C(NC1CCCc2c1[nH]c1ccc(Br)cc21)Oc1ccccc1] 75 | (6-Bromo-2,3,4,9-tetrahydro-1H-carbazol-1-yl)-carbamic acid phenyl ester | 248.11 [M − C$_7$H$_6$NO$_2$] | 3.70 | * |
| 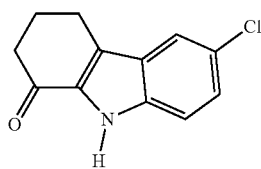 [SMILES: O=C1CCCc2c1[nH]c1ccc(Cl)cc21] 76 | 6-Chloro-2,3,4,9-tetrahydro-carbazol-1-one | 218.03 | 3.49 | * |
| 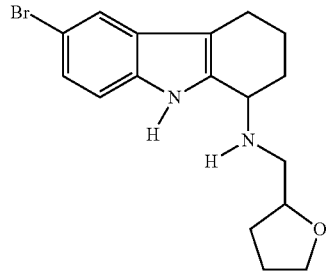 [SMILES: Brc1ccc2[nH]c3c(c2c1)CCCC3NCC1CCCO1] 77 | (6-Bromo-2,3,4,9-tetrahydro-1H-carbazol-1-yl)-(tetrahydro-furan-2-ylmethyl)-amine | 347/349 1:1 | 2.48 | * |
| 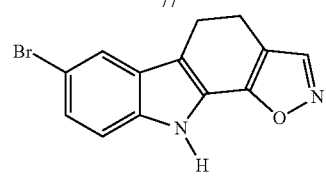 78 | 7-Bromo-4,10-dihydro-5H-1-oxa-2,10-diaza-cyclopenta[a]fluorine | 289.07 [M + H]+ | 3.78 | * |
| 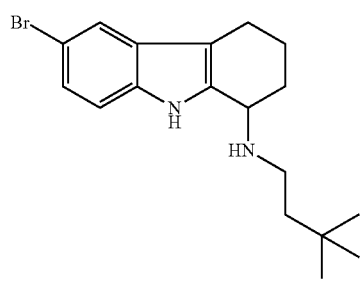 [SMILES: CC(C)(C)CCNC1CCCc2c1[nH]c1ccc(Br)cc21] 79 | (6-Bromo-2,3,4,9-tetrahydro-1H-carbazol-1-yl)-(3,3-dimethyl-butyl)-amine | 347/349 1:1 | 2.70 | * |
| 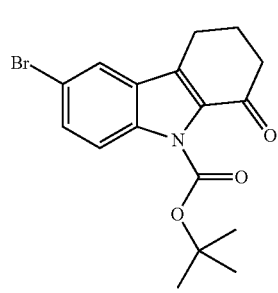 [SMILES: CC(C)(C)OC(=O)n1c2c(c3cc(Br)ccc31)CCCC2=O] 80 | 6-Bromo-1-oxo-1,2,3,4-tetrahydro-carbazole-9-carboxylic acid tert-butyl ester | 363.10 (M-Boc) | 4.47 | * |

TABLE 1-continued
| | | | | |
|---|---|---|---|---|
| 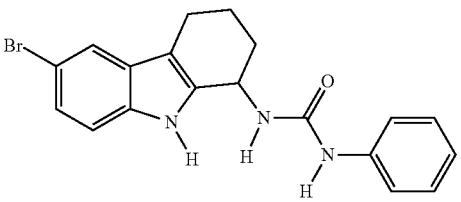 [SMILES: O=C(Nc1ccccc1)NC1CCCc2c1[nH]c1ccc(Br)cc21] 81 | 1-(6-Bromo-2,3,4,9-tetrahydro-1H-carbazol 1-yl)-3-phenyl-urea | 382.23 | 3.54 | * |
| 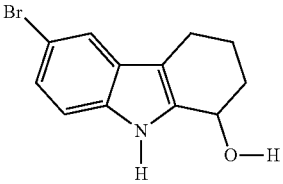 [SMILES: OC1CCCc2c1[nH]c1ccc(Br)cc21] 82 | 6-Bromo-9-methyl-2,3,4,9-tetrahydro-1H-carbazol-1-ol | 264.13 | 3.00 | * |
| 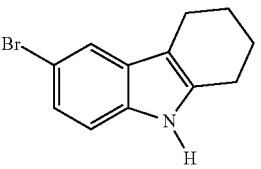 [SMILES: Brc1ccc2[nH]c3c(c2c1)CCCC3] 83 | 6-Bromo-2,3,4,9-tetrahydro-1H-carbazole | 248.11 | 3.95 | * |
| 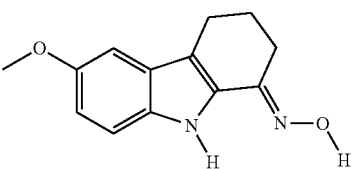 [SMILES: COc1ccc2[nH]c3c(c2c1)CCC/C3=N\O] 84 | 6-Methoxy-2,3,4,9-tetrahydro-carbazol-1 one oxime | 229.07/229.11 | 3.03/ 3.10 | * |
| 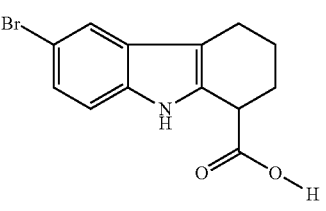 [SMILES: O=C(O)C1CCCc2c1[nH]c1ccc(Br)cc21] 85 | 6-Bromo-2,3,4,9-tetrahydro-1H-carbazole-1-carboxylic acid | | | * |
| 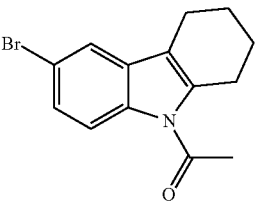 [SMILES: CC(=O)n1c2c(c3cc(Br)ccc31)CCCC2] 86 | 1-(6-Bromo-1,2,3,4-tetrahydro-carbazol-9-yl)-ethanone | 292.13 [M + H]+ | 4.32 | * |
| 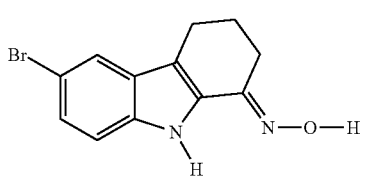 [SMILES: O/N=C1\CCCc2c1[nH]c1ccc(Br)cc21] 87 | 6-Bromo-2,3,4,9-tetrahydro-carbazol-1-one oxime | 277.02/22.02 | 3.53/ 3.55 | * |

TABLE 1-continued

| | | | | |
|---|---|---|---|---|
| 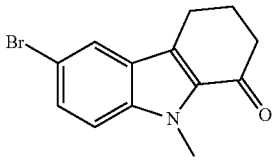 [SMILES: Cn1c2c(c3cc(Br)ccc31)CCCC2=O] 88 | 6-Bromo-9-methyl-2,3,4,9-tetrahydro-carbazol-1-one | tetra carboline | | * |
| 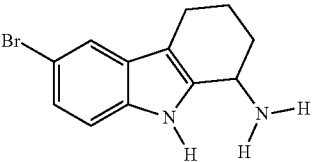 [SMILES: NC1CCCc2c1[nH]c1ccc(Br)cc21] 89 | 6-Bromo-2,3,4,9-tetrahydro-1H-carbazol-1-ylamine | 263.14 | 2.27 | * |
| 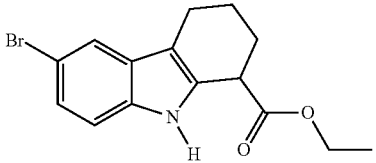 90 | 6-Bromo-2,3,4,9-tetrahydro-1H-carbazole-1-carboxylic acid ethyl ester | 322.17 | 4.15 | * |
| 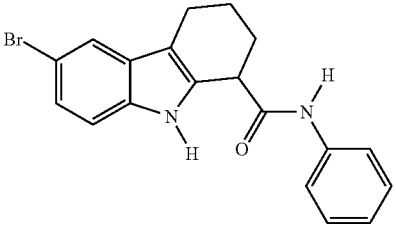 [SMILES: O=C(Nc1ccccc1)C1CCCc2c1[nH]c1ccc(Br)cc21] 91 | 6-Bromo-2,3,4,9-tetrahydro-1H-carbazole-1-carboxylic acid phenylamide | 365.17 | 3.75 | * |
| 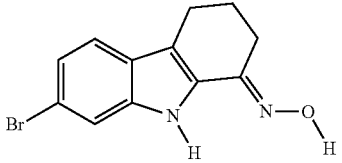 [SMILES: O/N=C1\CCCc2c1[nH]c1cc(Br)ccc21] 92 | 7-Bromo-2,3,4,9-tetrahydro-carbazol-1-one oxime | 277.00/277.01 | 3.55/ 3.65 | * |
| 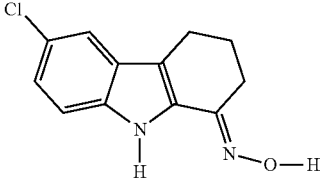 [SMILES: O/N=C1\CCCc2c1[nH]c1ccc(Cl)cc21] 93 | 6-Chloro-9-methyl-2,3,4,9-tetrahydro-carbazol-1-one oxime; compound with GENERIC INORGANIC NEUTRAL COMPONENT | 233.01/233.01 | 3.51/ 3.57 | * |
| 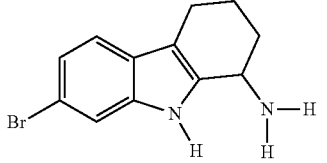 [SMILES: NC1CCCc2c1[nH]c1cc(Br)ccc21] 94 | 7-Bromo-2,3,4,9-tetrahydro-1H-carbazol-1-ylamine; compound with methane | 263.00 | 2.30 | * |

| | | | | |
|---|---|---|---|---|
| 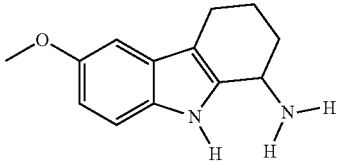 [SMILES: COc1ccc2[nH]c3c(c2c1)CCCC3N] 95 | 6-Methoxy-2,3,9-tetrahydro-1H-carbazol-1-ylamine | 200.08 [M − NH]+ | 1.72 | * |
| 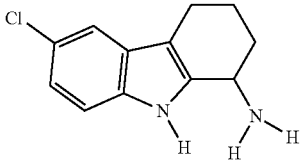 [SMILES: NC1CCCc2c1[nH]c1ccc(Cl)cc21] 96 | 6-Chloro-2,3,4,9-tetrahydro-1H-carbazol-1-ylamine | 219.09 | 2.34 | * |
| 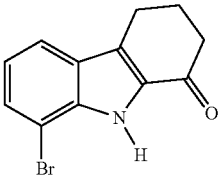 [SMILES: O=C1CCCc2c1[nH]c1c(Br)cccc21] 97 | 8-Bromo-2,3,4,9-tetrahydro-carbazol-1-one | 261.97 | 3.11 | * |
| 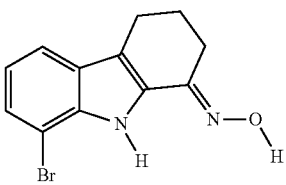 [SMILES: O/N=C1\CCCc2c1[nH]c1c(Br)cccc21] 98 | 8-Bromo-2,3,4,9-tetrahydro-carbazol-1-one oxime | 277.01 | 3.23 | * |
| 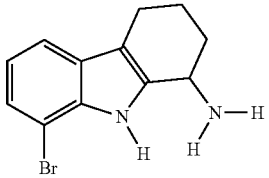 [SMILES: NC1CCCc2c1[nH]c1c(Br)cccc21] 99 | 8-Bromo-2,3,4,9-tetrahydro-1H-carbazol-1-ylamine | 263.03 | 1.90 | * |
| 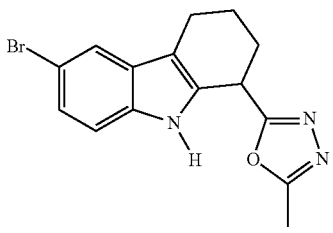 [SMILES: Cc1nnc(C2CCCc3c2[nH]c2ccc(Br)cc32)o1] 100 | 6-Bromo-1-(5-methyl-[1,3,4]oxadiazol-2-yl)-2,3,4,9-tetrahydro-1H-carbazole | 330.18 | 3.49 | * |
| 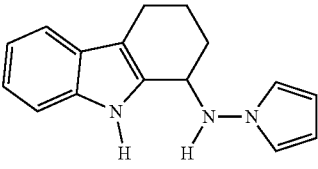 [SMILES: c1ccc2c3c([nH]c2c1)C(Nn1cccc1)CCC3] 101 | Pyrrol-1-yl-(2,3,4,9-tetrahydro-1H-carbazol-1-yl)-amine | 250.25 | 3.70 | * |

TABLE 1-continued
| | | | | |
|---|---|---|---|---|
| 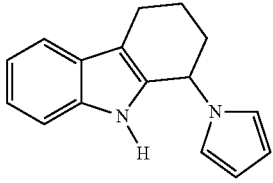 [SMILES: c1ccc2c3c([nH]c2c1)C(n1cccc1)CCC3] 102 | 1-Pyrrol-1-yl-2,3,4,9-tetrahydro-1H-carbazole | 235.20 | 3.82 | * |
| 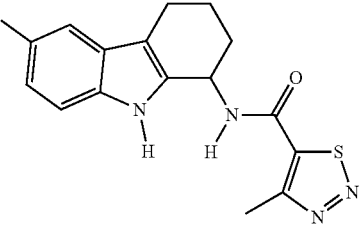 103 | 4-Methyl-[1,2,3]thiadiazole-5-carboxylic acid (6-bromo-2,3,4,9-tetrahydro-1H-carbazol-1-yl)-amide | 293.10 | 3.37 | ** |
| 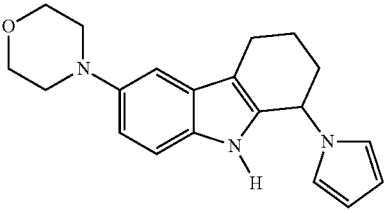 [SMILES: c1ccn(C2CCCc3c2[nH]c2ccc(N4CCOCC4)cc32)c1] 104 | 6-Morpholin-4-yl-1-pyrrol-1-yl-2,3,4,9-tetrahydro-1H-carbazole | 320.25 | 2.40 | * |
| 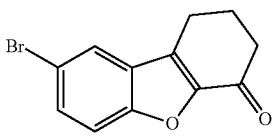 [SMILES: O=C1CCCc2c1oc1ccc(Br)cc21] 105 | 8-Bromo-2,3-dihydro-1H-dibenzofuran-4-one | 265.08 | 3.42 | * |
| 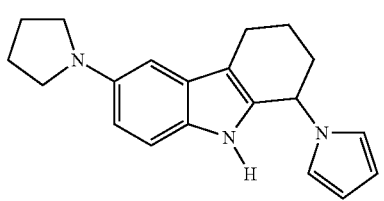 [SMILES: c1ccn(C2CCCc3c2[nH]c2ccc(N4CCCC4)cc32)c1] 106 | 6-Pyrrolidin-1-yl-1-pyrrol-1-yl-2,3,4,9-tetrahydro-1H-carbazole | 304.22 | 2.29 | * |
| 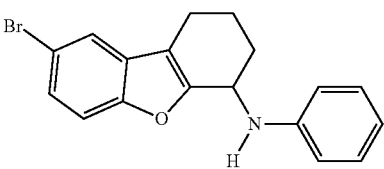 [SMILES: Brc1ccc2oc3c(c2c1)CCCC3Nc1ccccc1] 107 | (8-Bromo-1,2,3,4-tetrahydro-dibenzofuran-4-yl)-phenyl-amine | 547.15 | 4.44 | * |
| 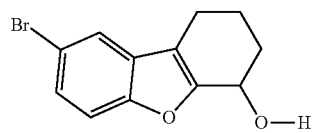 [SMILES: OC1CCCc2c1oc1ccc(Br)cc21] 108 | 8-Bromo-1,2,3,4-tetrahydro-dibenzofuran-4-ol | 268.13 | 3.14 | * |

TABLE 1-continued
| | | | | |
|---|---|---|---|---|
| 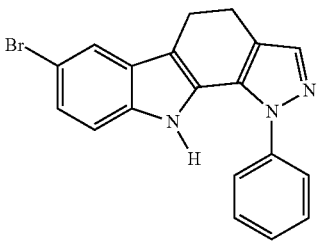 [SMILES: Brc1ccc2[nH]c3c(c2c1)CCc1cnn(-c2ccccc2)c1-3] 109 | 7-Bromo-1-phenyl-1,4,5,10-tetrahydro-1,2,10-triaza-cyclopenta[a]fluorine | 362.07 | 4.04 | * |
| 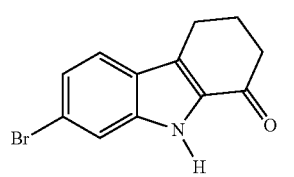 [SMILES: O=C1CCCc2c1[nH]c1cc(Br)ccc21] 110 | 7-Bromo-2,3,4,9-tetrahydro-carbazol-1-one | 261.99 | 3.21 | * |
| 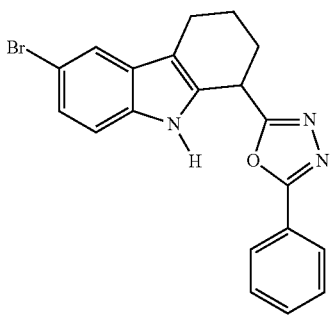 [SMILES: Brc1ccc2[nH]c3c(c2c1)CCCC3c1nnc(-c2ccccc2)o1] 111 | 6-Bromo-1-(5-phenyl-[1,3,4]oxadiazol-2-yl)-2,3,4,9-tetrahydro-1H-carbazole | 394.2 [M + H]+ | 4.25 | * |
| 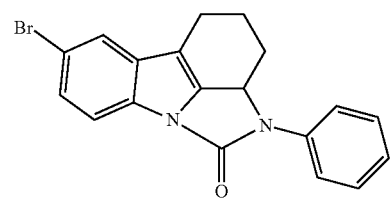 [SMILES: O=C1N(c2ccccc2)C2CCCc3c2n1c1ccc(Br)cc31] 112 | 7-Bromo-2-phenyl-2a,3,4,5-tetrahydro-2H-2,9b-diaza-cyclopenta[jk]fluoren-1-one | 368.15 [M + H]+ | 4.60 | * |
| 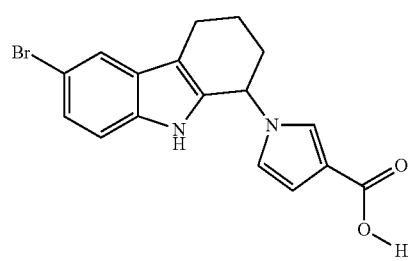 [SMILES: O=C(O)c1ccn(C2CCCc3c2[nH]c2ccc(Br)cc32)c1] 113 | 1-(6-Bromo-2,3,4,9-tetrahydro-1H-carbazol-1-yl)-1H-pyrrole-3-carboxylic acid | 357.02 | 3.33 | * |

TABLE 1-continued
| Structure | Name | MS | RT | * |
|---|---|---|---|---|
| 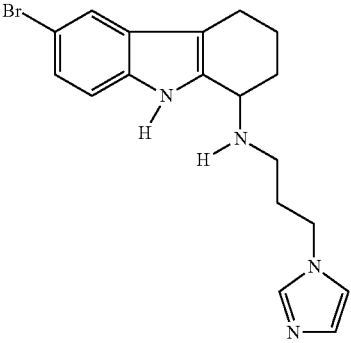 [SMILES: Brc1ccc2[nH]c3c(c2c1)CCCC3NCCCn1ccnc1] 114 | (6-Bromo-2,3,4,9-tetrahydro-1H-carbazol-1-yl)-(3-imidazol-1-yl-propyl)-amine | 371/373 1:1 | 2.00 | * |
| 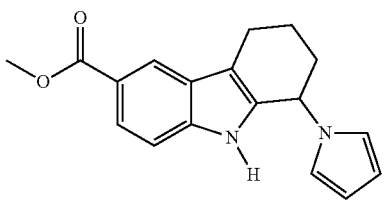 [SMILES: COC(=O)c1ccc2[nH]c3c(c2c1)CCCC3n1cccc1] 115 | 8-Pyrrol-1-yl-6,7,8,9-tetrahydro-5H-carbazole-3-carboxylic acid methyl ester | 293.29 | 3.40 | * |
| 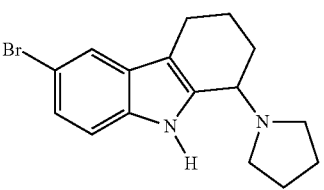 [SMILES: Brc1ccc2[nH]c3c(c2c1)CCCC3N1CCCC1] 116 | 6-Bromo-1-pyrrolidin-1-yl-2,3,4,9-tetrahydro-1H-carbazole | 317.09 | 2.41 | * |
| 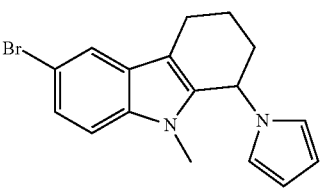 [SMILES: Cn1c2c(c3cc(Br)ccc31)CCCC2n1cccc1] 117 | 6-Bromo-9-methyl-1-pyrrol-1-yl-2,3,4,9-tetrahydro-1H-carbazole | 329.08 [M + H]+ | 4.63 | * |
| 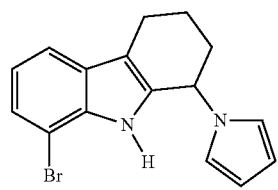 [SMILES: Brc1cccc2c3c([nH]c12)C(n1cccc1)CCC3] 118 | 8-Bromo-1-pyrrol-1-yl-2,3,4,9-tetrahydro-1H-carbazole | 313.22 | 3.82 | * |
| 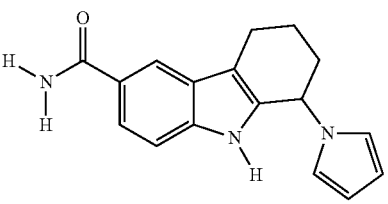 [SMILES: NC(=O)c1ccc2[nH]c3c(c2c1)CCCC3n1cccc1] 119 | 8-Pyrrol-1-yl-6,7,8,9-tetrahydro-5H-carbazole-3-carboxylic acid amide | 278.18 | 2.93 | * |

TABLE 1-continued
| Structure | Name | MW | RT | Activity |
|---|---|---|---|---|
| 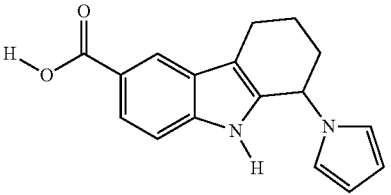 [SMILES: O=C(O)c1ccc2[nH]c3c(c2c1)CCCC3n1cccc1] 120 | 8-Pyrrol-1-yl-6,7,8,9-tetrahydro-5H-carbazole-3-carboxylic acid | 279.20 | 3.25 | * |
| 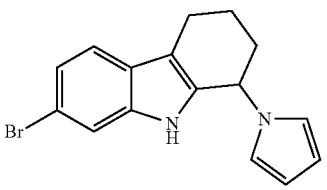 [SMILES: Brc1ccc2c3c([nH]c2c1)C(n1cccc1)CCC3] 121 | 7-Bromo-1-pyrrol-1-yl-2,3,4,9-tetrahydro-1H-carbazole | 313.07 | 4.26 | * |
| 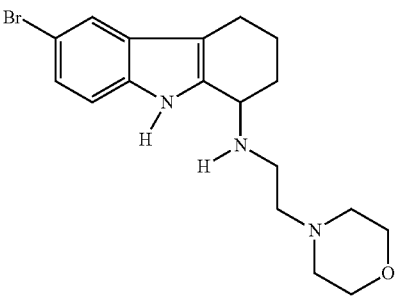 [SMILES: Brc1ccc2[nH]c3c(c2c1)CCCC3NCCN1CCOCC1] 122 | (6-Bromo-2,3,4,9-tetrahydro-1H-carbazol-1-yl)-(2-morpholin-4-yl-ethyl)-amine | 376/378 1:1 | 2.15 | * |
| 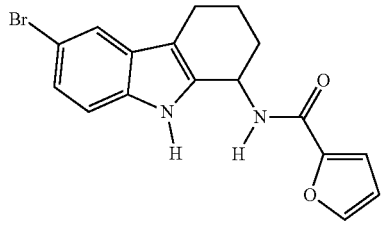 123 | Furan-2-carboxylic acid (6-bromo-2,3,4,9-tetrahydro-1H-carbazol-1-yl)-amide | | | **** |
| 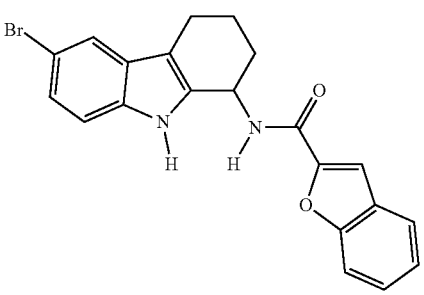 [SMILES: O=C(NC1CCCc2c1[nH]c1ccc(Br)cc21)c1cc2ccccc2o1] 124 | Benzofuran-2-carboxylic acid (6-bromo-2,3,4,9-tetrahydro-1H-carbazol-1-yl)-amide | 407.01 | 4.09 | ** |

TABLE 1-continued
| | | | | |
|---|---|---|---|---|
| 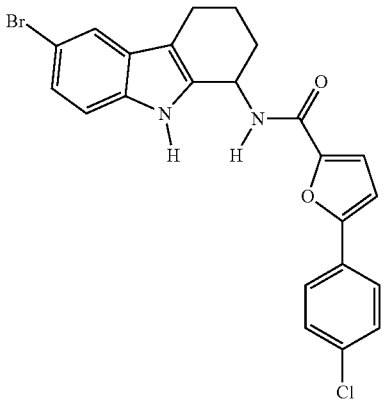 [SMILES: O=C(NC1CCCc2c1[nH]c1ccc(Br)cc21)c1ccc(-c2ccc(Cl)cc2)o1]  125 | 5-(4-Chloro-phenyl)-furan-2-carboxylic acid (6-bromo-2,3,4,9-tetrahydro-1H-carbazol-1-yl)-amide | | | *** |
| 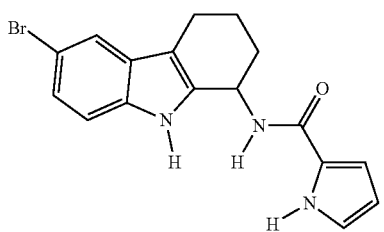 [SMILES: O=C(NC1CCCc2c1[nH]c1ccc(Br)cc21)c1ccc[nH]1]  126 | 1H-Pyrrole-2-carboxylic acid (6-bromo-2,3,4,9-tetrahydro-1H-carbazol-1-yl)-amide | 356.06 | 3.64 | *** |
| 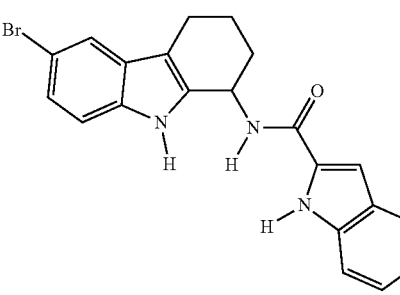  127 | 1H-Indole-2-carboxylic acid (6-bromo-2,3,4,9-tetrahydro-1H-carbazol-1-yl)-amide | 406.06 | 3.92 | *** |
| 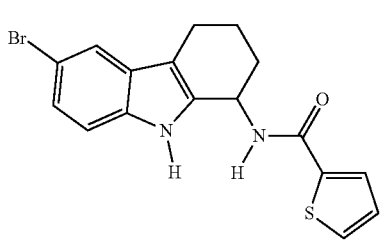  128 | Thiophene-2-carboxylic acid (6-bromo-2,3,4,9-tetrahydro-1H-carbazol-1-yl)-amide | 315.07 [M + H]+ | 3.68 | ***** |
| 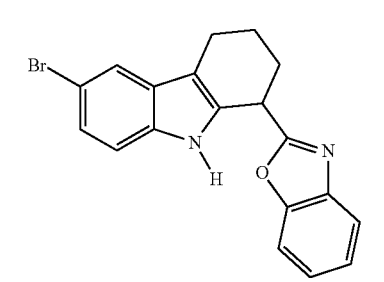 [SMILES: Brc1ccc2[nH]c3c(c2c1)CCCC3c1nc2ccccc2o1]  129 | 1-Benzooxazol-2-yl-6-bromo-2,3,4,9-tetrahydro-1H-carbazole | 265.01 | 4.18 | ***** |

TABLE 1-continued
| | | | | |
|---|---|---|---|---|
| 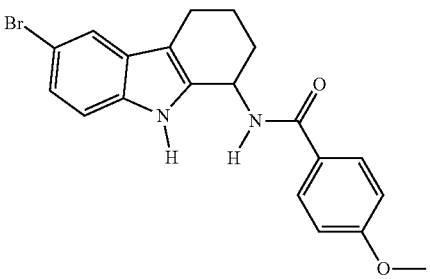 130 | N-(6-Bromo-2,3,4,9-tetrahydro-1H-carbazol-1-yl)-4-methoxy-benzamide | 397.24 | 3.57 | **** |
| 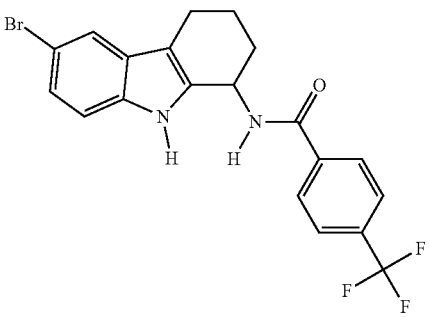 [SMILES: O=C(NC1CCCc2c1[nH]c1ccc(Br)cc21)c1ccc(C(F)(F)F)cc1] 131 | N-(6-Bromo-2,3,4,9-tetrahydro-1H-carbazol-1-yl)-4-trifluoromethyl-benzamide | 435.23 | 3.80 | **** |
| 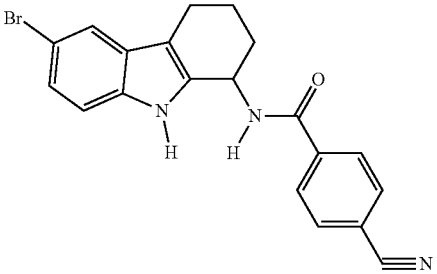 [SMILES: N#Cc1ccc(C(=O)NC2CCCc3c2[nH]c2ccc(Br)cc32)cc1] 132 | N-(6-Bromo-2,3,4,9-tetrahydro-1H-carbazol-1-yl)-4-cyano-benzamide | 392.23 | 3.52 | **** |
| 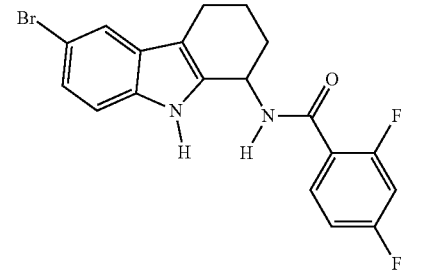 [SMILES: O=C(NC1CCCc2c1[nH]c1ccc(Br)cc21)c1ccc(F)cc1F] 133 | N-(6-Bromo-2,3,4,9-tetrahydro-1H-carbazol-1-yl)-2,4-difluoro-benzamide | 403.21 | 3.65 | ***** |
| 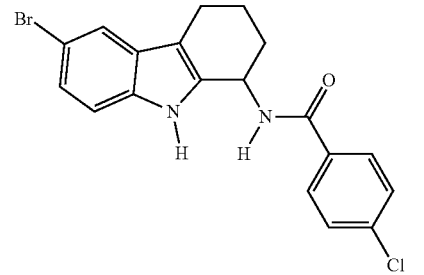 [SMILES: O=C(NC1CCCc2c1[nH]c1ccc(Br)cc21)c1ccc(Cl)cc1] 134 | N-(6-Bromo-2,3,4,9-tetrahydro-1H-carbazol-1-yl)-4-chloro-benzamide | 401.17 | 3.75 | **** |

TABLE 1-continued

| | | | | |
|---|---|---|---|---|
| 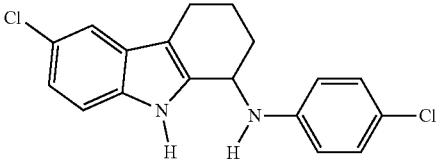 [SMILES: Clc1ccc(NC2CCCc3c2[nH]c2ccc(Cl)cc32)cc1] 135 | (4-Chloro-phenyl)-(6-chloro-2,3,4,9-tetrahydro-1H-carbazol-1-yl)-amine | 329.21 | 4.31 | **** |
| 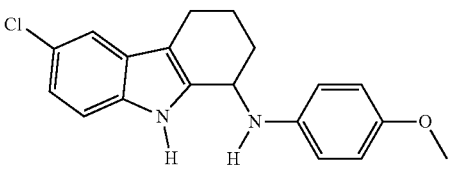 [SMILES: COc1ccc(NC2CCCc3c2[nH]c2ccc(Cl)cc32)cc1] 136 | (6-Chloro-2,3,4,9-tetrahydro-1H-carbazol-1-yl)-(4-methoxy-phenyl)-amine | 325.25 | 3.59 | ***** |
| 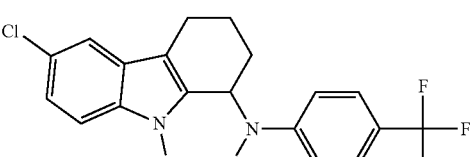 137 | (6-Chloro-2,3,4,9-tetrahydro-1H-carbazol-1-yl)-(4-trifluoromethyl-phenyl)-amine | 363.21 | 4.37 | ***** |
| 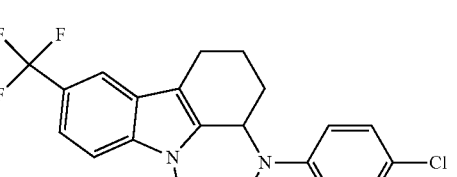 138 | (4-Chloro-phenyl)-(6-trifluoromethyl-2,3,4,9-tetrahydro-1H-carbazol-1-yl)-amine | 363.21 | 4.34 | **** |
| 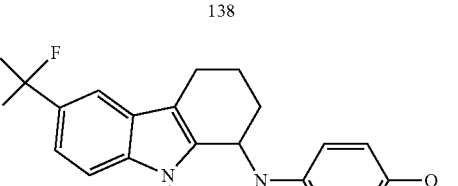 139 | (4-Methoxy-phenyl)-(6-trifluoromethyl-2,3,4,9-tetrahydro-1H-carbazol-1-yl)-amine | 359.26 | 3.79 | **** |
| 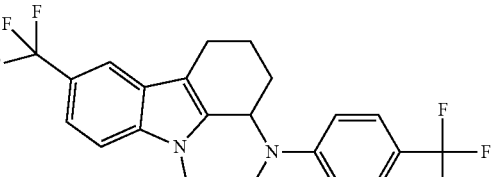 140 | (4-Trifluoromethyl-phenyl)-(6-trifluoromethyl-2,3,4,9-tetrahydro-1H-carbazol-1-yl)-amine | 397.22 | 4.39 | **** |
| 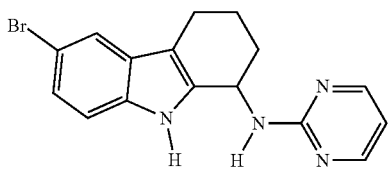 [SMILES: Brc1ccc2[nH]c3c(c2c1)CCCC3Nc1ncccn1] 141 | (6-Bromo-2,3,4,9-tetrahydro-1H-carbazol-1-yl)-pyrimidin-2-yl-amine | 341.23 | 3.37 | ***** |

TABLE 1-continued
| Structure | Name | MW | LogP | Activity |
|---|---|---|---|---|
| 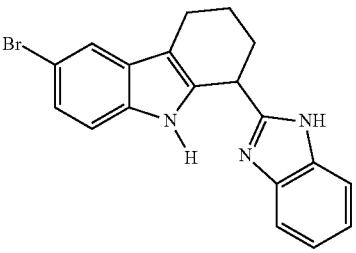 [SMILES: Brc1ccc2[nH]c3c(c2c1)CCCC3c1nc2ccccc2[nH]1] 142 | 1-(1H-Benzoimidazol-2-yl)-6-bromo-2,3,4,9-tetrahydro-1H-carbazole | 364.17 | 2.30 | **** |
| 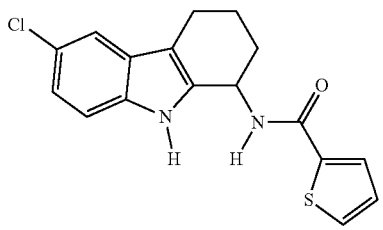 143 | Thiophene-2-carboxylic acid (6-chloro-2,3,4,9-tetrahydro-1H-carbazol-1-yl)-amide | 329.22 | 3.68 | *** |
| 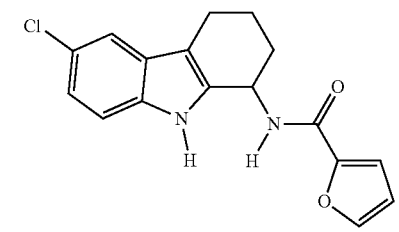 [SMILES: O=C(NC1CCCc2c1[nH]c1ccc(Cl)cc21)c1ccco1] 144 | Furan-2-carboxylic acid (6-chloro-2,3,4,9-tetrahydro-1H-carbazol-1-yl)-amide | 313.21 | 3.52 | *** |
| 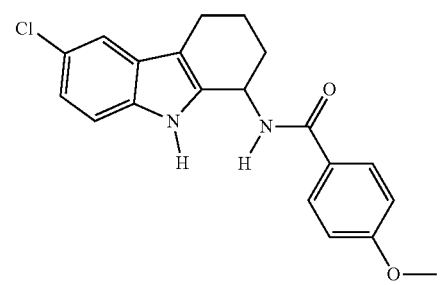 [SMILES: COc1ccc(C(=O)NC2CCCc3c2[nH]c2ccc(Cl)cc32)cc1] 145 | N-(6-Chloro-2,3,4,9-tetrahydro-1H-carbazol-1-yl)-4-methoxy-benzamide | 353.26 | 3.71 | **** |
| 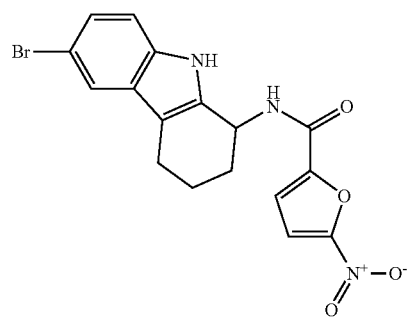 [SMILES: O=C(NC1CCCc2c1[nH]c1ccc(Br)cc21)c1ccc([N+](=O)[O-])o1] 146 | 5-Nitro-furan-2-carboxylic acid (6-bromo-2,3,4,9-tetrahydro-1H-carbazol-1-yl)-amide | 402.13 | 3.75 | *** |

| | | | | |
|---|---|---|---|---|
| 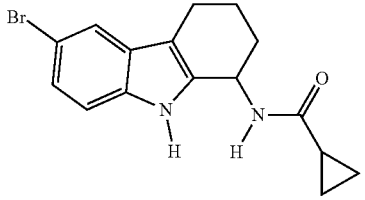 [SMILES: O=C(NC1CCCc2c1[nH]c1ccc(Br)cc21)C1CC1] 147 | Cyclopropanecarboxylic acid (6-bromo-2,3,4,9-tetrahydro-1H-carbazol-1-yl)-amide | 331.17 | 3.48 | *** |
| 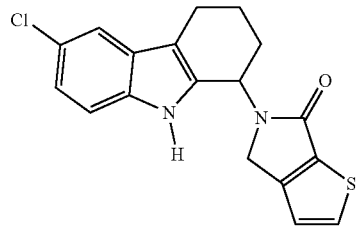 [SMILES: O=C1c2sccc2CN1C1CCCc2c1[nH]c1ccc(Cl)cc21] 148 | 5-(6-Chloro-2,3,4,9-tetrahydro-1H-carbazol-1-yl)-4,5-dihydro-thieno[2,3-c]pyrrol-6-one | 341.14 | 3.68 | ***** |
| 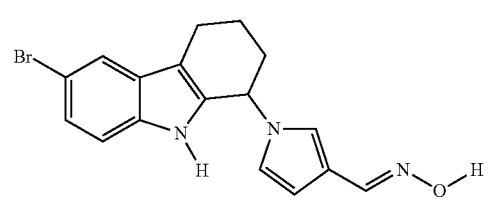 [SMILES: O/N=C/c1ccn(C2CCCc3c2[nH]c2ccc(Br)cc32)c1] 149 | 1-(6-Bromo-2,3,4,9-tetrahydro-1H-carbazol-1-yl)-1H-pyrrole-3-carbaldehyde oxime | 356.11 | 3.54 | *** |
| 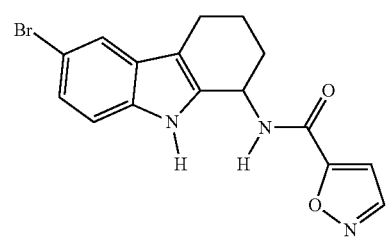 [SMILES: O=C(NC1CCCc2c1[nH]c1ccc(Br)cc21)c1ccno1] 150 | isoxazole-5-carboxylic acid (6-bromo-2,3,4,9-tetrahydro-1H-carbazol-1-yl)-amide | 358.15 | 3.48 | **** |
| 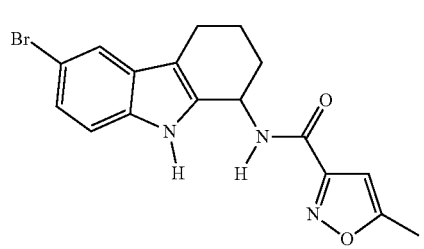 [SMILES: Cc1cc(C(=O)NC2CCCc3c2[nH]c2ccc(Br)cc32)no1] 151 | 5-Methyl-isoxazole-3-carboxylic acid (6-bromo-2,3,4,9-tetrahydro-1H-carbazol-1-yl)-amide | 372.23 | 3.47 | **** |
| 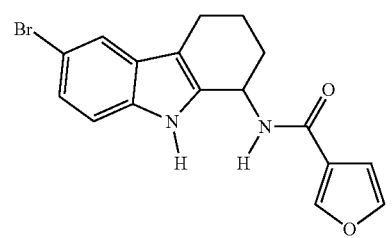 [SMILES: O=C(NC1CCCc2c1[nH]c1ccc(Br)cc21)c1ccoc1] 152 | Furan-3-carboxylic acid (6-bromo-2,3,4,9-tetrahydro-1H-carbazol-1-yl)-amide | 357.16 | 3.54 | ** |

TABLE 1-continued

| | | | | |
|---|---|---|---|---|
| 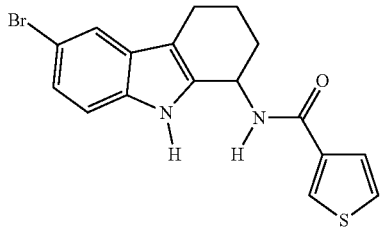 [SMILES: O=C(NC1CCCc2c1[nH]c1ccc(Br)cc21)c1ccsc1] 153 | Thiophene-3-carboxylic acid (6-bromo-2,3,4,9-tetrahydro-1H-carbazol-1-yl)-amide | 373.14 | 3.66 | *** |
| 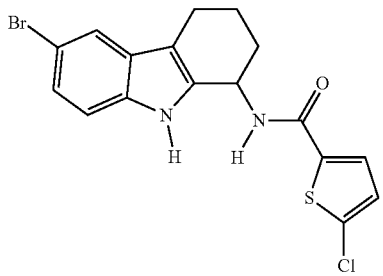 [SMILES: O=C(NC1CCCc2c1[nH]c1ccc(Br)cc21)c1ccc(Cl)s1] 154 | 5-Chloro-thiophene-2-carboxylic acid (6-bromo-2,3,4,9-tetrahydro-1H-carbazol-1-yl)-amide | 407.13 | 4.00 | ***** |
| 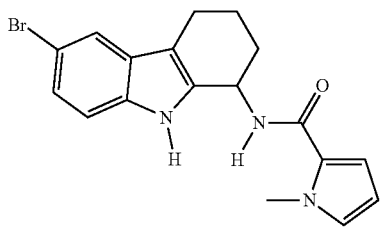 [SMILES: Cn1cccc1C(=O)NC1CCCc2c1[nH]c1ccc(Br)cc21] 155 | 1-Methyl-1H-pyrrole-2-carboxylic acid (6-bromo-2,3,4,9-tetrahydro-1H-carbazol-1-yl)-amide | 370.17 | 3.87 | **** |

Purchased compounds 156-188

| Compound | Compound Name | ELISA EC50 μM | ELISA Activity |
|---|---|---|---|
| 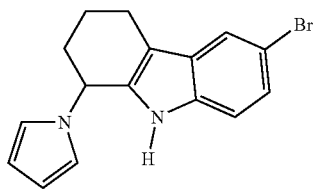 [SMILES: Brc1ccc2[nH]c3c(c2c1)CCCC3n1cccc1] 156 | 6-Bromo-1-pyrrol-1-yl-2,3,4,9-tetrahydro-1H-carbazole | 0.010 | ***** |
| 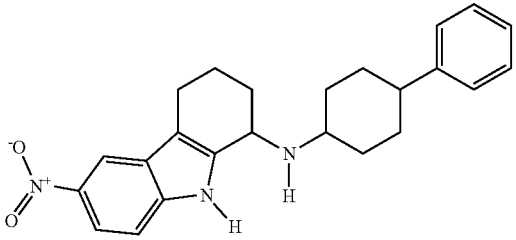 157 | (6-Nitro-2,3,4,9-tetrahydro-1H-carbazol-1-yl)-(4-phenyl- | 0.0149 | **** |

TABLE 1-continued
| | | | |
|---|---|---|---|
| 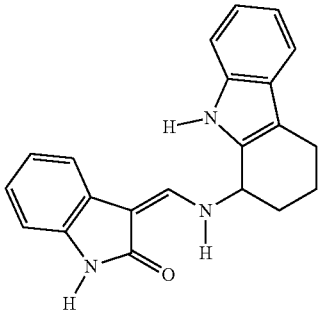 [SMILES: O=C1Nc2ccccc2/C1=C/NC1CCCc2c1[nH]c1ccccc21] 158 | 3-[(2,3,4,9-Tetrahydro-1H-carbazol-1-ylamino)-methylene]-1,3-dihydro-indol-2-one | 0.2671 | ** |
| 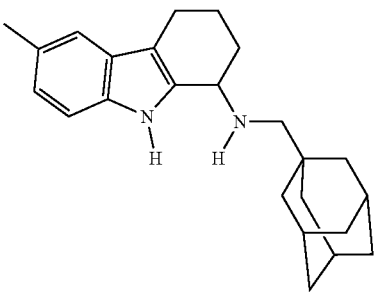 [SMILES: Cc1ccc2[nH]c3c(c2c1)CCCC3NCC12CC3CC(CC(C3)C1)C2] 159 | Adamantan-1-ylmethyl-(6-methyl-2,3,4,9-tetrahydro-1H-carbazol-1-yl)-amine | 0.3600 | ** |
| 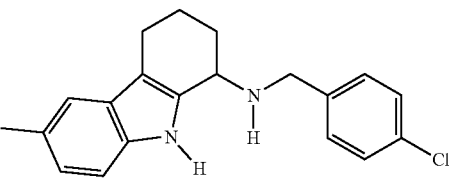 [SMILES: Cc1ccc2[nH]c3c(c2c1)CCCC3NCc1ccc(Cl)cc1] 160 | (4-Chloro-benzyl)-(6-methyl-2,3,4,9-tetrahydro-1H-carbazol-1-yl)-amine | 0.42 | ** |
| 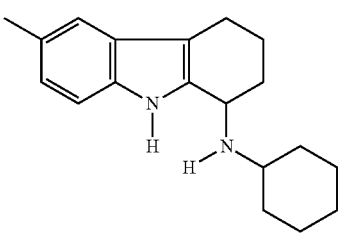 [SMILES: Cc1ccc2[nH]c3c(c2c1)CCCC3NC1CCCCC1] 161 | Cyclohexyl-(6-methyl-2,3,4,9-tetrahydro-1H-carbazol-1-yl)-amine | 0.67 | ** |
| 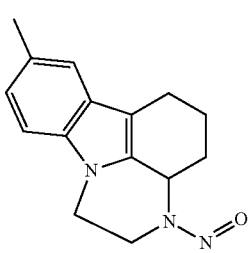 [SMILES: Cc1ccc2c(c1)c1c3n2CCN(N=O)C3CCC1] 162 | 8-Methyl-3-nitroso-2,3,3a,4,5,6-hexahydro-1H-pyrazino[3,2,1-jk]carbazole | 0.89 | ** |

TABLE 1-continued
| Structure | Name | Value | |
|---|---|---|---|
| 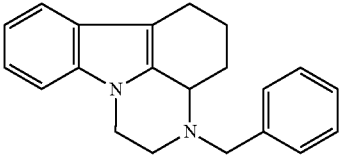 [SMILES: c1ccc(CN2CCn3c4c(c5ccccc53)CCCC42)cc1] 163 | 3-Benzyl-2,3,3a,4,5,6-hexahydro-1H-pyrazino[3,2,1-jk]carbazole | 1.79 | * |
| 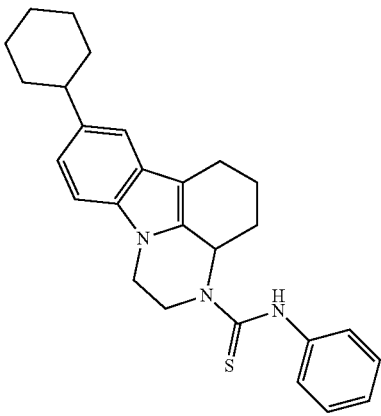 [SMILES: S=C(Nc1ccccc1)N1CCn2c3c(c4cc(C5CCCCC5)ccc42)CCCC31] 164 | 8-Cyclohexyl-1,2,3a,4,5,6-hexahydro-pyrazino[3,2,1-jk]carbazole-3-carbothioic acid phenylamide | 2.17 | * |
| 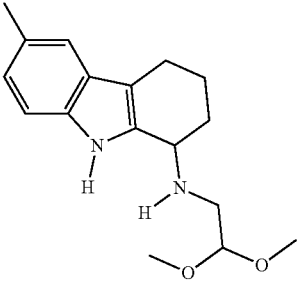 165 | (2,2-Dimethoxy-ethyl)-(6-methyl-2,3,4,9-tetrahydro-1H-carbazol-1-yl)-amine | 5.2 | * |
| 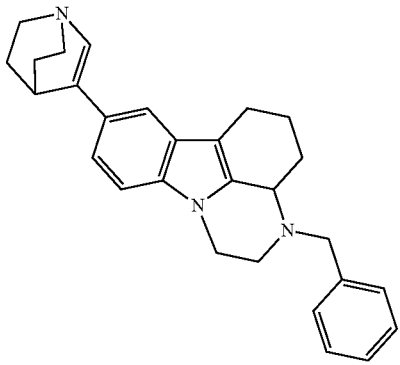 [SMILES: C1=C(c2ccc3c(c2)c2c4n3CCN(Cc3ccccc3)C4CCC2)C2CCN1CC2] 166 | 8-(1-Aza-bicyclo[2.2.2]oct-2-en-3-yl)-3-benzyl-2,3,3a,4,5,6-hexahydro-1H-pyrazino[3,2,1-jk]carbazole | 6.631 | * |
| 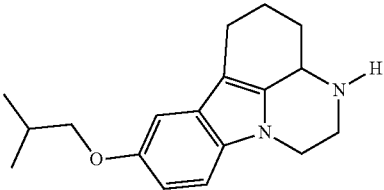 [SMILES: CC(C)COc1ccc2c(c1)c1c3n2CCNC3CCC1] 167 | 8-Isobutoxy-2,3,3a,4,5,6-hexahydro-1H-pyrazino[3,2,1-jk]carbazole | 6.93 | * |

TABLE 1-continued

| | | | |
|---|---|---|---|
| 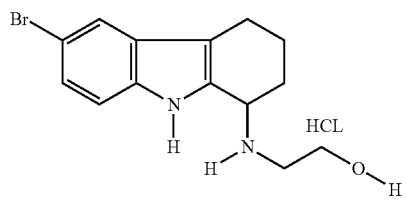 [SMILES: OCCNC1CCCc2c1[nH]c1ccc(Br)cc21]<br>168 | 2-(6-Bromo-2,3,4,9-tetrahydro-1H carbazol-1-ylamino)-ethanol hydrochloride | 7.72 | * |
| 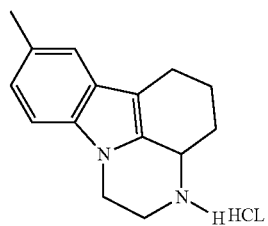 [SMILES: Cc1ccc2c(c1)c1c3n2CCNC3CCC1]<br>169 | 8-Methyl-2,3,3a,4,5,6-hexahydro-1H-pyrazino[3,2,1-jk]carbazole hydrochloride | >10 | * |
| 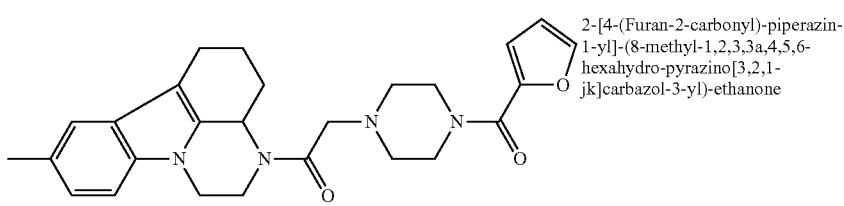<br>170 | 2-[4-(Furan-2-carbonyl)-piperazin-1-yl]-(8-methyl-1,2,3,3a,4,5,6-hexahydro-pyrazino[3,2,1-jk]carbazol-3-yl)-ethanone | >10 | * |
| 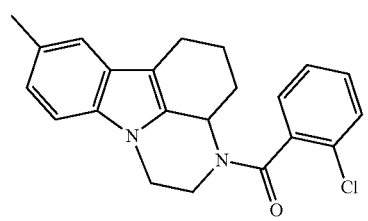 [SMILES: Cc1ccc2c(c1)c1c3n2CCN(C(=O)c2ccccc2Cl)C3CCC1]<br>171 | (2-Chloro-phenyl)-(8-methyl-1,2,3,3a,4,5,6-hexahydro-pyrazino[3,2,1-jk]carbazol-3-yl)-methanone | >10 | * |
| 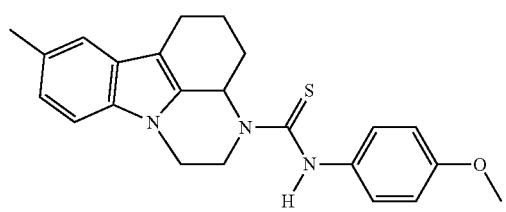<br>172 | 8-Methyl-1,2,3,3a,4,5,6-hexahydro-pyrazino[3,2,1-jk]carbazole-3-carbothioic acid (4-methoxy-phenyl)-amide | >10 | * |
| 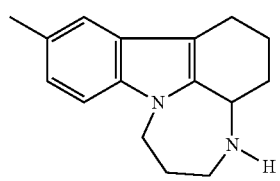 [SMILES: Cc1ccc2c(c1)c1c3n2CCCNC3CCC1]<br>173 | 11-Methyl-1,2,3,3a,4,5,6,7-octahydro-[1,4]diazepino[3,2,1-jk]carbazole | >10 | * |

TABLE 1-continued
| | | | | |
|---|---|---|---|---|
| 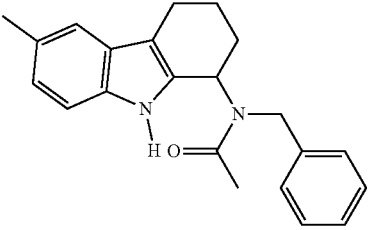 [SMILES: CC(=O)N(Cc1ccccc1)C1CCCc2c1[nH]c1ccc(C)cc21] 174 | N-Benzyl-N-(6-methyl-2,3,4,9-tetrahydro-1H-carbazol-1-yl)-acetamide | >10 | * | |
| 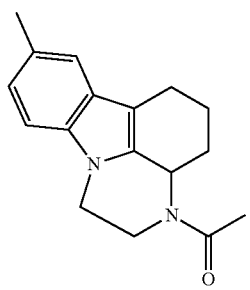 [SMILES: CC(=O)N1CCn2c3c(c4cc(C)ccc42)CCCC31] 175 | 1-(8-Methyl-1,2,3a,4,5,6-hexahydro-pyrazino[3,2,1-jk]carbazol-3-yl)-ethanone | >10 | * | |
| 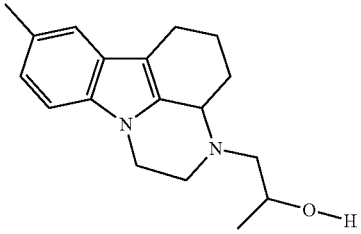 [SMILES: Cc1ccc2c(c1)c1c3n2CCN(CC(C)O)C3CCC1] 176 | 1-(8-Methyl-1,2,3a,4,5,6-hexahydro-pyrazino[3,2,1-jk]carbazol-3-yl)-propan-2-ol | >10 | * | |
| 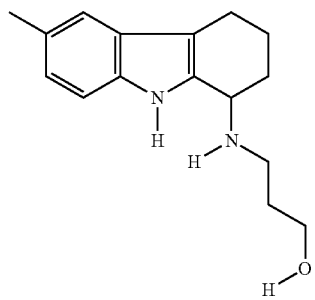 [SMILES: Cc1ccc2[nH]c3c(c2c1)CCCC3NCCCO] 177 | 3-(6-Methyl-2,3,4,9-tetrahydro-1H-carbazol-1-ylamino)-propan-1-ol | >10 | * | |
| 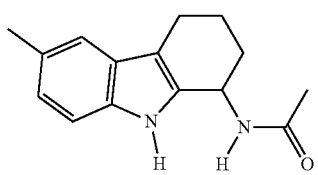 [SMILES: CC(=O)NC1CCCc2c1[nH]c1ccc(C)cc21] 178 | N-(6-Methyl-2,3,4,9-tetrahydro-1H-carbazol-1-yl)-acetamide | >10 | * | |

TABLE 1-continued
| | | | |
|---|---|---|---|
| 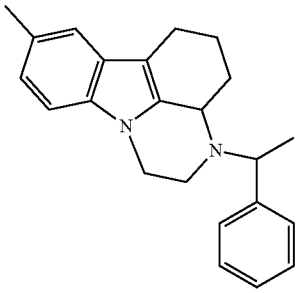 [SMILES: Cc1ccc2c(c1)c1c3n2CCN(C(C)c2ccccc2)C3CCC1] 179 | 8-Methyl-3-(1-phenyl-ethyl)-2,3,3a,4,5,6-hexahydro-1H-pyrazino[3,2,1-jk]carbazole | >10 | * |
| 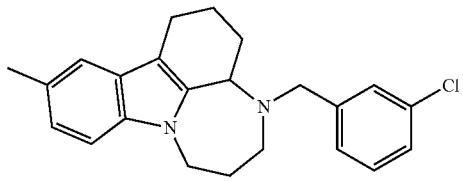 [SMILES: Cc1ccc2c(c1)c1c3n2CCCN(Cc2cccc(Cl)c2)C3CCC1] 180 | 4-(3-Chloro-benzyl)-11-methyl-1,2,3,3a,4,5,6,7-octahydro-[1,4]diazepino[3,2,1-jk]carbazole | >10 | * |
| 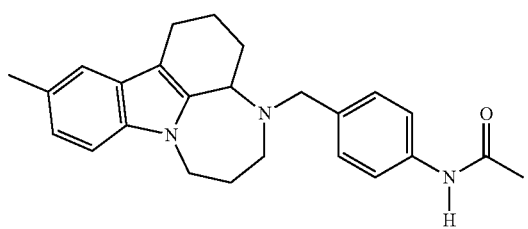 [SMILES: CC(=O)Nc1ccc(CN2CCCn3c4c(c5cc(C)ccc53)CCCC42)cc1] 181 | N-[4-(11-Methyl-1,2,3,3a,6,7-hexahydro-5H-[1,4]diazepino[3,2,1-jk]carbazol-4-ylmethyl)-phenyl]-acetamide | >10 | * |
| 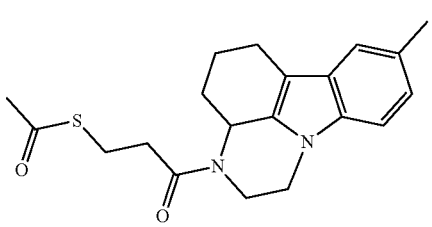 [SMILES: CC(=O)SCCC(=O)N1CCn2c3c(c4cc(C)ccc42)CCCC31] 182 | Thioacetic acid S-[3-(8-methyl-1,2,3a,4,5,6-hexahydro-pyrazino[3,2,1-jk]carbazol-3-yl)-3-oxo-propyl] ester | >10 | * |
| 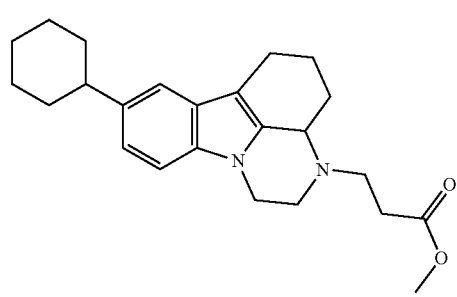 [SMILES: COC(=O)CCN1CCn2c3c(c4cc(C5CCCCC5)ccc42)CCCC31] 183 | 3-(8-Cyclohexyl-1,2,3a,4,5,6-hexahydro-pyrazino[3,2,1-jk]carbazol-3-yl)-propionic acid | >10 | * |

TABLE 1-continued
| | | | |
|---|---|---|---|
| 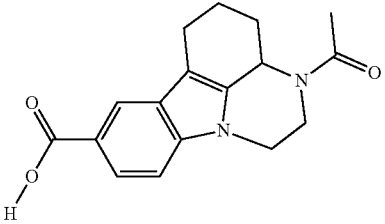 [SMILES: CC(=O)N1CCn2c3c(c4cc(C(=O)O)ccc42)CCCC31]<br>184 | 3-Acetyl-2,3,3a,4,5,6-hexahydro-1H-pyrazino[3,2,1-jk]carbazole-8-carboxylic acid | >10 | * |
| 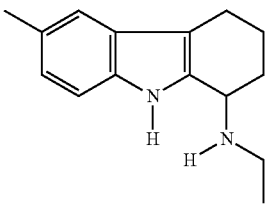 [SMILES: CCNC1CCCc2c1[nH]c1ccc(C)cc21]<br>185 | Ethyl-(6-methyl-2,3,4,9-tetrahydro-1H-carbazol-1-yl)-amine | >10 | * |
| 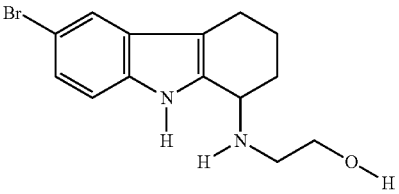 [SMILES: OCCNC1CCCc2c1[nH]c1ccc(Br)cc21]<br>186 | 2-(6-Bromo-2,3,4,9-tetrahydro-1H-carbazol-1-ylamino)-ethanol hydrochloride | 12.16 | * |
| 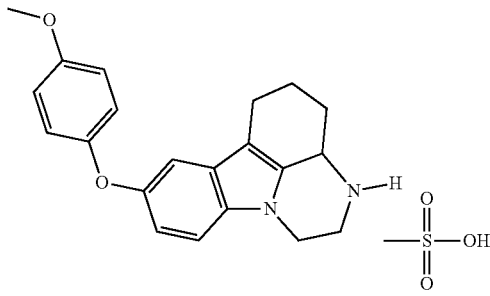<br>187 | 8-(4-Methoxy-phenoxy)-2,3,3a,4,5,6-hexahydro-1H-pyrazino[3,2,1-jk]carbazole methanesulfonic acid | 18 | * |
| 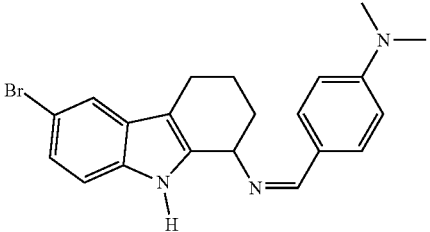 [SMILES: CN(C)c1ccc(/C=N\C2CCCc3c2[nH]c2ccc(Br)cc32)cc1]<br>188 | | | |

TABLE 1-continued

| Compound | Compound Name | LCMS [M + H] | RT (min) | MW | ELISA Activity EC50 (uM) |
|---|---|---|---|---|---|
| 191 | | 372.23 (M − H) | 3.47 | 373.23 | ***** |
| 192 | | 356.40 | 4.33 | 356.26 | ***** |
| 193 | | 342.36 | 3.85 | 342.23 | **** |
| 194 | | 398.34 | 4.10 | 398.29 | ***** |

TABLE 1-continued
| | | | | |
|---|---|---|---|---|
| 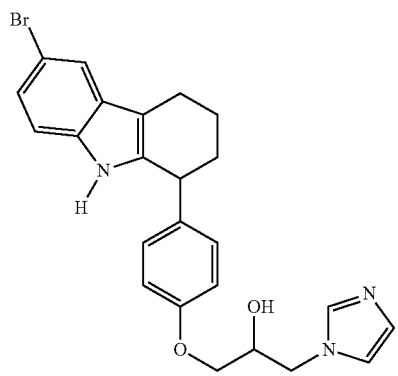 195 | 466.39 | 2.77 | 466.37 | ***** |
| 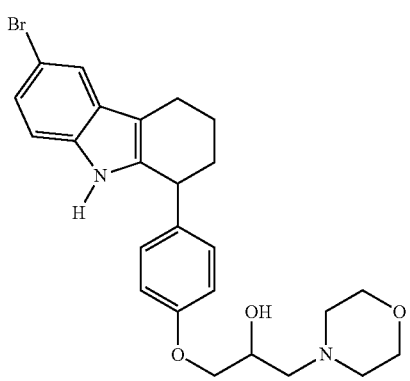 196 | 485.41 | 2.70 | 485.41 | ***** |
| 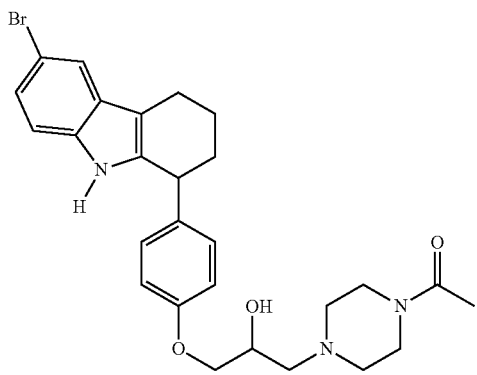 197 | 526.42 | 2.92 | 526.46 | ***** |

TABLE 1-continued
| | | | | |
|---|---|---|---|---|
| 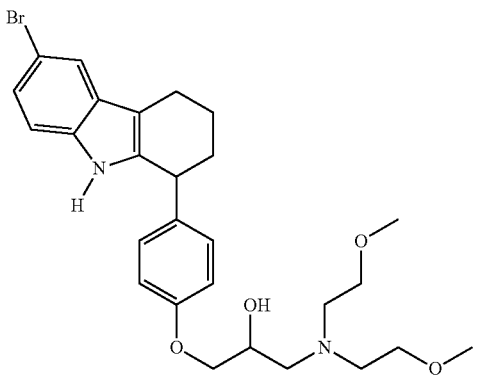  198 | 531.45 | 3.12 | 531.47 | ***** |
| 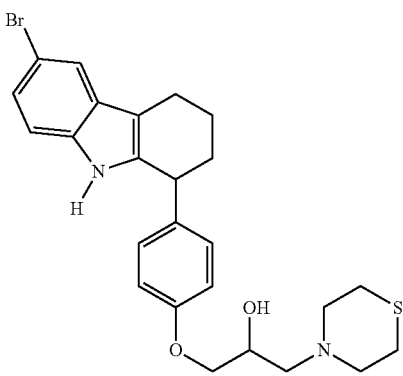  199 | 501.38 | 3.07 | 501.47 | ***** |
| 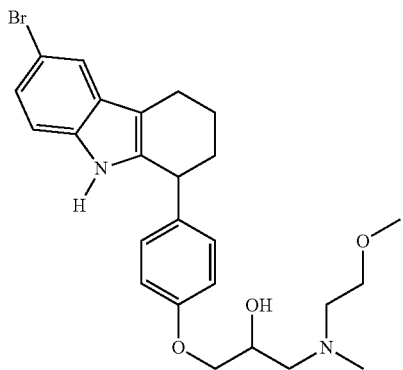  200 | 487.40 | 3.02 | 487.42 | ***** |
| 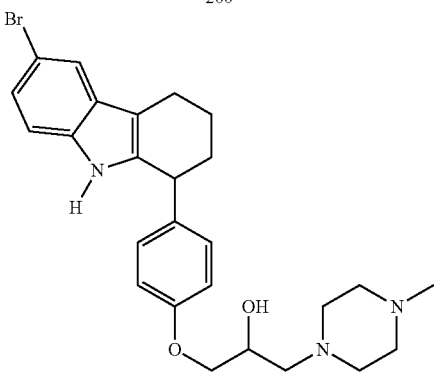  201 | 498.42 | 2.77 | 498.45 | **** |

TABLE 1-continued
| | | | | |
|---|---|---|---|---|
| 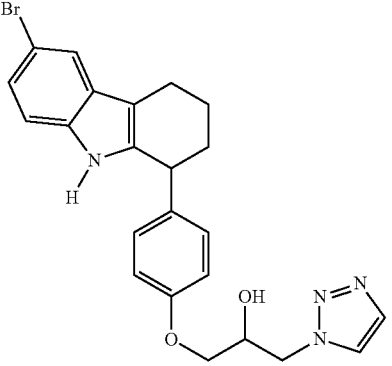 [SMILES: OC(COc1ccc(C2CCCc3c2[nH]c2ccc(Br)cc32)cc1)Cn1ccnn1] 202 | 467.35 | 3.68 | 467.35 | ***** |
| 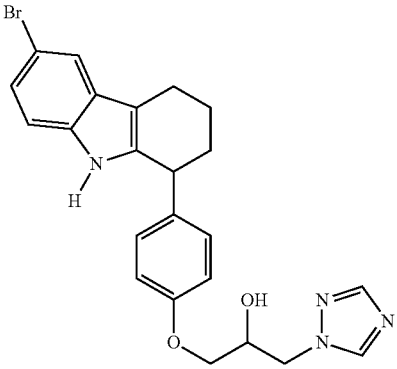 203 | 467.35 | 3.60 | 467.35 | **** |
| 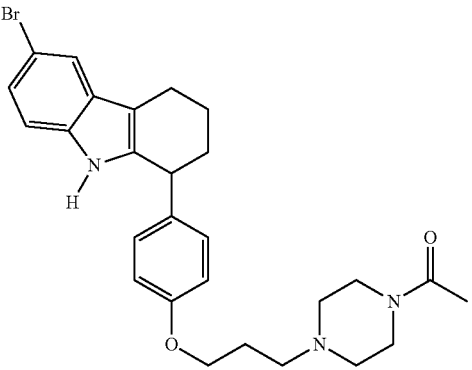 [SMILES: CC(=O)N1CCN(CCCOc2ccc(C3CCCc4c3[nH]c3ccc(Br)cc43)cc2)CC1] 204 | 510.33 | 2.57 | 510.466 | **** |
| 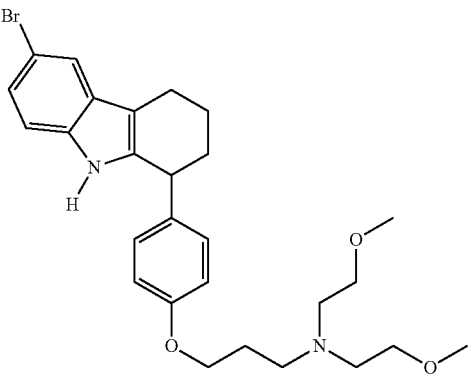 [SMILES: COCCN(CCCOc1ccc(C2CCCc3c2[nH]c2ccc(Br)cc32)cc1)CCOC] 205 | 516.36 | 2.72 | 515.48 | **** |

TABLE 1-continued
| | | | | |
|---|---|---|---|---|
| 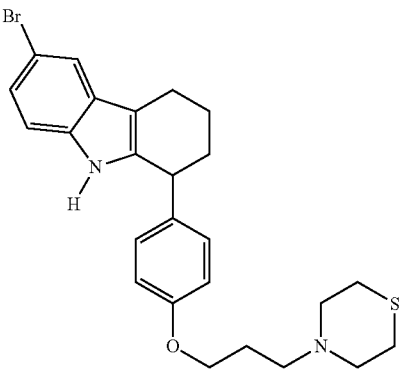 [SMILES: Brc1ccc2[nH]c3c(c2c1)CCCC3c1ccc(OCCCN2CCOCC2)cc1] 206 | 485.30 | 2.70 | 485.48 | ***** |
| 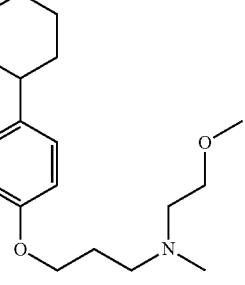 207 | 471.32 | 2.63 | 471.43 | **** |
| 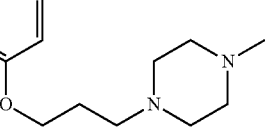 208 | 483.34 | 2.50 | 482.46 | *** |
| 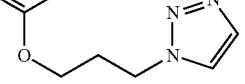 209 | 451.29 | 3.70 | 451.36 | ***** |

TABLE 1-continued
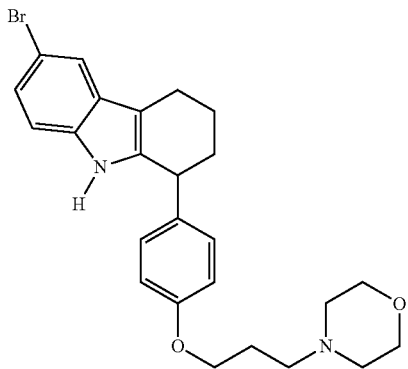
210
469.29 2.62 469.41 *****
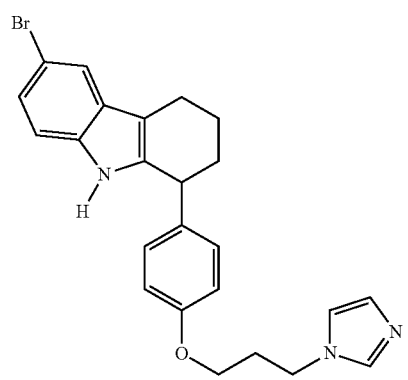 [SMILES: Brc1ccc2[nH]c3c(c2c1)CCCC3c1ccc(OCCCn2ccnc2)cc1]
211
450.28 2.63 450.37 *****
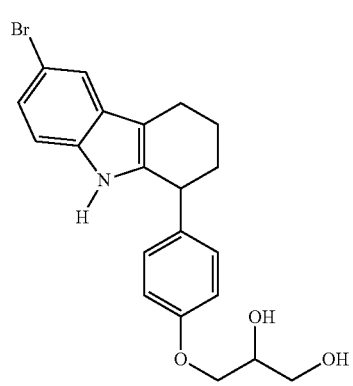 [SMILES: OCC(O)COc1ccc(C2CCCc3c2[nH]c2ccc(Br)cc32)cc1]
212
416.47 3.28 416.31 *****
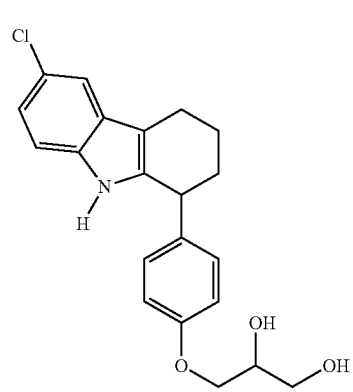 [SMILES: OCC(O)COc1ccc(C2CCCc3c2[nH]c2ccc(Cl)cc32)cc1]
213
372.36 3.25 371.86 ****

TABLE 1-continued

| Structure | MW | RT | MS | Activity |
|---|---|---|---|---|
| 214 | 482.59 | 2.42 | 482.01 | *** |
| 215 | 441.51 | 2.47 | 440.96 | **** |
| 216 | 487.57 | 2.57 | 487.03 | **** |
| 217 | 457.51 | 2.52 | 457.03 | **** |

TABLE 1-continued
| | | | | |
|---|---|---|---|---|
| 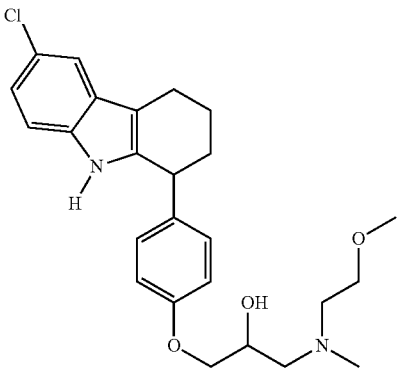 [SMILES: COCCN(C)CC(O)COc1ccc(C2CCCc3c2[nH]c2ccc(Cl)cc32)cc1] 218 | 443.55 | 2.48 | 442.98 | **** |
| 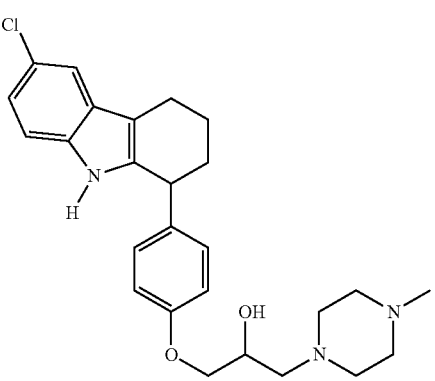 [SMILES: CN1CCN(CC(O)COc2ccc(C3CCCc4c3[nH]c3ccc(Cl)cc43)cc2)CC1] 219 | 454.58 | 2.35 | 454.00 | **** |
| 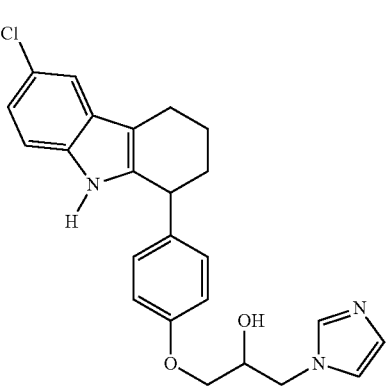 [SMILES: OC(COc1ccc(C2CCCc3c2[nH]c2ccc(Cl)cc32)cc1)Cn1ccnc1] 220 | 422.50 | 2.49 | 421.92 | **** |
| 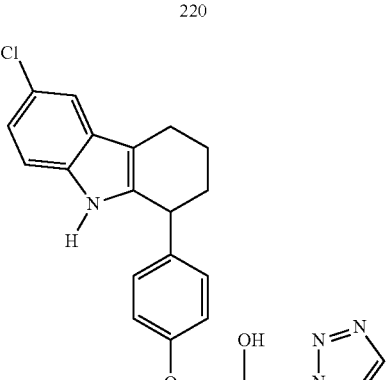 221 | 423.51 | 3.35 | 422.91 | **** |

US 9,271,960 B2
151 152
TABLE 1-continued
| | | | | |
|---|---|---|---|---|
| 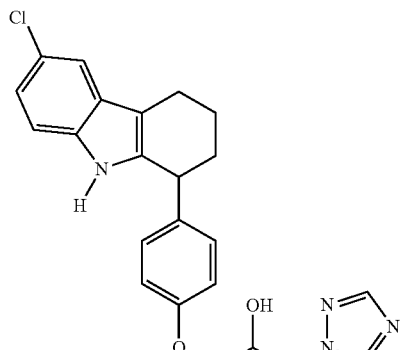<br>222 | 423.51 | 3.28 | 422.91 | *** |
| 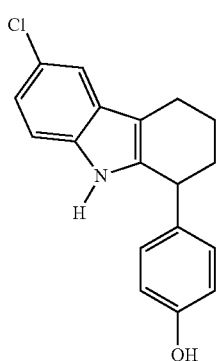 [SMILES: Oc1ccc(C2CCCc3c2[nH]c2ccc(Cl)cc32)cc1]<br>223 | 298.27 | 3.65 | 297.78 | *** |
| 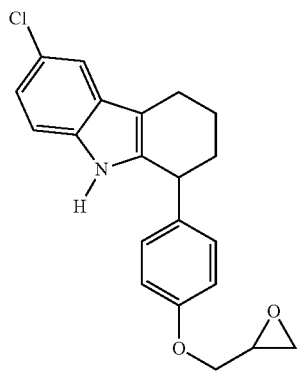 [SMILES: Clc1ccc2[nH]c3c(c2c1)CCCC3c1ccc(OCC2CO2)cc1]<br>224 | 354.45 | 3.82 | 353.84 | ***** |
| 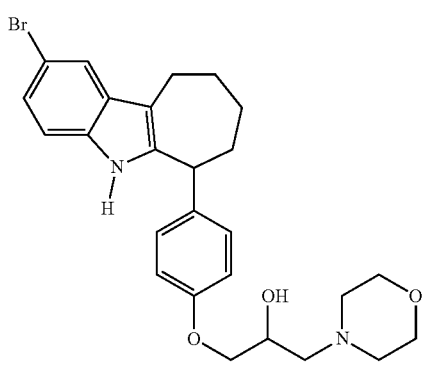 [SMILES: OC(COc1ccc(C2CCCCc3c2[nH]c2ccc(Br)cc32)cc1)CN1CCOCC1]<br>225 | 499.42 | 2.40 | 499.44 | *** |

TABLE 1-continued
| | | | | |
|---|---|---|---|---|
| 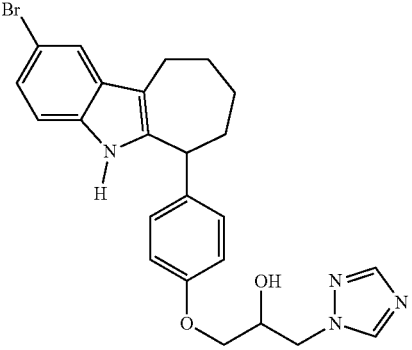 [SMILES: OC(COc1ccc(C2CCCCc3c2[nH]c2ccc(Br)cc32)cc1)Cn1cncn1]226 | 481.38 | 3.63 | 481.3851 | *** |
| 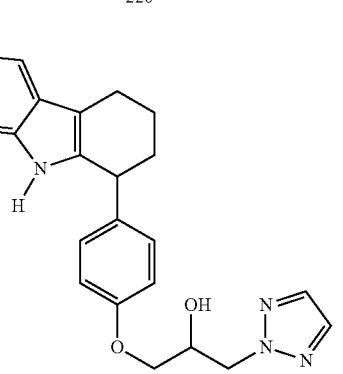227 | 465.22 (ES−) | 3.90 | 467.3585 | ***** |
| 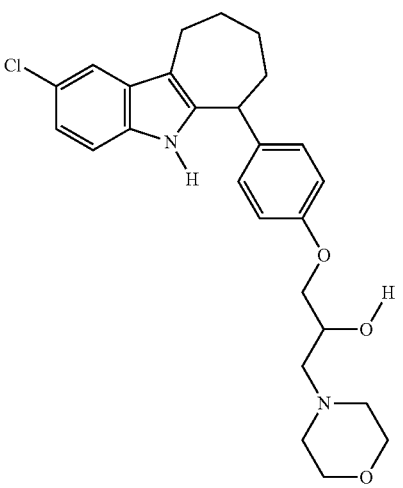 [SMILES: OC(COc1ccc(C2CCCCc3c2[nH]c2ccc(Cl)cc32)cc1)CN1CCOCC1]228 | 455.5 | 4.68 | 454.99 | **** |
| 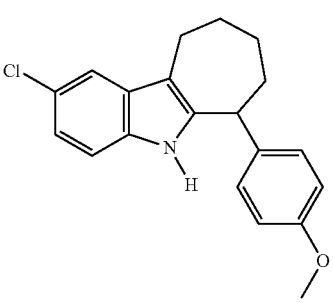 [SMILES: COc1ccc(C2CCCCc3c2[nH]c2ccc(Cl)cc32)cc1]229 | 326.5 | 5.58 | 325.83 | **** |

TABLE 1-continued
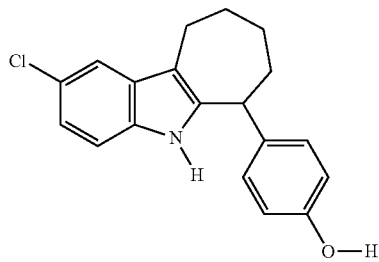 [SMILES: Oc1ccc(C2CCCCc3c2[nH]c2ccc(Cl)cc32)cc1]
230
312.0  5.08  311.81  *****
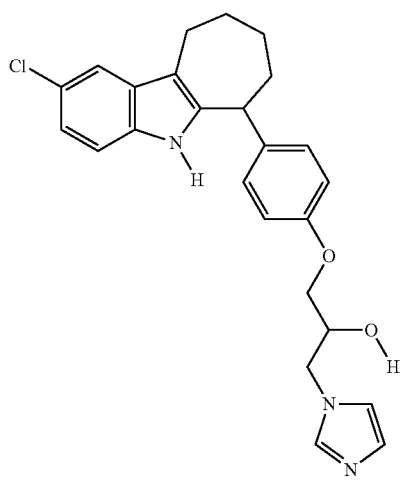 [SMILES: OC(COc1ccc(C2CCCCc3c2[nH]c2ccc(Cl)cc32)cc1)Cn1ccnc1]
231
436.5  4.79  435.95  *****
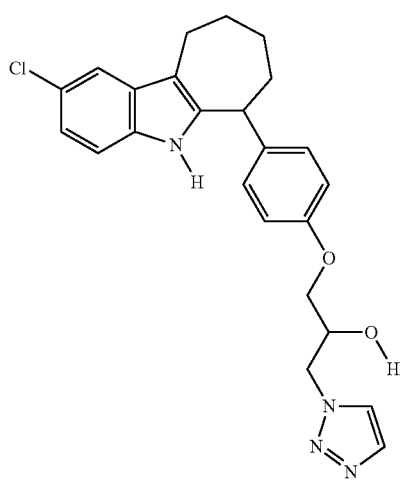 [SMILES: OC(COc1ccc(C2CCCCc3c2[nH]c2ccc(Cl)cc32)cc1)Cn1ccnn1]
232
437.5  4.99  436.93  ****

TABLE 1-continued
| | | | |
|---|---|---|---|
| 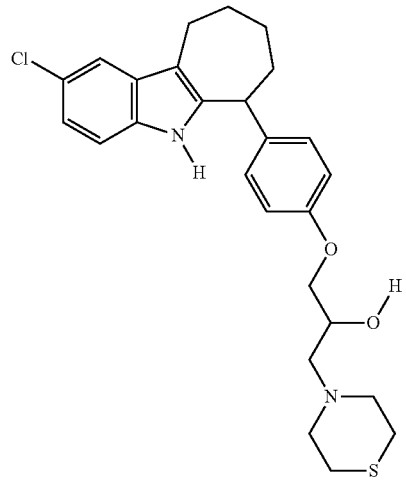 [SMILES: OC(COc1ccc(C2CCCCc3c2[nH]c2ccc(Cl)cc32)cc1)CN1CCSCC1]233 | 471.0 | 5.11 | 471.06 | ***** |
| 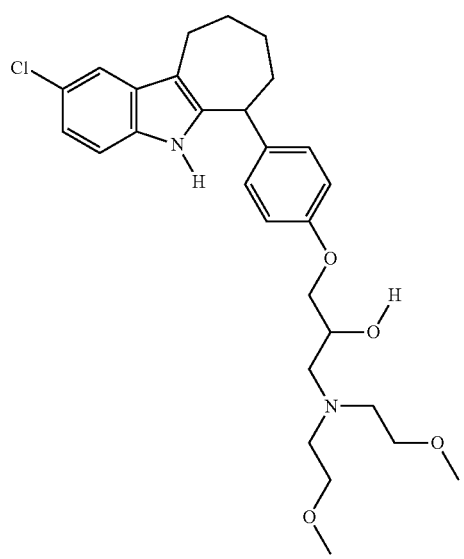 [SMILES: COCCN(CCOC)CC(O)COc1ccc(C2CCCCc3c2[nH]c2ccc(Cl)cc32)cc1]234 | 501.5 | 5.32 | 501.06 | ***** |
| 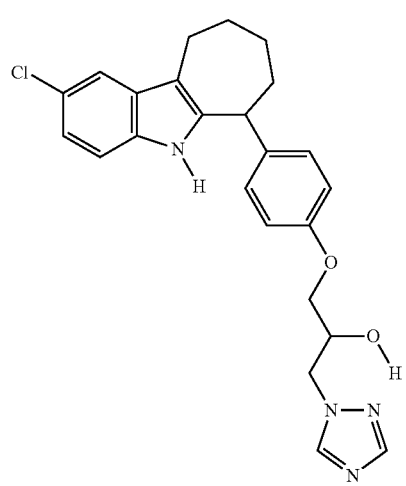 [SMILES: OC(COc1ccc(C2CCCCc3c2[nH]c2ccc(Cl)cc32)cc1)Cn1cncn1]235 | 437.0 | 4.91 | 436.93 | **** |

TABLE 1-continued

| Structure | | | |
|---|---|---|---|
| 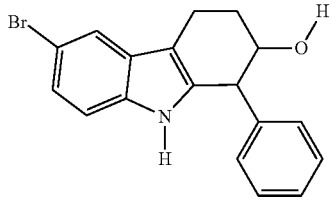 [SMILES: OC1CCc2c([nH]c3ccc(Br)cc23)C1c1ccccc1] 236 | 342.24 (ES+) | 3.69 | 342.24 | *** |
| 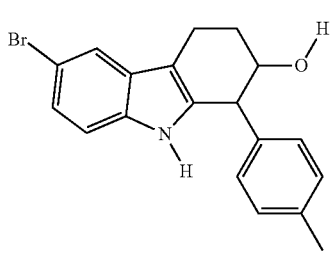 [SMILES: Cc1ccc(C2c3[nH]c4ccc(Br)cc4c3CCC2O)cc1] 237 | 354.17 | 3.77 | 356.26 | ** |
| 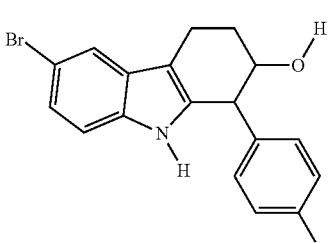 238 | 374.09 | 3.86 | 376.68 | ***** |
| 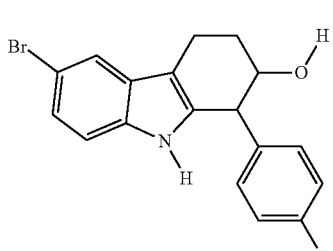 239 | 358.14 | 3.67 | 360.23 | ***** |

Example 3

Compounds of the Invention Inhibit VEGF Expression and Tumor Growth in an In Vivo Tumor Growth PD Model Compounds of the invention also showed activity in the following pharmacodynamic model that assesses intratumor VEGF levels. Briefly, HT1080 cells (a human fibrosarcoma cell line) were implanted subcutaneously in nude mice. After seven days, mice were administrated compounds orally at a desired dosage range, e.g., 200 mg/kg/day, for seven days. The tumors were then excised from mice and homogenized in Tris-HCl buffer containing proteinase inhibitors. Intratumor VEGF levels were subsequently measured using a human VEGF ELISA kit (R&D System). Protein concentrations of the homogenates were measured with a Bio-Rad Protein assay kit and intratumor VEGF levels were normalized to the protein concentrations.

Preferred compounds of the invention, when used for one week on a 100 $mm^3$ tumor, will generally inhibit tumor growth by at least 50%, as compared to the vehicle-treated control groups (data not shown).

The compounds shown below in Table 2 numbered 156-188 are commercially available. These compounds are generally known as drug-like compounds, and were purchased for the purpose of determining new uses of the compounds. Their commercial information is as follows:

TABLE 2
| Commercially Available Compounds | | |
|---|---|---|
| Compound | Supplier Information | Catalog Information |
| 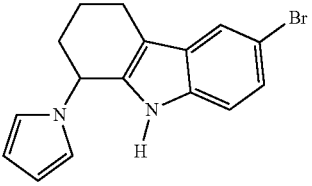 156 | ChemBridge | 5920301 |
| 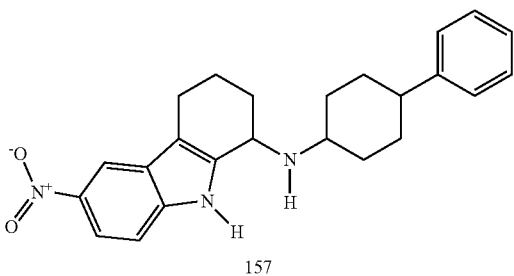 [SMILES: O=[N+]([O-])c1ccc2[nH]c3c(c2c1)CCCC3NC1CCC(c2ccccc2)CC1] 157 | ChemBridge | 5781451 |
| 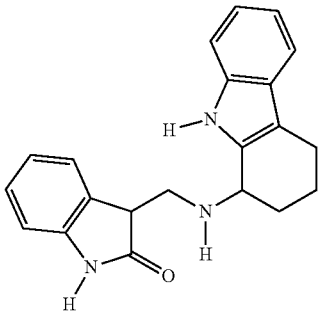 158 | ChemBridge | 5666718 |
| 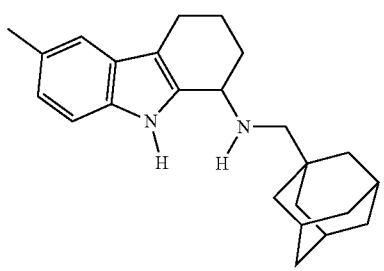 159 | ChemBridge | |
| 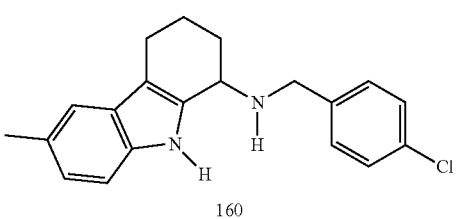 [SMILES: Cc1ccc2[nH]c3c(c2c1)CCCC3NCc1ccc(Cl)cc1] 160 | ChemBridge | 5219670 |

TABLE 2-continued

| Commercially Available Compounds | | |
|---|---|---|
| Compound | Supplier Information | Catalog Information |
| 161 | ChemBridge | 5303009 |
| 162 | ChemBridge | 5133291 |
| 163 | ChemBridge | 5309760 |
| 164 | ChemDiv | 8010-1969 |

TABLE 2-continued

Commercially Available Compounds

| Compound | Supplier Information | Catalog Information |
|---|---|---|
| 165 | ChemBridge | 5259158 |
| 166 | Tripos | 2000-13782 |
| 167 | Chem Div | 3606-0172 |
| 168 (HCl salt) | ChemDiv | 3474-0005 |

TABLE 2-continued

Commercially Available Compounds

| Compound | Supplier Information | Catalog Information |
|---|---|---|
| 169 (HCl salt) | ChemDiv | 0075-0033 |
| 170 | ChemDiv | 3606-0516 |
| 171 | Tripos | 2000-12661 |
| 172 | Tripos | 2000-00255 |
| 173 | Tripos | 2000-13573 |
| 174 | Tripos | 2000-13758 |

TABLE 2-continued
Commercially Available Compounds
| Compound | Supplier Information | Catalog Information |
|---|---|---|
| 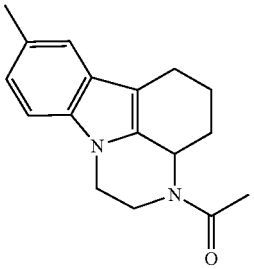<br>175 | ChemBridge | 5133287 |
| 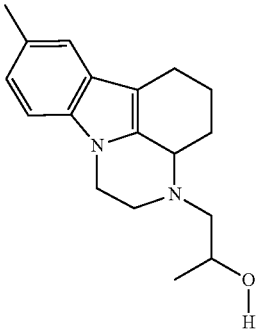<br>176 | ChemBridge | 5259311 |
| 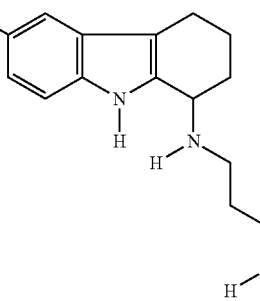<br>177 | ChemBridge | 5257392 |
| 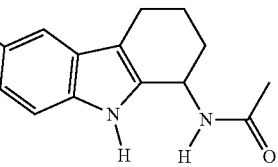<br>178 | ChemBridge | 5373714 |
| 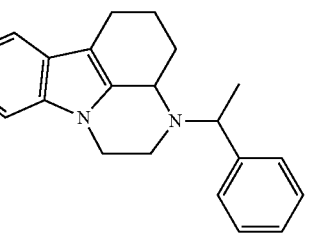<br>179 | ChemBridge | 5475174 |

TABLE 2-continued
Commercially Available Compounds
| Compound | Supplier Information | Catalog Information |
|---|---|---|
| 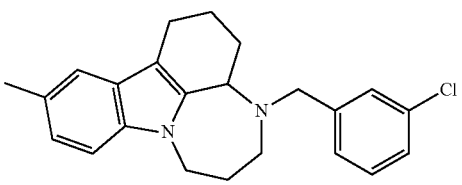<br>180 | ChemBridge | 5782156 |
| 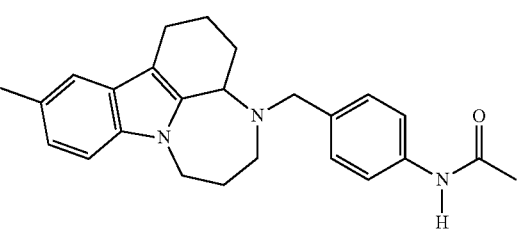<br>181 | ChemBridge | 5782195 |
| 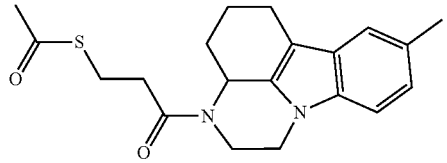<br>182 | ChemBridge | 5915049 |
| 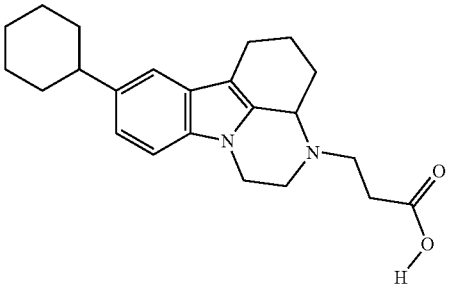<br>183 | ChemBridge | 5920645 |
| 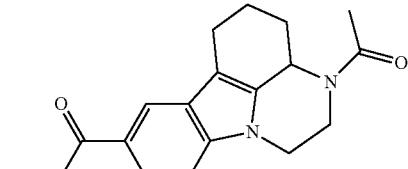<br>184 | ChemBridge | 7111705 |
| 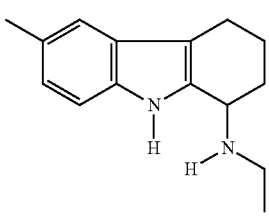<br>185 | ChemBridge | 5277652 |

TABLE 2-continued

Commercially Available Compounds

| Compound | Supplier Information | Catalog Information |
|---|---|---|
| 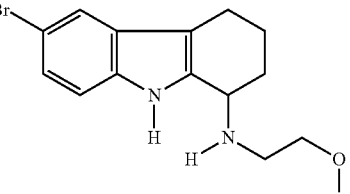 186 | ChemDiv | 3474-0005 |
| 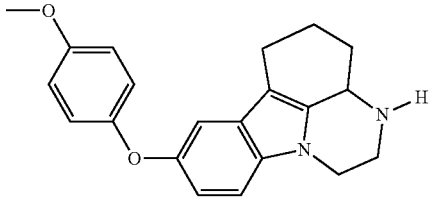 187 | ChemDiv | 3606-0161 |
| 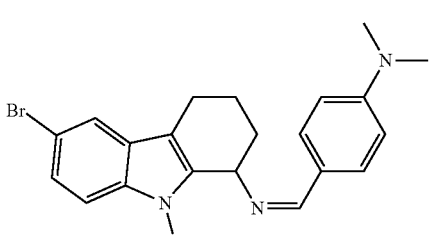 188 | ChemDiv | 8005-8953 |

REFERENCES

1. Carmeliet P. Angiogenesis in health and disease. Nat Med. 9(6):653-60, 2003.
2. Ferrara N. Role of vascular endothelial growth factor in physiologic and pathologic angiogenesis: therapeutic implications. Semin Oncol. 29(6 Suppl 16):10-4, 2002.
3. Witmer A N, Vrensen G F, Van Noorden C J, Schlingemann R O. Vascular endothelial growth factors and angiogenesis in eye disease. Prog Retin Eye Res. 22(1):1-29, 2003.
4. Clark A and Yorio T. Ophthalmic drug discovery. Nat. Rev. Drug discovery. 2:448-459, 2003.
5. Ferrara N, Alitalo K. Clinical applications of angiogenic growth factors and their inhibitors. Nat Med. 5(12):1359-64, 1999
6. Kerbel R, Folkman J. Clinical translation of angiogenesis inhibitors. Nat Rev Cancer. 2(10):727-39, 2002
7. Rofstad E K, Halsor E F. Vascular endothelial growth factor, interleukin 8, platelet-derived endothelial cell growth factor, and basic fibroblast growth factor promote angiogenesis and metastasis in human melanoma xenografts. Cancer Res. 60(17):4932-8, 2000.
8. Leung D W, Cachianes G, Kuang W J, Goeddel D V, Ferrara N. Vascular endothelial growth factor is a secreted angiogenic mitogen. Science 246:1306-1309, 1989.
9. Plouet J, Schilling J, Gospodarowicz D. Isolation and characterization of a newly identified endothelial cell mitogen produced by AtT-20 cells. EMBO J. 8:3801-3806, 1989.
10. Connolly D T, Olander J V, Heuvelman D, Nelson R, Monsell R, Siegel N, Haymore B L, Leimgruber R, Feder J. Human vascular permeability factor. Isolation from U937 cells. J. Biol. Chem 0.264:20017-20024, 1989.
11. Tischer E, Mitchell R, Hartman T, Silva M, Godpodarowicz D, Fiddes J C, and Abraham J A. The human gene for vascular endothelial growth factor. Multiple protein forms are encoded through alternative exon splicing. J. Biol. Chem. 266:11947-11954, 1991.
12. Ortega N, Hutchings H, and Plouet J. Signal relays in the VEGF system. Front. Biosci. 4:D141-52, 1999.
13. Sato Y, Kanno S, Oda N, Abe M, Ito M, Shitara K and Shibuya M. Properties of two VEGF receptors, Flt-1 and KDR, in signal transduction. Annals of New York Academy of Science, 902:201-207, 2000.
14. Shalaby F. et al. Failure of blood island formation and vasculogenesis in Flk-1-deficient mice. Nature 376: 62-66, 1995.
15. Fong G H, Rossant J, Gertenstein M and Breitman M L. Role of the Flt-1 receptor tyrosine kinase in regulating assembly of vascular endothelium. Nature 376: 66-70, 1995.
16. Folkman J. Tumor angiogenesis: therapeutic implications. N Engl J Med. 18; 285(21):1182-6. 1971.
17. Matter A. Tumor angiogenesis as a therapeutic target. Drug Discovery Today 6:1005-1024, 2001.
18. Yancopoulos G D, Davis S, Gale N W, Rudge J S, Wiegand S J and Holash J. Vascular-specific growth factors and blood vessel formation. Nature 407: 242-248, 2000.

19. Hanahan D and Folkman J. Patterns and emerging mechanisms of the angiogenic switch during tumorigenesis. Cell 86:353-364, 1996.

20. Gasparini G, Tai M, Gion M, Verderio P, Dittadi R, Hanatani M, Matsubara Vinante O, Bonoldi E, Boracchi P, Gatti C, Suzuki H, Tominaga T. Prognostic significance of vascular endothelial growth factor protein in node-negative breast carcinoma. J. Natl. Cancer Inst. 89:139-147, 1997.

21. Ferrara N and Davis-Smyth T. The biology of vascular endothelial growth factor. Endocr. Rev. 18: 4-25, 1997.

22. Dirix L Y, Vermeulen P B, Pawinski A, Prove A, Benoy I, De Pooter C, Martin M, Van Oosterom A T. Elevated levels of the angiogenic cytokines basic fibroblast growth factor and vascular endothelial growth factor in sera of cancer patients. Br. J. Cancer 76:238-243, 1997.

23. Carmeliet P, Ferreira V, Breier G, Pollefeyt S, Kieckens L, Gertsenstein M, Fahrig M, Vandenhoeck A, Harpal K, Eberhardt C, Declercq C, Pawling J, Moons L, Cohen D, Risau W, Nagy A. Abnormal blood vessel development and lethality in embryos lacking a single VEGF allele. Nature 380:435-439, 1996.

24. Kim K J, Li B, Wine J, Armanini M, Gillett N, Phillips H S, and Ferrara N. Inhibition of vascular endothelial growth factor-induced angiogenesis suppresses tumor growth in vivo. Nature 362: 841-844, 1993.

25. Hichlin D J, Witte L, Zhu Z, Liao F, Wu Y, Li Y. and Bohlen P. Monoclonal antibody strategies to block angiogenesis. Drug Discovery Today 6: 517-528, 2001.

26. Lin P, Sankar S, Shan S, Dewhirst M W, Polverini P J, Quinn T Q, Peters K G. Inhibition of tumor growth by targeting tumor endothelium using a soluble vascular endothelial growth factor receptor. Cell Growth Differ. 9(1):49-58, 1998.

27. Borgstrom P, Bourdon M A, Milan K J, Sriramarao P, Ferrara N. Neutralizing anti-vascular endothelial growth factor antibody completely inhibits angiogenesis and growth of human prostate carcinoma micro tumors in vivo. Prostate 35:1-10, 1998.

28. Yuan F, Chen Y, Dellian M, Safabakhsh N, Ferrara N, Jain R K. Time-dependent vascular regression and permeability changes in established human tumor xenografts induced by an anti-vascular endothelial growth factor/vascular permeability factor antibody. Proc. Natl. Acad. Sci. USA, 93:14765-14770, 1996.

29. Funatsu H, Yamashita H, Ikeda T, Nakanishi Y, Kitano S, Hori S. Angiotensin II and vascular endothelial growth factor in the vitreous fluid of patients with diabetic macular edema and other retinal disorders. Am J Ophthalmol. 133(4): 537-43, 2002.

30. Lip P L, Blann A D, Hope-Ross M, Gibson J M, Lip G Y. Age-related macular degeneration is associated with increased vascular endothelial growth factor, hemorheology and endothelial dysfunction. Ophthalmology. 108(4):705-10, 2001.

31. Schwesinger C, Yee C, Rohan R M, Joussen A M, Fernandez A, Meyer T N, Poulaki V, Ma J J, Redmond T M, Liu S, Adamis A P, D'Amato R J. Intrachoroidal neovascularization in transgenic mice overexpressing vascular endothelial growth factor in the retinal pigment epithelium. Am J Pathol. 158(3):1161-72, 2001

32. Ohno-Matsui K, Hirose A, Yamamoto S, Saikia J, Okamoto N, Gehlbach P, Duh E J, Hackett S, Chang M, Bok D, Zack D J, Campochiaro P A. Inducible expression of vascular endothelial growth factor in adult mice causes severe proliferative retinopathy and retinal detachment. Am J Pathol. 2002 February; 160(2):711-9, 2002.

33. Eyetech Study Group. Preclinical and phase 1A clinical evaluation of an anti-VEGF pegylated aptamer (EYE001) for the treatment of exudative age-related macular degeneration. 22(2):143-52, 2002.

34. Krzystolik M G, Afshari M A, Adamis A P, Gaudreault J, Gragoudas E S, Michaud N A, Li W, Connolly E, O'Neill C A, Miller J W. Prevention of experimental choroidal neovascularization with intravitreal anti-vascular endothelial growth factor antibody fragment. Arch Ophthalmol. 120(3):338-46, 2002.

35. Shen W Y, Garrett K L, Wang C G, Zhang K, Ma Z Z, Constable I J, Rakoczy P E. Preclinical evaluation of a phosphorothioate oligonucleotide in the retina of rhesus monkey. Lab Invest. 2002 February; 82(2):167-82, 2002.

36. Honda M, Sakamoto T, Ishibashi T, Inomata H, Ueno H. Experimental subretinal neovascularization is inhibited by adenovirus-mediated soluble VEGF/flt-1 receptor gene transfection: a role of VEGF and possible treatment for SRN in age-related macular degeneration. Gene Ther. 7(11):978-85, 2000.

37. Saishin Y, Saishin Y, Takahashi K, Lima e Silva R, Hylton D, Rudge J S, Wiegand S J, Campochiaro P A. VEGF-TRAP(R1R2) suppresses choroidal neovascularization and VEGF-induced breakdown of the blood-retinal barrier. J Cell Physiol. 195(2):241-8, 2003.

38. Maxwell P H, Wiesener M S, Chang G W, Clifford S C, Vaux E C, Cockman M E, Wykoff C C, Pugh C W, Maher E R, Ratcliffe P J. The tumour suppressor protein VHL targets hypoxia-inducible factors for oxygen-dependent proteolysis. Nature 399:271-275, 1999.

39. Rak J, Mitsuhashi Y, Sheehan C, Tamir A, Viloria-Petit A, Filmus J, Mansour S J, Ahn N G, Kerbel R S. Oncogenes and tumor angiogenesis: differential modes of vascular endothelial growth factor up-regulation in ras-transformed epithelial cells and fibroblasts. Cancer Res. 60:490-498, 2000.

40. Ikeda E, Achen M G, Breier G, Risau W. Hypoxia-induced transcriptional activation and increased mRNA stability of vascular endothelial growth factor in C6 glioma cells. J. Biol. Chem. 270:19761-19766, 1995.

41. Stein I, Itin A, Einat P, Skaliter R, Grossman Z and Keshet E. Translation of Vascular endothelial growth factor mRNA by internal ribosome entry: implication for translation under hypoxia. Mol. Cell. Biol. 18: 3112-3119, 1998.

42. Levy A P, Levy N S, and Goldberg M A. Post-transcriptional regulation of vascular endothelial growth factor by hypoxia. J. Biol. Chem. 271: 2746-2753, 1996.

43. Liu Y, Cox S R, Morita T, Kourembanas S. Hypoxia regulates vascular endothelial growth factor gene expression in endothelial cells. Identification of a 5' enhancer. Circ. Res. 77:638-643, 1995.

44. Semenza G L. Regulation of mammalian 02 homeostasis by hypoxia-inducible factor 1. Annu. Rev. Cell. Dev. Biol, 5:551-578, 1999.

45. Goldberg I, Furneaux H and Levy A P. A 40 bp element that mediates stabilization of VEGF mRNA by HuR. J. Biol. Cell. J Biol Chem. 2002 Apr. 19; 277(16):13635-40, 2002.

46. Kraggerud S M, Sandvik J A, Pettersen E O. Regulation of protein synthesis in human cells exposed to extreme hypoxia. Anticancer Res. 15:683-686, 1995.

47. Huez I, Creancier L, Audigier S, Gensac M C, Prats A C and Prats H. Two independent internal ribosome entry sites are involved in translation initiation of vascular endothelial growth factor mRNA. Mol. Cell. Biol. 18: 6178-6190, 1998.

48. Akiri G, Nahari D, Finkelstein Y, Le S Y, Elroy-Stein O and Levi B Z. Regulation of vascular endothelial growth factor (VEGF) expression is mediated by internal initiation of translation and alternative initiation of transcription. Oncogene 17: 227-236, 1998.

49. Zhu Z and Witte L. Inhibition of tumor growth and metastasis by targeting tumor-associated angiogenesis with antagonists to the receptors of vascular endothelial growth factor. Invest. New Drugs 17:195-212, 1999.

50. Carmeliet P and Jain R K. Angiogenesis in cancer and other diseases. Nature 407:249-257, 2000.

51. Millauer B, Shawver L K, Plate K H, Risau W and Ullrich A. Glioblastoma growth inhibited in vivo by a dominant-negative Flk-1 mutant. Nature 367: 576-579, 1994.

52. Fong T A, et al. SU5416 is a potent and selective inhibitor of the vascular endothelial growth factor receptor (Flk-1/KDR) that inhibits tyrosine kinase catalysis, tumor vascularizatiion, and growth of multiple tumor types. Cancer Res. 59: 99-106, 1999.

53. Geng L, Donnelly E, McMahon G, Lin P C, Sierra-Rivera E, Oshinka H, and Hallahan D E. Inhibition of vascular endothelial growth factor receptor signaling leads to reversal of tumor resistance to radiotherapy. Cancer Res. 61: 2413-2419, 2001.

54. Ryan, A. M., Eppler, D. B., Hagler, K. E., Bruner, R. H., Thomford, P. J., Hall, R. L., Shopp, G. M. and O'neill, C. A. Preclinical safety evaluation of rhuMAbVEGF, an antiangiogenic humanized antibody. Toxicol. Pathol., 27: 78-86, 1999.

55. Ferrara, N., Chen, H., Davis-Smyth, T., Gerber, H-P., Nguyen, T-N., Peers, D., Chisholm, V., Hffian, K. J., and Schwall, R. H. Vascular endothelial growth factor is essential for corpus luteum angiogenesis. Nat. Med., 4: 336-340, 1998.

56. Holash J, Maisonpierre P C, Compton D, Boland P, Alexander C R, Zagzag D, Yancopoulos G D, Wiegand S J. Vessel cooption, regression, and growth in tumors mediated by angiopoietins and VEGF. Science 284:1994-1998, 1999.

57. Ozaki H, Seo M S, Ozaki K, Yamada H, Yamada E, Okamoto N, Hofmann F, Wood J M, Campochiaro P A. Blockade of vascular endothelial cell growth factor receptor signaling is sufficient to completely prevent retinal neovascularization. Am J Pathol. 156(2):697-707, 2000.

58. Reich S J, Fosnot J, Kuroki A, Tang W, Yang X, Maguire A M, Bennett J, Tolentino M J. Small interfering RNA (siRNA) targeting VEGF effectively inhibits ocular neovascularization in a mouse model. Mol Vis. 30; 9:210-6, 2003.

59. Asano M, Yukita A, Suzuki H. Wide spectrum of anti-tumor activity of a neutralizing monoclonal antibody to human vascular endothelial growth factor. Jpn J Cancer Res. 90(1):93-100, 1999.

60. Brekken R A, Overholser J P, Stastny V A, Waltenberger J, Minna J D, Thorpe P E. Selective inhibition of vascular endothelial growth factor (VEGF) receptor 2 (KDR/Flk-1) activity by a monoclonal anti-VEGF antibody blocks tumor growth in mice. Cancer Res. 60(18):5117-24, 2000.

61. Laird A D. et al. SU6668 is a potent antiangiogenic and antitumor agent that induces regression of established tumors. Cancer Res. 60(15):4152-60, 2000.

62. Wedge S R, Ogilvie D J, Dukes M, Kendrew J, Curwen J O, Hennequin L F, Thomas A P, Stokes E S, Curry B, Richmond G H, Wadsworth P F. ZD4190: an orally active inhibitor of vascular endothelial growth factor signaling with broad-spectrum antitumor efficacy. Cancer Res. 60(4):970-5, 2000.

63. Parry T J, Cushman C, Gallegos A M, Agrawal A B, Richardson M, Andrews L E, Maloney L, Molder V R, Wincott F E, Pavco P A. Bioactivity of anti-angiogenic ribozymes targeting Flt-1 and KDR mRNA. Nucleic. Acids. Res. 27:2569-2577, 1999.

64. Ellis L M, Liu. W, Wilson M. Down-regulation of vascular endothelial growth factor in human colon carcinoma cell lines by antisense transfection decreases endothelial cell proliferation. Surgery 120:871-878, 1996.

65. Filleur S, Courtin A, Ait-Si-Ali S, Guglielmi J, Merle C, Harel-Bellan A, Clezardin P, Cabon F. SiRNA-mediated Inhibition of Vascular Endothelial Growth Factor Severely Limits Tumor Resistance to Antiangiogenic Thrombospondin-1 and Slows Tumor Vascularization and Growth. Cancer Res. 63(14):3919-22, 2003.

66. Giles F J. Et al. Phase II study of SU5416—a small-molecule, vascular endothelial growth factor tyrosine-kinase receptor inhibitor—in patients with refractory myeloproliferative diseases. Cancer. 97(8):1920-8, 2003.

67. Sugimoto H, Hamano Y, Charytan D, Cosgrove D, Kieran M, Sudhakar A, Kalluri R. Neutralization of circulating vascular endothelial growth factor (VEGF) by anti-VEGF antibodies and soluble VEGF receptor 1 (sFlt-1) induces proteinuria. J Biol Chem. 278(15):12605-8, 2003.

68. Bergsland E. et al. A randomized phase II trial comparing rhuMAb VEGF (recombinant humanized mAb to vascular endothelial cell growth factor) plus 5-fluorouracil/leucovorin (FU/LV) to FU/LV alone in patients with metastatic colorectal cancer. American Society of Clinical Oncology 36$^{th}$ Annual Meeting, 20-23 May, 2000, New Orleans, La., USA, Abstract 939.

69. DeVore, R. F. et al. A randomized Phase II trial comparing rhuMAb VEGF (recombinant humanized mAb to vascular endothelial cell growth factor) plus Carboplatin/Paclitaxel (CP) to CP alone in patients with stage IIIB/IV NSCLC. American Society of Clinical Oncology 36$^{th}$ Annual Meeting, 20-23 May, 2000, New Orleans, La., USA, Abstract 1896

What is claimed is:

1. A method for inhibiting VEGF production in a subject, comprising administering to the subject a VEGF-inhibiting amount of a compound of Formula (Ia)

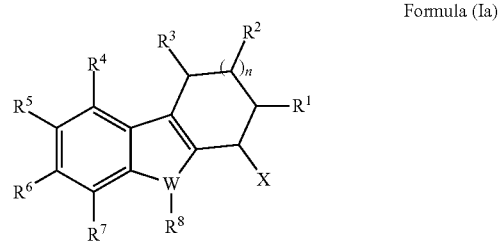

Formula (Ia)

or an enantiomer, a diastereomer, a pharmaceutically acceptable salt, or a mixture thereof, wherein:

(a) X is selected from the group consisting of:

a substituted or unsubstituted

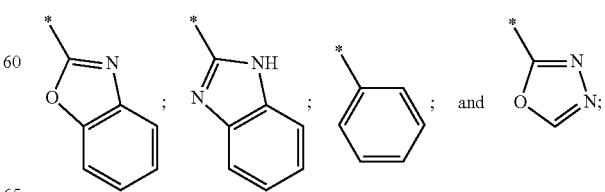

and $NR^9R^{10}$;

wherein NR⁹R¹⁰ is selected from the group consisting of: a substituted or unsubstituted

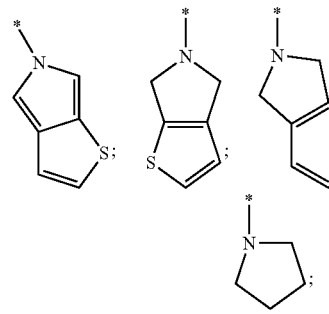

wherein X is optionally substituted with substituents selected from the group consisting of:

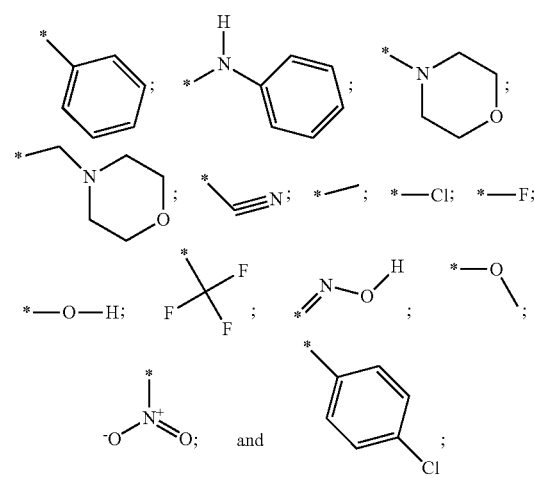

(b) $R^1$, $R^2$ and $R^3$ are each —H;
(c) n is 1 or 2;
(d) $R^4$, $R^6$ and $R^7$ are each independently —H, or halo;
(e) $R^5$ is independently —OH, substituted or unsubstituted $C_{1-6}$ alkyl, substituted or unsubstituted alkoxy, halo, haloalkyl, haloalkoxy, nitro, cyano, substituted or unsubstituted heterocyclic ring, substituted or unsubstituted amino, substituted or unsubstituted phenyl, substituted or unsubstituted phenoxy, substituted or unsubstituted cycloalkyl, substituted or unsubstituted alkenyl, substituted or unsubstituted alkynyl, or substituted or unsubstituted alkoxycarbonyl, or hydroxycarbonyl;
(f) $R^8$ is H; and
(g) W is N;
wherein the term "substituted" in $R^5$ denotes that a moiety has one or more hydrogen atoms replaced by one or more substituents selected from the group consisting of:

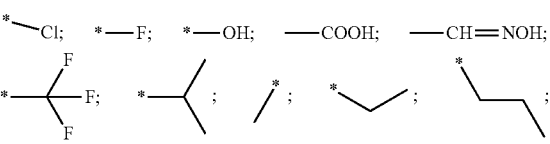

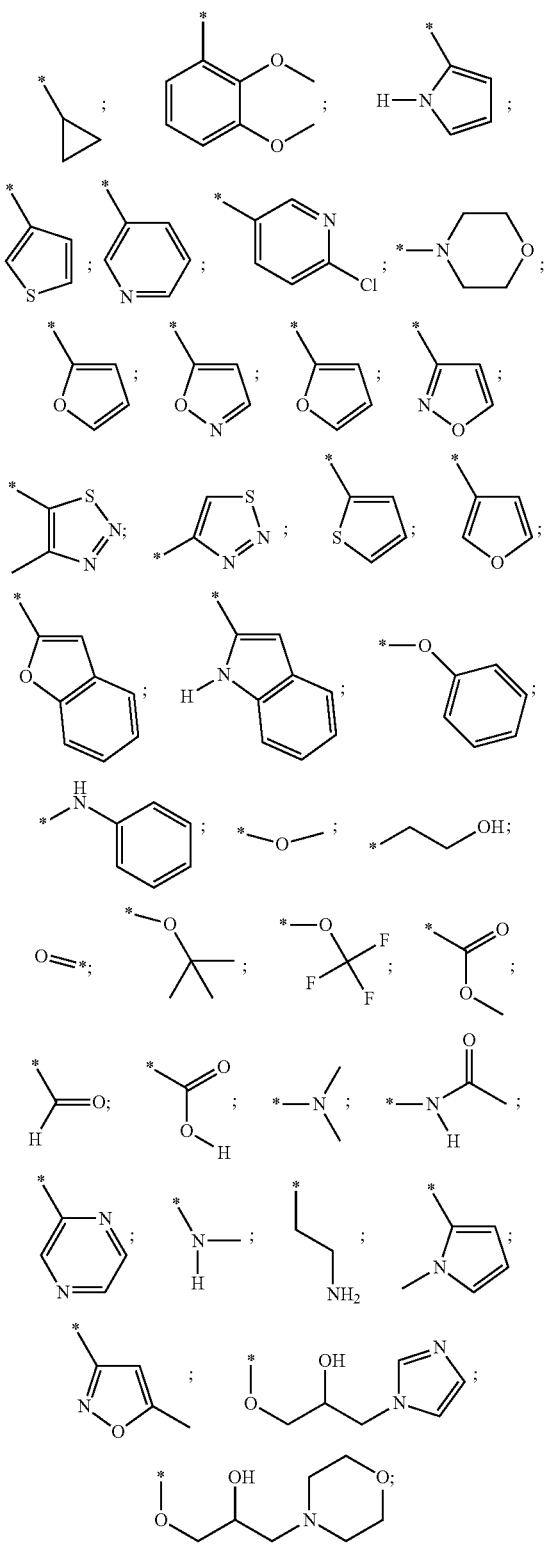

-continued

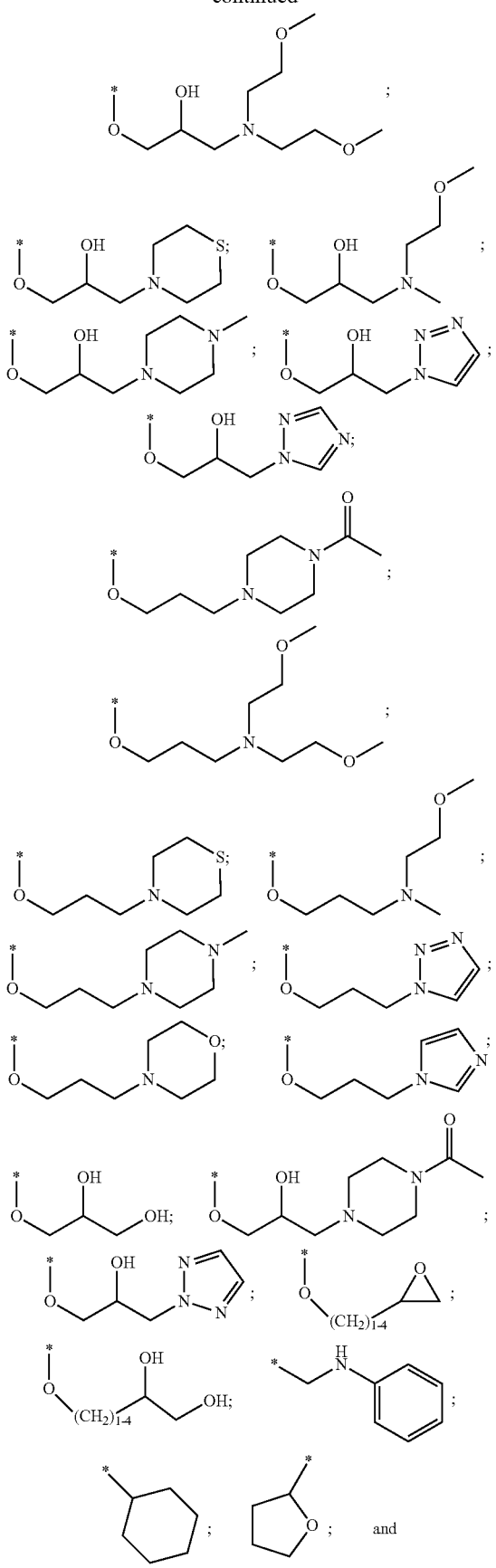

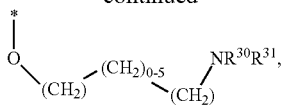

wherein $R^{30}$ and $R^{31}$ are each independently H or alkyl; or $R^{30}$ and $R^{31}$ together with the nitrogen to which they are bound form a 5-7 membered nitrogen containing heterocyclic ring; and (h) with the proviso that a compound of Formula (Ia) is not a compound having the structure:

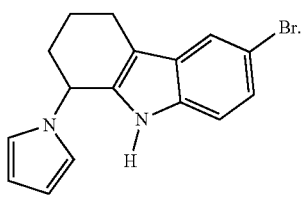

2. A method for inhibiting angiogenesis in a subject, comprising administering to the subject an anti-angiogenic amount of a compound of Formula (Ia)

Formula (Ia)

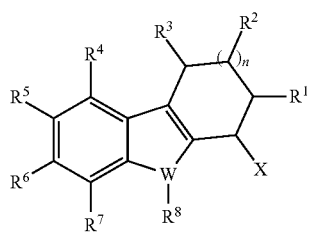

or an enantiomer, a diastereomer, a pharmaceutically acceptable salt, or a mixture thereof, wherein:

(a) X is selected from the group consisting of: a substituted or unsubstituted

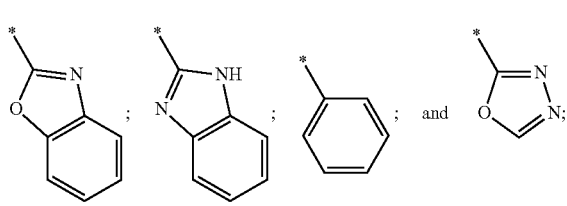

and $NR^9R^{10}$;

wherein $NR^9R^{10}$ is selected from the group consisting of: a substituted or unsubstituted

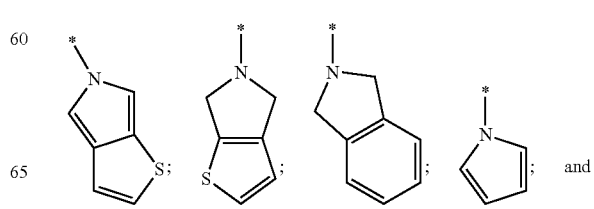

-continued

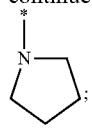

wherein X is optionally substituted with substituents selected from the group consisting of:

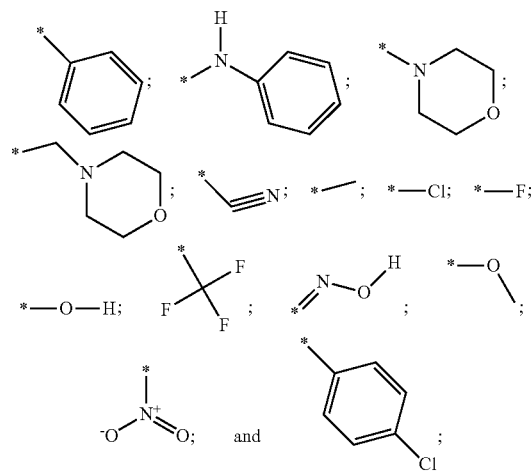

(b) R¹, R² and R³ are each —H;
(c) n is 1 or 2;
(d) R⁴, R⁶ and R⁷ are each independently —H or halo;
(e) R⁵ is independently —OH, substituted or unsubstituted $C_{1-6}$ alkyl, substituted or unsubstituted alkoxy, halo, haloalkyl, haloalkoxy, nitro cyano, substituted or unsubstituted heterocyclic ring, substituted or unsubstituted amino, substituted or unsubstituted phenyl, substituted or unsubstituted phenoxy, substituted or unsubstituted cycloalkyl, substituted or unsubstituted alkenyl, substituted or unsubstituted alkynyl, or substituted or unsubstituted alkoxycarbonyl, or hydroxycarbonyl;
(f) R⁸ is H; and
(g) W is N;
wherein the term "substituted" in R⁵ denotes that a moiety has one or more hydrogen atoms replaced by one or more substituents selected from the group consisting of:

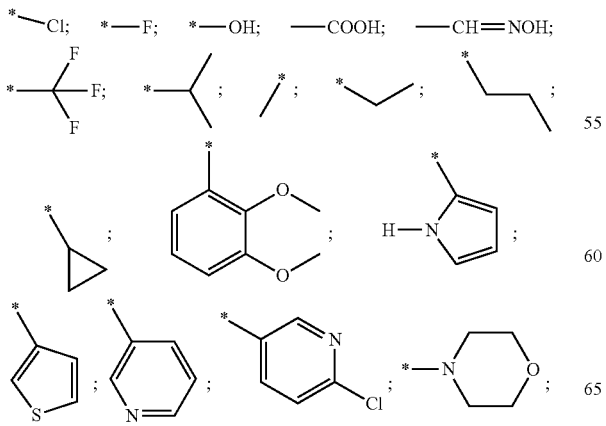

-continued

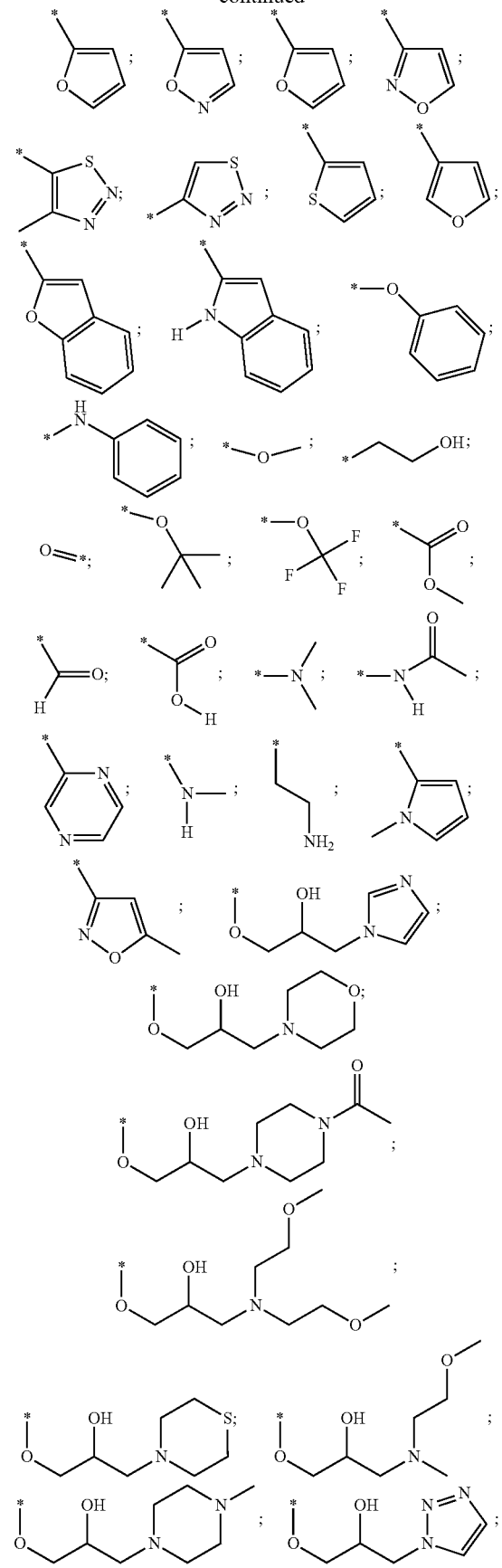

185
-continued

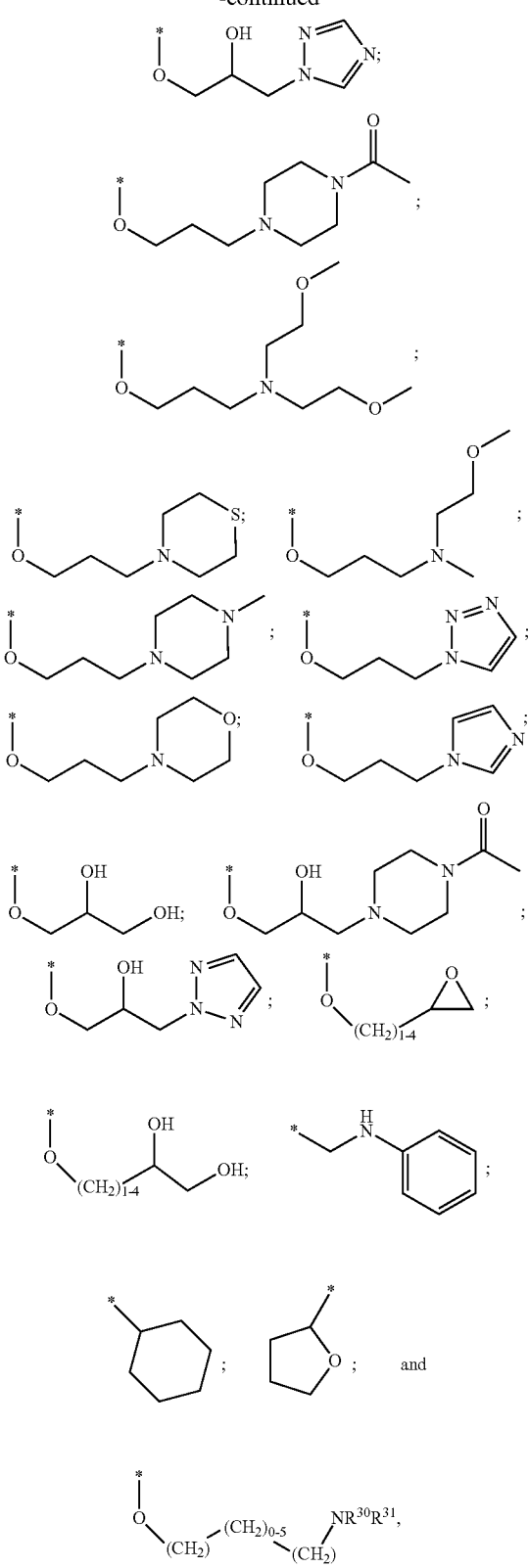

wherein $R^{30}$ and $R^{31}$ are each independently H or alkyl; or $R^{30}$ and $R^{31}$ together with the nitrogen to which they are bound form a 5-7 membered nitrogen containing heterocyclic ring; and (h) with the proviso that a compound of Formula (Ia) is not a compound having the structure:

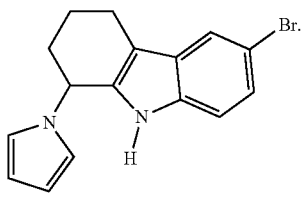 [SMILES: Brc1ccc2[nH]c3c(c2c1)CCCC3n1cccc1]

3. A method for treating a disease selected from the group consisting of cancer, diabetic retinopathy, exudative macular degeneration, rheumatoid arthritis, psoriasis, atherosclerosis, obesity, and chronic inflammation in a subject, comprising administering to the subject a therapeutically effective amount of a compound of Formula (Ia)

Formula (Ia)

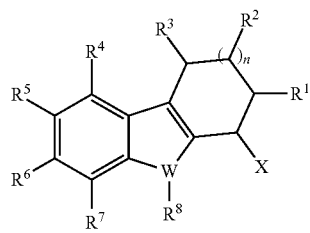

or an enantiomer, a diastereomer, a pharmaceutically acceptable salt, or a mixture thereof, wherein:

(a) X is selected from the group consisting of:

a substituted or unsubstituted

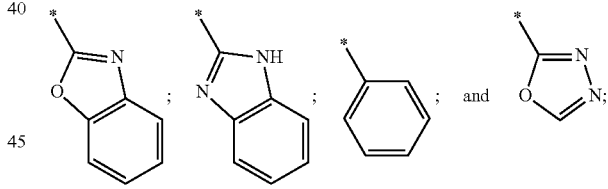

and $NR^9R^{10}$;

wherein $NR^9R^{10}$ is selected from the group consisting of:

a substituted or unsubstituted

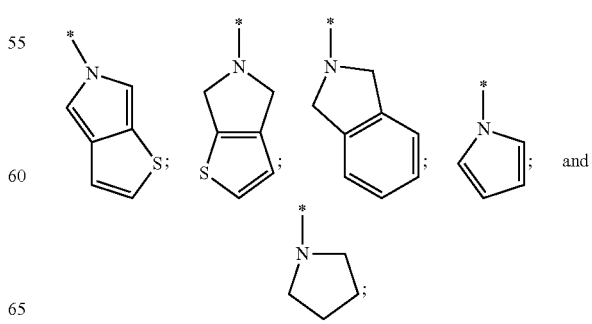

wherein X is optionally substituted with substituents selected from the group consisting of:

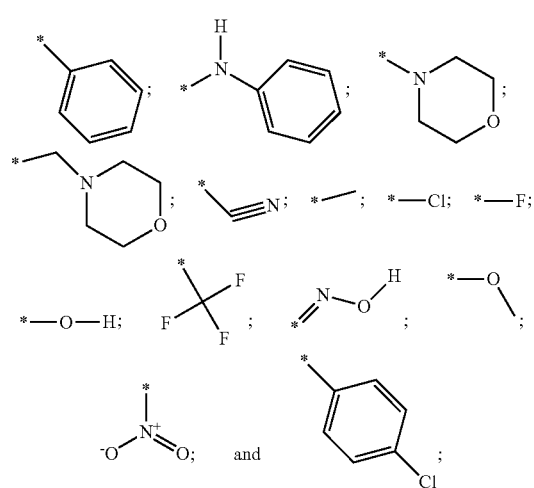

(b) $R^1$, $R^2$ and $R^3$ are each —H;
(c) n is 1 or 2;
(d) $R^4$, $R^6$ and $R^7$ are each independently —H or halo;
(e) $R^5$ is independently —OH, substituted or unsubstituted $C_{1-6}$ alkyl, substituted or unsubstituted alkoxy, halo, haloalkyl, haloalkoxy, nitro cyano, substituted or unsubstituted heterocyclic ring, substituted or unsubstituted amino, substituted or unsubstituted phenyl, substituted or unsubstituted phenoxy, substituted or unsubstituted cycloalkyl, substituted or unsubstituted alkenyl, substituted or unsubstituted alkynyl, or substituted or unsubstituted alkoxycarbonyl, or hydroxycarbonyl;
(f) $R^8$ is H; and
(g) W is N;
wherein the term "substitued" in $R^5$ denotes that a moiety has one or more hydrogen atoms replaced by one or more substituents selected from the group consisting of:

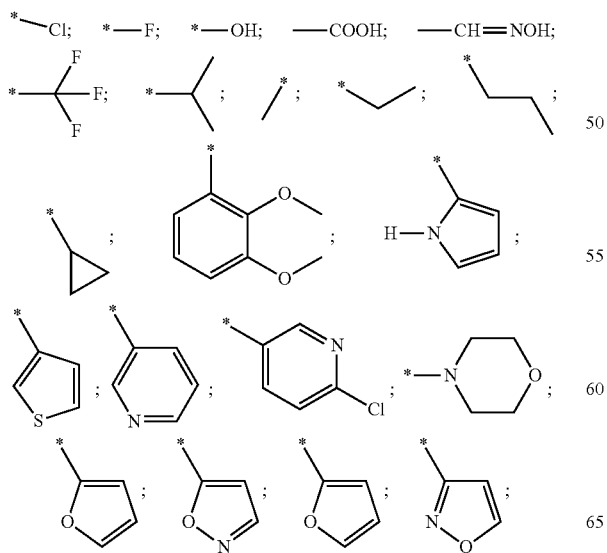

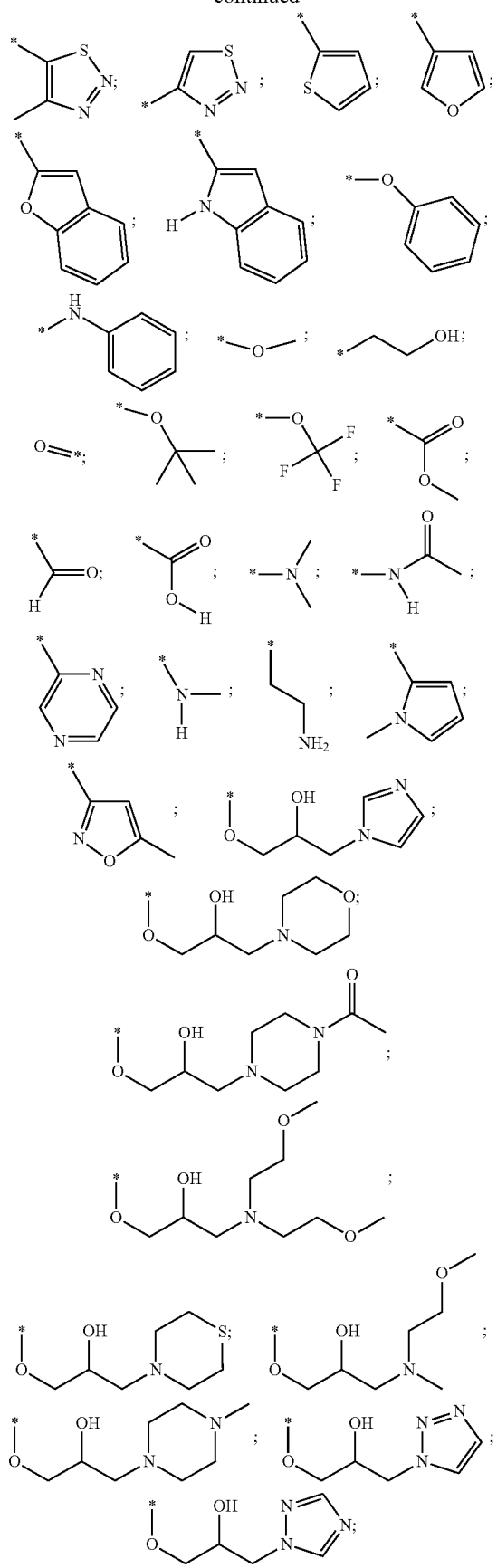

-continued

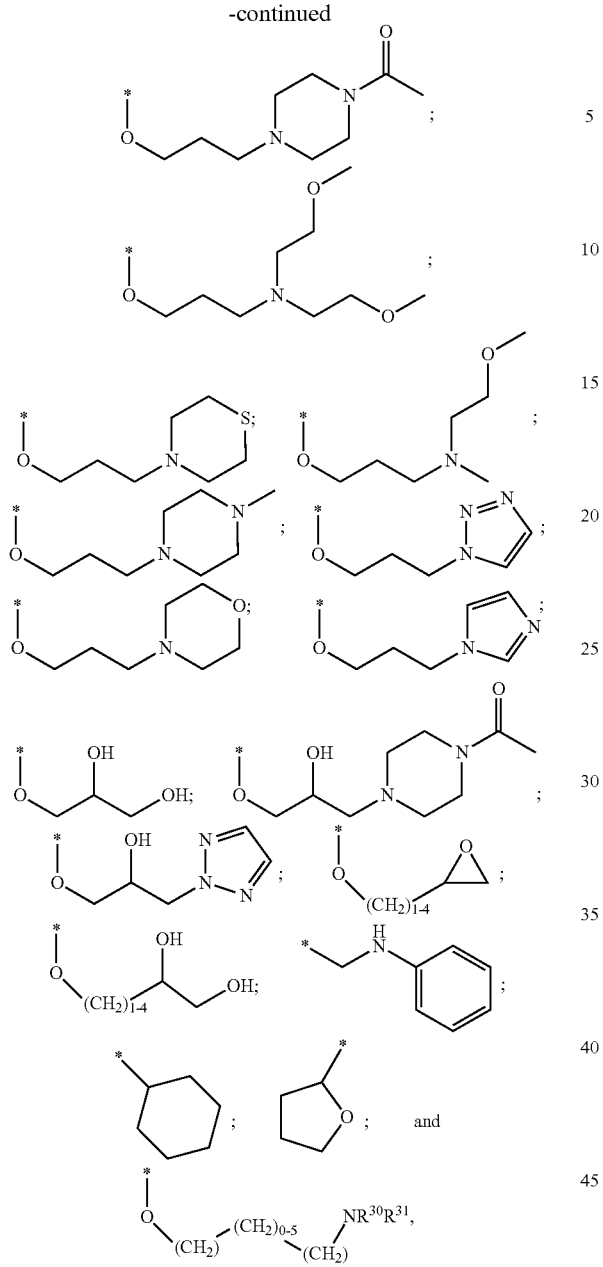

wherein $R^{30}$ and $R^{31}$ are each independently H or alkyl; or $R^{30}$ and $R^{31}$ together with the nitrogen to which they are bound form a 5-7 membered nitrogen containing heterocyclic ring; and (h) with the proviso that a compound of Formula (Ia) is not a compound having the structure:

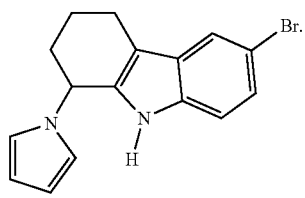 [SMILES: Brc1ccc2[nH]c3c(c2c1)CCCC3n1cccc1]

4. A method for inhibiting VEGF production in a subject, comprising administering to the subject a VEGF-inhibiting amount of a compound selected from the group consisting of:

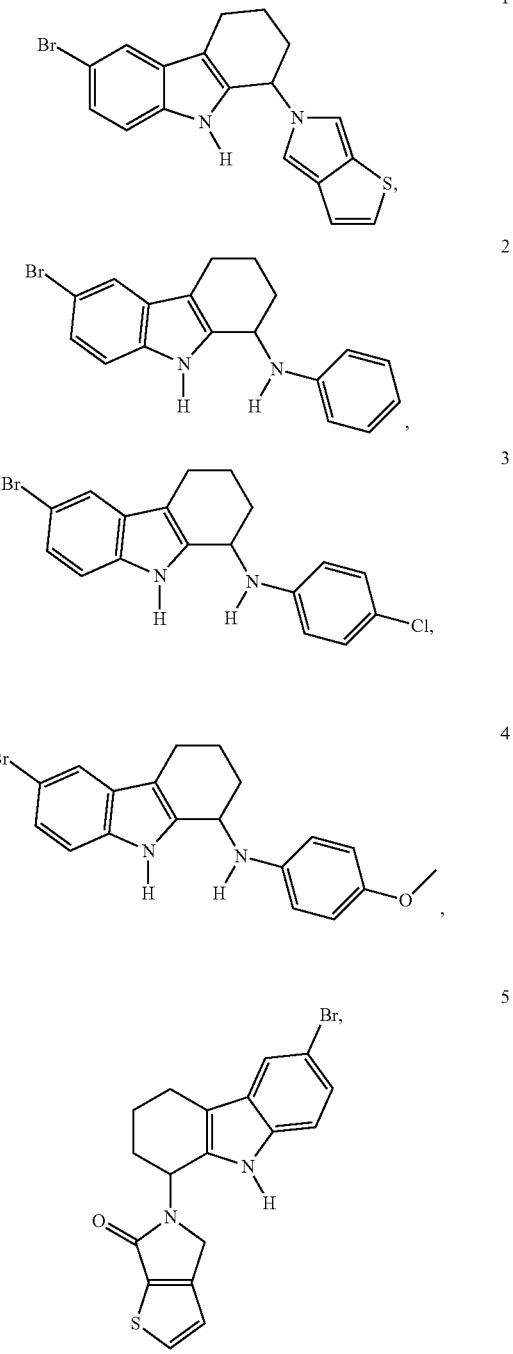

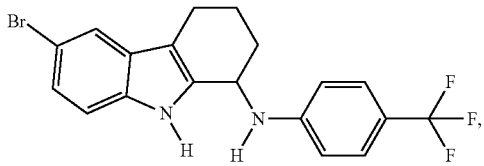

7
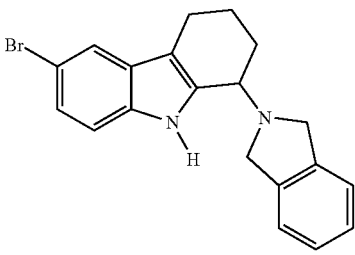
8
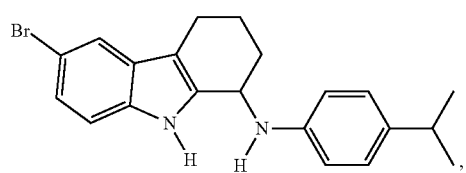
9
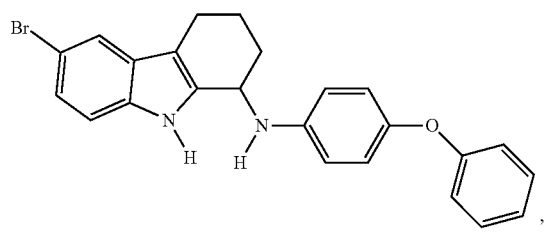
10
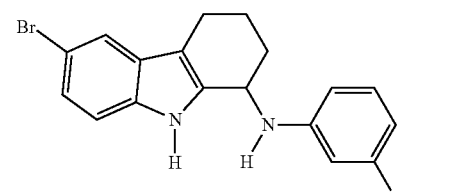
11
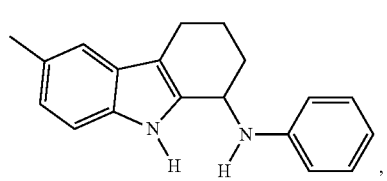
12
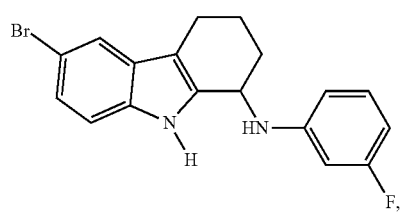
13
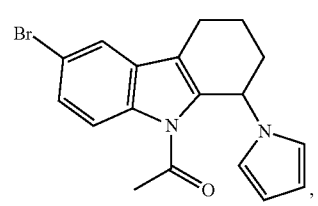
14
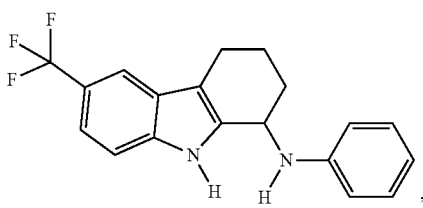
15
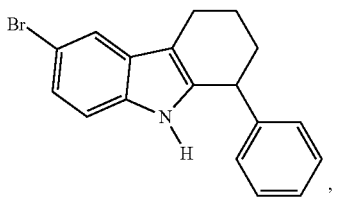
16
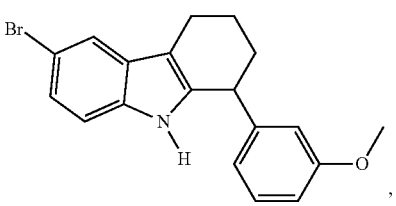
17
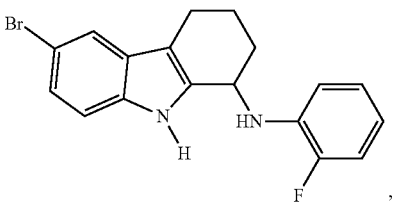
18
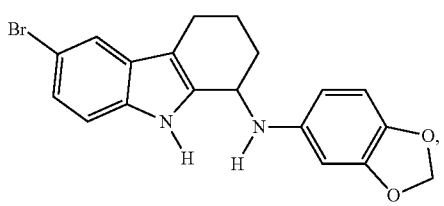
19
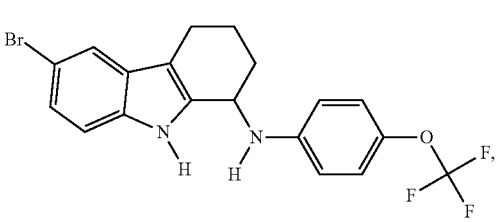
20
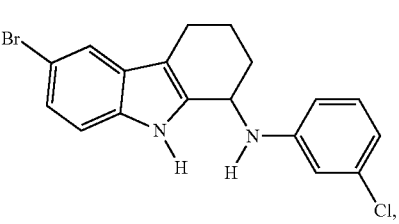

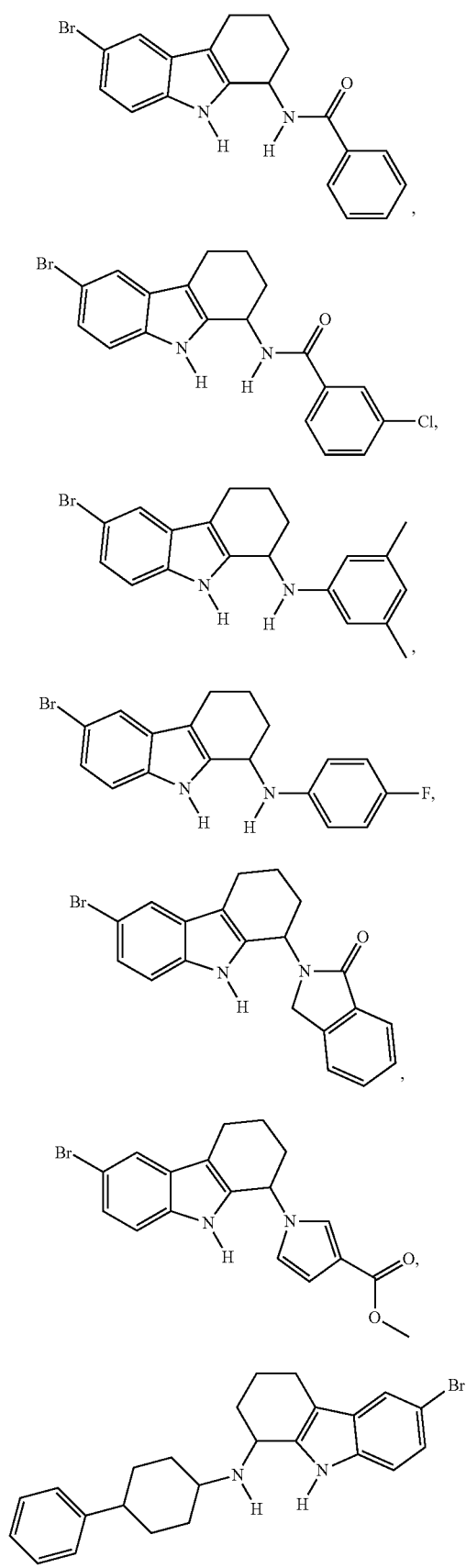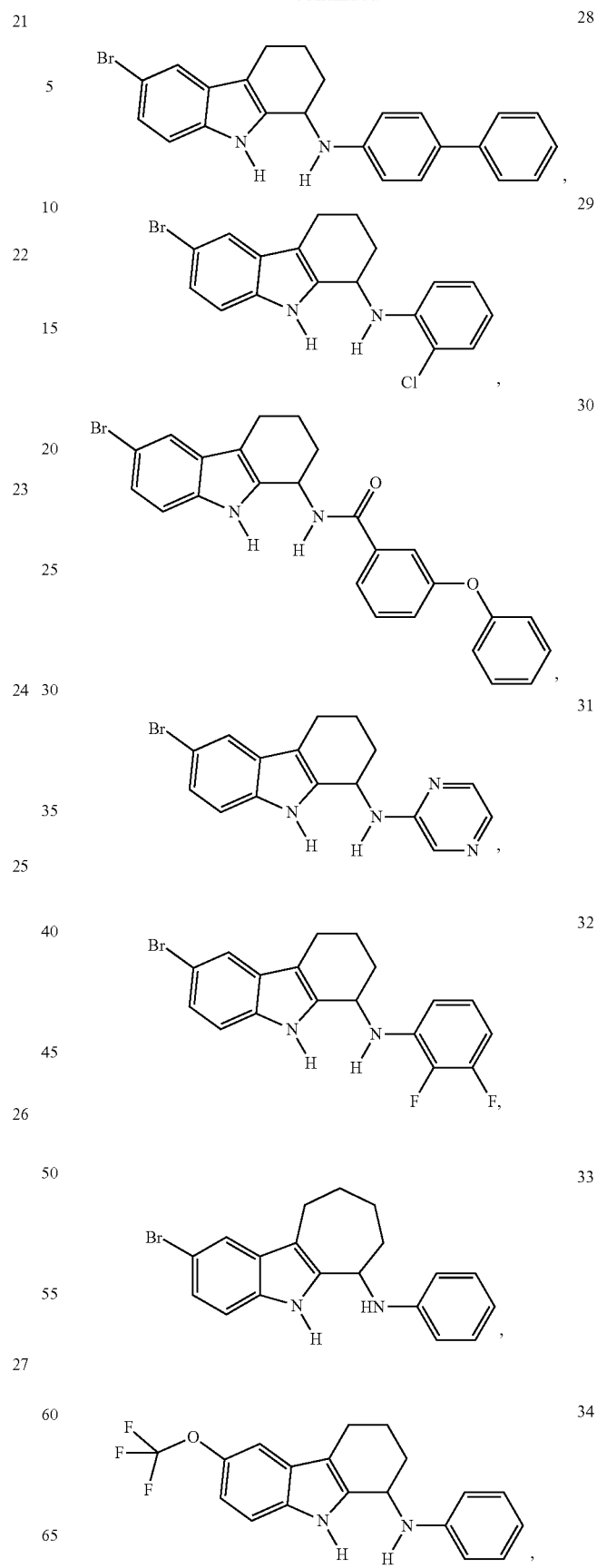

35
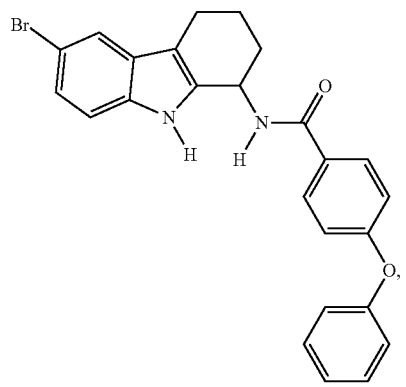
36
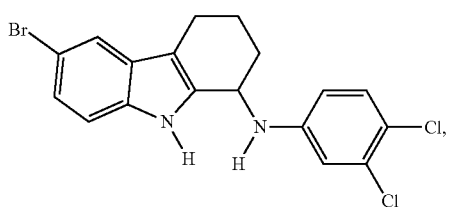
37
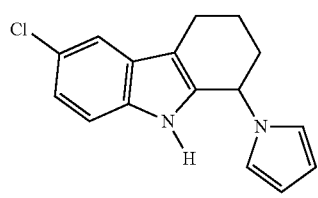
38
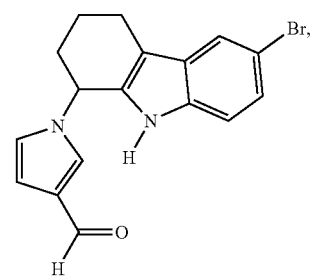
39
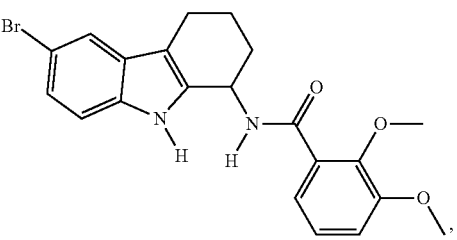
40
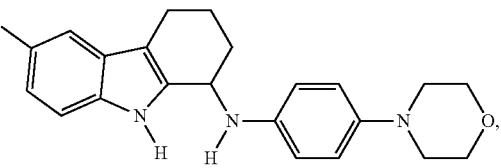
41
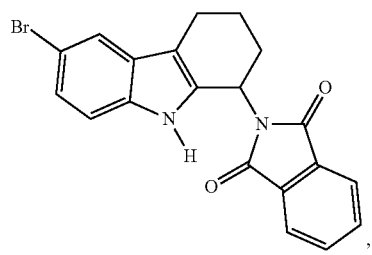
42
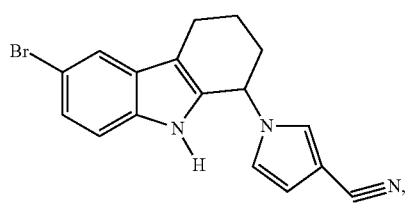
43
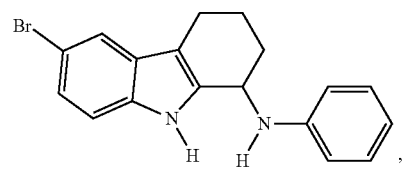
44
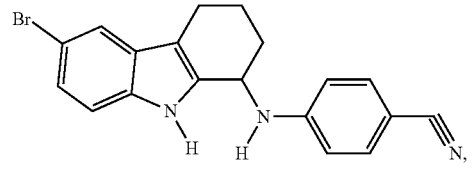
45
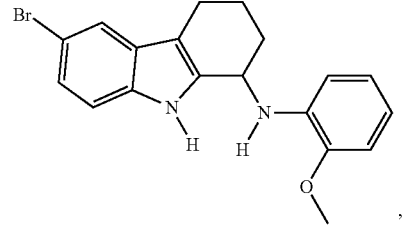
46
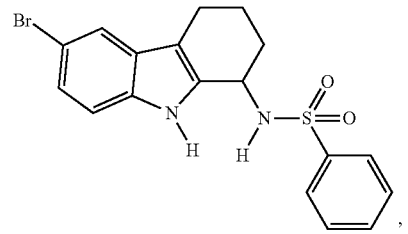
47
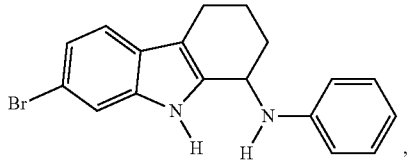

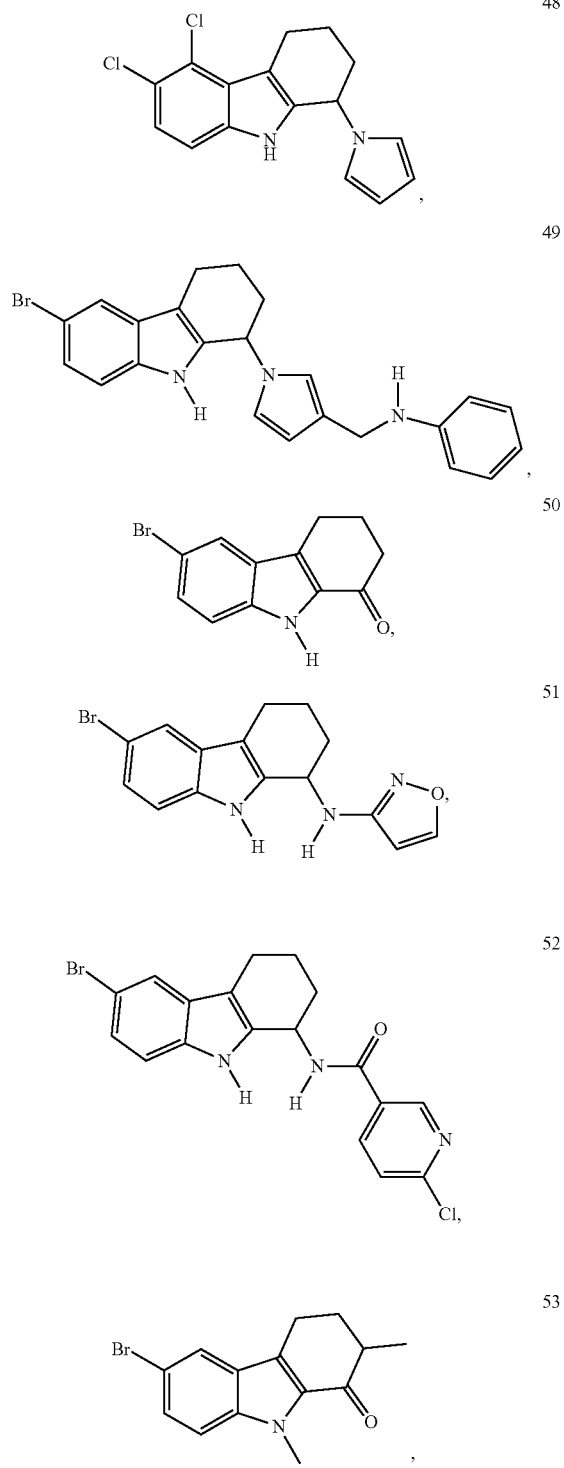
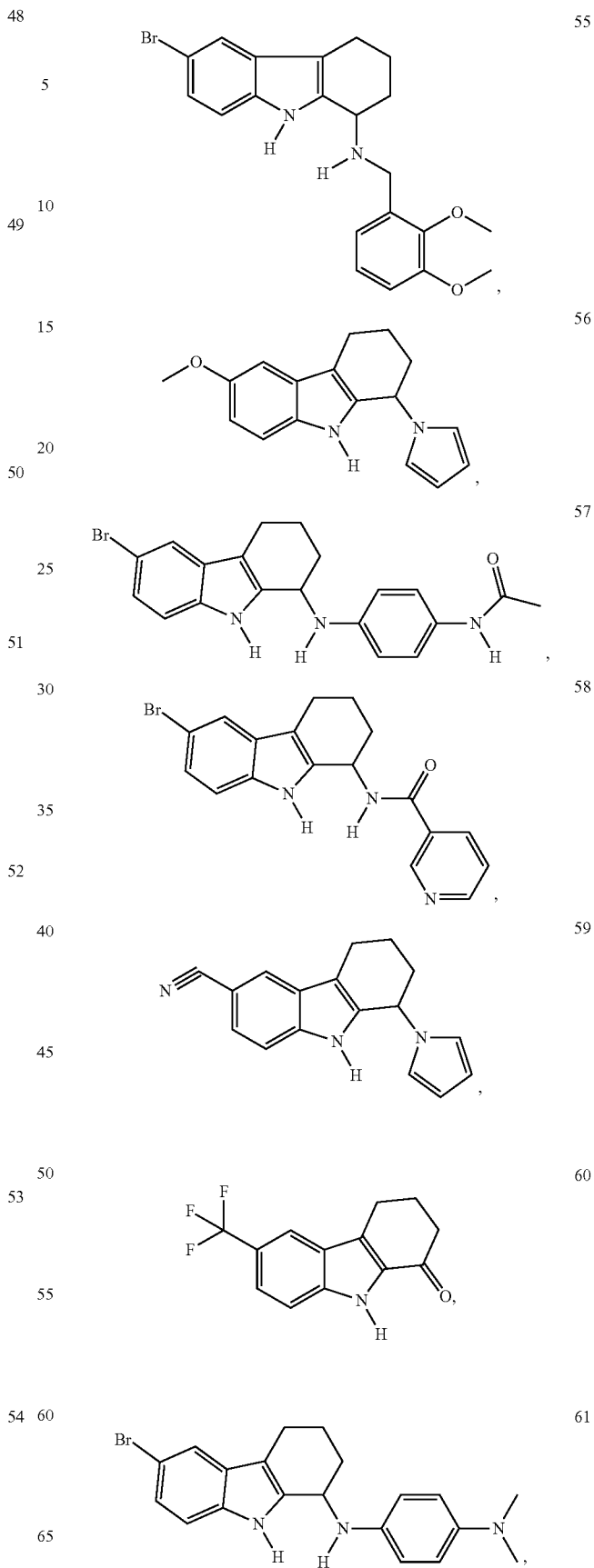

199
-continued
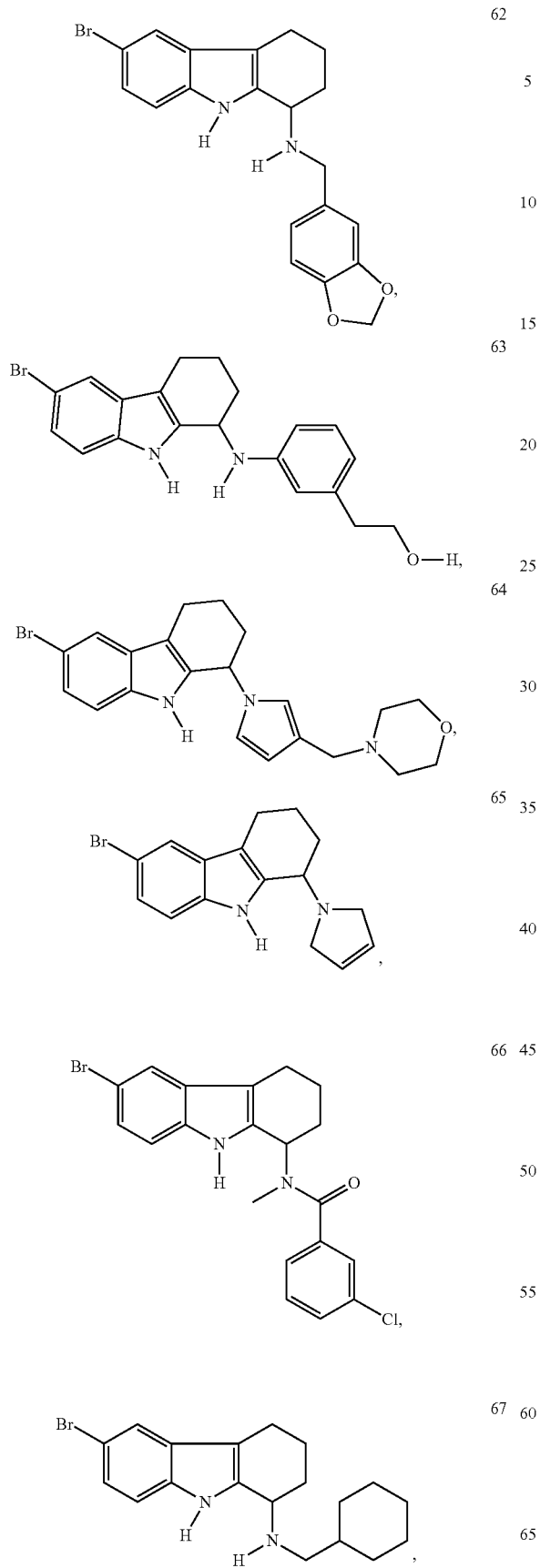
200
-continued
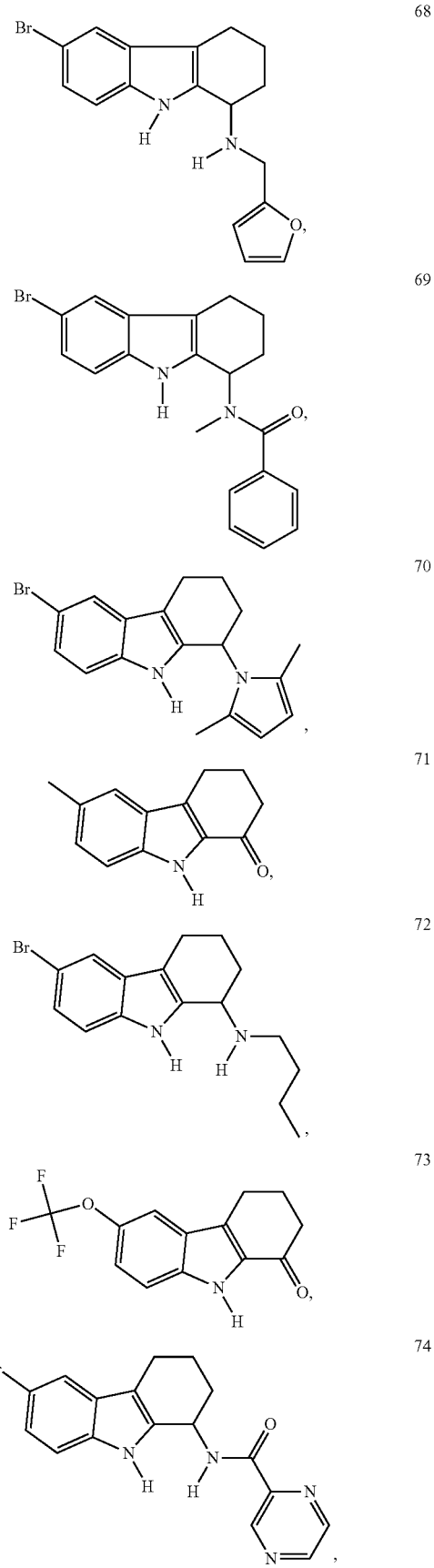

-continued

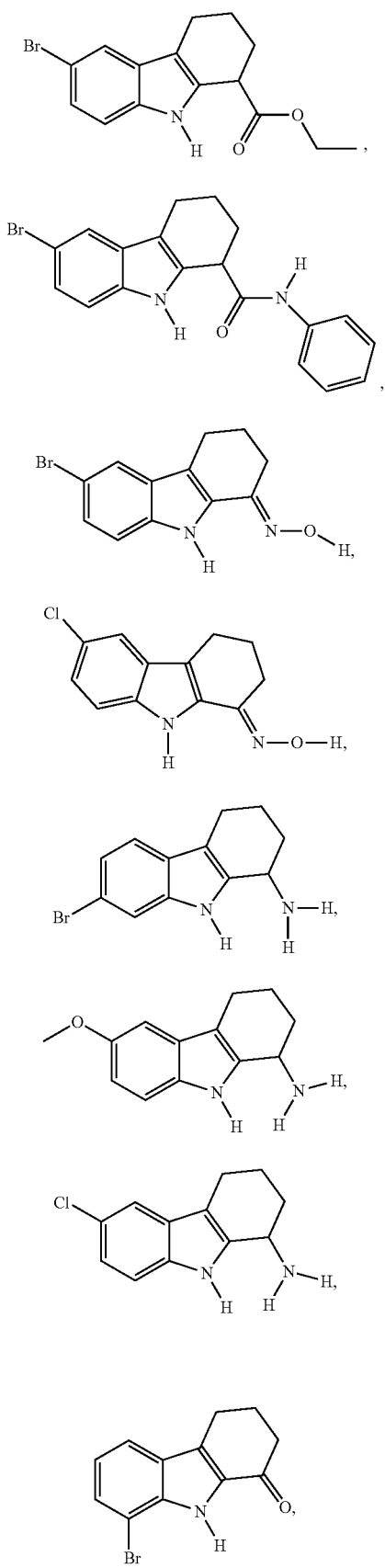
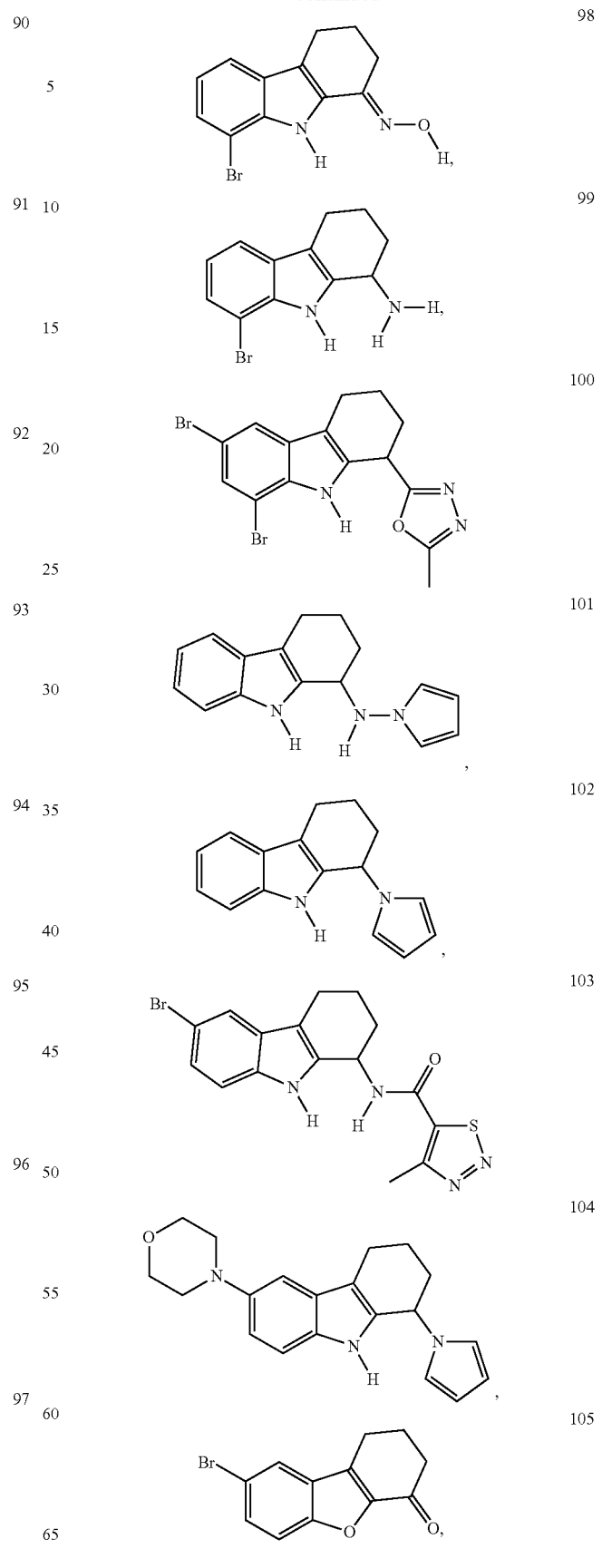

-continued
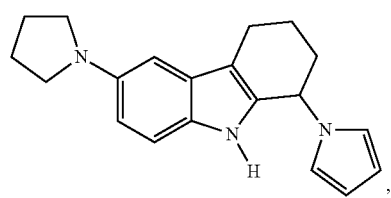
106
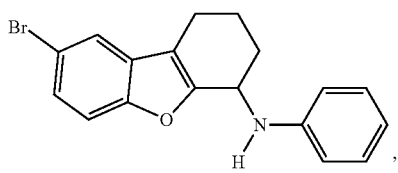
107
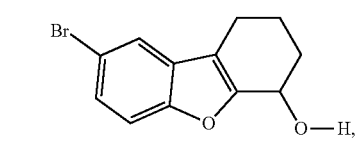
108
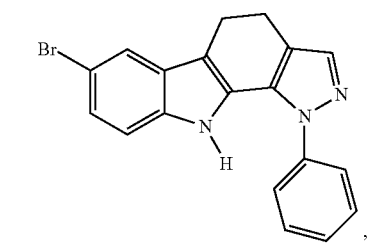
109
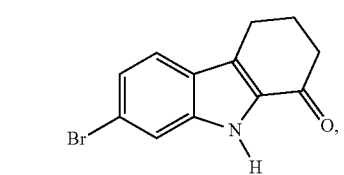
110
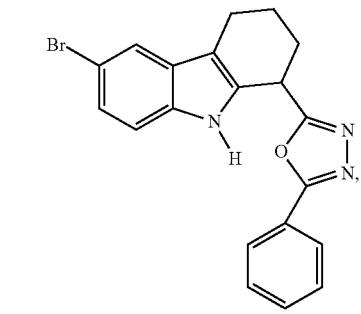
111
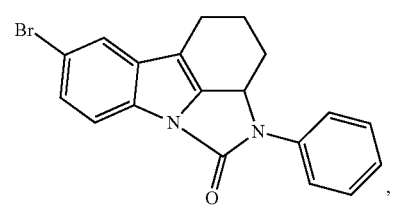
112
-continued
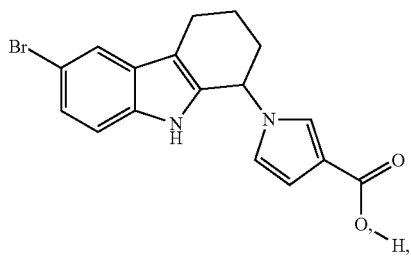
113
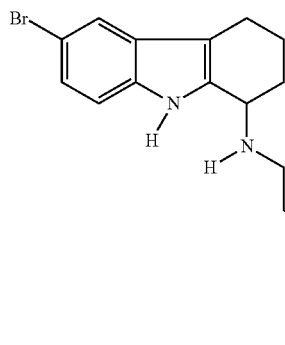
114
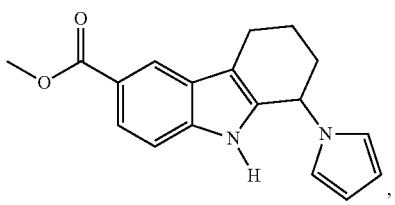
115
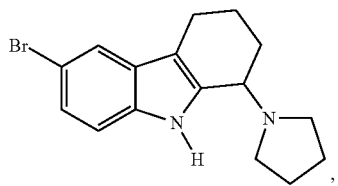
116
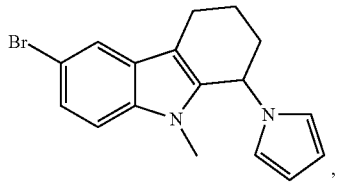
117
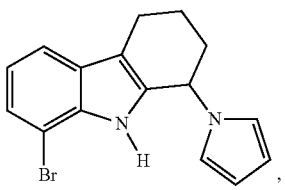
118
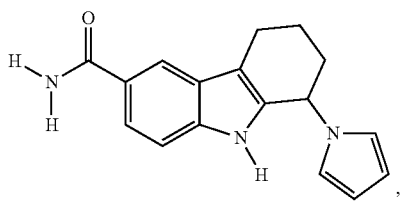
119

-continued
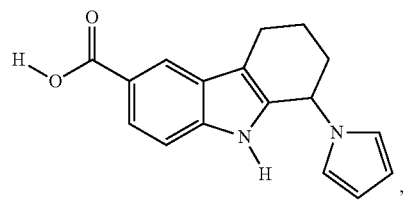
120
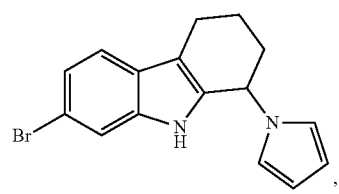
121
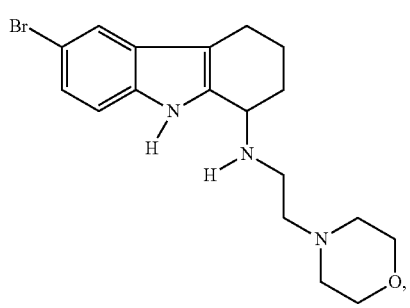
122
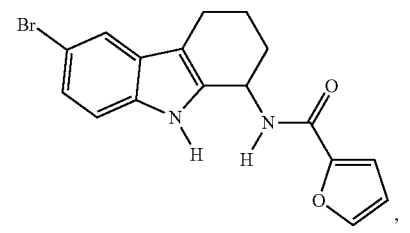
123
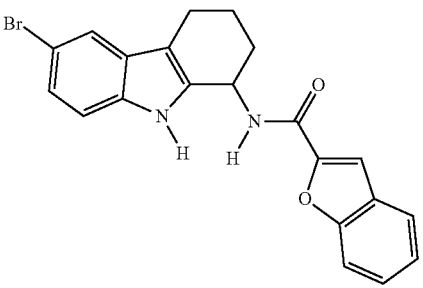
124
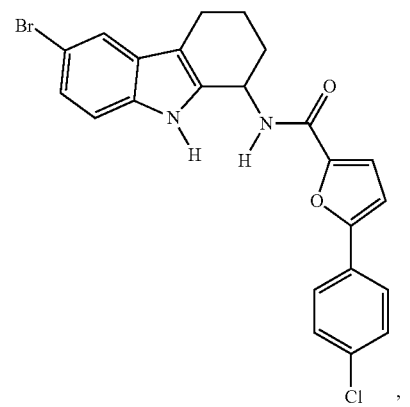
125
-continued
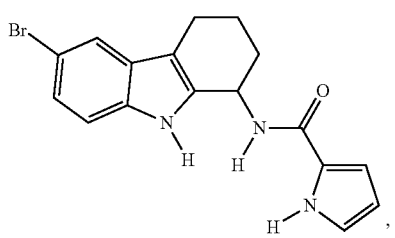
126
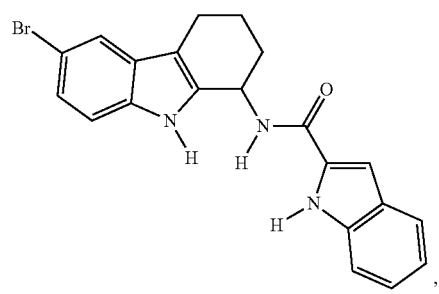
127
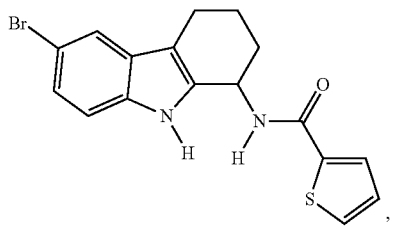
128
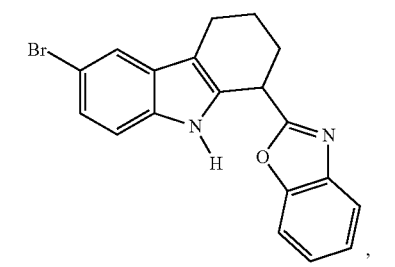
129
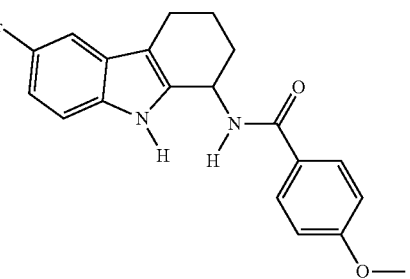
130
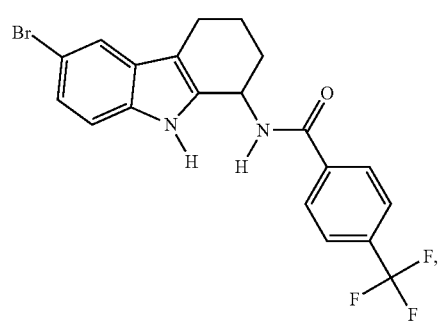
131

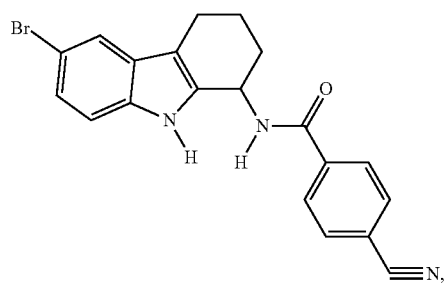
132
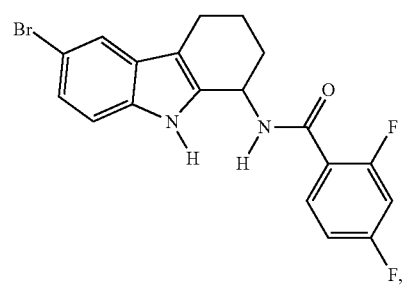
133
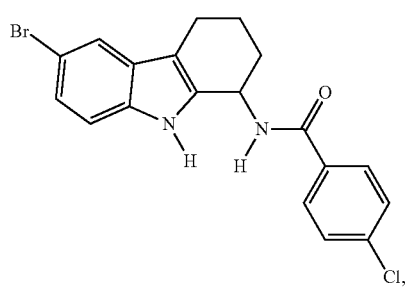
134
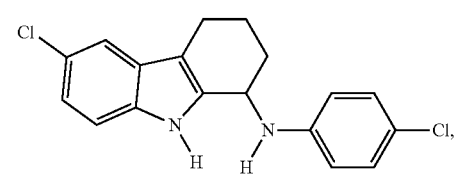
135
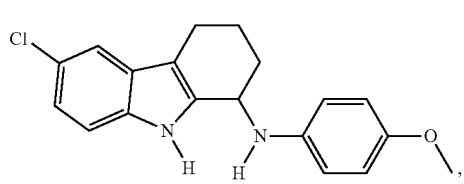
136
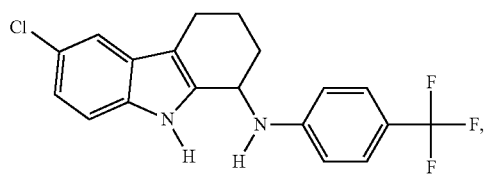
137
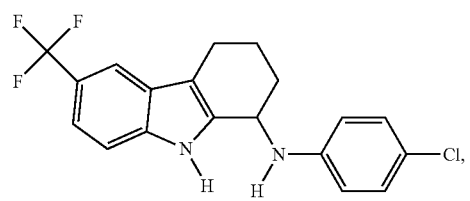
138
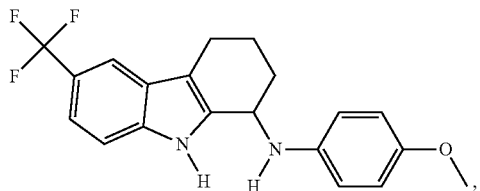
139
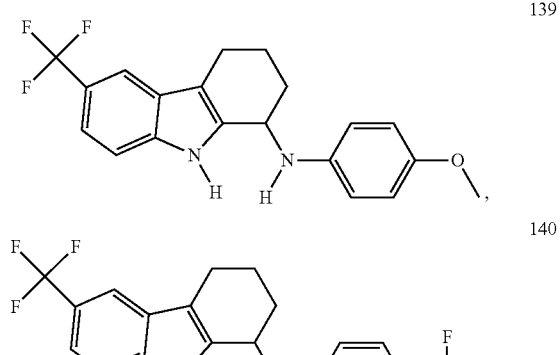
140
141
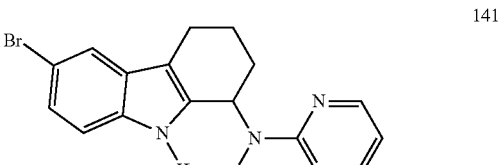
142
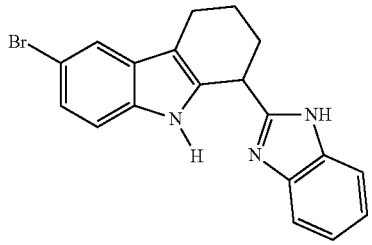
143
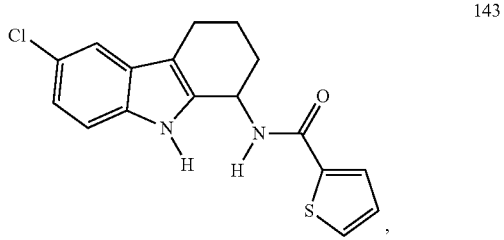
144
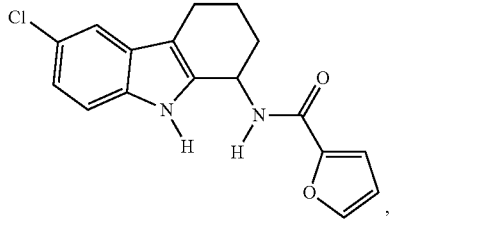
145

211
-continued
146
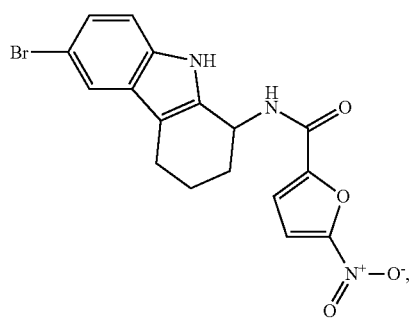
147
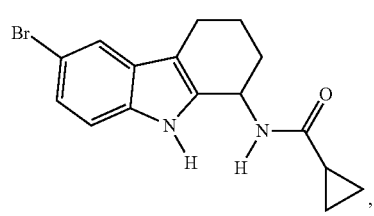
148
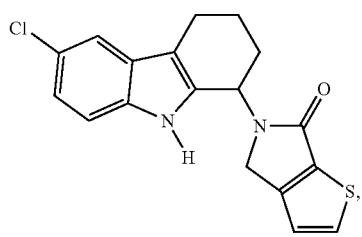
149
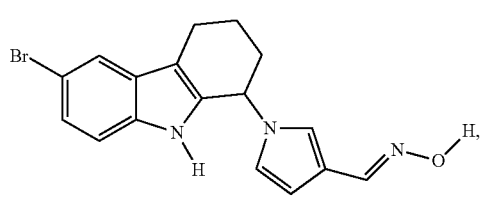
150
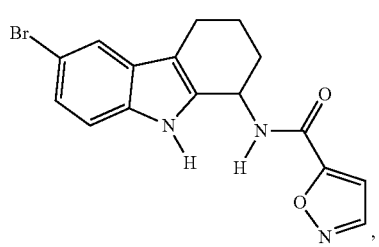
151
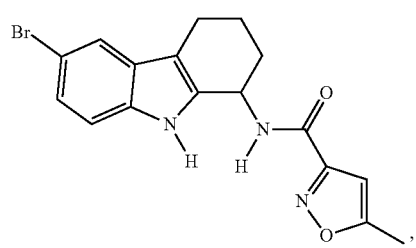
212
-continued
152
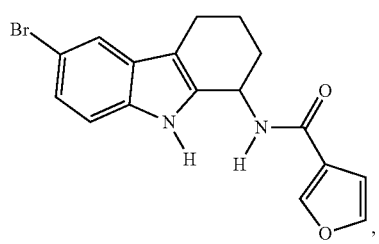
153
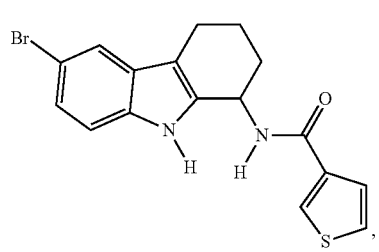
154
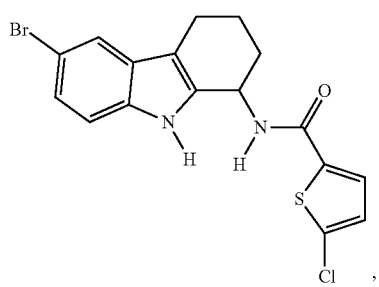
155
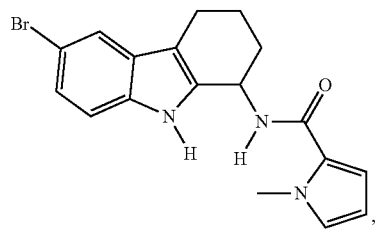
156
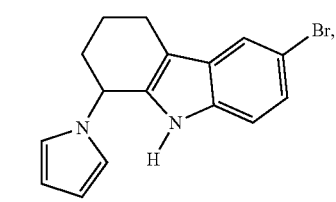
157
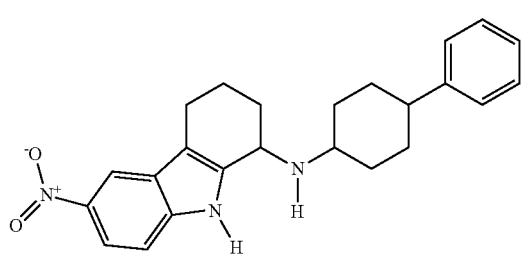

-continued
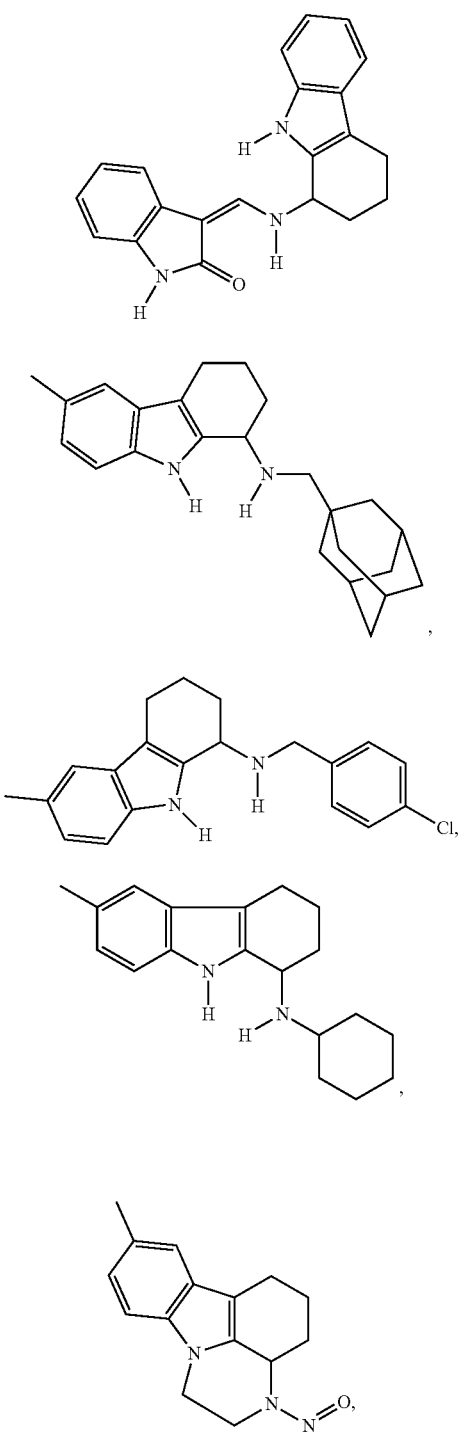
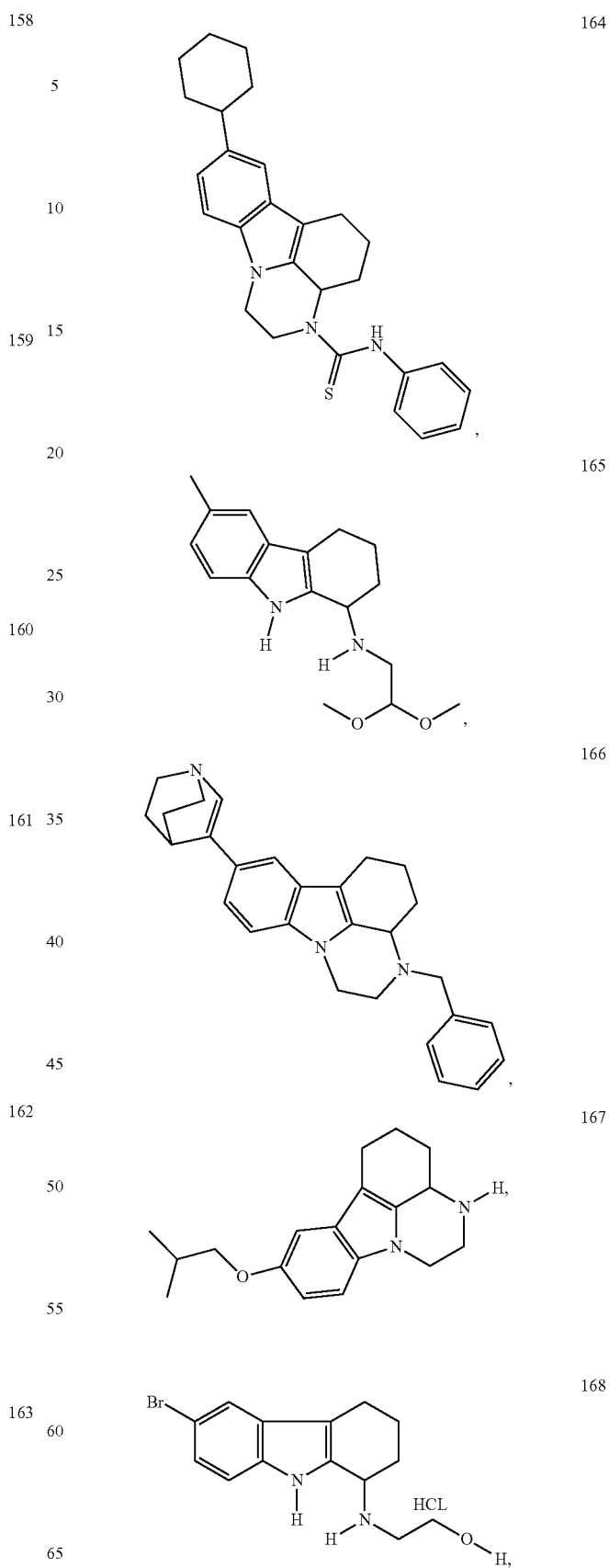

-continued
168A
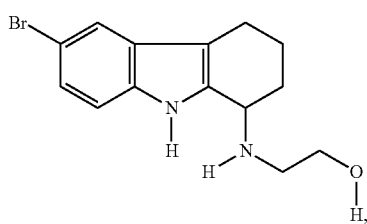
169
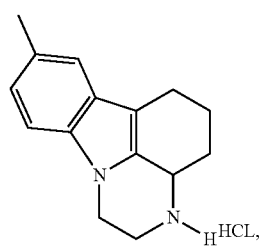
169A
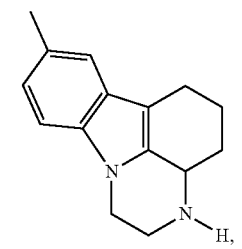
170
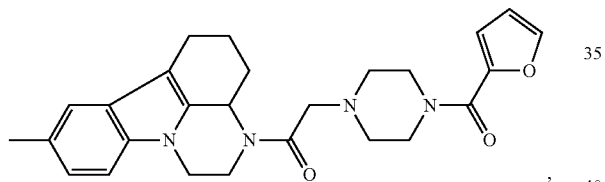
171
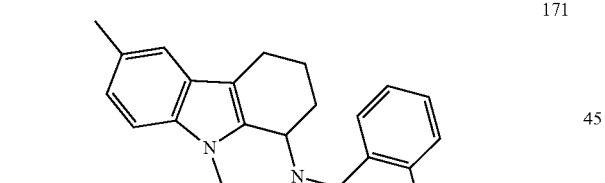
172
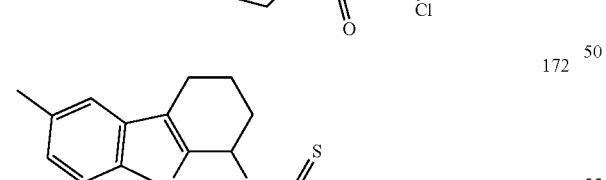
173
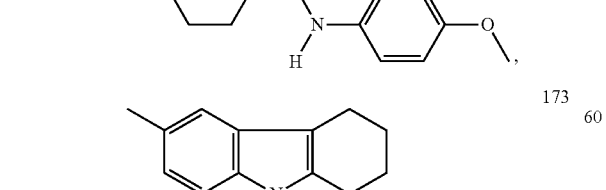
-continued
174
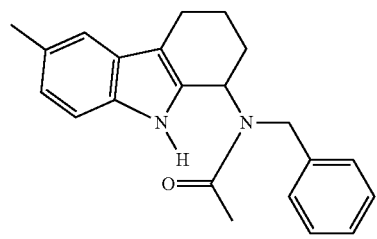
175
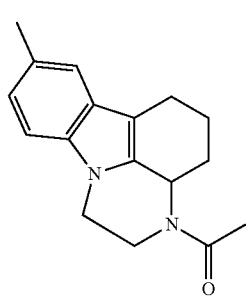
176
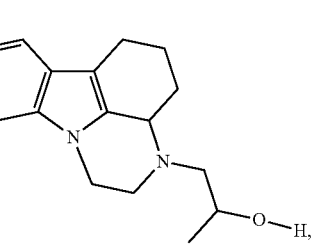
177
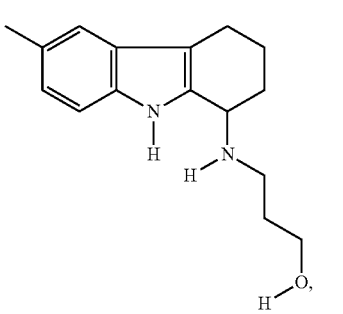
178
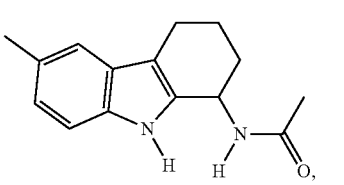
179
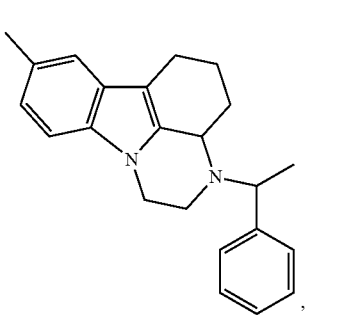

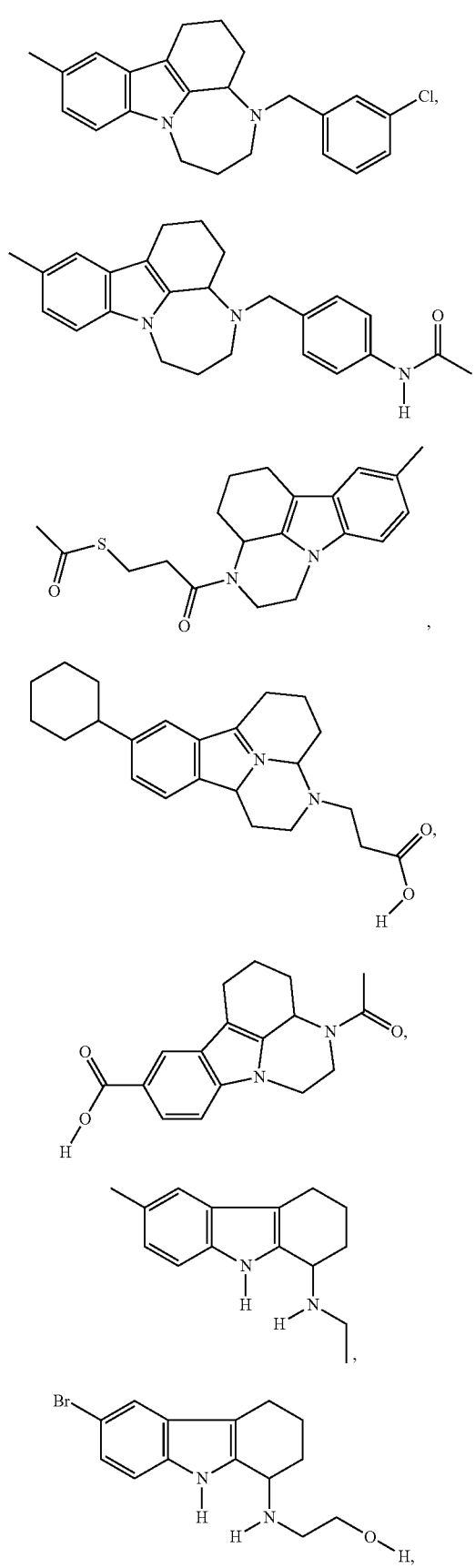
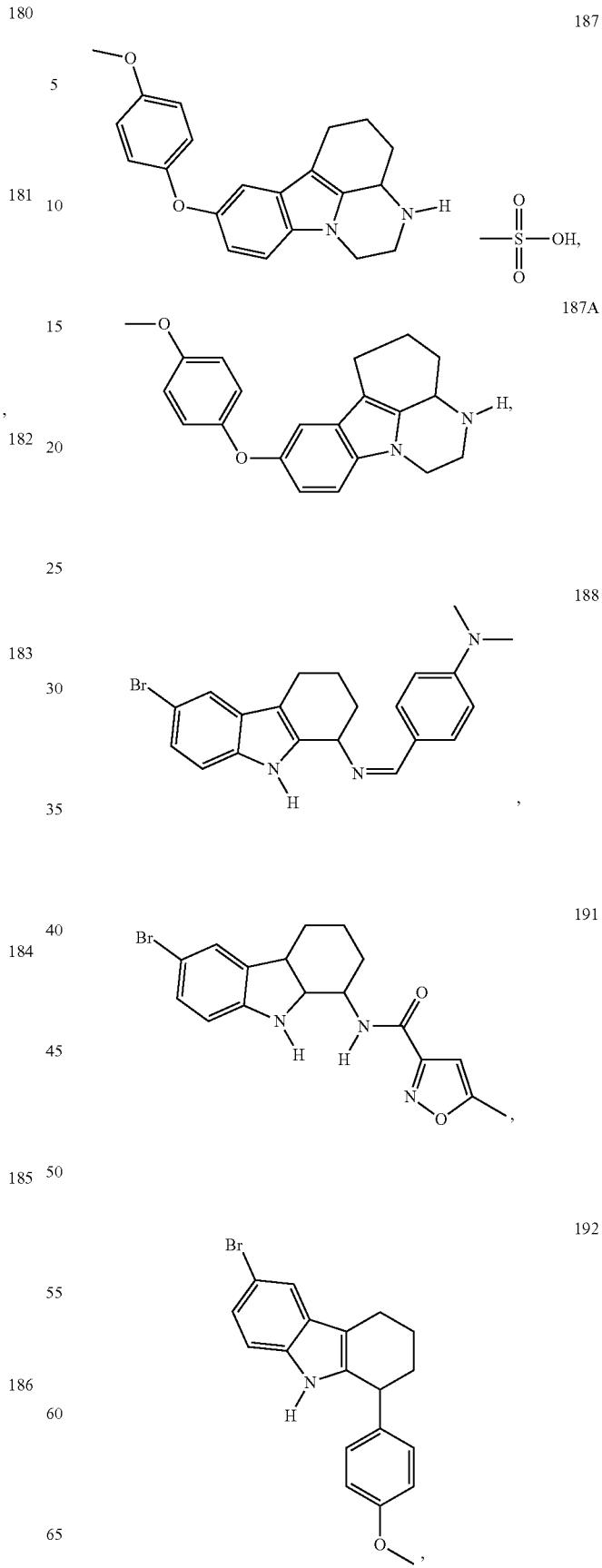

193 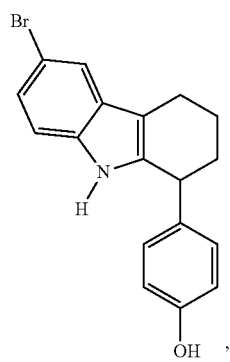
194 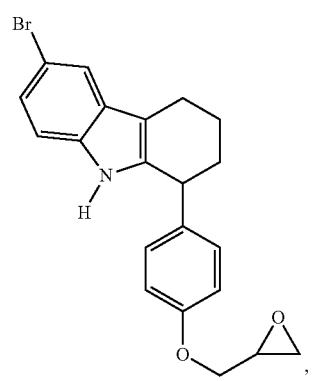
195 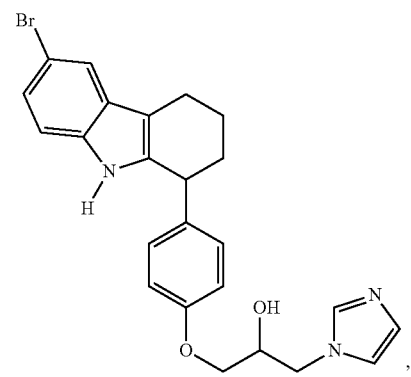
196 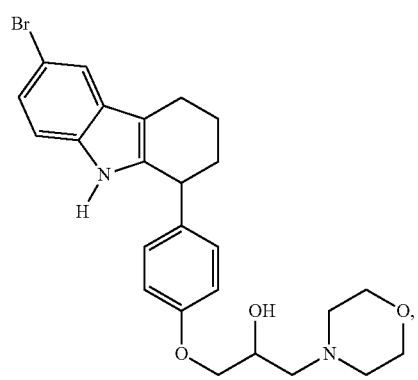
197 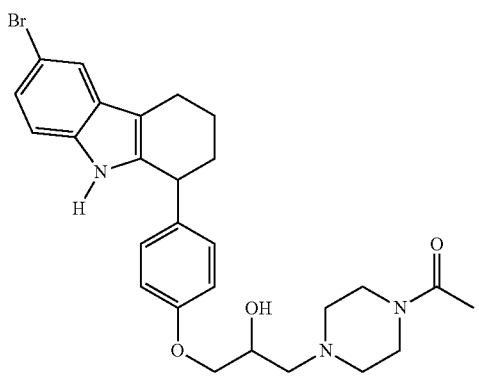
198 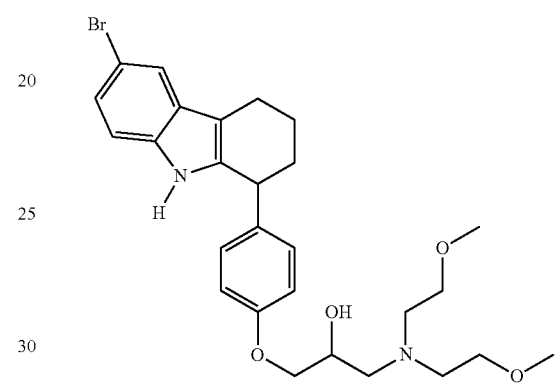
199 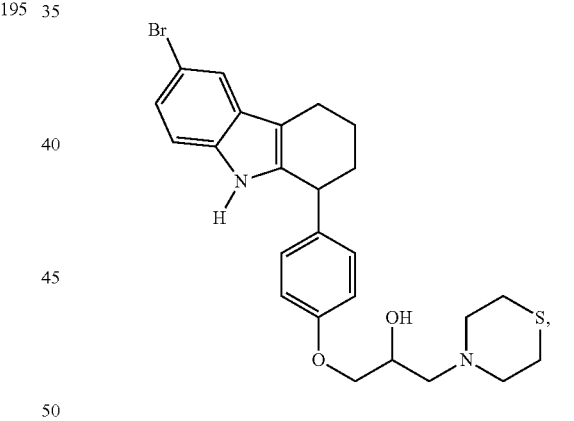
200 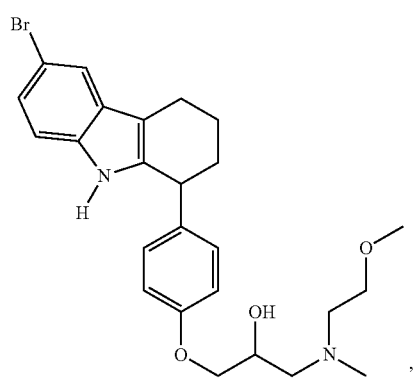

201 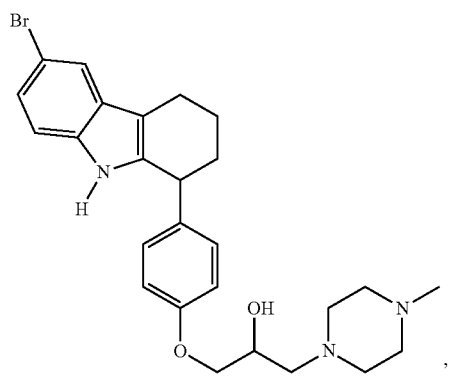
202 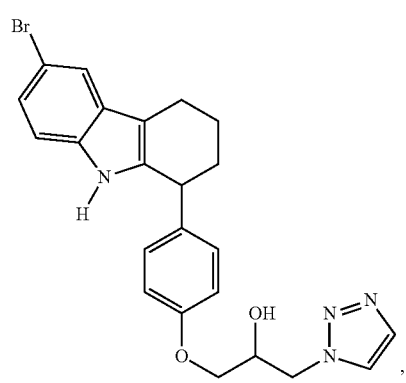
203 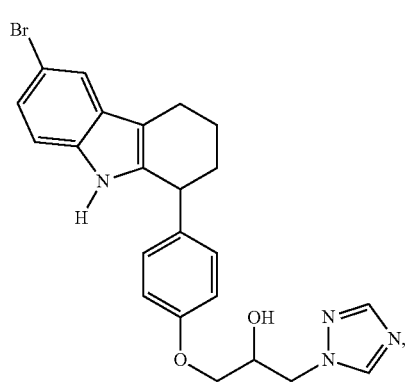
204 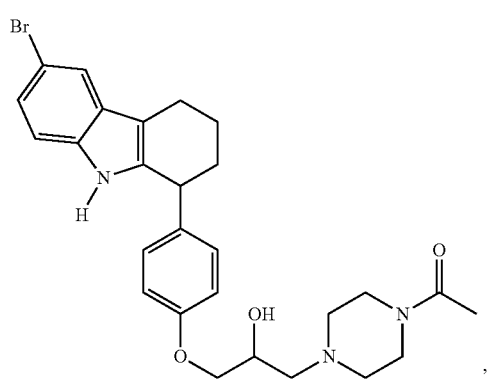
205 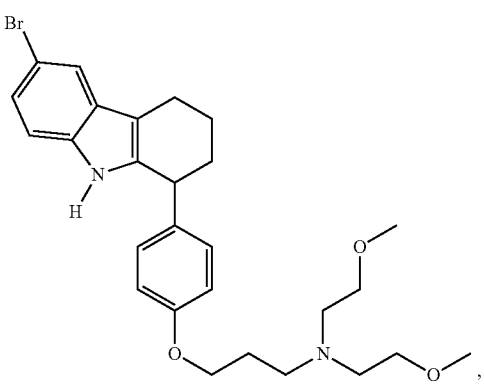
206 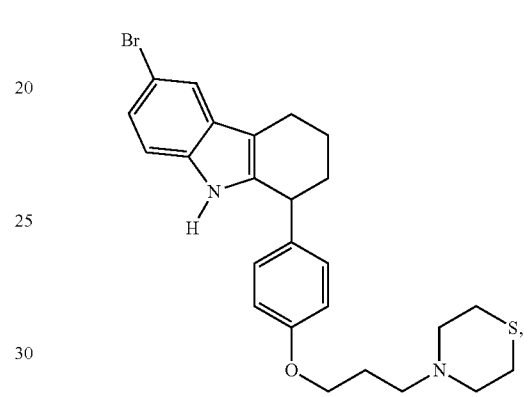
207 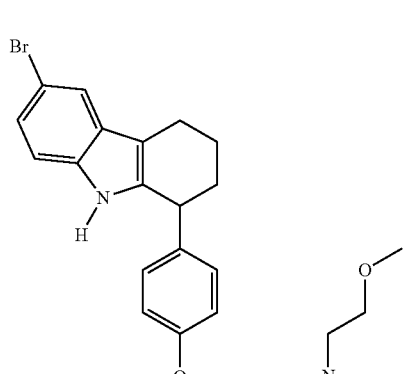
208 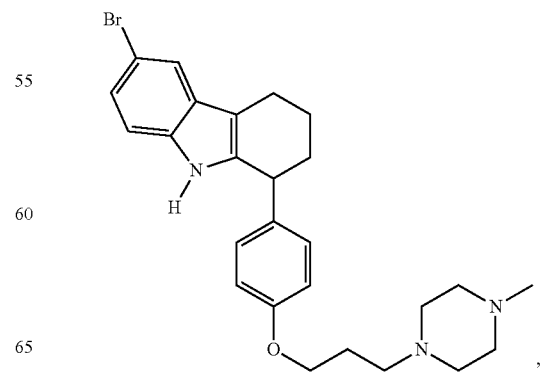

209 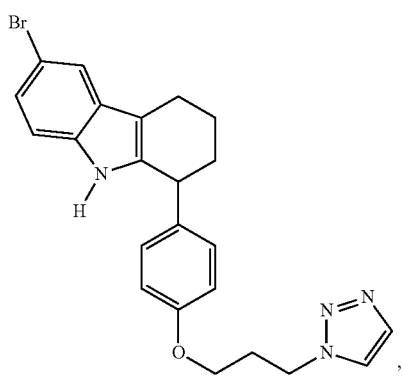
210 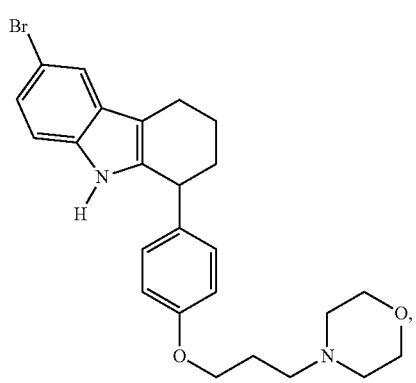
211 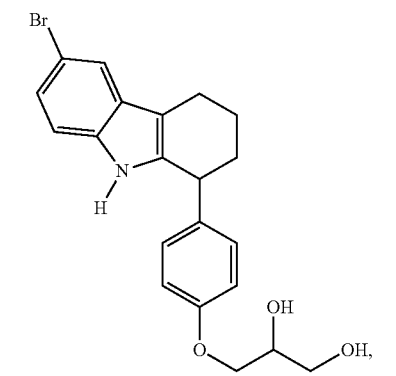
213 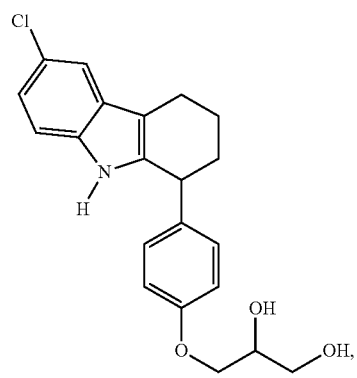
214 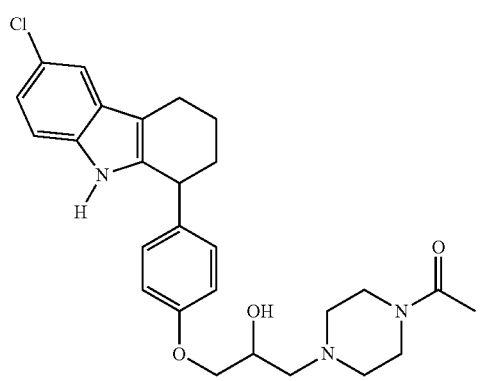
215 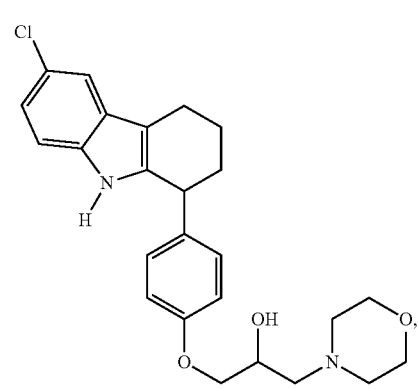
212
216 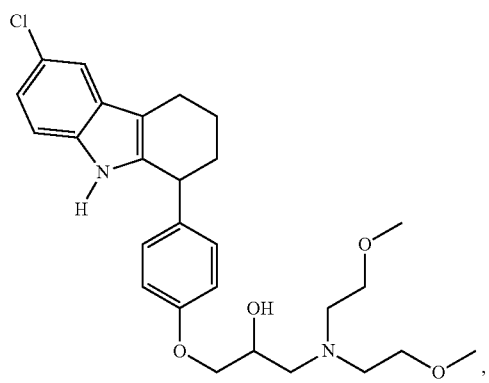

225
-continued
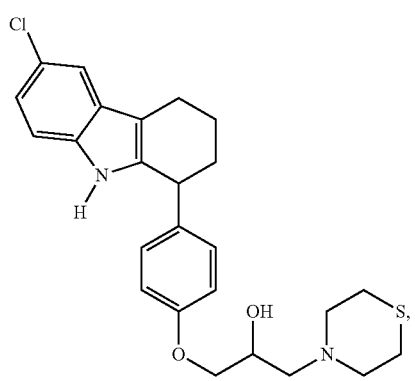
217
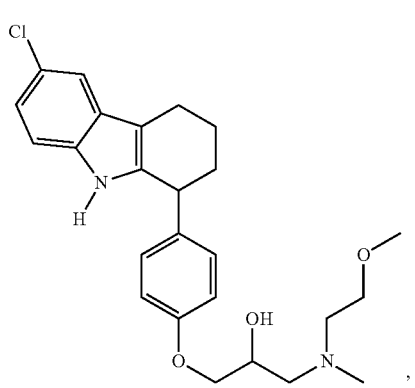
218
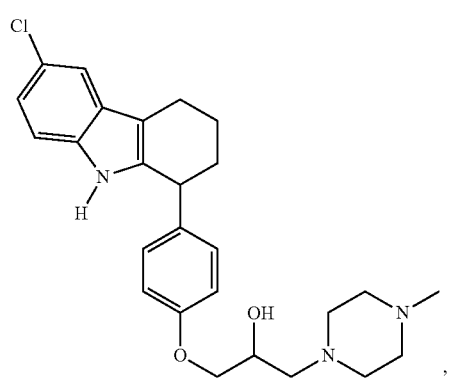
219
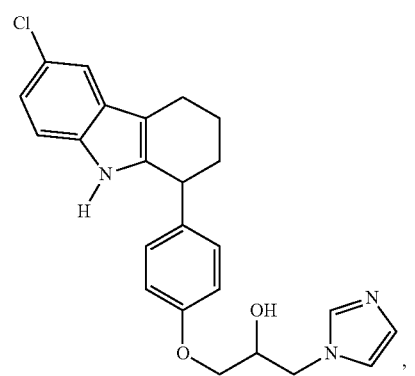
220
226
-continued
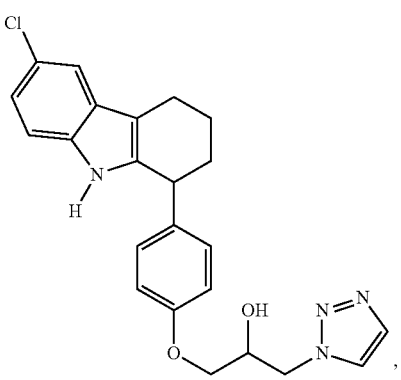
221
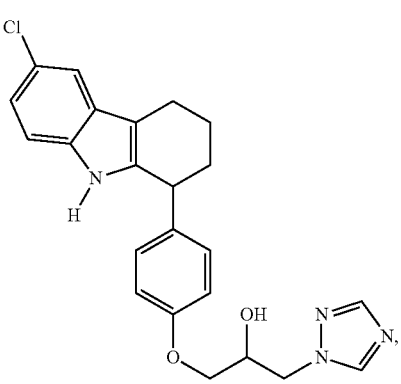
222
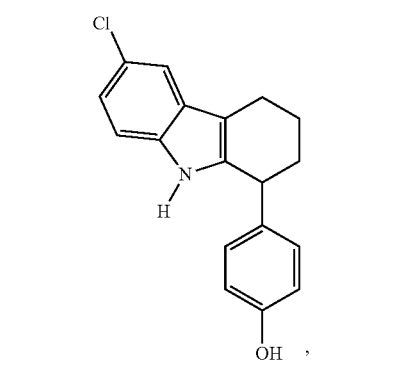
223
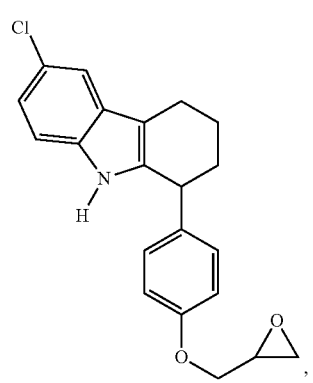
224

225
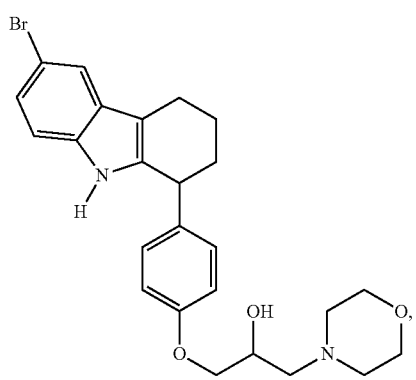
226
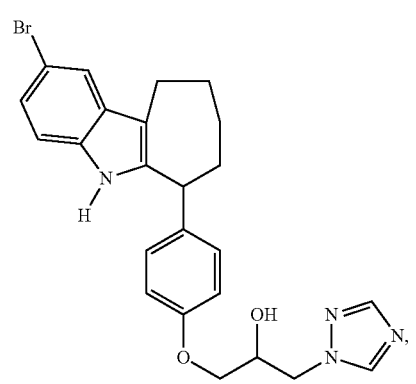
227
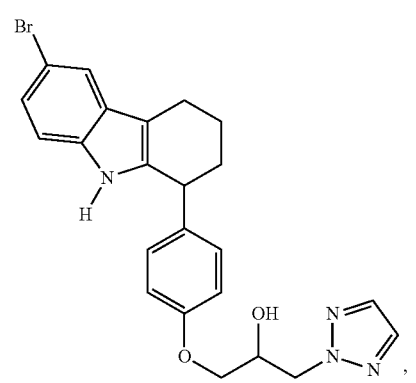
228
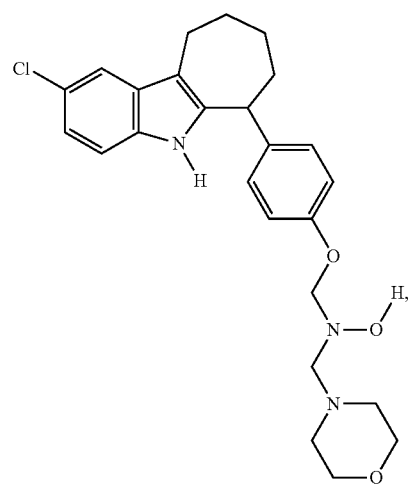
229
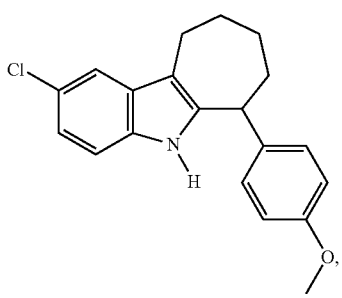
230
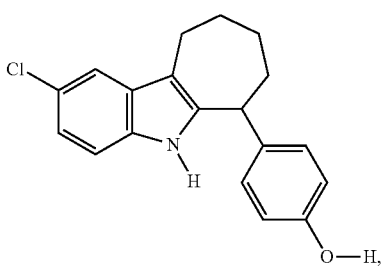
231
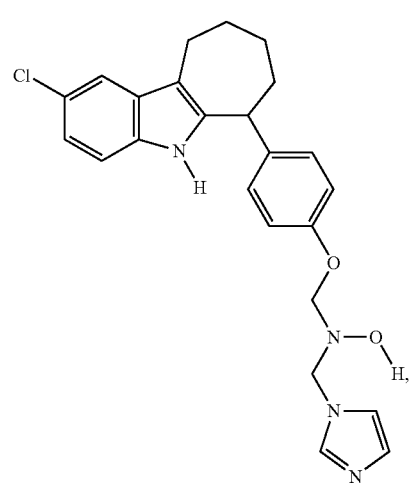
232
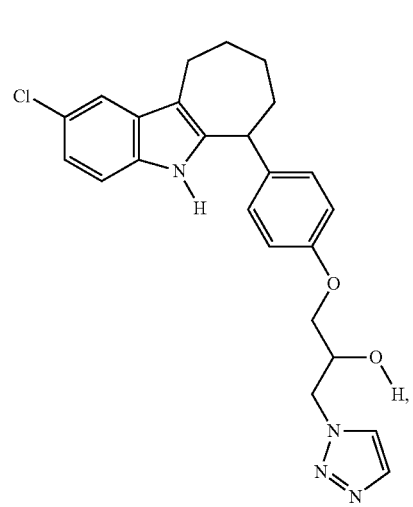

233 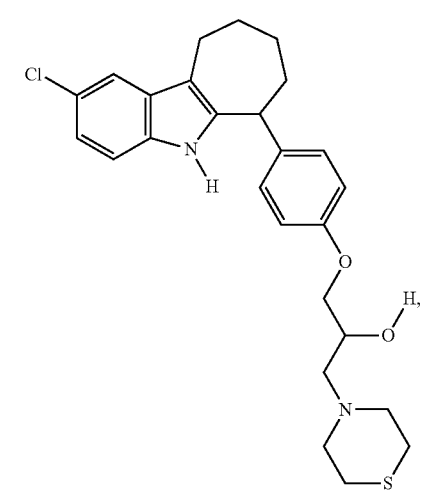
234 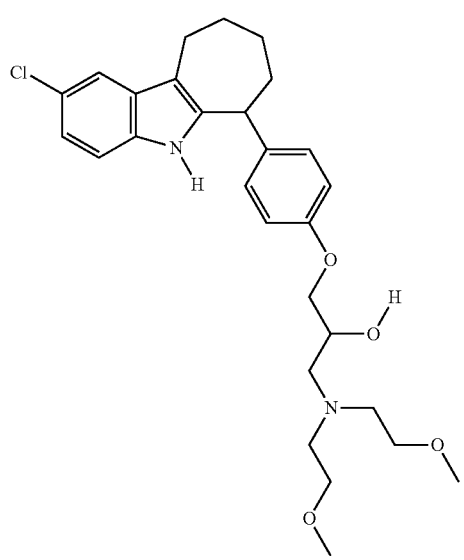
235 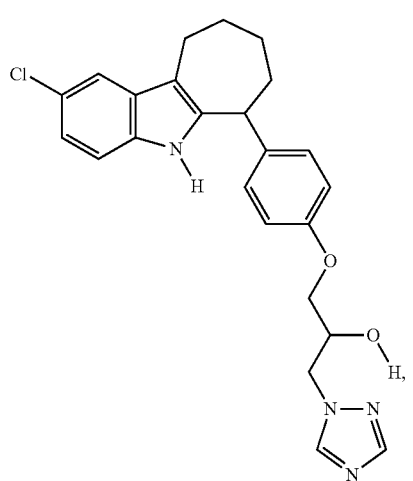
236 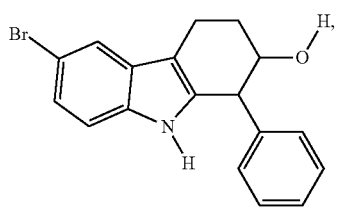
237 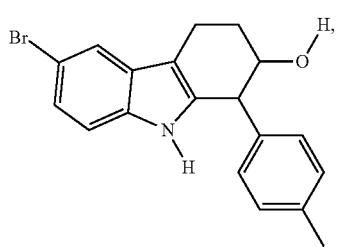
238 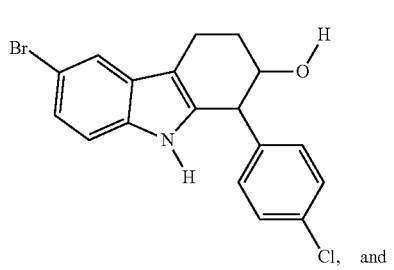
239 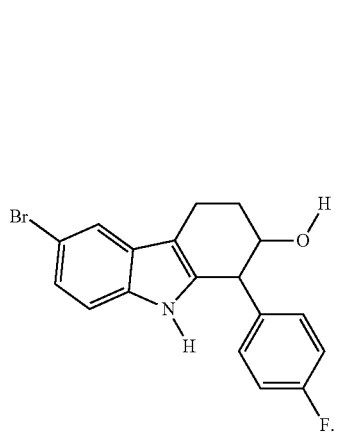
* * * * *